United States Patent
Goldberg et al.

(10) Patent No.: US 9,850,236 B2
(45) Date of Patent: Dec. 26, 2017

(54) TRIFLUOROMETHYL ALCOHOLS AS MODULATORS OF RORγT

(71) Applicant: Janssen Pharmaceutica NV, Beerse (BE)

(72) Inventors: Steven Goldberg, Carlsbad, CA (US); Hariharan Venkatesan, San Diego, CA (US); Virginia Tanis, Vista, CA (US); Olaf Kinzel, Heidelberg (DE); Christian Gege, Ehingen (DE); Christoph Steeneck, Heidelberg (DE); Gerald Kleymann, Bad Salzuflen (DE); Thomas Hoffmann, Speyer (DE); Anne M. Fourie, San Diego, CA (US); Xiaohua Xue, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/927,499

(22) Filed: Oct. 30, 2015

(65) Prior Publication Data

US 2016/0122336 A1    May 5, 2016

Related U.S. Application Data

(60) Provisional application No. 62/072,563, filed on Oct. 30, 2014.

(51) Int. Cl.
| | |
|---|---|
| *A61K 31/426* | (2006.01) |
| *C07D 277/56* | (2006.01) |
| *C07D 417/06* | (2006.01) |
| *A61K 31/454* | (2006.01) |
| *A61K 45/06* | (2006.01) |
| *C07D 487/08* | (2006.01) |
| *A61K 31/427* | (2006.01) |
| *C07D 495/10* | (2006.01) |
| *C07D 417/14* | (2006.01) |
| *A61K 31/4709* | (2006.01) |
| *A61K 31/541* | (2006.01) |
| *A61K 31/4439* | (2006.01) |

(52) U.S. Cl.
CPC .......... *C07D 417/06* (2013.01); *A61K 31/426* (2013.01); *A61K 31/427* (2013.01); *A61K 31/4439* (2013.01); *A61K 31/454* (2013.01); *A61K 31/4709* (2013.01); *A61K 31/541* (2013.01); *A61K 45/06* (2013.01); *C07D 277/56* (2013.01); *C07D 417/14* (2013.01); *C07D 487/08* (2013.01); *C07D 495/10* (2013.01)

(58) Field of Classification Search
CPC .......... A61K 31/426; A61K 31/427; A61K 31/4439; A61K 31/454; A61K 31/4709; A61K 31/541; C07D 277/56; C07D 417/06; C07D 417/14; C07D 487/08; C07D 495/109

USPC .......... 514/336, 365; 546/269.7; 548/200
See application file for complete search history.

(56) References Cited

U.S. PATENT DOCUMENTS

| | | |
|---|---|---|
| 5,342,835 A | 8/1994 | Pepin et al. |
| 2015/0038350 A1 | 2/2015 | Nishinaga et al. |
| 2015/0072890 A1 | 3/2015 | Nishinaga et al. |

FOREIGN PATENT DOCUMENTS

| | | |
|---|---|---|
| EP | 360701 A1 | 3/1990 |
| EP | 2738170 | 6/2014 |
| WO | WO 1996003392 A1 | 2/1996 |
| WO | WO 2002083111 A2 | 10/2002 |
| WO | WO 2003015776 A1 | 2/2003 |
| WO | WO 2006124687 A1 | 11/2006 |
| WO | WO 2007087427 A2 | 8/2007 |
| WO | WO 2008064317 A1 | 5/2008 |
| WO | WO 2008064318 A2 | 5/2008 |
| WO | WO 2009011850 | 1/2009 |
| WO | WO 2010006713 | 1/2010 |

(Continued)

OTHER PUBLICATIONS

Zhang et al, "Decarboxylative Cross-Coupling of Azoyl Carboxylic Acids with Aryl Halids," Organic Letters (2010), vol. 12(21), pp. 4745-4747.*

(Continued)

*Primary Examiner* — Kathrien Cruz
*Assistant Examiner* — Janet L Coppins
(74) *Attorney, Agent, or Firm* — Yuriy P. Stercho

(57) ABSTRACT

The present invention comprises compounds of Formula I.

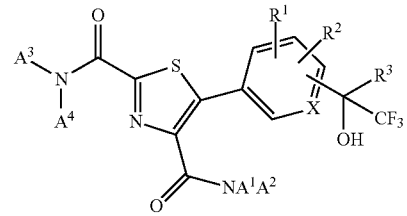

Formula I wherein:
X, $A^1$, $A^2$, $A^3$, $A^4$, $R^1$, $R^2$, and $R^3$ are defined in the specification.
The invention also comprises a method of treating or ameliorating a syndrome, disorder or disease, wherein said syndrome, disorder or disease is rheumatoid arthritis or psoriasis. The invention also comprises a method of modulating RORγt activity in a mammal by administration of a therapeutically effective amount of at least one compound of claim 1.

43 Claims, No Drawings

(56) References Cited

FOREIGN PATENT DOCUMENTS

| WO | WO 2011053948 A1 | 5/2011 |
|---|---|---|
| WO | WO 2011112263 A1 | 9/2011 |
| WO | WO 2011112264 A1 | 9/2011 |
| WO | WO 2011115892 A1 | 9/2011 |
| WO | WO 2012027965 | 3/2012 |
| WO | WO 2012074547 A2 | 6/2012 |
| WO | WO 2012129491 | 9/2012 |
| WO | WO 2012158784 A2 | 11/2012 |
| WO | WO 2013036912 A2 | 3/2013 |
| WO | WO 2013079223 A | 6/2013 |
| WO | WO 2013092939 A1 | 6/2013 |
| WO | WO 2013178362 A1 | 12/2013 |
| WO | WO 2015035278 A1 | 3/2015 |
| WO | WO 2015042212 A1 | 3/2015 |
| WO | WO 2015082533 A1 | 6/2015 |
| WO | WO 2015103507 A1 | 7/2015 |
| WO | WO 2015103508 A1 | 7/2015 |
| WO | WO 2015103509 A1 | 7/2015 |
| WO | WO 2015103510 A1 | 7/2015 |
| WO | WO 2015145371 A1 | 10/2015 |

OTHER PUBLICATIONS

Liegault, et al., "Establishment of Broadly Applicable reaction condisions for the Palladium-Catalyzed Direct Arylation of Heteroatom-Containing Aromatic Compounds", The Journal of Organic Chemistry, (2009), vol. 74, No. 5, 6, pp. 1826-1834.

Kumar N, "The Benzenesulfoamide T0901317 [N-(2,2,2-Trifluoroethyl)-N-[4-[2,2,2- trifluoro-1-hydroxy-1-(trifluoromethyl)ethyl]phenyl]-benzenesulfonamide] Is a Novel Retinoic Acid Receptor-Related Orphan Receptor-α/γ Inverse Agonist", Molecular Pharmacology (2010), 77(2), 228-236.

Chang M, "Pharmacologic Repression of Retinoic Acid Receptor—Related Orphan Nuclear Receptor γ Is Therapeutic in the Collagen-Induced Arthritis Experimental Model", Arthritis & Rheumatology (2014), 66(3), 579-588.

Yao, et al, "Preparation Method of N-butyl-5-phenylthiazole-4-Formamide Derivative Via Coupling Reaction Under Catalysis of Copper Catalyst", Database accession No. 2014:924023.

Zhang, et al., "Decarboxylative Cross-Coupling of Azoyl Carboxylic Acids with Aryl Halides", Organic Letters, (2010) vol. 12, No. 21, pp. 4745-47457.

PCT/US2015/058193, International Search Report, Dated Jan. 26, 2016.

PCT/US2015/058198, International Search Report, Dated Jan. 21, 2016.

PCT/US2015/058200, International Search Report, Dated Jan. 27, 2016.

U.S. Appl. No. 14/927,502.

U.S. Appl. No. 14/927,501.

PCT/US2015/058193, Written Opinion dated Jan. 26, 2016.

PCT/US2015/058198, Written Opinion dated Jan. 21, 2016.

PCT/US2015/058200, Written Opinion dated Jan. 27, 2016.

Fauber et al., J. Med. Chem. 2014, 57, 5871-5892.

Yang et al., Trends in Pharmacological Sciences, Oct. 2014, vol. 35, No. 10, 493-500.

Steven Goldberg et al., U.S. Appl. No. 15/497,565.

Barczyk, A., W. Pierzchala, et al. (2003). "Interleukin-17 in sputum correlates with airway hyperresponsiveness to methacholine." Respir Med 97(6): 726-33.

Beurel, E., Harrington, L. E., Jope, R. S. (2013) "Inflammatory T helper 17 cells promote depression-like behavior in mice." Biol Psychiatry 73(7): 622-30.

Bowes, J. and A. Barton "The genetics of psoriatic arthritis: lessons from genome-wide association studies." Discov Med 10(52): 177-83 (2010).

Chang, M. R. et al. (2015) "Antiobesity Effect of a Small Molecule Repressor of RORγ." Mol Pharmacol. 88(1): 48-56.

Chen, Y., et al. (2011). "Emerging tendency towards autoimmune process in major depressive patients: A novel insight from Th17 cells." Psychiatry Research 188(2): 224-230.

Cua, D. J., J. Sherlock, et al. (2003). "Interleukin-23 rather than interleukin-12 is the critical cytokine for autoimmune inflammation of the brain." Nature 421(6924): 744-8.

Dong, C. (2006). "Diversification of T-helper-cell lineages: finding the family root of IL-17-producing cells." Nat Rev Immunol 6(4): 329-33.

Fujino, S., A. Andoh, et al. (2003). "Increased expression of interleukin 17 in inflammatory bowel disease." Gut 52(1): 65-70.

Garber K. (2011). "Psoriasis: from bed to bench and back" Nat Biotech 29, 563-566.

Gazouli, M., I. Pachoula, et al. "NOD2/CARD15, ATG16L1 and IL23R gene polymorphisms and childhood-onset of Crohn's disease." World J Gastroenterol 16(14): 1753-8 (2010).

Hueber, W., Patel, D.D., Dryja, T., Wright, A.M., Koroleva, I., Bruin, G., Antoni, C., Draelos, Z., Gold, M.H., Durez, P., Tak, P.P., Gomez-Reino, J.J., Foster, C.S., Kim, R.Y., Samson, C.M., Falk, N. S., Chu, D.S., Callanan, D., Nguyen, Q.D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.

Ivanov, Il, B. S. McKenzie, et al. (2006). "The orphan nuclear receptor RORgammat directs the differentiation program of proinflammatory IL-17+ T helper cells." Cell 126(6): 1121-33.

Kochi, Y., Y. Okada, et al. "(2010) A regulatory variant in CCR6 is associated with rheumatoid arthritis susceptibility." Nat Genet 42(6): 515-9.

Kolls, J. K. And A. Linden (2004). "Interleukin-17 family members and inflammation." Immunity 21(4): 467-76.

Korn, T., E. Bettelli, et al. (2009). "IL-17 and Th17 Cells." Annu Rev Immunol 27: 485-517.

Krueger, J. G., S. Fretzin, et al. "IL-17A is essential for cell activation and inflammatory gene circuits in subjects with psoriasis." J Allergy Clin Immunol 13(1): 145-154 e9 (2012).

Langrish, C. L., Y. Chen, et al. (2005). "IL-23 drives a pathogenic T cell population that induces autoimmune inflammation." J Exp Med 201(2): 233-40.

Leonardi, C., R. Matheson, et al. "Anti-interleukin-17 monoclonal antibody ixekizumab in chronic plaque psoriasis." N. Engl J Med 366(13): 1190-9 (2012).

Lock, C., G. Hermans, et al. (2002). "Gene-microarray analysis of multiple sclerosis lesions yields new targets validated in autoimmune encephalomyelitis." Nat Med 8(5): 500-8.

Matulis, D., Kranz, J. K., Salemme, F. R., and Todd, M. J. (2005) Thermodynamic stability of carbonic anhydrase: measurements of binding affinity and stoichiometry using ThermoFluor. Biochemistry 44, 5258-66.

McKenzie, B. S., R. A. Kastelein, et al. (2006). "Understanding the IL-23-IL-17 immune pathway." Trends Immunol 27(1): 17-23.

Meissburger, B. et al. (2011) "Adipogenesis and insulin sensitivity in obesity are regulated by retinoid-related orphan receptor gamma." EMBO Mol Med. 3(11): 637-651.

Nunez, C., B. Dema, et al. (2008). "IL23R: a susceptibility locus for celiac disease and multiple sclerosis?" Genes Immun 9(4): 289-93.

Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. J Biomol Screen 6, 429-40.

Papp, K. A., "Brodalumab, an anti-interleukin-17-receptor antibody for psoriasis." N Engl J Med 2012 366(13): 1181-9.

Stamp, L. K., M. J. James, et al. (2004). "Interleukin-17: the missing link between T-cell accumulation and effector cell actions in rheumatoid arthritis" Immunol Cell Biol 82(1): 1-9.

Tonel, G., C. Conrad, et al. "Cutting edge: A critical functional role for IL-23 in psoriasis." J Immunol 185(10): 5688-91 (2010).

Yen, D., J. Cheung, et al. (2006). "IL-23 is essential for T cell-mediated colitis and promotes inflammation via IL-17 and IL-6." J Clin Invest 116(5): 1310-6.

\* cited by examiner

SEQUENCE LISTING

```
<160> NUMBER OF SEQ ID NOS: 4

<210> SEQ ID NO 1
<211> LENGTH: 3054
<212> TYPE: DNA
<213> ORGANISM: Homo sapiens

<400> SEQUENCE: 1
agagagctag gtgcagagct tcaggctgag gcgctgctga gagggcctcg ccccgcctct      60
gccgccagct gcaccccact cctggaccac cccctgctga gaaggacagg gagccaaggc     120
cggcagagcc aaggctcagt catgagaaca caaattgaag tgatcccttg caaaatctgt     180
ggggacaagt cgtctgggat ccactacggg gttatcacct gtgaggggtg caagggcttc     240
ttccgccgga gccagcgctg taacgcggcc tactcctgca cccgtcagca gaactgcccc     300
atcgaccgca ccagccgaaa ccgatgccag cactgccgcc tgcagaaatg cctggcgctg     360
ggcatgtccc gagatgctgt caagttcggc cgcatgtcca agaagcagag ggacagcctg     420
catgcagaag tgcagaaaca gctgcagcag cggcaacagc agcaacagga accagtggtc     480
aagacccctc cagcagggc ccaaggagca gataccctca cctacacctt ggggctccca     540
gacgggcagc tgcccctggg ctcctcgcct gacctgcctg aggcttctgc ctgtcccct     600 ggcctcctga aagcctcagg ctctgggccc tcatattcca caacttggc caaggcaggg     660 ctcaatgggg cctcatgcca ccttgaatac agccctgagc ggggcaaggc tgagggcaga     720
gagagcttct atagcacagg cagccagctg acccctgacc gatgtggact tcgttttgag     780
gaacacaggc atcctgggct tggggaactg ggacagggcc cagacagcta cggcagcccc     840
agtttccgca gcacaccgga ggcaccctat gcctccctga cagagataga gcacctggtg     900
cagagcgtct gcaagtccta cagggagaca tgccagctgc ggctggagga cctgctgcgg     960
cagcgctcca acatcttctc ccgggaggaa gtgactggct accagaggaa gtccatgtgg    1020
gagatgtggg aacggtgtgc ccaccacctc accgaggcca ttcagtacgt ggtggagttc    1080
```

```
gccaagaggc tctcaggctt tatggagctc tgccagaatg accagattgt gcttctcaaa    1140
gcaggagcaa tggaagtggt gctggttagg atgtgccggg cctacaatgc tgacaaccgc    1200
acggtctttt ttgaaggcaa atacggtggc atggagctgt tccgagcctt gggctgcagc    1260
gagctcatca gctccatctt tgacttctcc cactccctaa gtgccttgca cttttccgag    1320
gatgagattg ccctctacac agcccttgtt ctcatcaatg cccatcggcc agggctccaa    1380
gagaaaagga agtagaaaca gctgcagtac aatctggagc tggcctttca tcatcatctc    1440
tgcaagactc atcgccaaag catcctggca aagctgccac ccaaggggaa gcttcggagc    1500
ctgtgtagcc agcatgtgga aaggctgcag atcttccagc acctccaccc catcgtggtc    1560
caagccgctt tccctccact ctacaaggag ctcttcagca ctgaaaccga gtcacctgtg    1620
gggctgtcca agtgacctgg aagagggact ccttgcctct ccctatggcc tgctggccca    1680
cctcctggga ccccgttcca ccctcaccct tttcctttcc catgaaccct ggagggtggt    1740
ccccaccagc tctttggaag tgagcagatg ctgcggctgg ctttctgtca gcaggccggc    1800
ctggcagtgg gacaatcgcc agagggtggg gctggcagaa caccatctcc agcctcagct    1860
ttgacctgtc tcatttccca tattccttca cacccagctt ctggaaggca tggggtggct    1920
gggatttaag gacttctggg ggaccaagac atcctcaaga aaacaggggc atccagggct    1980
ccctggatga atagaatgca attcattcag aagctcagaa gctaagaata agcctttgaa    2040
atacctcatt gcatttccct ttgggcttcg gcttggggag atggatcaag ctcagagact    2100
ggcagtgaga gcccagaagg acctgtataa aatgaatctg gagctttaca ttttctgcct    2160
ctgccttcct cccagctcag caaggaagta tttgggcacc ctacccttta cctggggtct    2220
aaccaaaaat ggatgggatg aggatgagag gctggagata attgttttat gggatttggg    2280
tgtgggacta gggtacaatg aaggccaaga gcatctcaga catagagtta aaactcaaac    2340
ctcttatgtg cactttaaag atagacttta ggggctggca caaatctgat cagagacaca    2400
tatccataca caggtgaaac acatacagac tcaacagcaa tcatgcagtt ccagagacac    2460
atgaacctga cacaatctct cttatccttg aggccacagc ttggaggagc ctagaggcct    2520
caggggaaag tcccaatcct gagggaccct cccaaacatt tccatggtgc tccagtccac    2580
tgatctgggg tctggggtga tccaaatacc accccagctc cagctgtctt ctaccactag    2640
aagacccaag agaagcagaa gtcgctcgca ctggtcagtc ggaaggcaag atcagatcct    2700
ggaggacttt cctggcctgc cgccagcccc tgctcttgtt gtggagaagg aagcagatgt    2760
gatcacatca ccccgtcatt gggcaccgct gactccagca tggaggacac cagggagcag    2820
ggcctgggcc tgtttcccca gctgtgatct tgcccagaac ctctcttggc ttcataaaca    2880
gctgtgaacc ctcccctgag ggattaacag caatgatggg cagtcgtgga gttggggggg    2940
ttgggggtgg gattgtgtcc tctaagggga cgggttcatc tgagtaaaca taaacccaa    3000 cttgtgccat tctttataaa atgatttta aggcaaaaaa aaaaaaaaa aaaa            3054
```

<210> SEQ ID NO 2
<211> LENGTH: 786
<212> TYPE: DNA
<213> ORGANISM: Homo sapiens

<400> SEQUENCE: 2

```
agcacaccgg aggcaccta tgcctccctg acagagatag agcacctggt gcagagcgtc      60
tgcaagtcct acagggagac atgccagctg cggctggagg acctgctgcg gcagcgctcc    120
aacatcttct cccgggagga agtgactggc taccagagga agtccatgtg ggagatgtgg    180
```

```
gaacggtgtg cccaccacct caccgaggcc attcagtacg tggtggagtt cgccaagagg    240
ctctcaggct ttatggagct ctgccagaat gaccagattg tgcttctcaa agcaggagca    300
atggaagtgg tgctggttag gatgtgccgg gcctacaatg ctgacaaccg cacggtcttt    360
tttgaaggca aatacggtgg catggagctg ttccgagcct tgggctgcag cgagctcatc    420
agctccatct ttgacttctc ccactcccta agtgccttgc acttttccga ggatgagatt    480
gccctctaca cagcccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tctacaagga gctcttcagc actgaaaccg agtcacctgt ggggctgtcc    780
aagtga                                                              786
```

```
<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
            20                  25                  30

Thr Glu Ile Glu His Leu Val Gln Ser Val Cys Lys Ser Tyr Arg Glu
        35                  40                  45

Thr Cys Gln Leu Arg Leu Glu Asp Leu Leu Arg Gln Arg Ser Asn Ile
    50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
            100                 105                 110

Asp Gln Ile Val Leu Leu Lys Ala Gly Ala Met Glu Val Val Leu Val
        115                 120                 125

Arg Met Cys Arg Ala Tyr Asn Ala Asp Asn Arg Thr Val Phe Phe Glu
    130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175
```

```
Phe Ser Glu Asp Glu Ile Ala Leu Tyr Thr Ala Leu Val Leu Ile Asn
            180                 185                 190

Ala His Arg Pro Gly Leu Gln Glu Lys Arg Lys Val Glu Gln Leu Gln
        195                 200                 205

Tyr Asn Leu Glu Leu Ala Phe His His His Leu Cys Lys Thr His Arg
        210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
                260                 265                 270

Thr Glu Thr Glu Ser Pro Val Gly Leu Ser Lys
        275                 280
```

TRIFLUOROMETHYL ALCOHOLS AS MODULATORS OF RORγT

CROSS-REFERENCE TO RELATED APPLICATIONS

This application claims priority from U.S. Application No. 62/072,563, filed on Oct. 30, 2014, which is incorporated herein by reference.

FIELD OF THE INVENTION

The invention is directed to substituted thiazole compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of $CD4^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+ T helper cells." Cell 126(6): 1121-33). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8; Krueger, J. G., S. Fretzin, et al. "IL-17A is essential for cell activation and inflammatory gene circuits in subjects with psoriasis." J Allergy Clin Immunol 130(1): 145-154 e9). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272).

All the above evidence supports inhibition of the Th17 pathway by modulating RORγt activity as an effective strategy for the treatment of immune-mediated inflammatory diseases.

SUMMARY OF THE INVENTION

The present invention comprises a compound of Formula I.

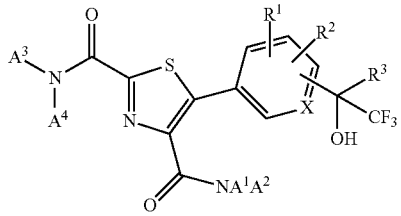

Formula I wherein

X is CH, CR$^1$, or N;

A$^1$ is C$_{(1-2)}$alkyl;

A$^2$ is cyclobutyl, or C$_{(1-4)}$alkyl, wherein said C$_{(1-4)}$alkyl is optionally substituted with OCH$_3$ or up to three fluorine atoms;

or A$^1$ and A$^2$ are taken together with their attached nitrogen to form a ring selected the group consisting of azetidinyl, piperidinyl, pyrrolidinyl,

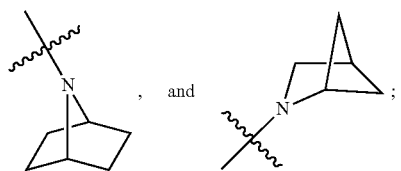 [SMILES: *N1C2CCC1CC2 ; *N1CC2CC1C2]

wherein said ring is optionally substituted with up to three substituents independently selected from the group consisting of F, CF$_3$, CH$_3$, —CN, and CH$_2$OH;

R$^1$ is Cl, C(CH$_3$)$_3$, CH$_2$CH$_3$, OCF$_3$, CF$_3$, OCH(CH$_3$)$_2$, CHF$_2$, OCHF$_2$, OCH$_3$, F, CH$_3$, or —CN;

R$^2$ is H, F, or Cl;

or R$^1$ and R$^2$ may be taken together with their attached phenyl to form a naphthalenyl, or quinolinyl group;

R$^3$ is CF$_3$, or CH$_2$CH$_3$;

A$^3$ is H

A$^4$ is H, C$_{(1-5)}$alkyl,

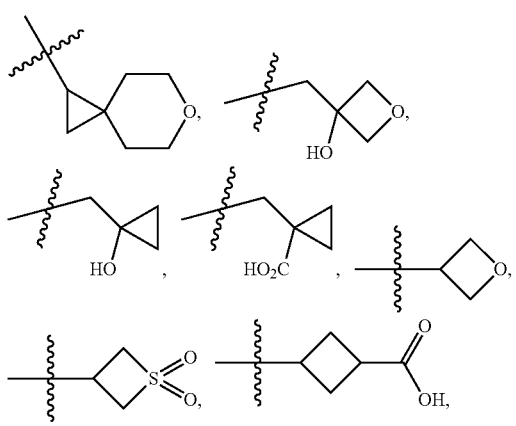

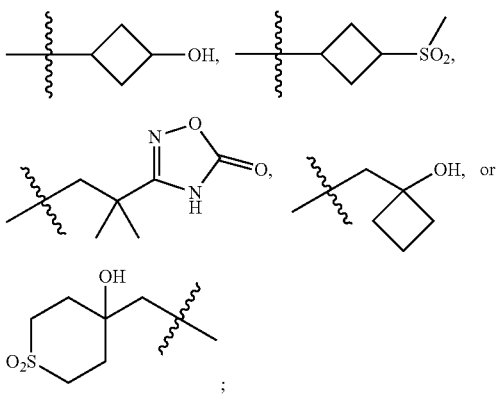

wherein said C$_{(1-5)}$alkyl is optionally substituted with one to two substituents independently selected from COOH, CONH$_2$, —CN, and OH;

or A$^3$ and A$^4$ may be taken together with their attached nitrogen to make a ring selected from the group consisting of

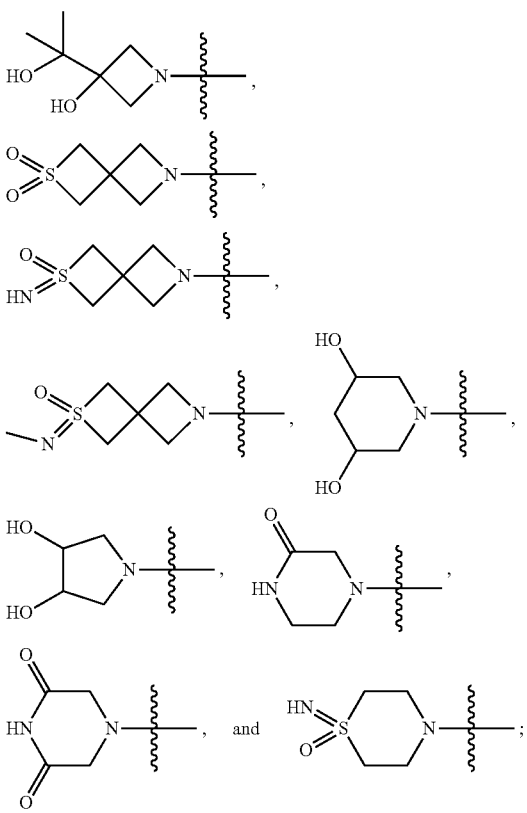

and pharmaceutically acceptable salts thereof.

DETAILED DESCRIPTION OF THE INVENTION

The present invention comprises a compound of Formula I.

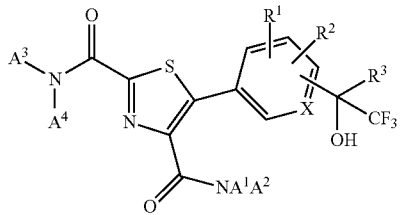
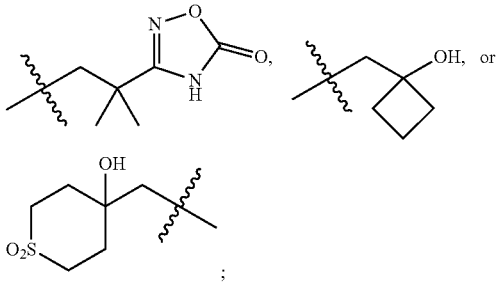

Formula I wherein
X is CH, CR$^1$, or N;
A$^1$ is C$_{(1-2)}$alkyl;
A$^2$ is cyclobutyl, or C$_{(1-4)}$alkyl, wherein said C$_{(1-4)}$alkyl is optionally substituted with OCH$_3$ or up to three fluorine atoms;
 or A$^1$ and A$^2$ are taken together with their attached nitrogen to form a ring selected the group consisting of azetidinyl, piperidinyl, pyrrolidinyl,

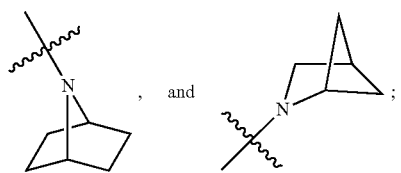 [SMILES: *N1C2CCC1CC2 ; *N1CC2CC1C2]

, and wherein said ring is optionally substituted with up to three substituents independently selected from the group consisting of F, CF$_3$, CH$_3$, —CN, and CH$_2$OH;
R$^1$ is Cl, C(CH$_3$)$_3$, CH$_2$CH$_3$, OCF$_3$, CF$_3$, OCH(CH$_3$)$_2$, CHF$_2$, OCHF$_2$, OCH$_3$, F, CH$_3$, or —CN;
R$^2$ is H, F, or Cl;
 or R$^1$ and R$^2$ may be taken together with their attached phenyl to form a naphthalenyl, or quinolinyl group;
R$^3$ is CF$_3$, or CH$_2$CH$_3$;
A$^3$ is H
A$^4$ is H, C$_{(1-5)}$alkyl,

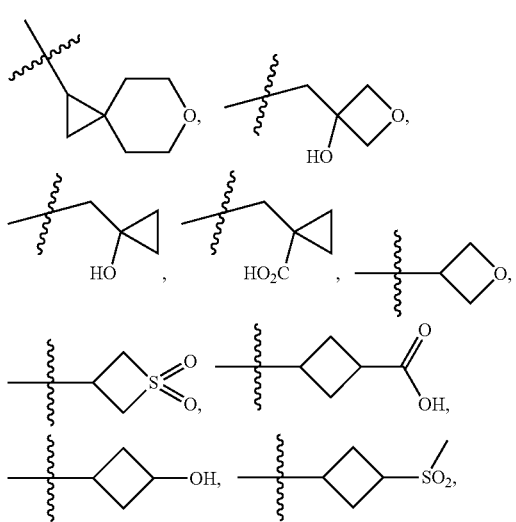

wherein said C$_{(1-5)}$alkyl is optionally substituted with one to two substituents independently selected from COOH, CONH$_2$, —CN, and OH;
 or A$^3$ and A$^4$ may be taken together with their attached nitrogen to make a ring selected from the group consisting of

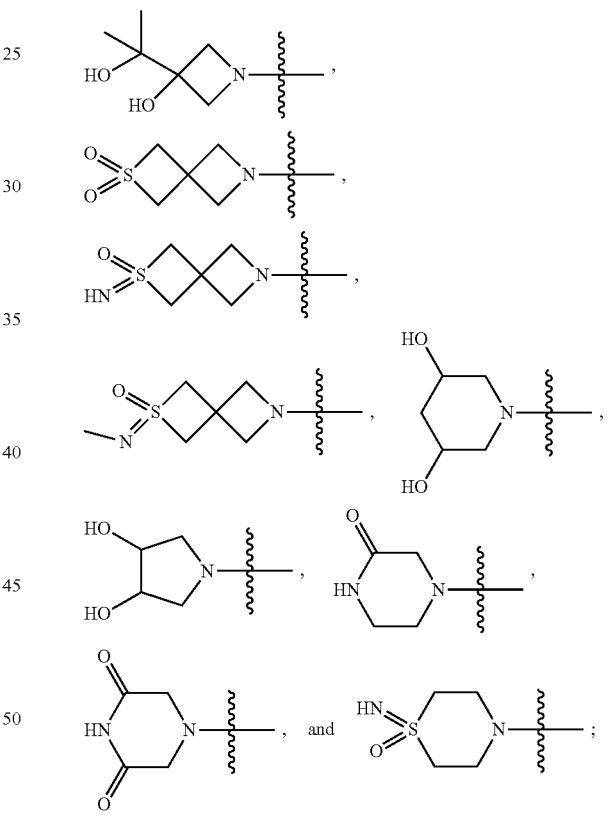

and pharmaceutically acceptable salts thereof.
In another embodiment of the invention:
X is CH, CR$^1$, or N;
A$^1$ is C$_{(1-2)}$alkyl;
A$^2$ is cyclobutyl, or C$_{(1-4)}$alkyl, wherein said C$_{(1-4)}$alkyl is optionally substituted with OCH$_3$ or up to three fluorine atoms;
 or A$^1$ and A$^2$ are taken together with their attached nitrogen to form a ring selected the group consisting of azetidinyl, piperidinyl, pyrrolidinyl,

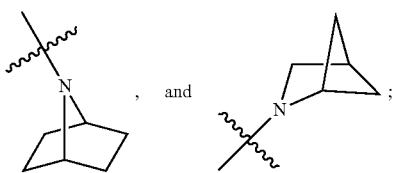 [SMILES: *N1C2CCC1CC2 ; *N1CC2CC1C2] and wherein said ring is optionally substituted with up to three substituents independently selected from the group consisting of F, CF$_3$, CH$_3$, —CN, and CH$_2$OH;

R$^1$ is Cl, C(CH$_3$)$_3$, CH$_2$CH$_3$, OCF$_3$, CF$_3$, OCH(CH$_3$)$_2$, CHF$_2$, OCHF$_2$, OCH$_3$, F, or CH$_3$;

R$^2$ is H, F, or Cl;

or R$^1$ and R$^2$ may be taken together with their attached phenyl to form a naphthalenyl, or quinolinyl group;

R$^3$ is CF$_3$, or CH$_2$CH$_3$;

A$^3$ is H

A$^4$ is H, C$_{(1-5)}$alkyl,

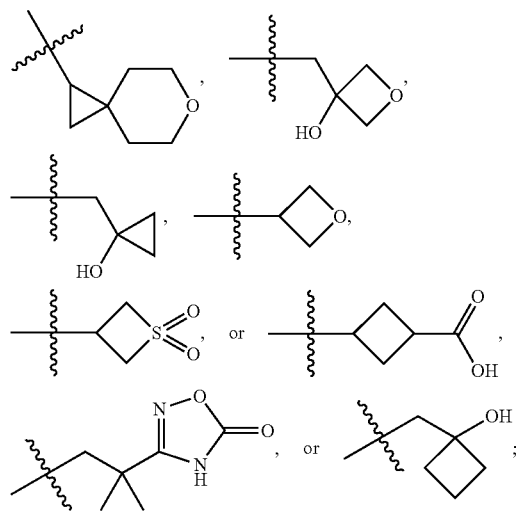

wherein said C$_{(1-5)}$alkyl is optionally substituted with one to two substituents independently selected from CONH$_2$, —CN, and OH;

or A$^3$ and A$^4$ may be taken together with their attached nitrogen to make a ring selected from the group consisting of

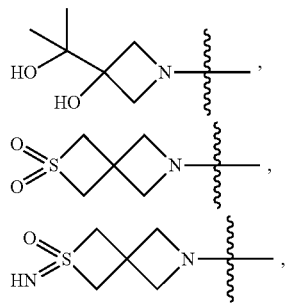

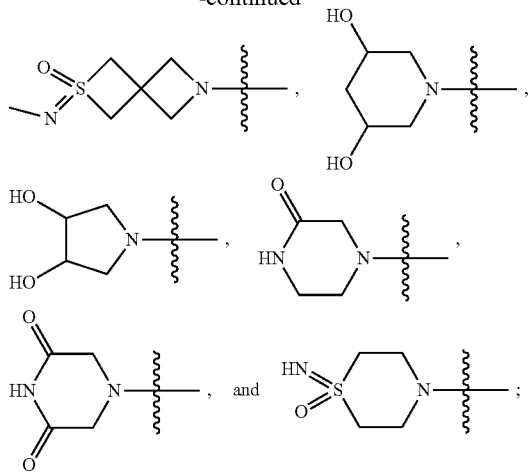

and pharmaceutically acceptable salts thereof.

Another embodiment of the invention is a compound of Formula II:

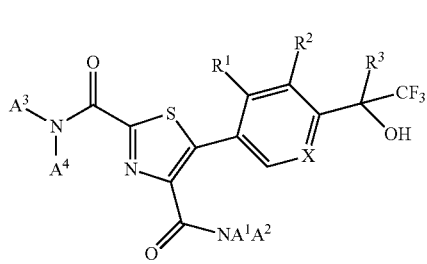

Formula II wherein

X is CH, CR$^1$, or N;

A$^1$ is C$_{(1-2)}$alkyl;

A$^2$ is cyclobutyl, or C$_{(1-4)}$alkyl, wherein said C$_{(1-4)}$alkyl is optionally substituted with OCH$_3$ or up to three fluorine atoms;

or A$^1$ and A$^2$ are taken together with their attached nitrogen to form a ring selected the group consisting of azetidinyl, piperidinyl, pyrrolidinyl,

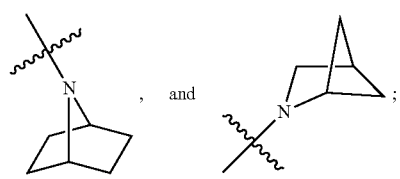 [SMILES: *N1C2CCC1CC2 ; *N1CC2CC1C2]

wherein said ring is optionally substituted with up to three substituents independently selected from the group consisting of F, CF$_3$, CH$_3$, —CN, and CH$_2$OH;

R$^1$ is Cl, C(CH$_3$)$_3$, CH$_2$CH$_3$, OCF$_3$, CF$_3$, OCH(CH$_3$)$_2$, CHF$_2$, OCHF$_2$, OCH$_3$, F, or CH$_3$;

R$^2$ is H, F, or Cl;

or R$^1$ and R$^2$ may be taken together with their attached phenyl to form a naphthalenyl, or quinolinyl group;

R$^3$ is CF$_3$, or CH$_2$CH$_3$;

A$^3$ is H

A$^4$ is H, C$_{(1-5)}$alkyl,

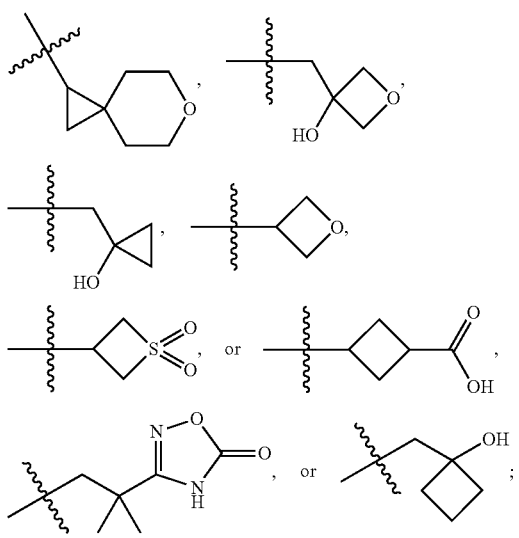

wherein said $C_{(1-5)}$alkyl is optionally substituted with one to two substituents independently selected from $CONH_2$, —CN, and OH;

or $A^3$ and $A^4$ may be taken together with their attached nitrogen to make a ring selected from the group consisting of

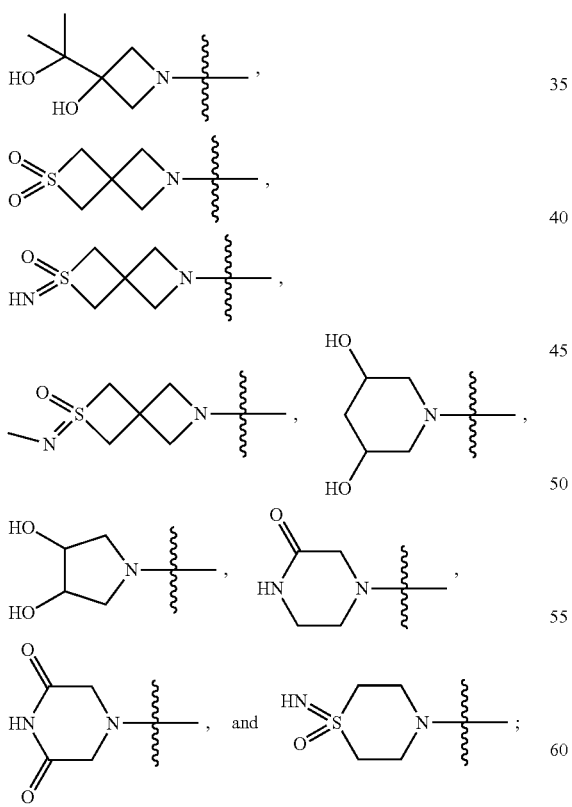

and pharmaceutically acceptable salts thereof.

Another embodiment of the invention is a compound selected from the group consisting of:

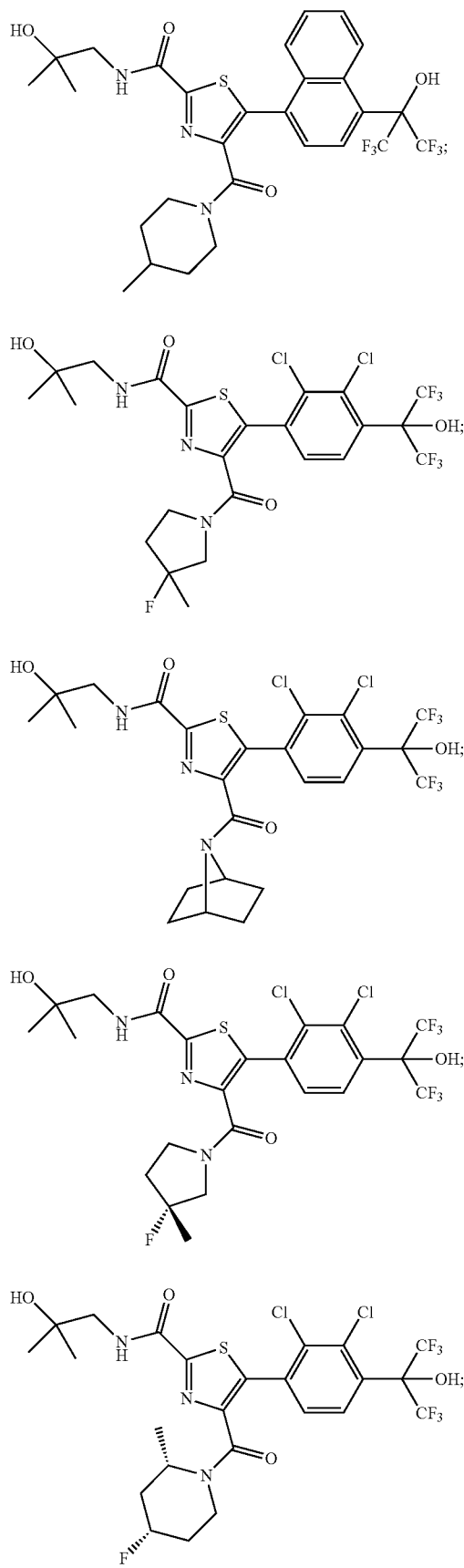

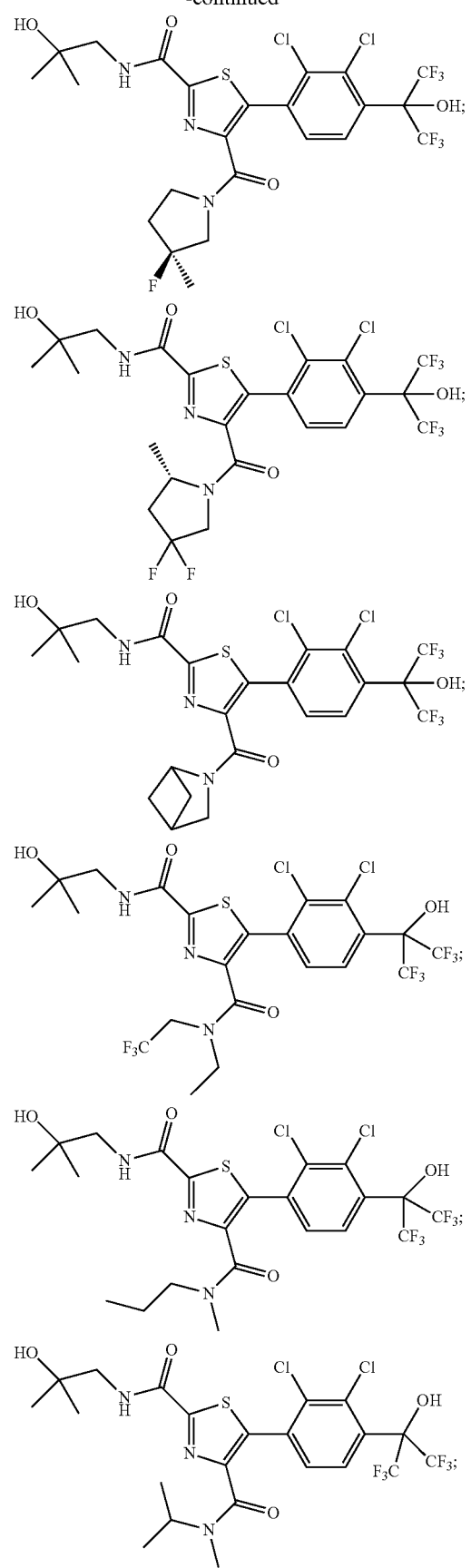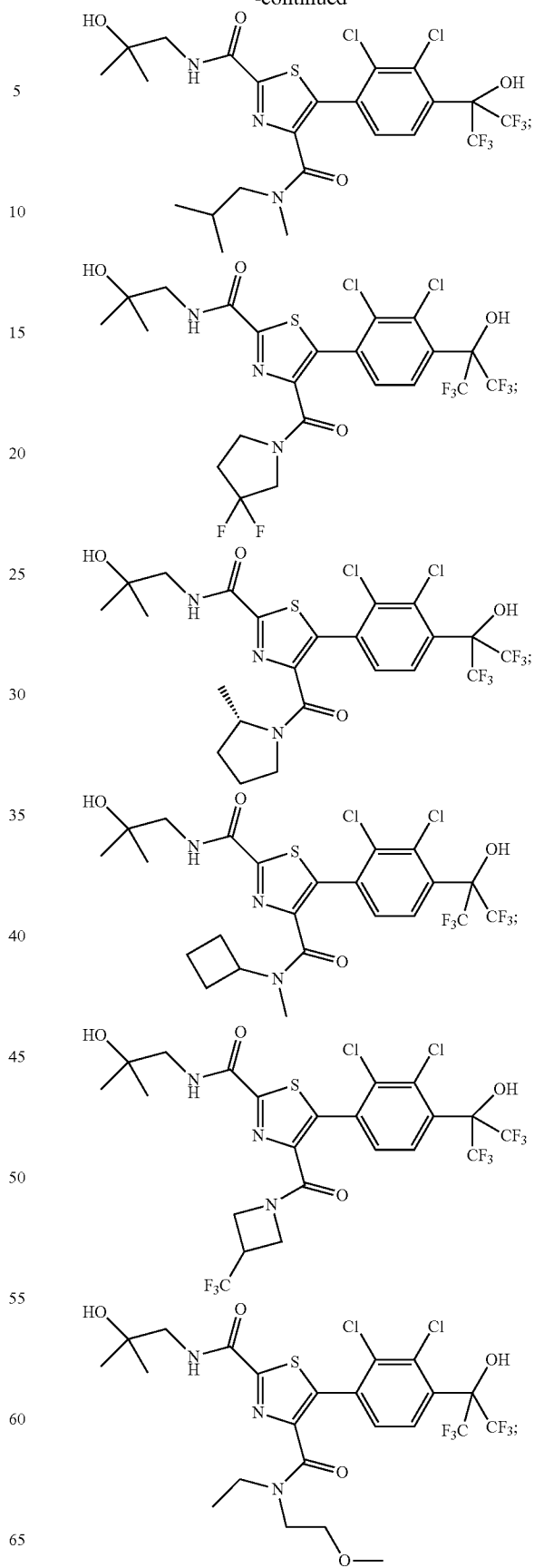

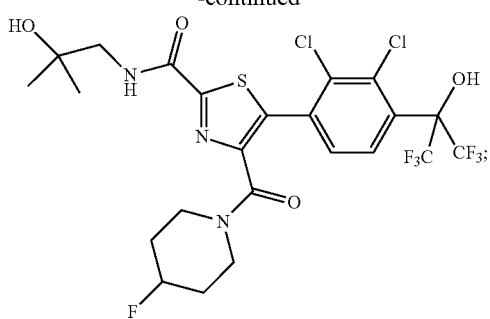
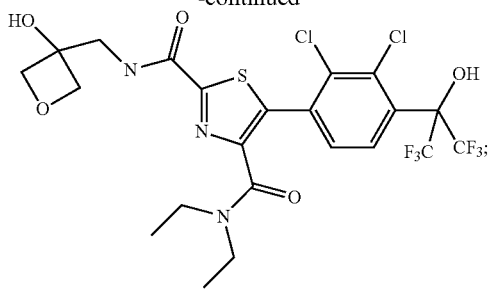
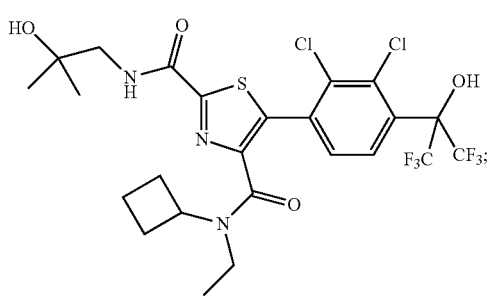
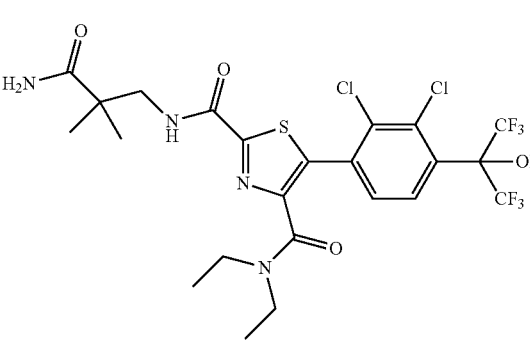
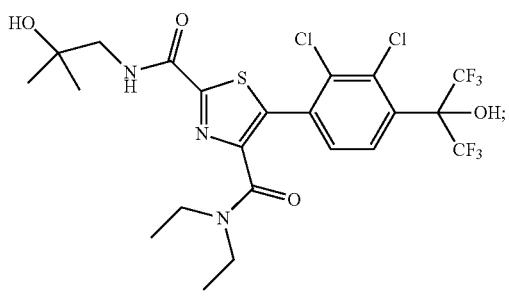
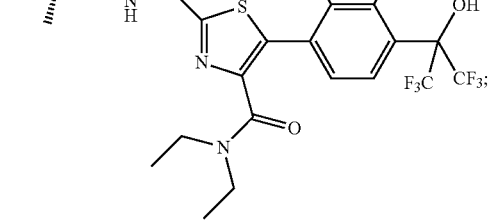
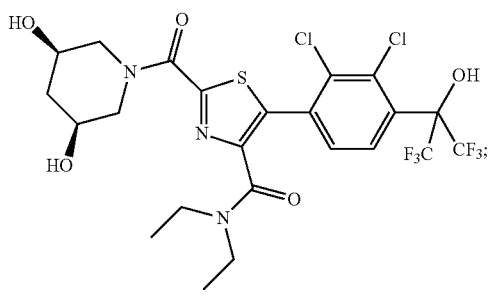
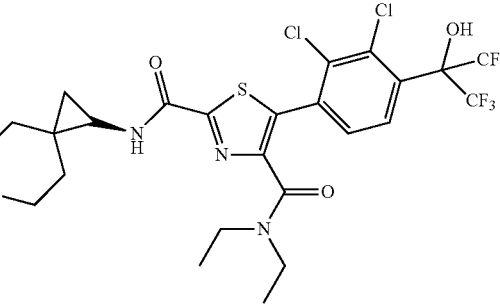
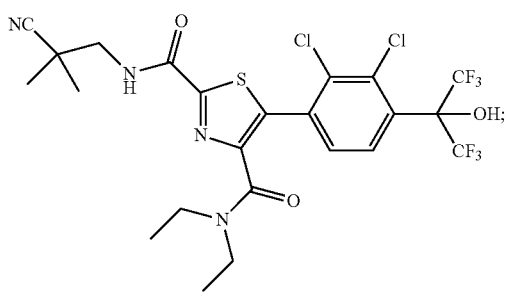
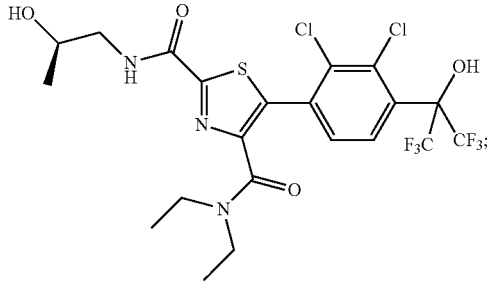

-continued
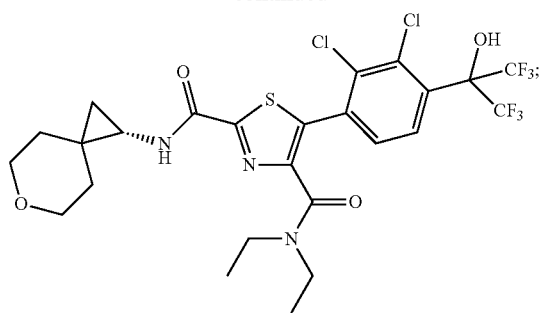
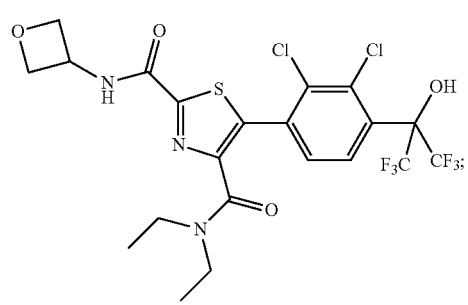
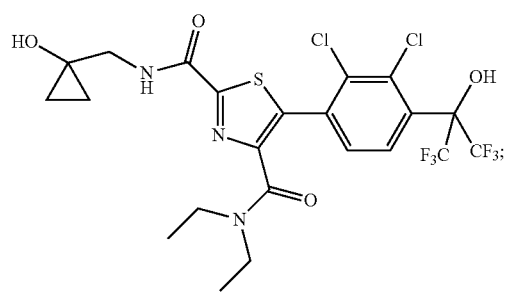
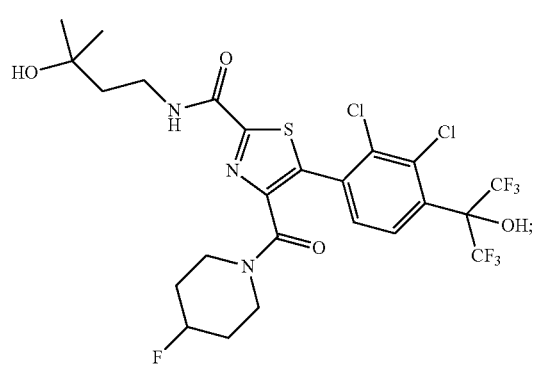
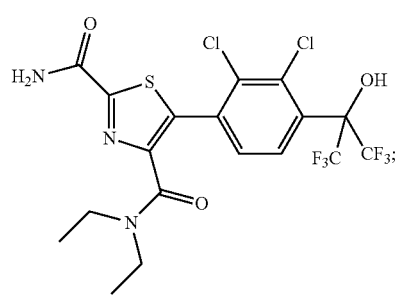
-continued
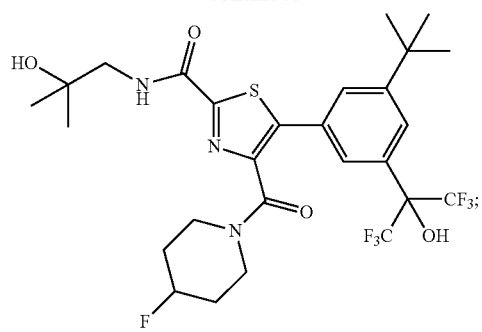
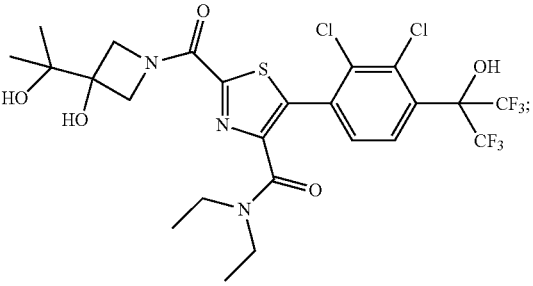
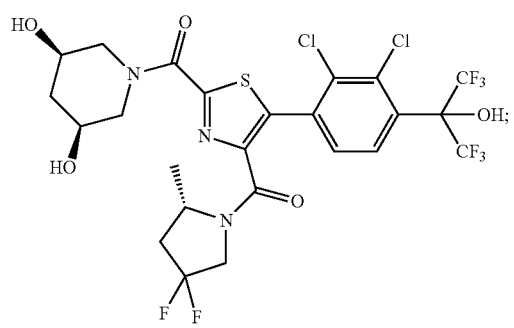
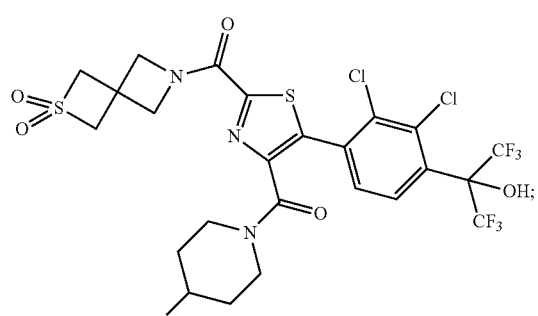
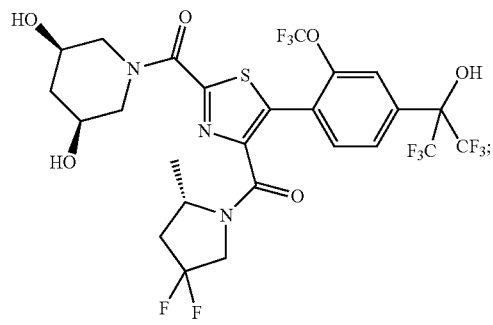

17
-continued
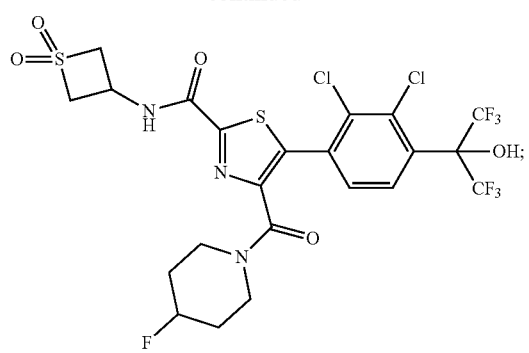
18
-continued
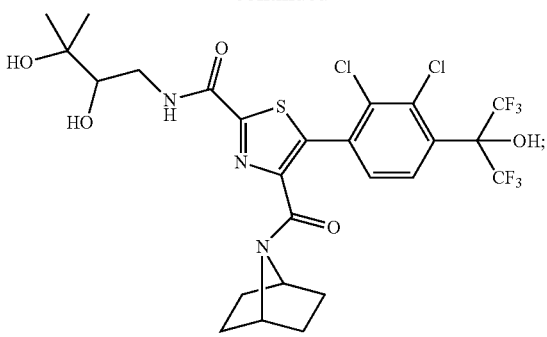
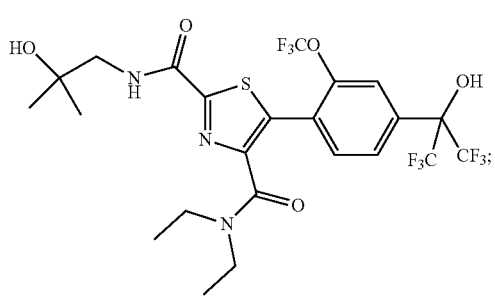
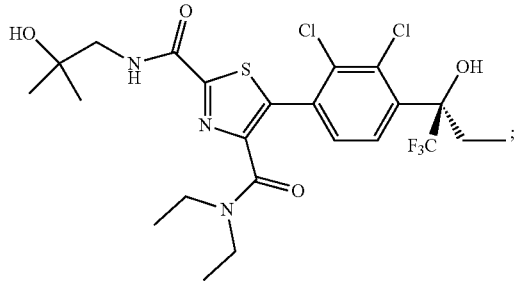
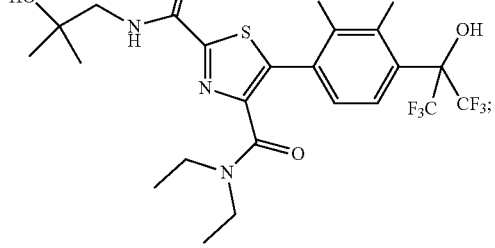
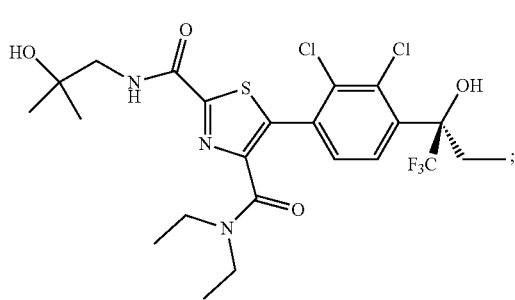

-continued
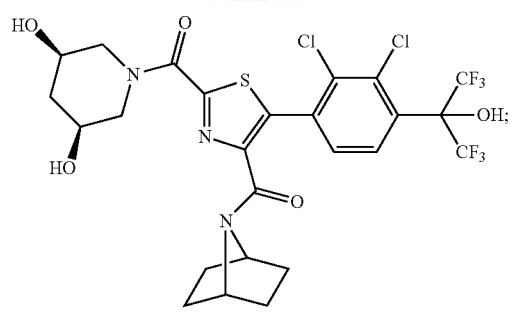
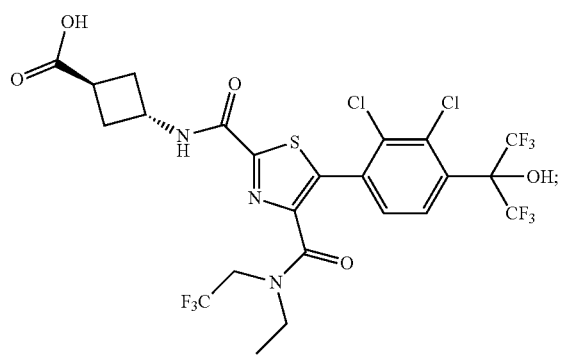
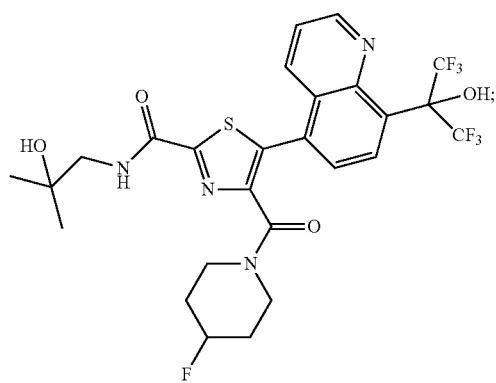
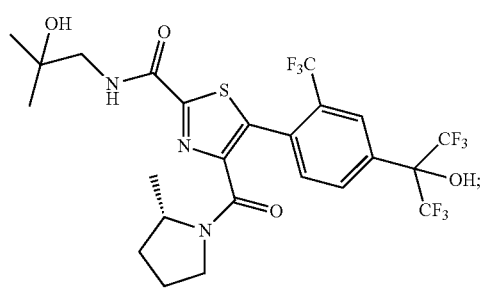
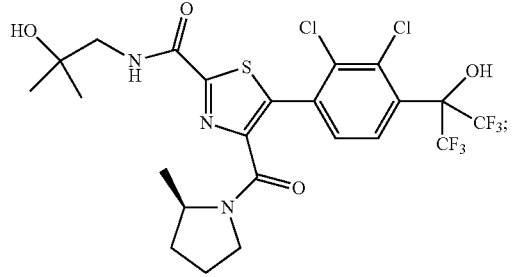
-continued
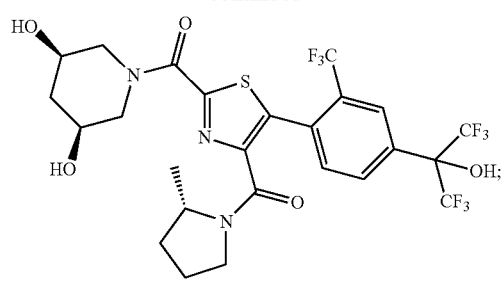
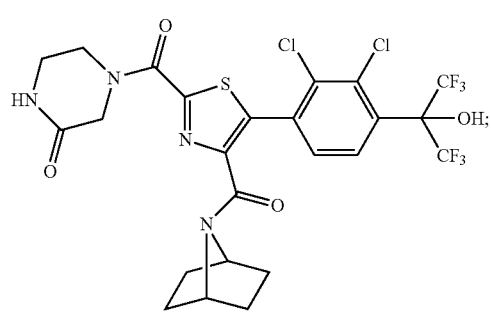
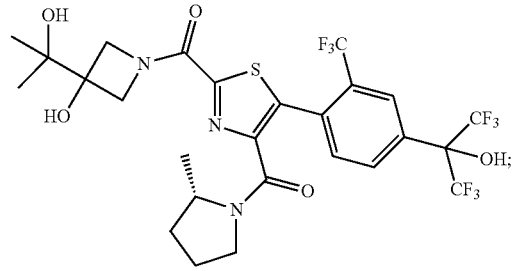
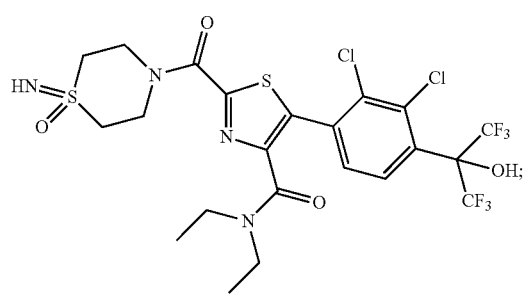
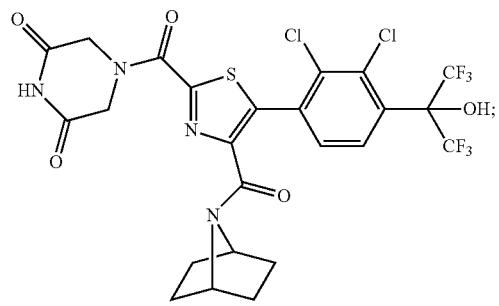

21
-continued
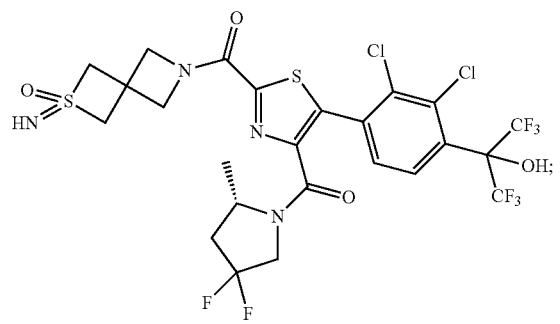
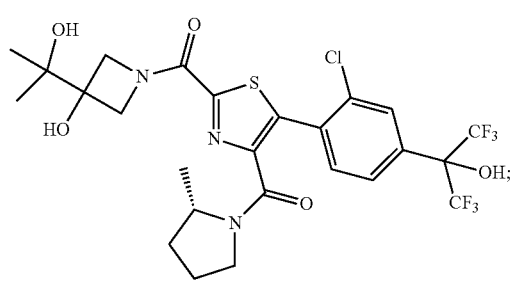
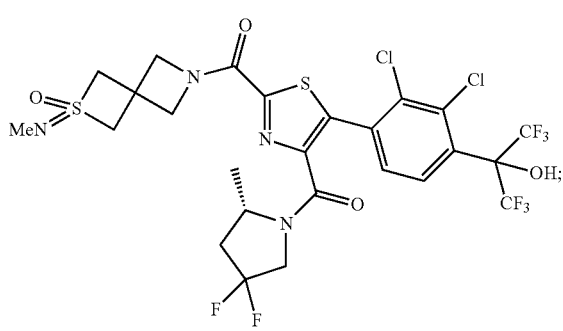
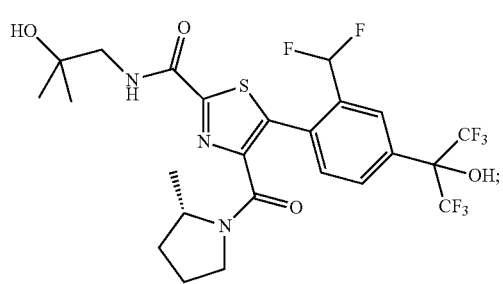
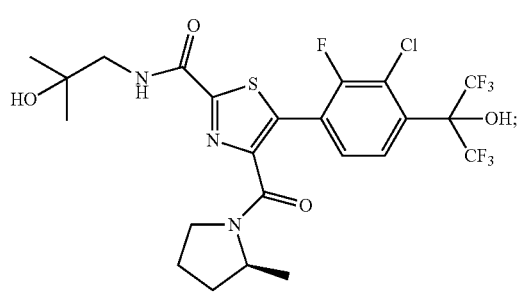
22
-continued
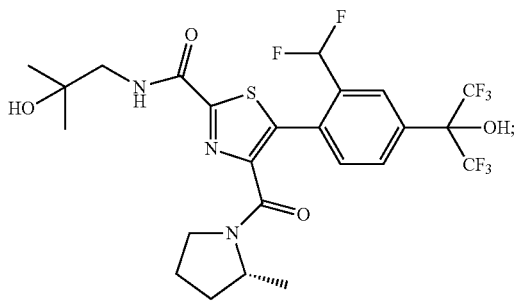
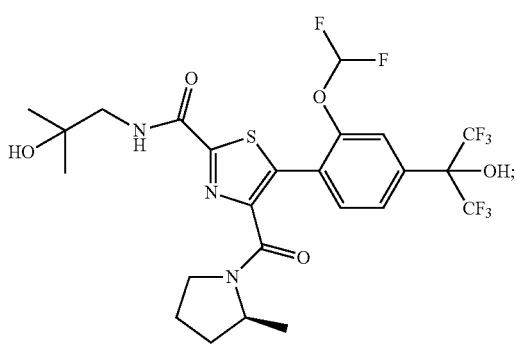
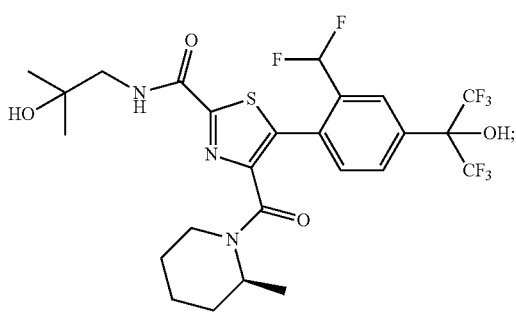
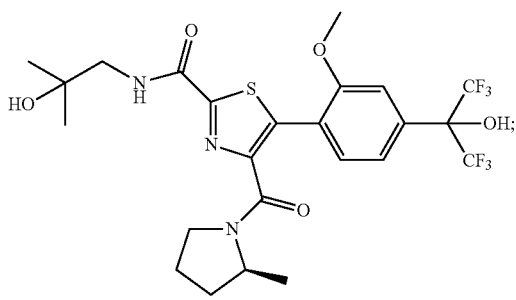
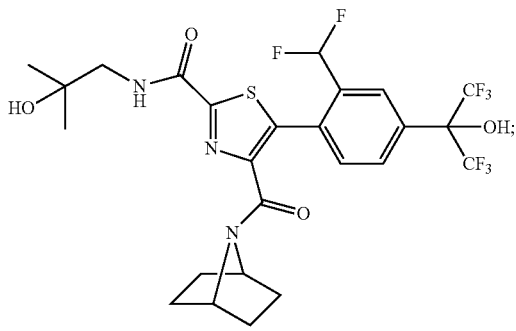

-continued
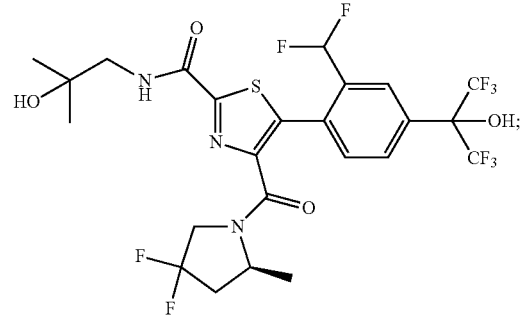
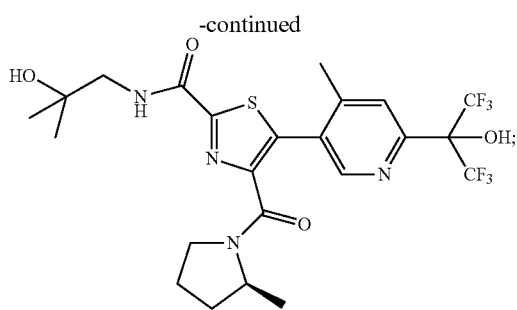
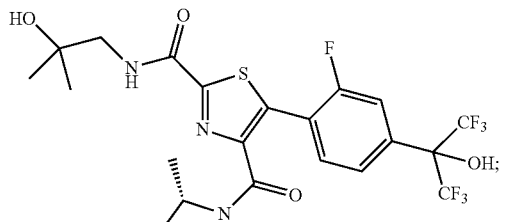
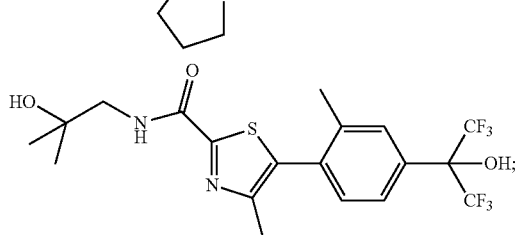
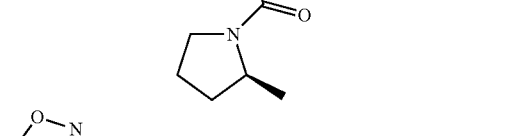
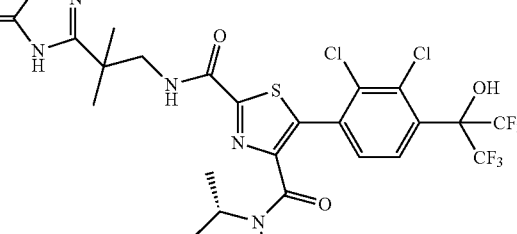
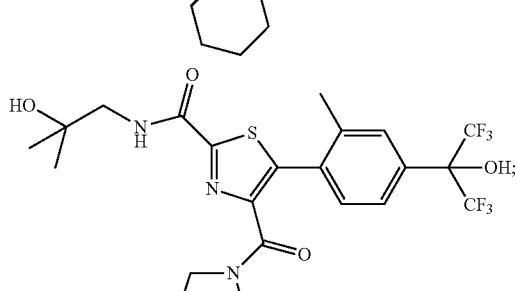
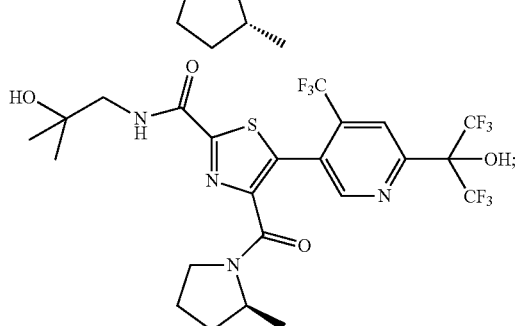

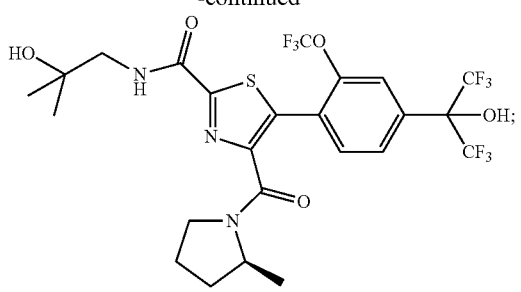
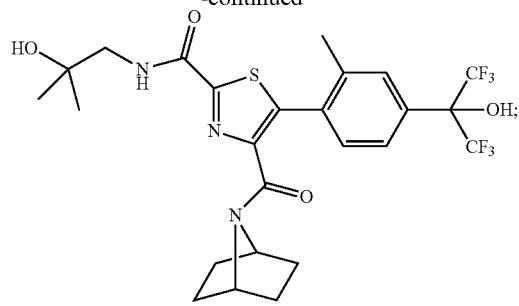
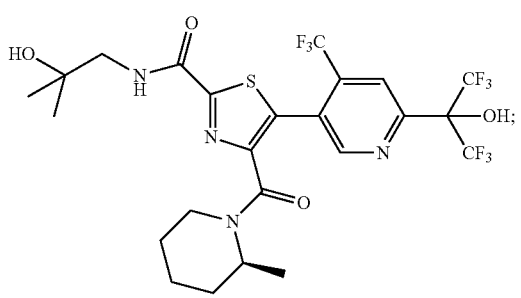
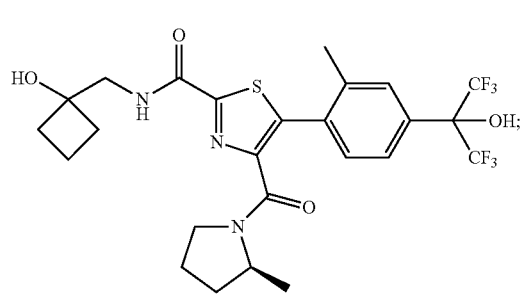
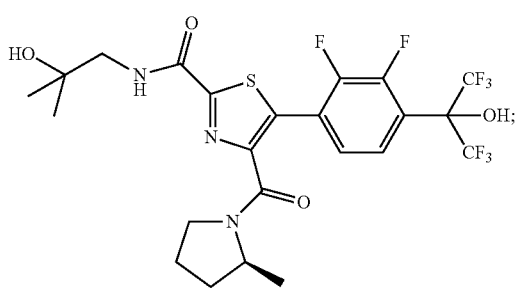
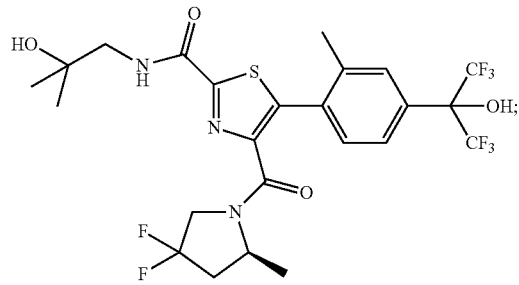
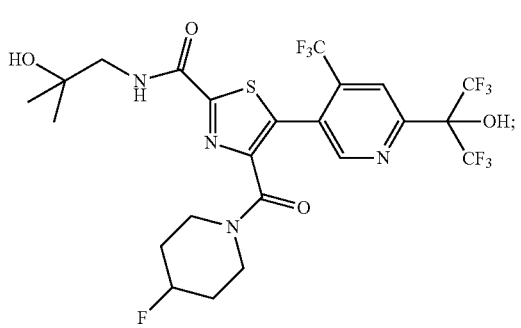
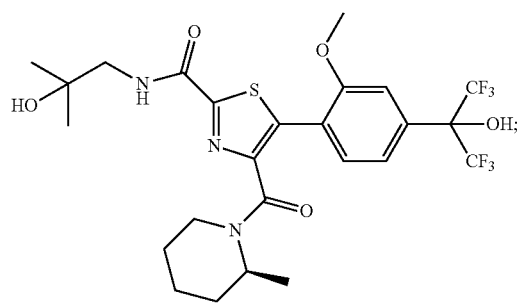
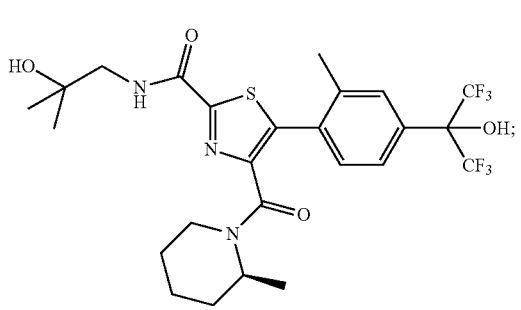
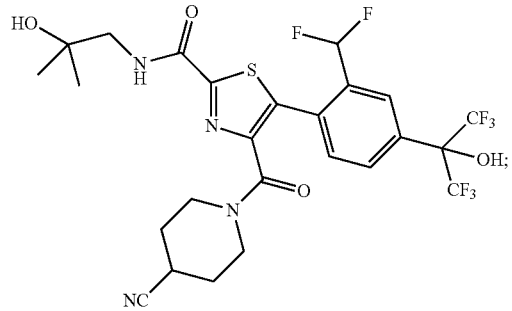

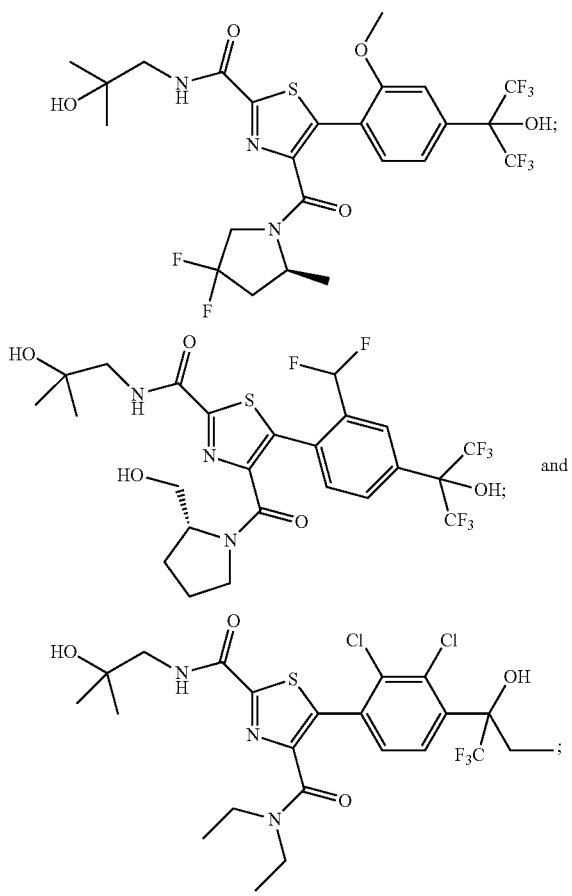
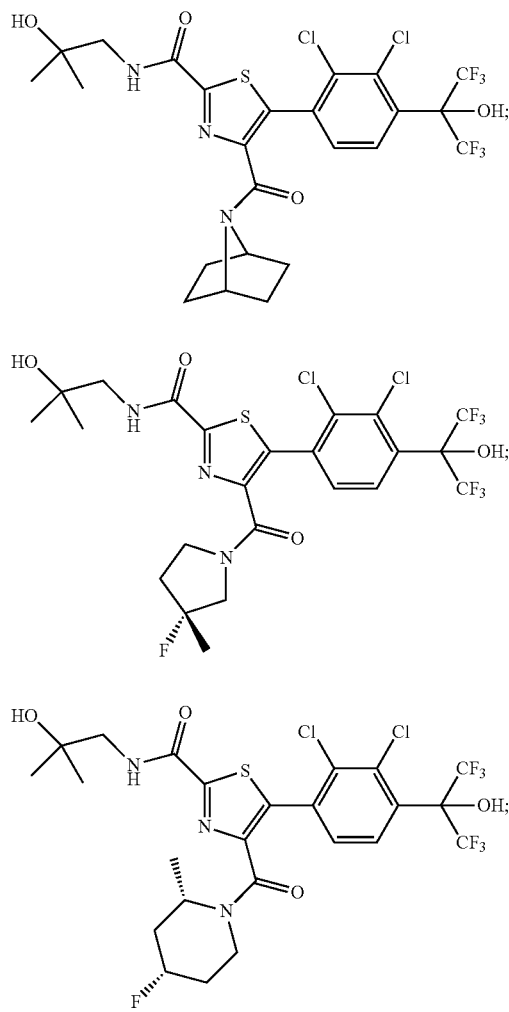
and pharmaceutically acceptable salts thereof.
Another embodiment of the invention is a compound selected from the group consisting of:
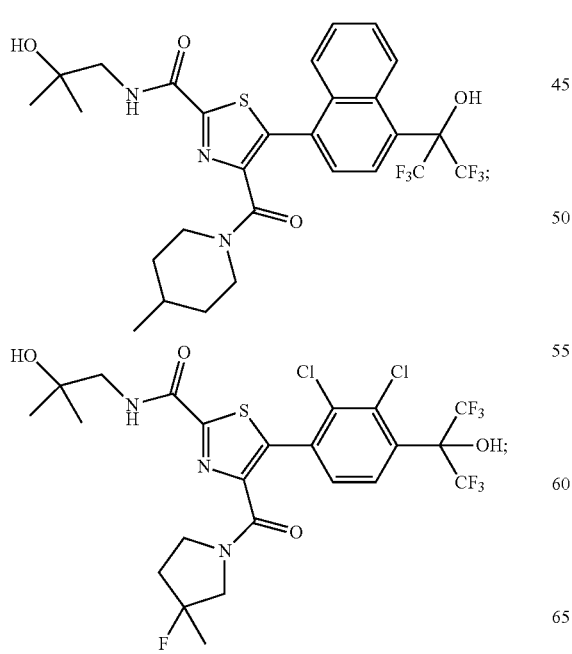
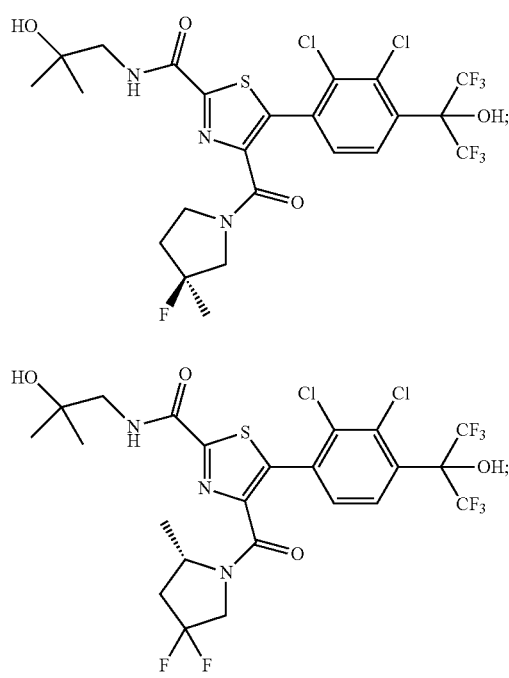

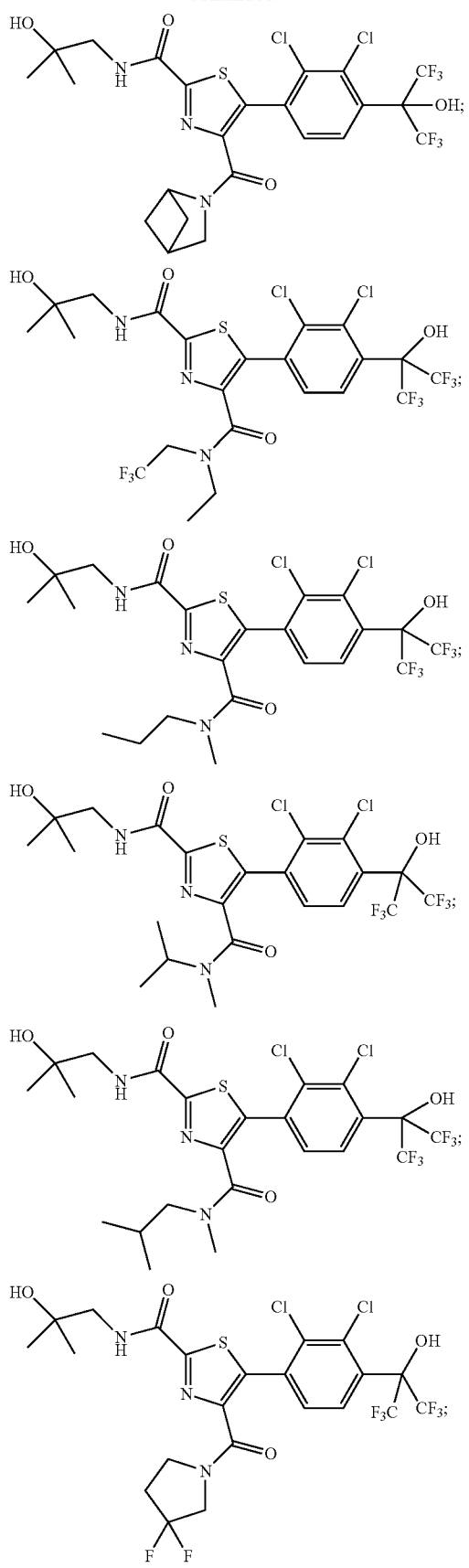
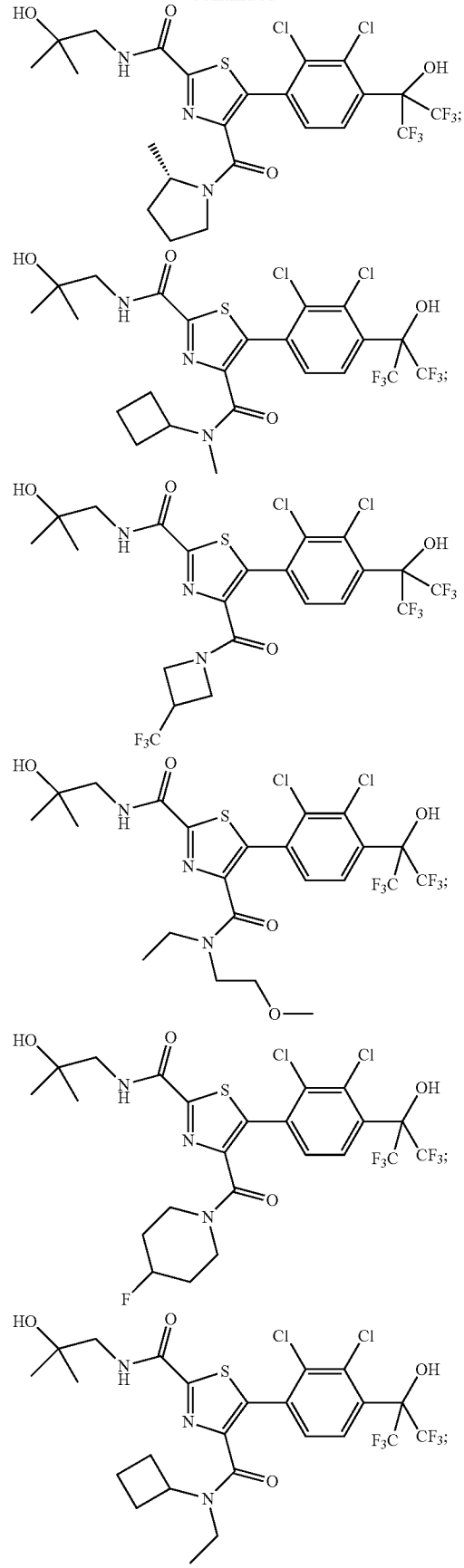

31
-continued
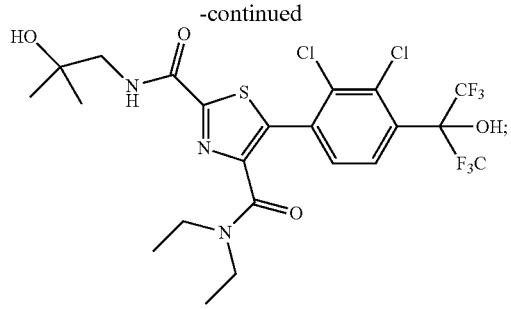
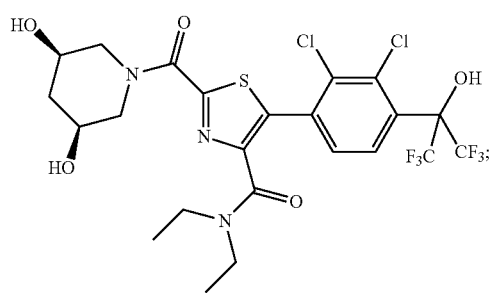
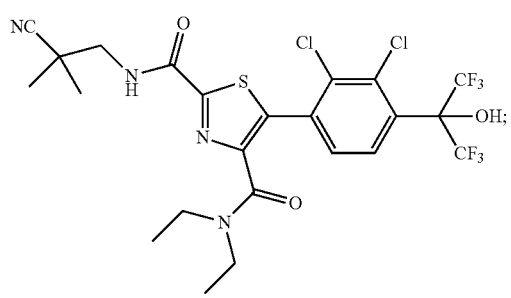
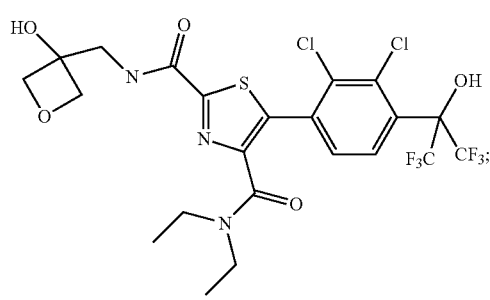
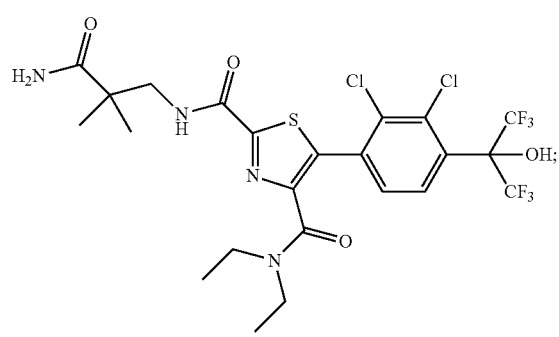
32
-continued
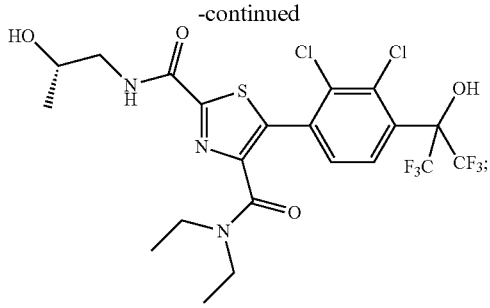
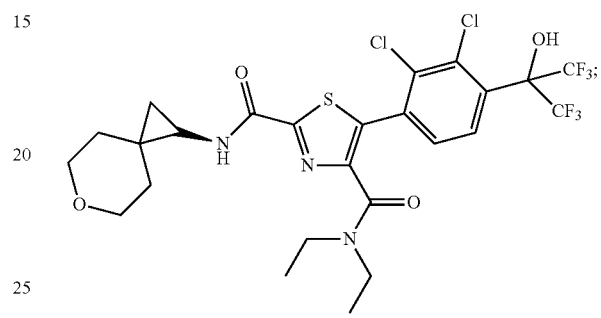
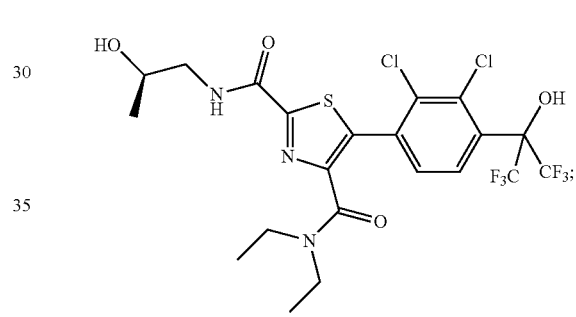
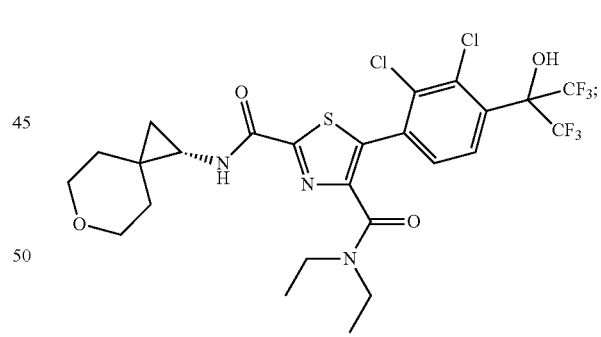
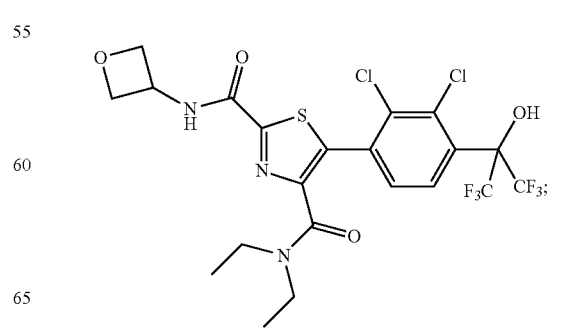

33
-continued
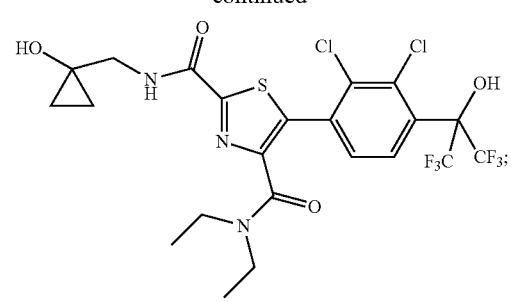
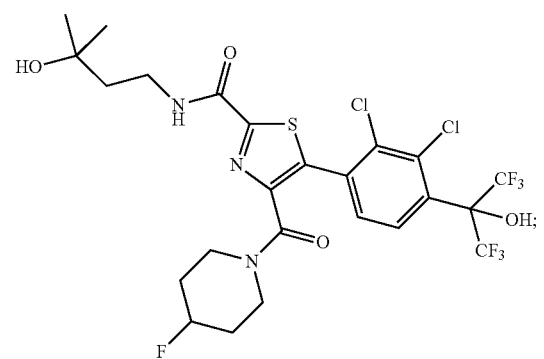
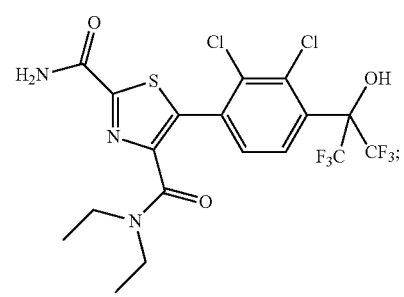
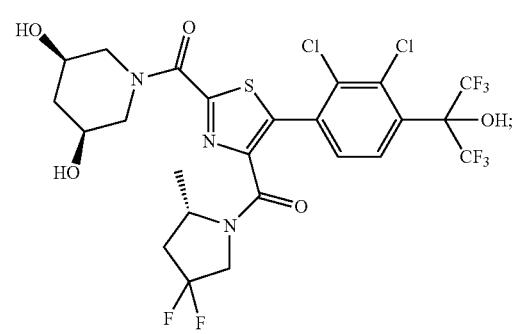
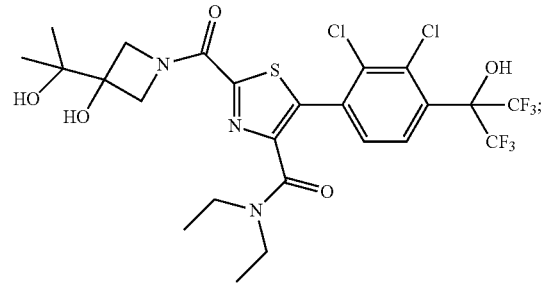
34
-continued
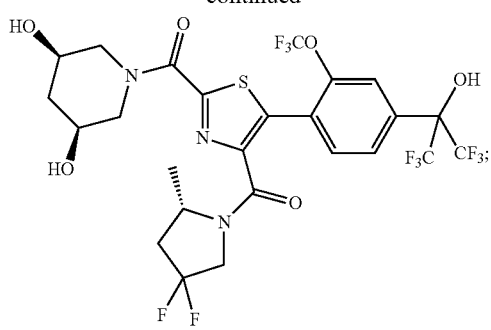
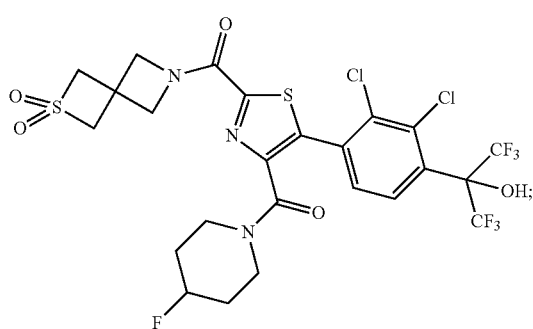
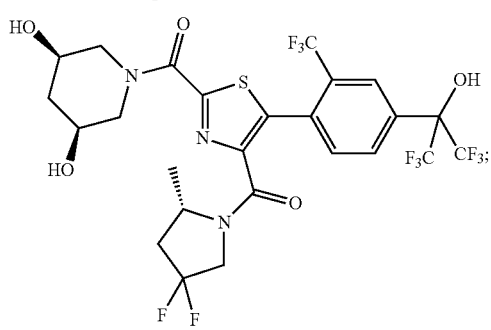
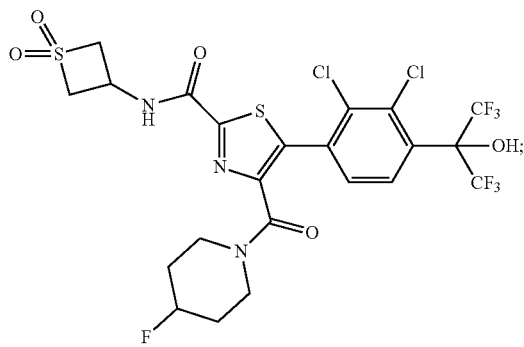
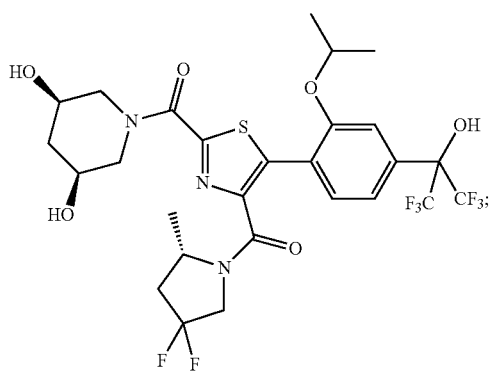

-continued
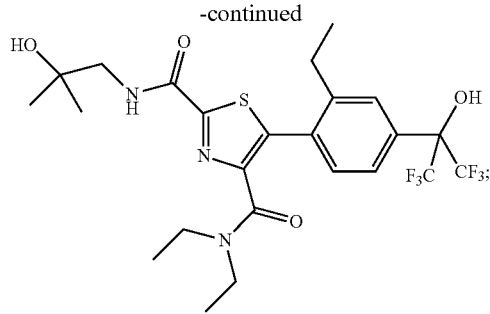
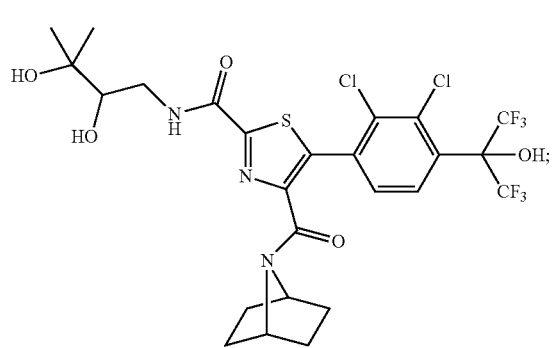
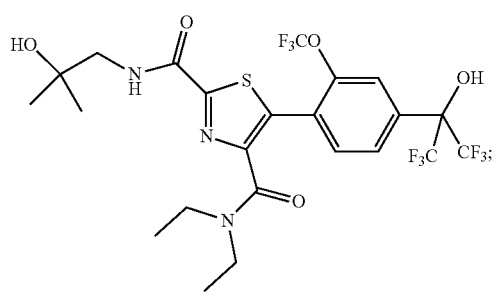
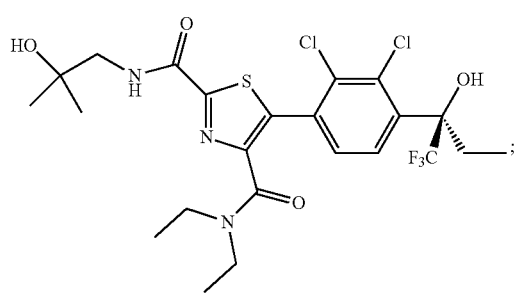
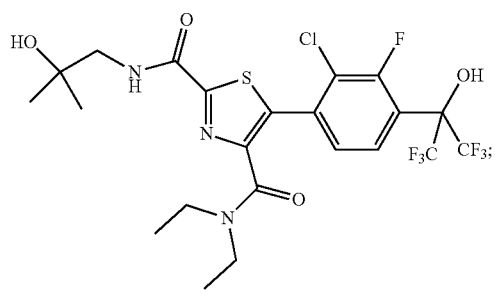
-continued
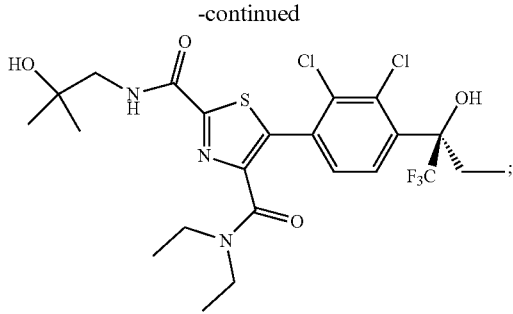
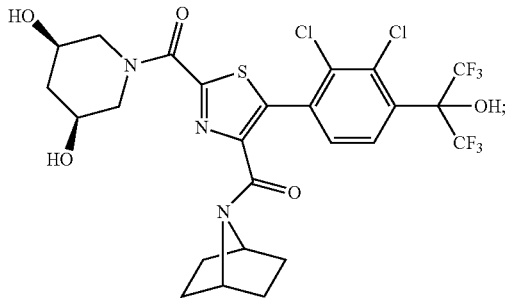
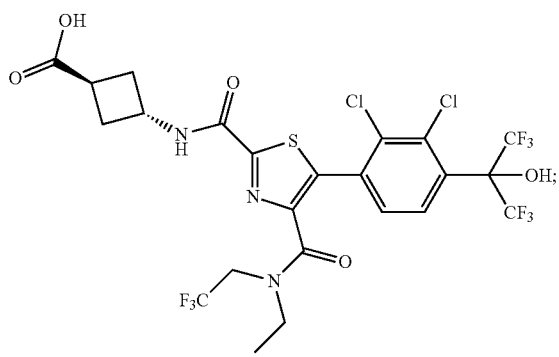
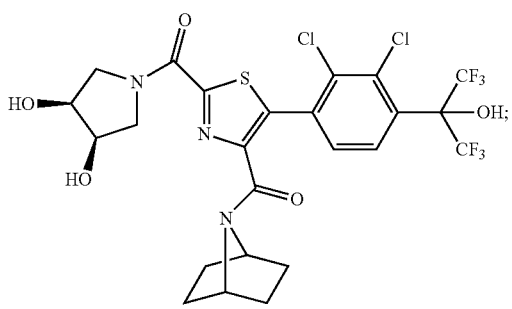
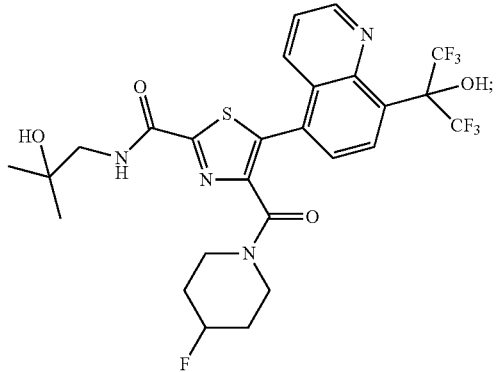

-continued
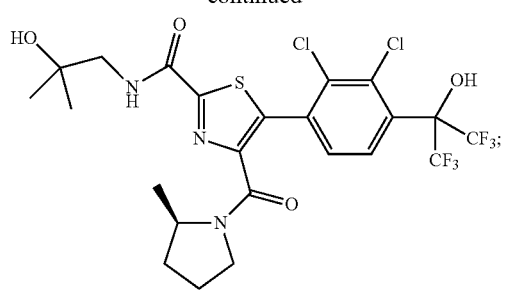
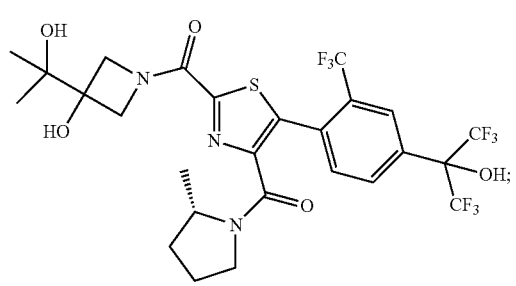
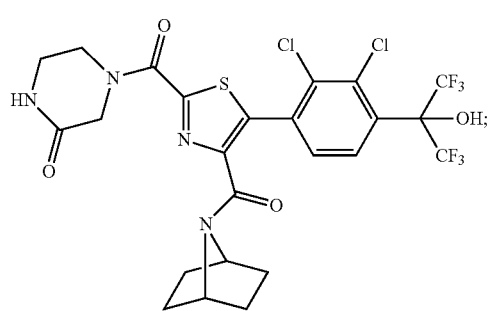
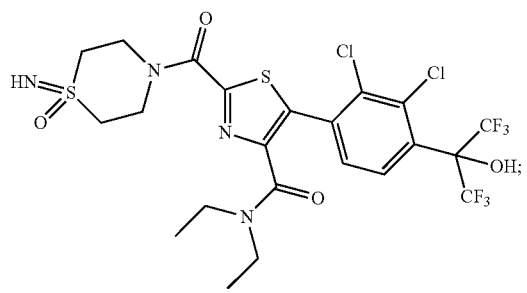
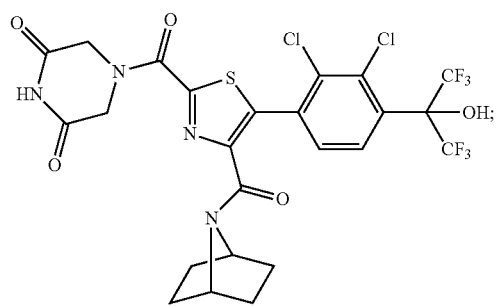
-continued
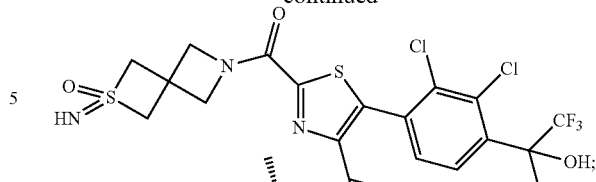
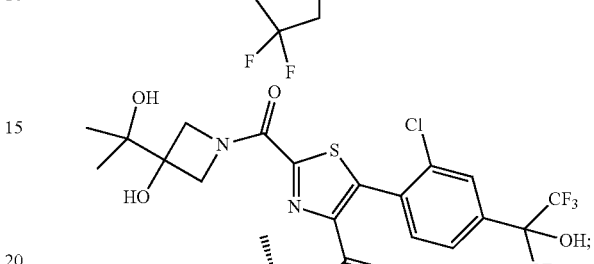
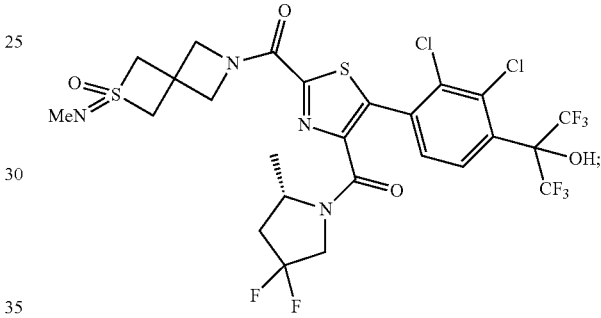
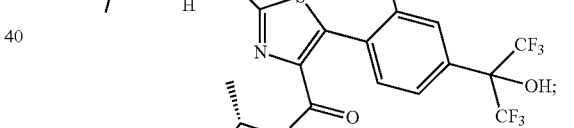
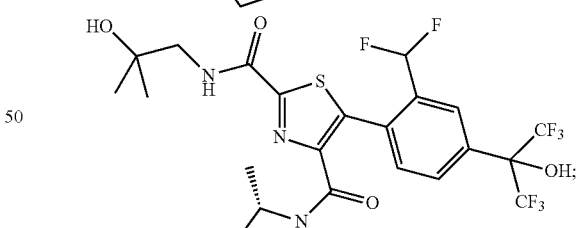
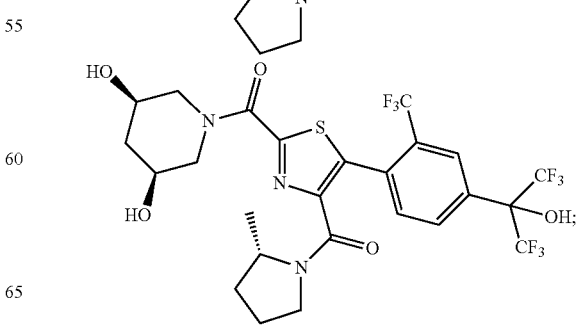

39
-continued
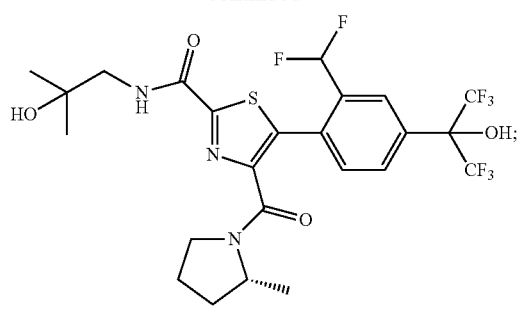
40
-continued
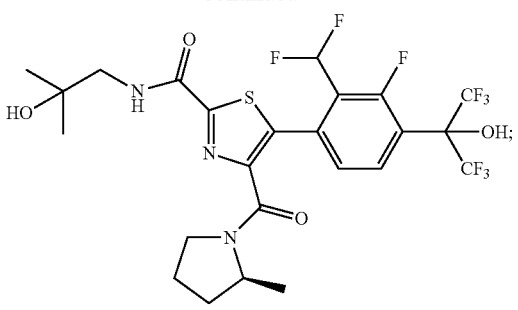
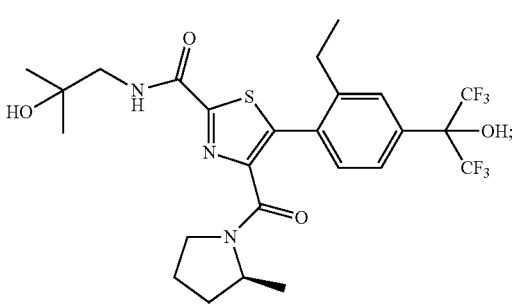
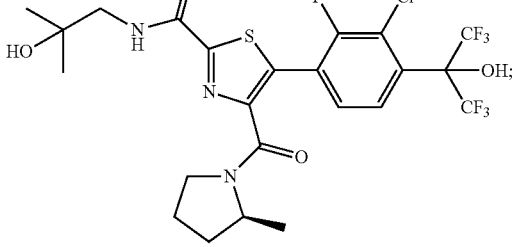
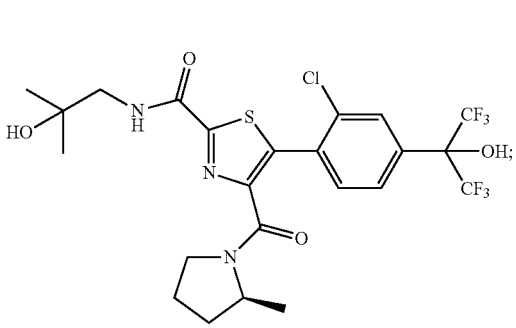
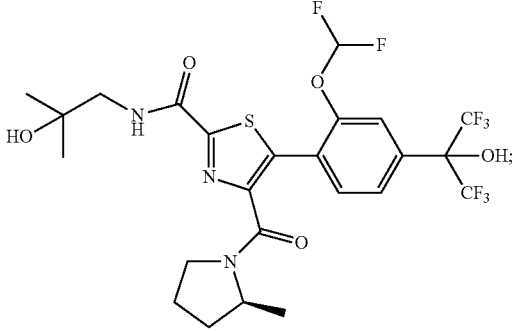

-continued
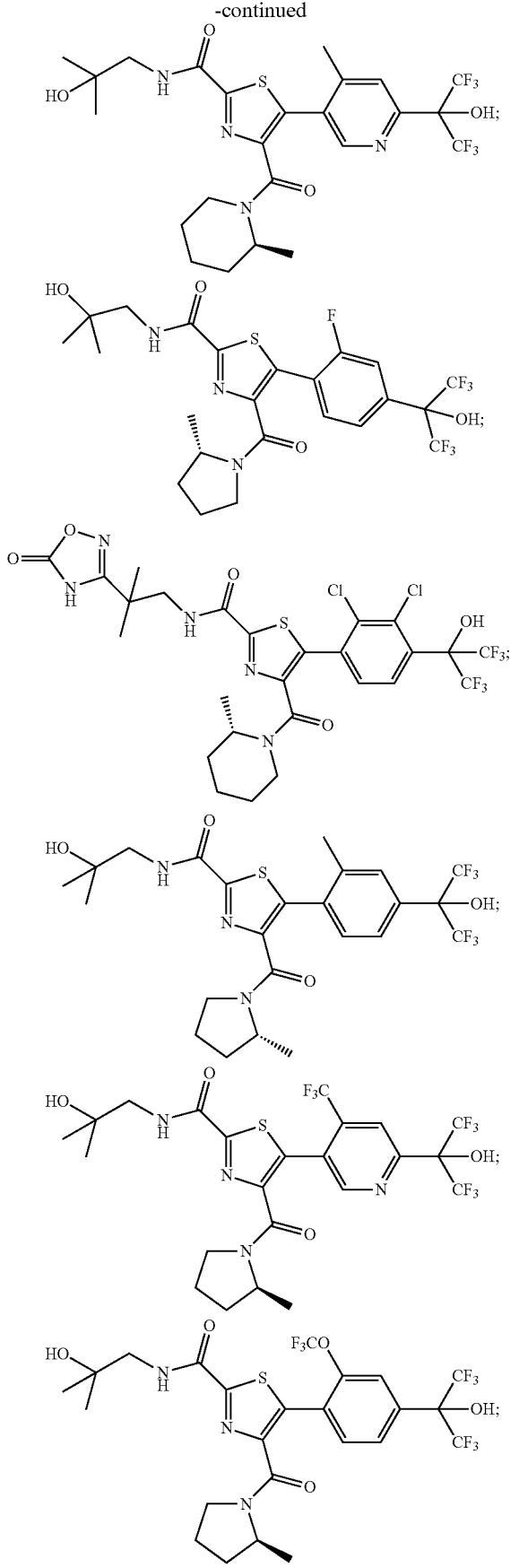
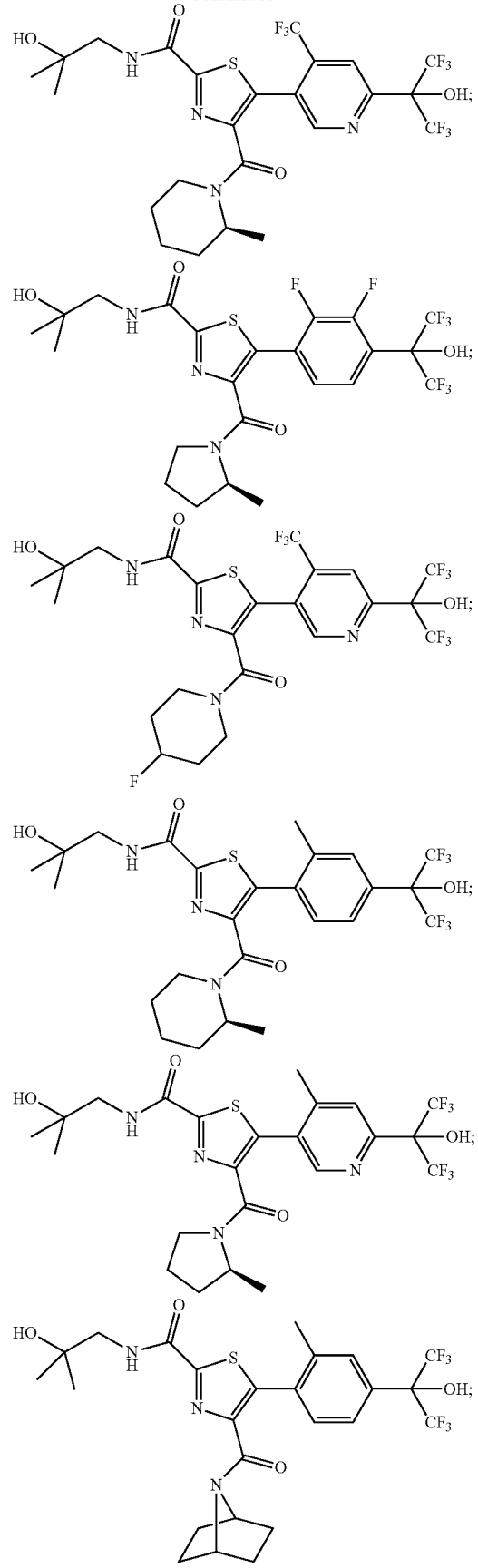

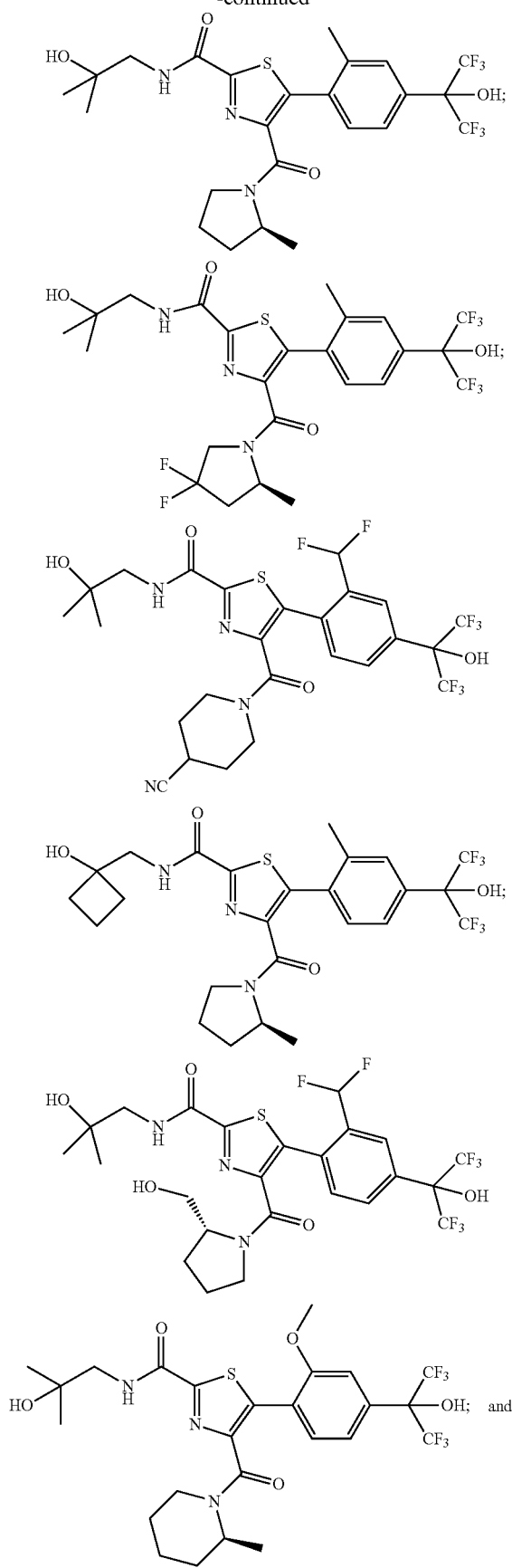
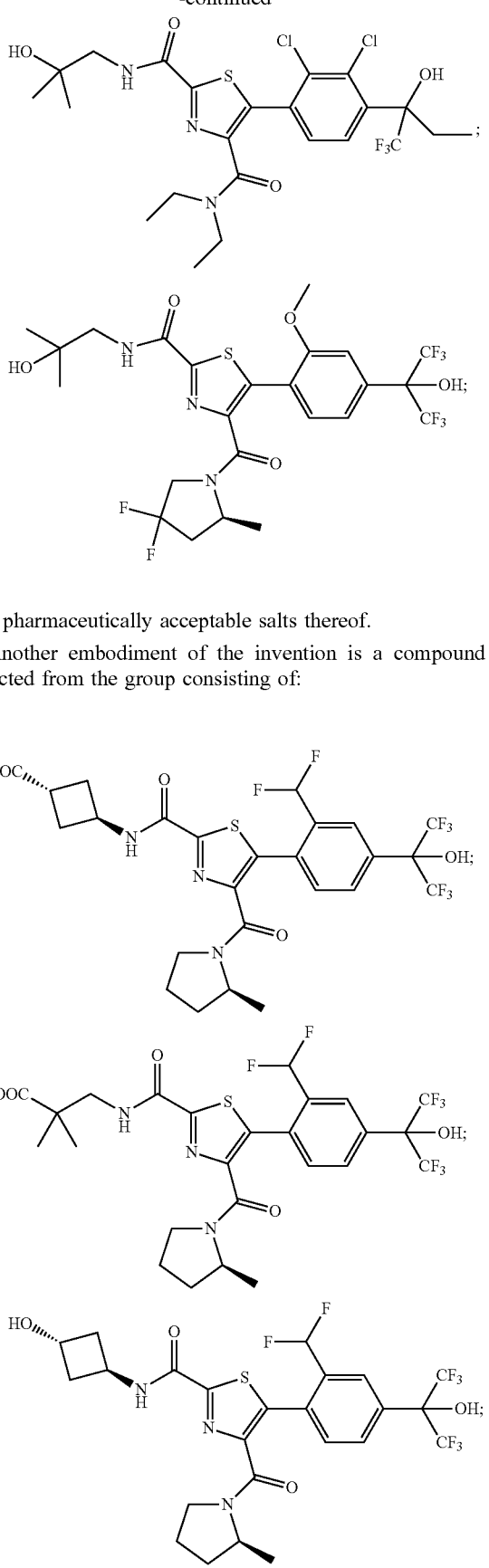
and pharmaceutically acceptable salts thereof.
Another embodiment of the invention is a compound selected from the group consisting of:

45
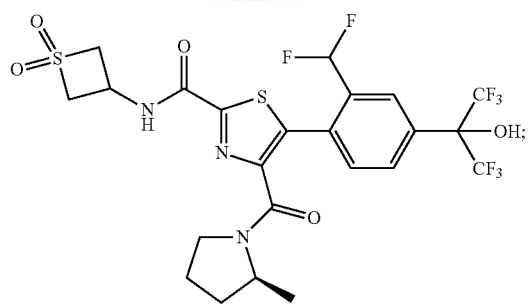
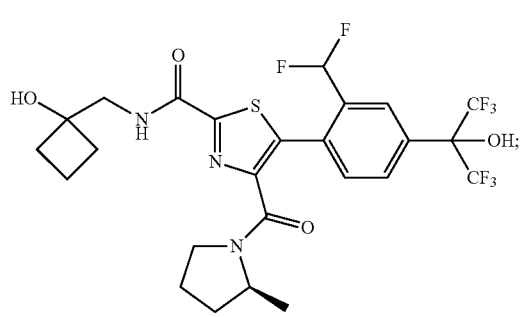
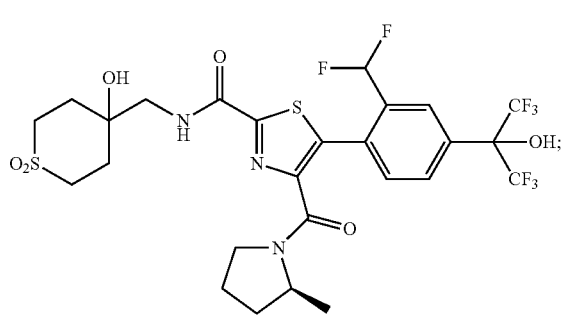
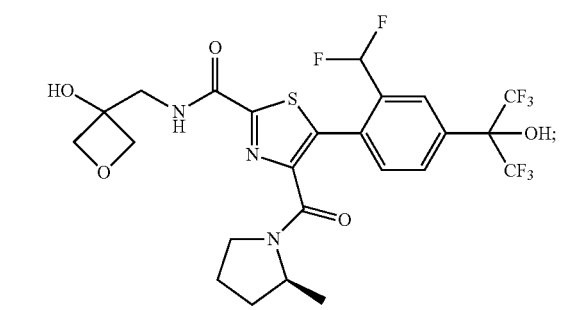
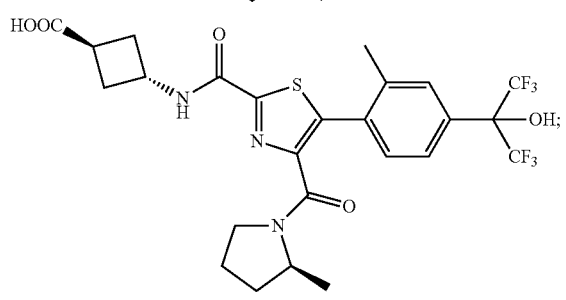
46
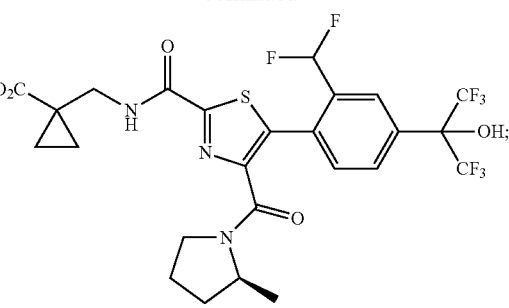
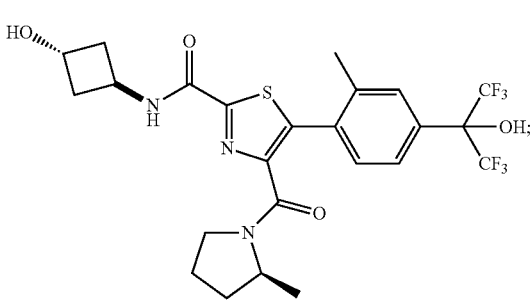
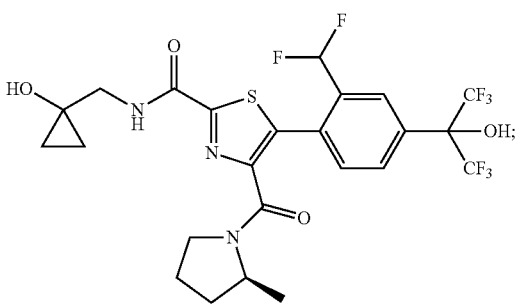
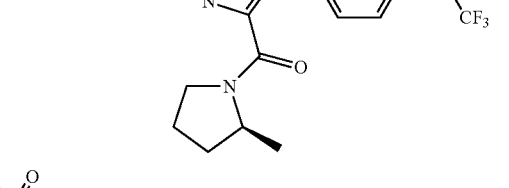
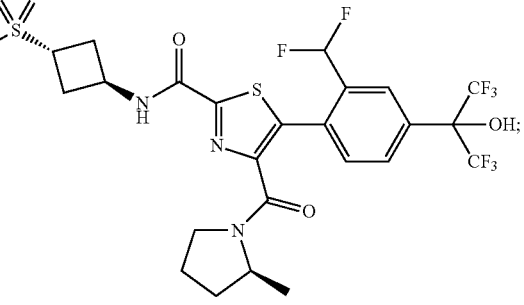

-continued

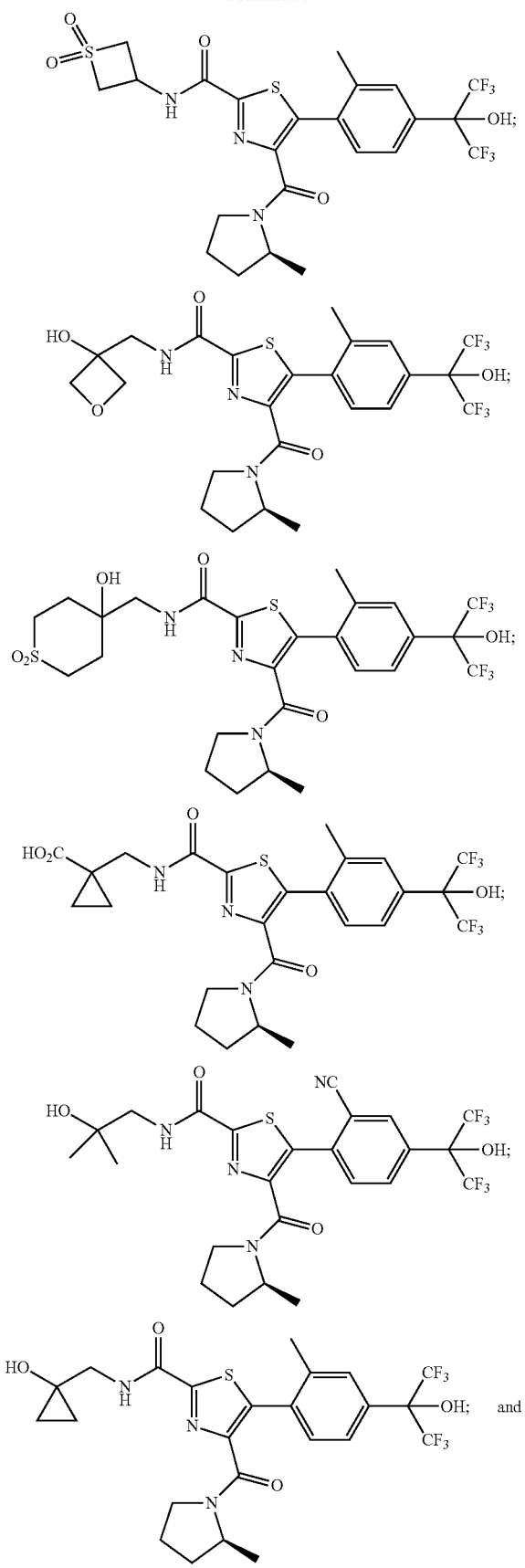

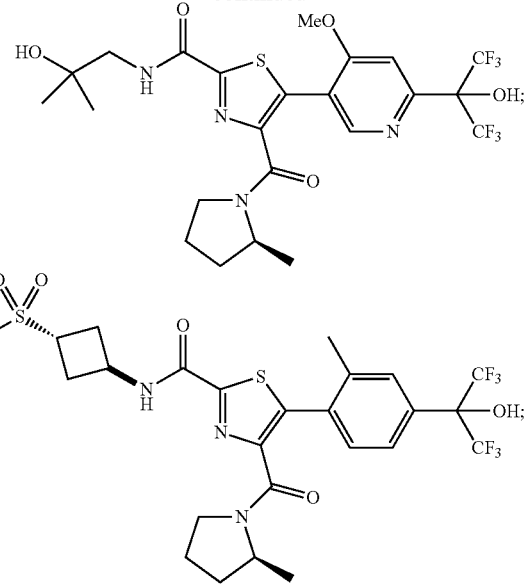

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodontis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

DEFINITIONS

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with aberrant RORγt expression or RORγt overexpression, or a patient with an inflammatory condition that accompanies syndromes, disorders or diseases associated with aberrant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

As used herein, the term "thiophenyl" is intended to describe the radical formed by removing a hydrogen atom from the molecule with the structure:

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding.

In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{13}C$ and $^{14}C$ and $^{16}O$ and $^{18}O$. The isotopes may be radioactive or non-radioactive. Radiolabelled compounds of Formula I may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

ABBREVIATIONS

Herein and throughout the application, the following abbreviations may be used.
Ac acetyl
br broad
bu butyl
cataCXium® A Di(1-adamantyl)-n-butylphosphine
CDI carbonyldiimidazole
cy cyclohexyl
d doublet
dba dibenzylideneacetone
DABCO 1,4-diazabicyclo[2.2.2]octane
DAST diethylaminosulfur trifluoride
DCM dichloromethane
DEA diethylamine
Dess-Martin Periodinane 1,1,1-tris(acetyloxy)-1,1-dihydro-1,2-benziodoxol-3-(1H)-one dppf 1,1'-bis(diphenylphosphino) ferrocine
DIPEA N,N-diisopropylethylamine (Hünig's base)
DME 1,2-dimethoxyethane
DMA N,N-dimethylacetamide
DMF N,N-dimethylformamide
DMSO dimethyl sulfoxide
EDCI 1-ethyl-3-(3-dimethylaminopropyl) carbodiimide
EtOAc ethyl acetate
ESI electrospray ionization
Et ethyl
FCC flash column chromatography
h hour(s)
HATU O-(7-azabenzotriazol-1-yl)-N,N,N'N'-tetramethyl-uronium hexafluorophosphate
HOBt 1-hydroxybenzotriazole
HOAt 1-hydroxy-7-azabenzotriazole
HPLC high pressure liquid chromatography
Hz Hertz
IPA isopropylalcohol
MS mass spectrometry
m multiplet
m-CPBA meta-chloroperoxybenzoic acid
M molar (moles/liter)
Me methyl
MPa megapascal
NBS N-bromosuccinimide
NMR nuclear magnetic resonance
PE petroleum ether
Ph phenyl
Piv pivaloyl (Me$_3$CCO)
PMB 4-methoxybenzyl
ppm parts per million
Psi pounds per square inch
q quartet
rt room temperature
s singlet
SEMCl (2-(chloromethoxy)ethyl)trimethylsilane
t triplet
t-bu tertiary butyl
TBAF tetrabutylammonium fluoride
TEA triethylamine
TEMPO (2,2,6,6-tetramethylpiperidin-1-yl)oxidanyl
TFA trifluoroacetic acid
TFAA trifluoroacetic acid anhydride
THF tetrahydrofuran
TLC thin layer chromatography
TMS trimethylsilyl
Ts tosyl General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

The compounds of the present invention can be prepared according to schemes 1 to 5. Coupling of an aryl group to the thiazole ring of compounds of Formula I can be accomplished by coupling the bromo-aryl/heteroaryl building blocks E-I/II or F-I to the thiazole derivates A-I-V in the presence of palladium catalysis, using appropriate ligands, solvents, additives and temperatures to form the 5-aryl/heteroaryl-substituted thiazoles B-I to B-VII (Scheme 1). The thiazole reactants can be 2- and 4-substituted either by an ester group (A-I, A-II, A-IV), an amide group (A-I-III, A-V) or an alkyl group (A-IV-V).

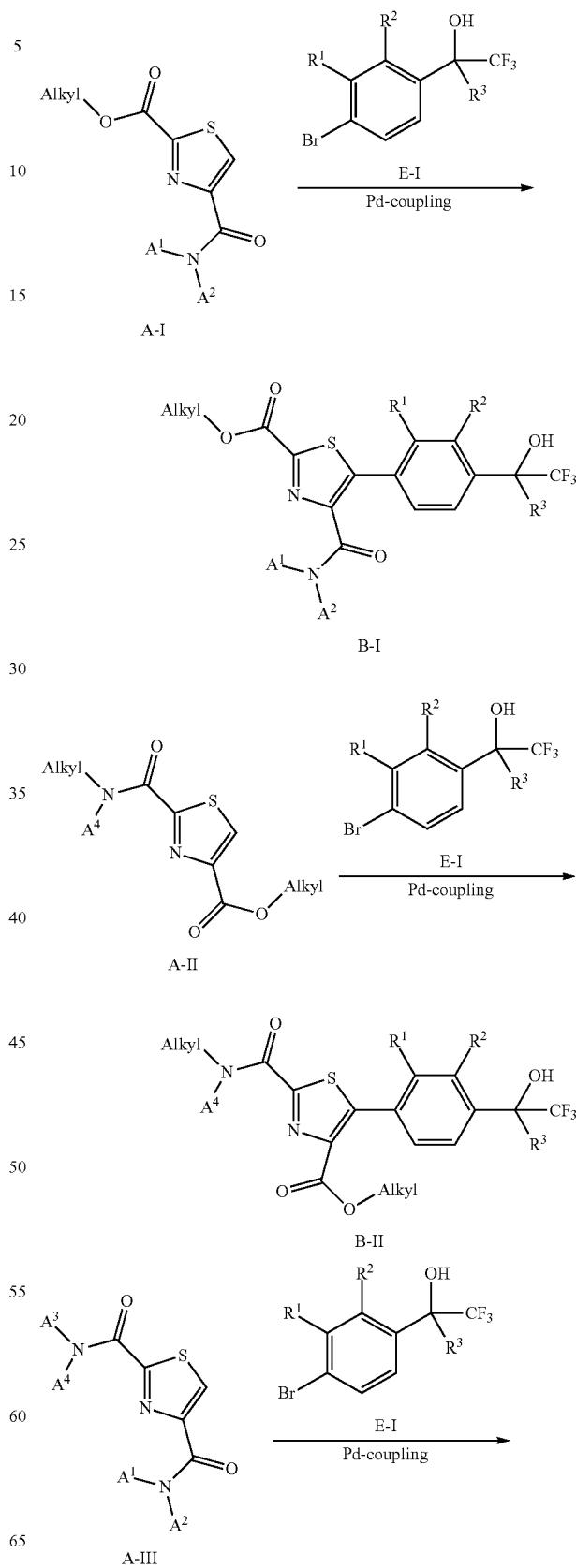

Scheme 1

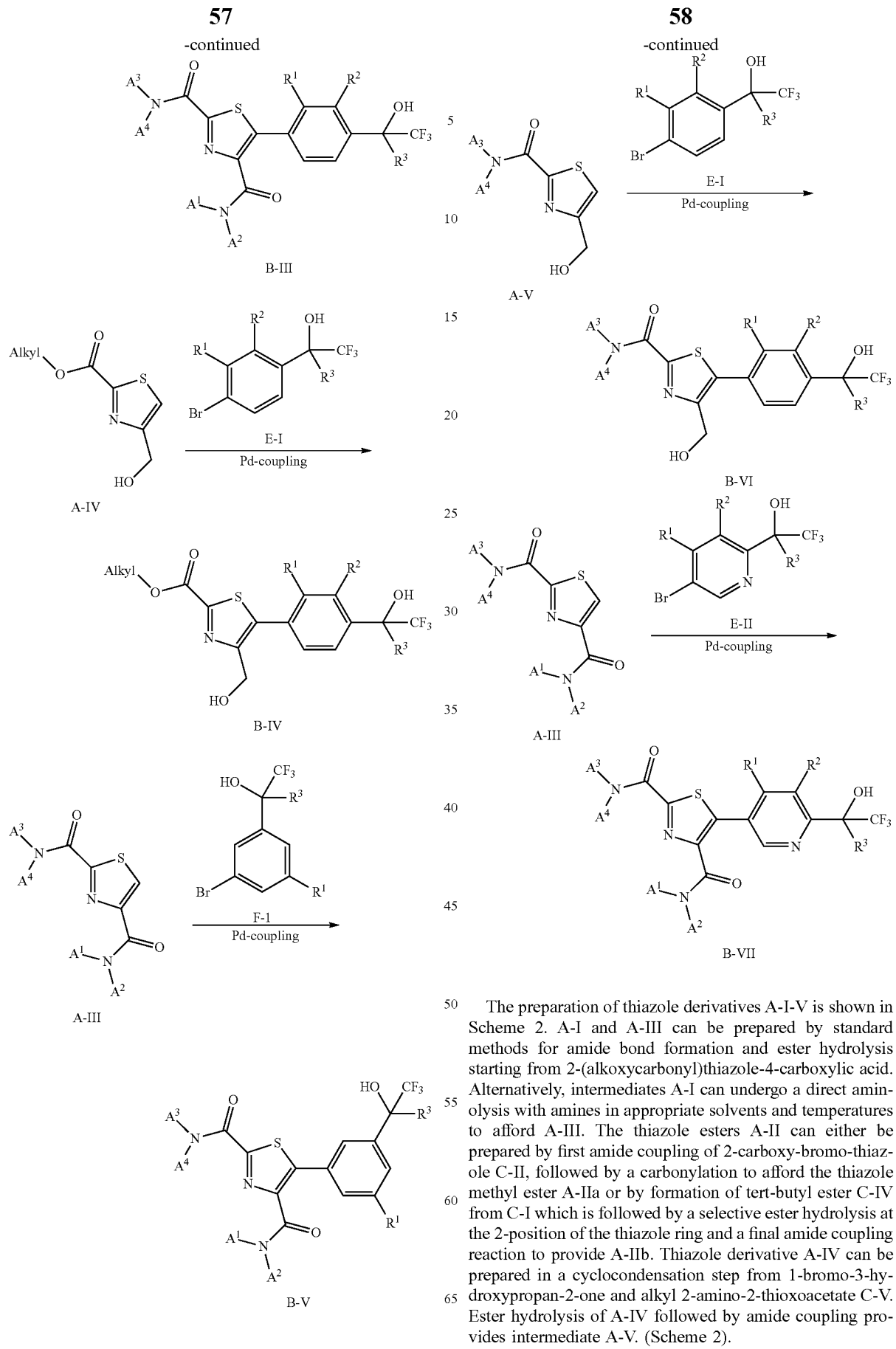

The preparation of thiazole derivatives A-I-V is shown in Scheme 2. A-I and A-III can be prepared by standard methods for amide bond formation and ester hydrolysis starting from 2-(alkoxycarbonyl)thiazole-4-carboxylic acid. Alternatively, intermediates A-I can undergo a direct aminolysis with amines in appropriate solvents and temperatures to afford A-III. The thiazole esters A-II can either be prepared by first amide coupling of 2-carboxy-bromo-thiazole C-II, followed by a carbonylation to afford the thiazole methyl ester A-IIa or by formation of tert-butyl ester C-IV from C-I which is followed by a selective ester hydrolysis at the 2-position of the thiazole ring and a final amide coupling reaction to provide A-IIb. Thiazole derivative A-IV can be prepared in a cyclocondensation step from 1-bromo-3-hydroxypropan-2-one and alkyl 2-amino-2-thioxoacetate C-V. Ester hydrolysis of A-IV followed by amide coupling provides intermediate A-V. (Scheme 2).

Scheme 2

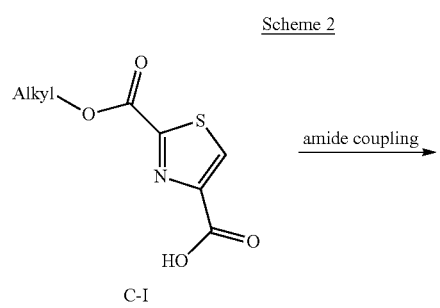

C-I

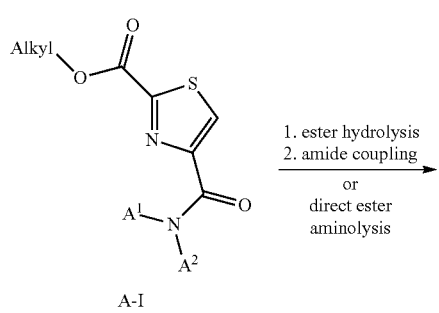

A-I

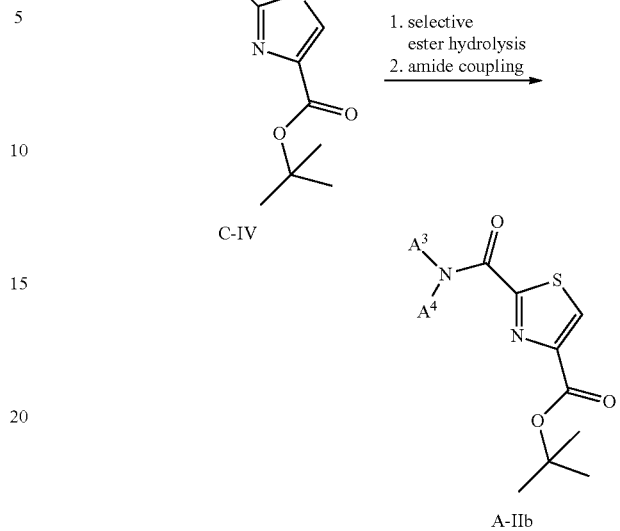

C-IV, A-IIb, C-V, A-IV, A-V

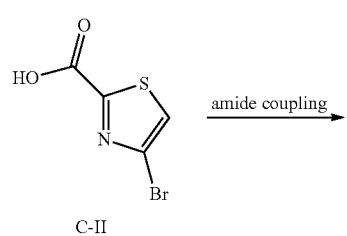

C-II

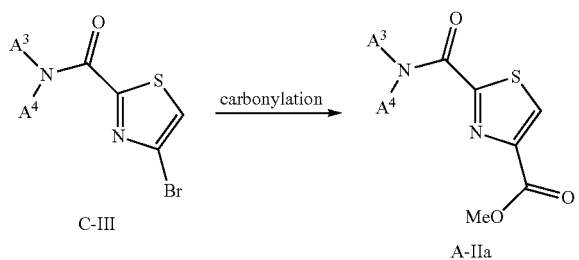

C-III, A-IIa

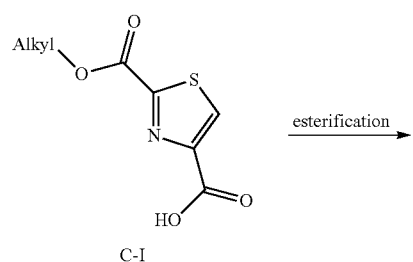

C-I

Preparation of the bromo-aryl/heteroaryl derivatives E-I/E-II/F-I are shown in Scheme 3. 1,4-Dibromo- or 1-bromo-4-iodo-aromatics can be used as reactants for a metallation reaction, e.g. a lithiation with n-butyl-lithium or Grignard formation using isopropyl magnesium chloride. The 1,4-dibromo aromatics should have identical substituents $R^1$ and $R^2$. The metallated species can react with the Weinreb amide of trifluoroacetic acid to form 1-bromo-4-trifluoroacetyl derivates D-II. Alternatively, the metallated species can react with hexafluoroactone to directly form trifluoroacetone alcohols E-I where $R^3$ is a $CF_3$ group. The trifluoromethyl alcohols E-I can be formed by reaction of D-II with $TMSCF_3$ in the presence of a fluoride source or by reaction with an alkyl Grignard reagent. The intermediates D-II can also be formed by a reaction of 1-bromo-4-alkoxycarbonyl aromatics, which can be prepared from the corresponding 4-bromobenzoic acids (D-III) via esterificataion using reagents such as thionyl chloride and methanol, with $TMSCF_3$ in the presence of a fluoride source. Alternatively, intermediate D-II can be formed from 1-bromo-4-formyl aromatics by reaction with TMSCF₃ in the presence of a fluoride source and subsequent oxidation (Scheme 3). 5-Bromo-2-iodopyridines (D-VI) can be used as reactants for a metallation reaction, e.g. a lithiation with n-butyl-lithium, and the metallated species can react with the ethyl trifluoroacetate to form 5-bromo-2-trifluoroacetylpyridine derivates D-VII. The trifluoromethyl alcohols E-II can be formed by reaction of D-II with TMSCF₃ in the presence of a fluoride source. 1,3-Dibromoaryl derivatives F-II can be metallated, e.g. a lithiation with n-butyl-lithium, and subsequent reaction with the Weinreb amide of trifluoroacetic acid will form the 1-bromo-3-trifluoroacetyl derivates F-III. The trifluoromethyl alcohols F-I can be formed by reaction of F-III with TMSCF₃ in the presence of a fluoride source or by reaction with an alkyl Grignard reagent.

An alternative synthetic route to afford the compounds of formula B-III of the present invention is shown in scheme 4. Starting from the products of the palladium catalyzed coupling reactions B-IV, B-I or B-II (as shown in scheme 1), hydroxymethyl-intermediate B-IV can be oxidized to the corresponding carboxylic acid, which can be used in an amide coupling reaction to give intermediates B-I. B-I and B-II can both be transformed into the compounds of the present invention B-III by first an ester hydrolysis and a subsequent amide coupling reaction. Alternatively, intermediates B-I can undergo a direct aminolysis with amines in appropriate solvents and temperatures to afford the compounds of the present invention B-III in one step. In another alternative route compounds of formula B-III can be obtained from intermediate B-VI through oxidation followed by amide coupling (Scheme 4).

Scheme 3

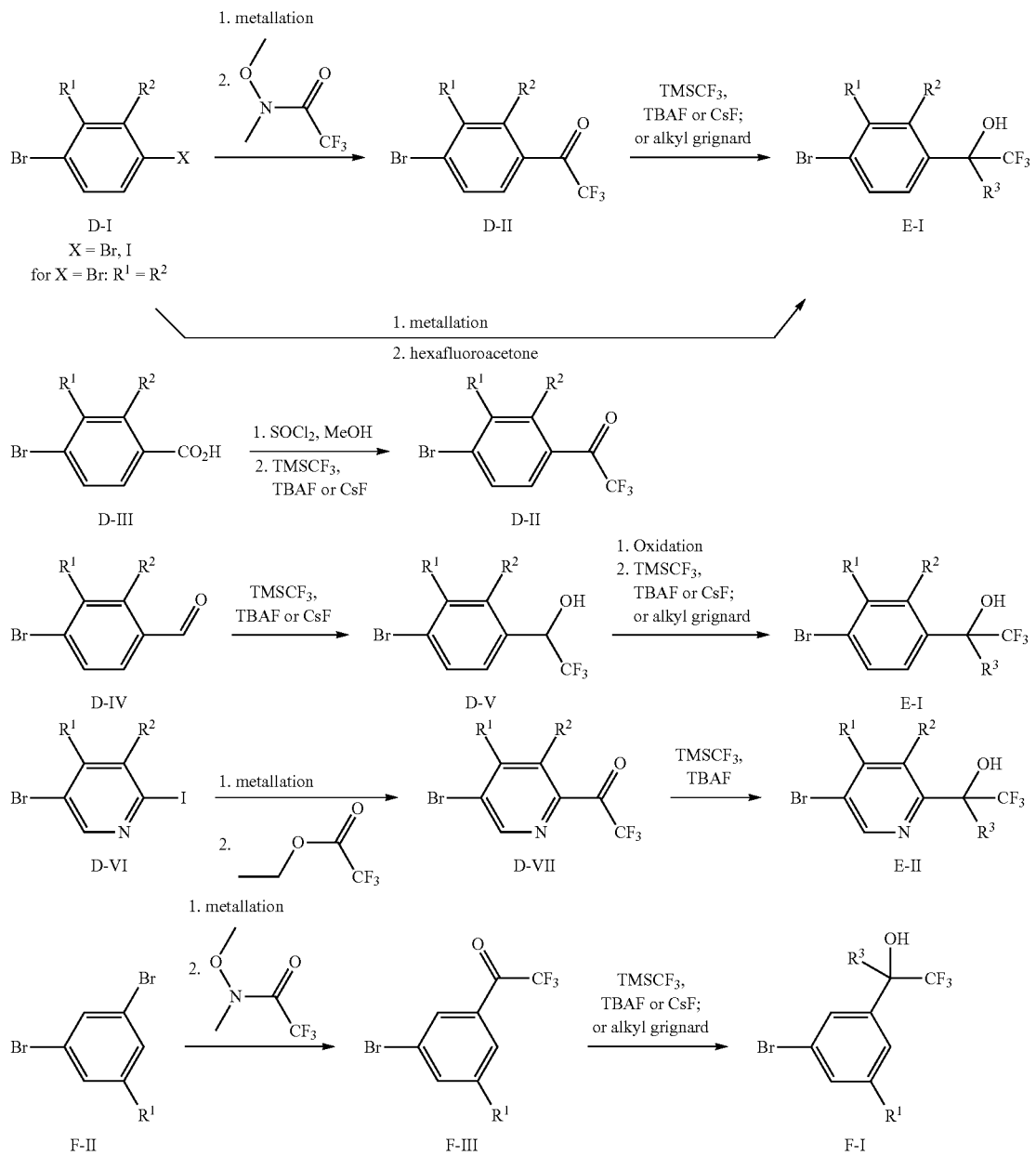

Scheme 4

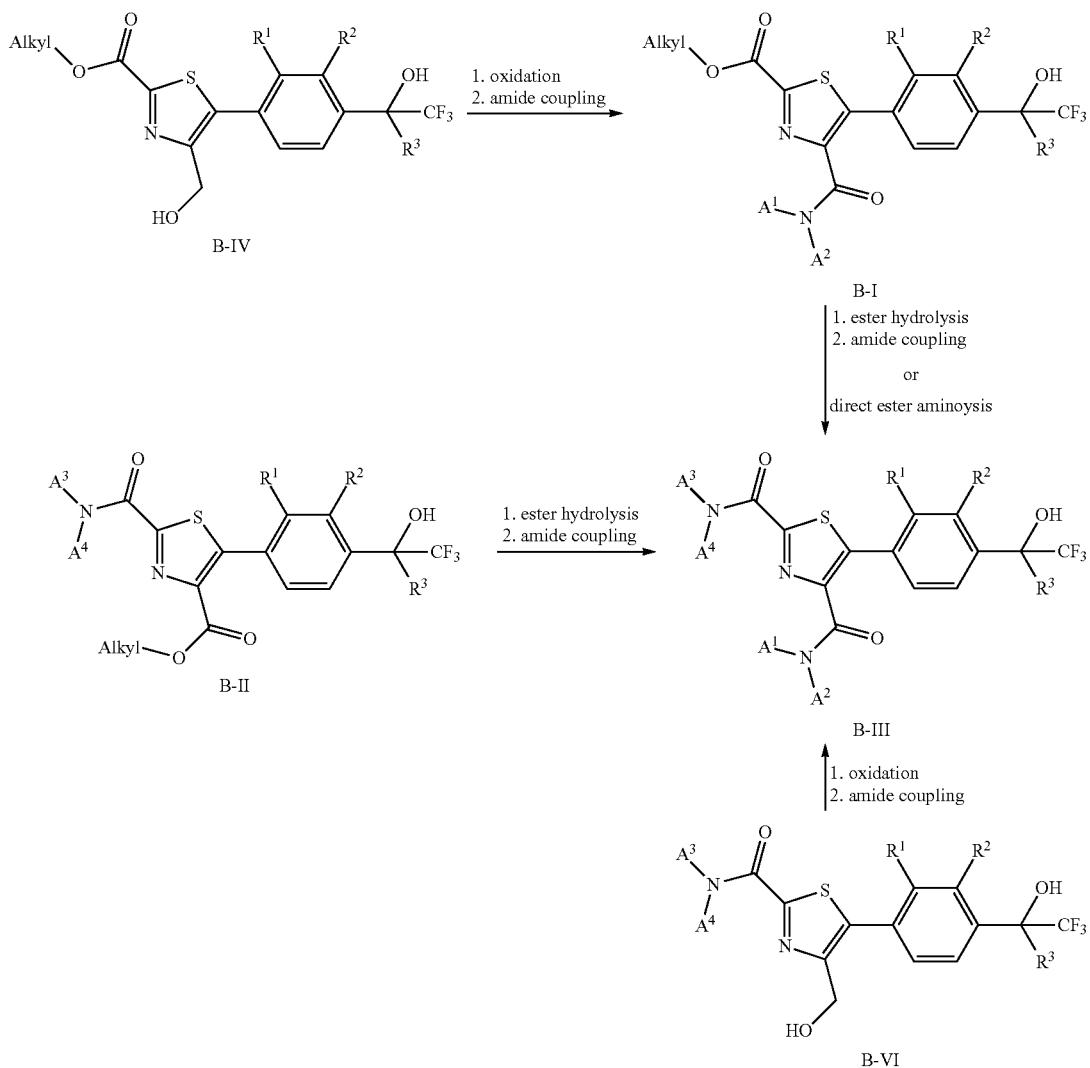

EXAMPLES

Compounds of the present invention can be prepared by methods known to those who are skilled in the art. The following examples are only meant to represent examples of the invention and are in no way meant to be a limit of the invention.

Intermediate 1

Step a 1-(4-Bromonaphthalen-1-yl)-2,2,2-trifluoroethanone

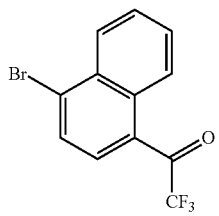

To a solution of 1,4-dibromonaphthalene (28.6 g, 100 mmol) in anhydrous THF (200 mL) was added n-BuLi (2.5 M in hexane, 44 mL, 110 mmol) at −78° C. under nitrogen, and the solution was stirred at this temperature for 30 minutes. The resulting solution was slowly added to a solution of 2,2,2-trifluoro-N-methoxy-N-methyl-acetamide (23.5 g, 148 mmol) in anhydrous THF (250 mL) at −78° C., and the solution was stirred for an additional 2 h. The solution was quenched with aqueous $NH_4Cl$ and extracted twice with EtOAc. The combined organic layers were washed with water and brine, dried over anhydrous $Na_2SO_4$, filtered and concentrated to dryness. The residue was purified by FCC on silica gel (PE/EtOAc=100/1) to give the title compound as a pale yellow oil.

Intermediate 1

2-(4-Bromonaphthalen-1-yl)-1,1,1,3,3,3-hexafluoropropan-2-ol

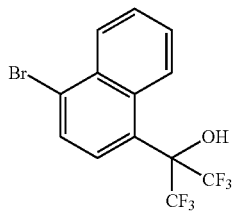

To a solution of 1-(4-bromonaphthalen-1-yl)-2,2,2-trifluoroethanone (27.4 g, 90.4 mmol, Intermediate 1, step a) and TMSCF$_3$ (64.1 g, 452 mmol) in anhydrous THF (250 mL) was added a solution of TBAF (35.9 g, 136 mmol) in anhydrous THF (350 mL) at 0° C., and the solution was stirred at rt overnight. The resulting solution was quenched with 1 N aqueous HCl, diluted with EtOAc and the two layers were separated. The organic layer was washed with water and brine, dried over anhydrous Na$_2$SO$_4$, filtered, concentrated to dryness and purified by FCC on silica gel (PE/EtOAc=5/1) to give the title compound as a yellow oil.

Intermediate 2

Step a

1-(4-Bromo-2,3-dichlorophenyl)-2,2,2-trifluoroethanone

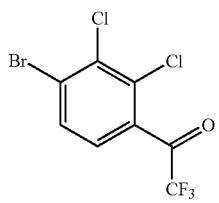

To a solution of 1-bromo-2,3-dichloro-4-iodobenzene (3.52 g, 10.0 mmol) in anhydrous THF (20 mL) was added n-BuLi (2.5 M in hexane, 4.4 mL, 11.0 mmol) at −78° C. under nitrogen, and the solution was stirred at this temperature for 30 minutes. The resulting solution was slowly added to a solution of 2,2,2-trifluoro-N-methoxy-N-methyl-acetamide (2.35 g, 14.8 mmol) in anhydrous THF (25.0 mL) at −78° C., and the solution was stirred for an additional 2 h. The solution was quenched with aqueous NH$_4$Cl and extracted with EtOAc twice. The combined organic layers were washed with water and brine, dried over anhydrous Na$_2$SO$_4$, filtered and concentrated to dryness. The residue was purified by FCC on silica gel (PE/EtOAc=100/1) to give the title compound as a pale yellow oil.

Alternate Synthesis of Intermediate 2

Step a

To a flask was added 1-bromo-2,3-dichloro-4-iodobenzene (30.0 g, 85.3 mmol) and THF (240 mL). This mixture was cooled to −85--78° C., and i-PrMgCl.LiCl (78.7 mL, 1.3 M in THF, 102 mmol) was added dropwise. Then 2,2,2-trifluoro-N-methoxy-N-methylacetamide (20.1 g, 128 mmol) was added in one portion. The mixture was warmed to 20-25° C. and stirred for 4 h. The reaction was quenched with saturated aqueous NH$_4$Cl (120 mL) and diluted with EtOAc (150 mL). The layers were separated and the aqueous phase was further extracted with EtOAc (90 mL). The combined organic phases were washed with water (60 mL) and brine (60 mL) successively, and concentrated under vacuum to give the title compound as a brown solid, which was used in the next step without further purification.

Intermediate 2

2-(4-Bromo-2,3-dichlorophenyl)-1,1,1,3,3,3-hexafluoropropan-2-ol

To a solution of 1-(4-bromo-2,3-dichlorophenyl)-2,2,2-trifluoroethanone (1.99 g, 6.18 mmol, Intermediate 2, step a) and TMSCF$_3$ (4.38 g, 30.9 mmol) in anhydrous THF (30 mL) was added a solution of TBAF (2.45 g, 9.27 mmol) in anhydrous THF (25 mL) at 0° C., and the solution was stirred at rt overnight. The resulting solution was quenched with 1 N aqueous HCl, diluted with EtOAc and the two layers were separated. The organic layer was washed with water and brine, dried over anhydrous Na$_2$SO$_4$, filtered, concentrated to dryness and purified by FCC on silica gel (PE/EtOAc=5/1) to give the title compound as a yellow oil.

Alternate Synthesis of Intermediate 2

To a flask was added 1-(4-bromo-2,3-dichlorophenyl)-2,2,2-trifluoroethanone (10.0 g, 31.1 mmol, Intermediate 2, step a), THF (10 mL) and TMSCF$_3$ (22.1 g, 155 mmol). This mixture stirred and was cooled to −15--10° C., and TBAF (14.3 g, 46.6 mmol) in THF (40 mL) was added dropwise. Then the reaction was quenched with 2 N aqueous HCl (78 mL), diluted with EtOAc (50 mL), and separated. The organic phase was washed with water (40 mL) and brine (40 mL) successively, and concentrated under vacuum. The residue was dissolved with heptane (50 mL), and DABCO (1.7 g, 15.2 mmol) was added in one portion. The mixture was stirred overnight, filtered, and the cake was washed with heptane (10 mL×2). The cake was dissolved with EtOAc (100 mL), washed with 1 N aqueous HCl (30 mL×3), and concentrated under vacuum to give the title compound as a brown liquid.

Intermediate 3

Step a 1-(4-Bromo-3-ethylphenyl)-2,2,2-trifluoroethanone

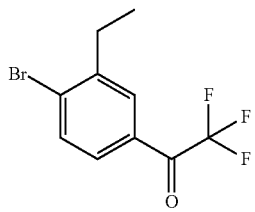

To a solution of methyl 4-bromo-3-ethylbenzoate (1.0 g, 4.11 mmol) and TMSCF$_3$ (901 mg, 6.17 mmol) in anhydrous toluene (15 mL) was slowly added TBAF (65.3 mg, 0.250 mmol) at 0° C., and the solution was stirred at rt for 20 h, and then heated at 50° C. for 1 h. The resulting solution was cooled to rt, quenched with 1 N aqueous HCl and diluted with EtOAc. The organic layer was washed with water and brine, dried over anhydrous Na$_2$SO$_4$, filtered and concentrated to dryness to give the crude title compound as a yellow oil.

Intermediate 3

2-(4-Bromo-3-ethylphenyl)-1,1,1,3,3,3-hexafluoropropan-2-ol

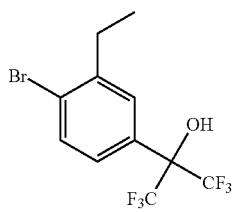

To a solution of 1-(4-bromo-3-ethylphenyl)-2,2,2-trifluoroethanone (1.63 g, 4.11 mmol, Intermediate 3, step a) and TMSCF$_3$ (901 mg, 6.17 mmol) in anhydrous THF (10 mL) was slowly added TBAF (65.3 mg, 0.25 mmol) at 0° C., and the solution was stirred at rt for 5 h. The resulting solution was quenched with 1 N aqueous HCl and diluted with EtOAc. The organic layer was washed with water and brine, dried over anhydrous Na$_2$SO$_4$, filtered, concentrated to dryness and purified by FCC on silica gel (PE) to give the title compound as a yellow oil.

Alternate Synthesis of Intermediate 3

Step Aa

2-Ethyl-4-iodoaniline

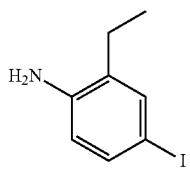

Iodine (46.0 g, 181 mmol) was added in portions to a solution of 2-ethylaniline (20.0 g, 165 mmol), NaHCO$_3$ (24.0 g, 286 mmol), MeOH (150 mL) and H$_2$O (150 mL) at 0° C. The resultant mixture was stirred for 16 hours with gradual warming to room temperature before pouring it into water (250 mL) and extracting with EtOAc (300 mL×2). The combined organic extracts were dried over anhydrous Na$_2$SO$_4$, filtered and concentrated to dryness to give the crude product, which was purified by FCC on silica gel (PE/EtOAc=100/1 to 50/1) to afford the title compound.

Alternate Synthesis of Intermediate 3

Step bb

1-Bromo-2-ethyl-4-iodobenzene

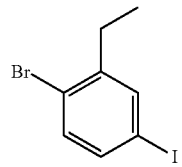

tert-Butyl nitrite (8.0 g, 78 mmol) was added drop wise to a solution consisting of 2-ethyl-4-iodoaniline (16 g, 65 mmol, Intermediate 3, step aa), p-toluenesulfonic acid monohydrate (14.6 g, 77.6 mmol), tetrabutylammonium bromide (41.7 g, 129 mmol), CuBr$_2$ (13 mg, 0.059 mmol) and acetonitrile (150 mL). The resultant mixture was stirred at room temperature for 16 h before pouring it into water (250 mL) and extracting with EtOAc (300 mL×3). The combined extracts were dried over anhydrous Na$_2$SO$_4$, filtered, and concentrated to dryness to give the crude product, which was purified by FCC on silica gel (PE/EtOAc=50/1 to 10/1) to afford the title compound.

Alternate Synthesis of Intermediate 3

Step Cc 1-(4-Bromo-3-ethylphenyl)-2,2,2-trifluoroethanone

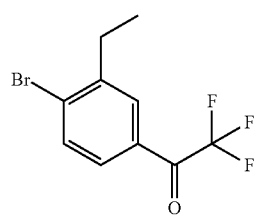

i-PrMgCl.LiCl (5.9 mL, 1.3 M in THF, 7.7 mmol) was added drop-wise to a solution of 1-bromo-2-ethyl-4-iodobenzene (2.0 g, 6.4 mmol, Intermediate 3, step bb) and anhydrous THF (30 mL) at −78° C. The resultant mixture was stirred at −78° C. for 10 minutes and then treated with 2,2,2-trifluoro-N-methoxy-N-methylacetamide (2.0 g, 13 mmol). The resultant mixture was stirred for 16 h with gradual warming to room temperature under N$_2$ before pouring it into water (50 mL) and extracting with EtOAc (50 mL×2). The combined organic extracts were dried over anhydrous Na$_2$SO$_4$, filtered, and concentrated to dryness to give the crude product, which was purified by FCC on silica gel (PE/EtOAc=100/1 to 50/1) to afford the title compound.

Alternate Synthesis of Intermediate 3

2-(4-Bromo-3-ethylphenyl)-1,1,1,3,3,3-hexafluoropropan-2-ol

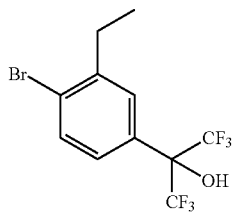

Tetrabutylammonium fluoride (32 mL, 1 M in THF, 32 mmol) was added drop-wise to a solution of 1-(4-bromo-3-ethylphenyl)-2,2,2-trifluoroethanone (6.0 g, 21 mmol, Intermediate 3, step cc), trimethyl(trifluoromethyl)silane (15.2 g, 107 mmol), and anhydrous THF (100 mL) at −15° C. The resultant mixture was stirred for 16 h with gradual warming to room temperature before pouring it into water (100 mL) and extracting with EtOAc (200 mL×2). The combined organic extracts were dried over anhydrous $Na_2SO_4$, filtered, and concentrated to dryness to give the crude product, which was purified by FCC on silica gel (PE/EtOAc=100/1 to 50/1) to afford the title compound.

Intermediate 3/1

2-(4-Bromo-3-chloro-2-fluorophenyl)-1,1,1,3,3,3-hexafluoropropan-2-ol

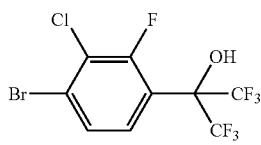

The title compound was prepared as described for Intermediate 3, using in step a methyl 4-bromo-3-chloro-2-fluorobenzoate in place of methyl 4-bromo-3-ethylbenzoate.

Intermediate 3/2

2-(4-Bromo-3-methylphenyl)-1,1,1,3,3,3-hexafluoropropan-2-ol

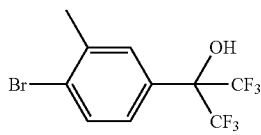

The title compound was prepared as described for Intermediate 3, using in step a methyl 4-bromo-3-methylbenzoate in place of methyl 4-bromo-3-ethylbenzoate.

Intermediate 3/3

Step a

Methyl 4-bromo-2,3-difluorobenzoate

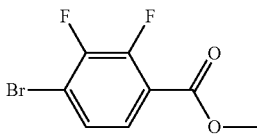

To a solution of 4-bromo-2,3-difluorobenzoic acid (10.6 g, 44.7 mmol) in MeOH (80 mL) was added $SOCl_2$ (10 mL, 137 mmol) dropwise. The mixture was stirred at 80° C. for 2 h and then the solvent was removed in vacuo. The residue was dissolved in EtOAc (200 mL), washed with water (2×200 mL), dried over anhydrous $Na_2SO_4$, filtered and concentrated to dryness. The residue was purified by FCC on silica gel (EtOAc/PE, 1/1) to provide the title compound as a white solid.

Intermediate 3/3

2-(4-Bromo-2,3-difluorophenyl)-1,1,1,3,3,3-hexafluoropropan-2-ol

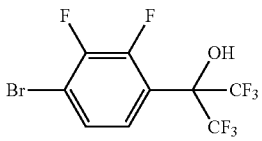

The title compound was prepared as described for Intermediate 3, using in step a methyl 4-bromo-2,3-difluorobenzoate (Intermediate 3/3, step a) in place of methyl 4-bromo-3-ethylbenzoate.

Intermediate 4

Step a (4-Bromo-3-(trifluoromethyl)phenyl)methanol

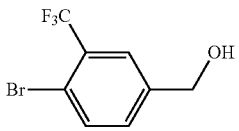

To a solution of methyl 4-bromo-3-(trifluoromethyl)benzoate (2.0 g, 7.1 mmol) in THF (20 mL) was added $LiAlH_4$ (403 mg, 10.6 mmol) at 0° C. under $N_2$. After addition, the reaction mixture was stirred at rt for 2 h. The reaction mixture was quenched with water (0.4 mL), 15% aqueous NaOH (0.4 mL) and water (1.2 mL) at 0° C. The mixture was filtered and the filtrate was concentrated to dryness to afford the crude title compound which was used in the next step without further purification.

Intermediate 4

Step b

4-Bromo-3-(trifluoromethyl)benzaldehyde

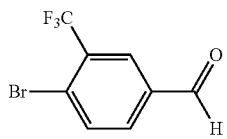

To a solution of (4-bromo-3-(trifluoromethyl)phenyl) methanol (1.5 g, crude, Intermediate 4, step a) in DCM (10 mL) was added Dess-Martin-periodinane (3.7 g, 8.82 mmol) at 0° C. The mixture was stirred at rt for 3 hours. The reaction mixture was diluted with saturated aqueous sodium bicarbonate (50 mL) and extracted with DCM (10 mL×3). The combined organic phase was dried over anhydrous Na$_2$SO$_4$ and concentrated to dryness to afford the crude title compound which was used in the next step without further purification.

Intermediate 4

Step c 1-(4-Bromo-3-(trifluoromethyl)phenyl)-2,2,2-trifluoroethanol

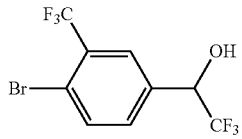

To a solution of 4-bromo-3-(trifluoromethyl)benzaldehyde (1.5 g, crude, Intermediate 4, step b) in THF (15 mL) was added TMSCF$_3$ (1.30 g, 9.15 mmol) and CsF (90 mg, 0.59 mmol) at 0° C. After addition, the reaction was stirred at rt overnight. To the reaction mixture was added 1 N aqueous HCl (10 mL) and the resulting mixture was stirred at rt for 30 minutes. The mixture was poured into water (30 mL) and extracted with EtOAc (10 mL×3). The combined organic phase was washed with brine, dried over anhydrous Na$_2$SO$_4$ and concentrated to dryness. The residue was purified by FCC on silica gel (PE/EtOAc=10/1) to afford the title compound as a yellow oil.

Intermediate 4

Step d 1-(4-Bromo-3-(trifluoromethyl)phenyl)-2,2,2-trifluoroethanone

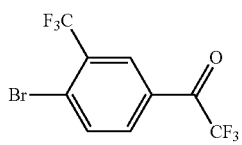

To a solution of 1-(4-bromo-3-(trifluoromethyl)phenyl)-2,2,2-trifluoroethanol (900 mg, 2.78 mmol, Intermediate 4, step c) in DCM (20 mL) was added Dess-Martin periodinane (1.8 g, 4.17 mmol) at 0° C. The mixture was stirred at rt for 2 h. The reaction mixture was diluted with saturated aqueous sodium bicarbonate (50 mL) and extracted with DCM (15 mL×3). The combined organic phase was dried over anhydrous Na$_2$SO$_4$ and concentrated to dryness. The residue was purified by FCC on silica gel (PE/EtOAc=50/1) to afford the title compound as a yellow oil.

Intermediate 4

2-(4-Bromo-3-(trifluoromethyl)phenyl)-1,1,1,3,3,3-hexafluoropropan-2-ol

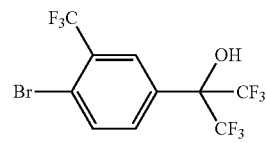

To a solution of 1-(4-bromo-3-(trifluoromethyl)phenyl)-2,2,2-trifluoroethanone (800 mg, 2.49 mmol, Intermediate 4, step d) in THF (6 mL) were added TMSCF$_3$ (723 mg, 4.98 mmol) and CsF (38 mg, 0.25 mmol) at 0° C. After addition, the reaction was stirred at rt overnight. To the reaction mixture was added 1 N aqueous HCl (10 mL) and the resulting mixture was stirred for 30 minutes. The mixture was poured into water (30 mL) and extracted with EtOAc (10 mL×3). The combined organic phase was washed with brine, dried over anhydrous Na$_2$SO$_4$ and concentrated to dryness to afford the title compound as a yellow oil.

Intermediate 4/1

2-(4-Bromo-3-(trifluoromethoxy)phenyl)-1,1,1,3,3,3-hexafluoropropan-2-ol

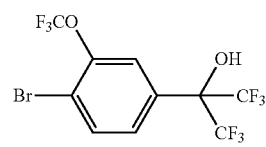

The title compound was prepared as described for Intermediate 4, using in step a methyl 4-bromo-3-(trifluoromethoxy)benzoate in place of methyl 4-bromo-3-(trifluoromethyl)benzoate.

Intermediate 4/2

2-(4-Bromo-3-isopropoxyphenyl)-1,1,1,3,3,3-hexafluoropropan-2-ol

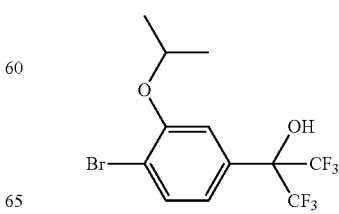

The title compound was prepared as described for Intermediate 4, using in step a methyl 4-bromo-3-(isopropoxy)benzoate in place of methyl 4-bromo-3-(trifluoromethyl)benzoate.

Intermediate 4/3

2-(4-Bromo-3-chlorophenyl)-1,1,1,3,3,3-hexafluoropropan-2-ol

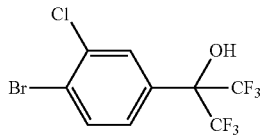

The title compound was prepared as described for Intermediate 4, starting in step c with 4-bromo-3-chlorobenzaldehyde in place of 4-bromo-3-(trifluoromethyl)benzaldehyde.

Intermediate 4/4

2-(4-Bromo-3-fluorophenyl)-1,1,1,3,3,3-hexafluoropropan-2-ol

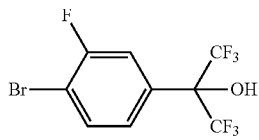

The title compound was prepared as described for Intermediate 4, starting in step c with 4-bromo-3-fluorobenzaldehyde in place of 4-bromo-3-(trifluoromethyl)benzaldehyde.

Intermediate 5

Step a 1-(3-Bromo-5-(tert-butyl)phenyl)-2,2,2-trifluoroethanone

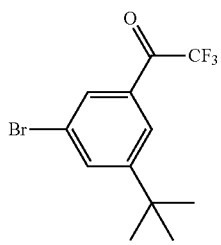 [SMILES: CC(C)(C)c1cc(Br)cc(C(=O)C(F)(F)F)c1]

To a solution of 1,3-dibromo-5-(tert-butyl)benzene (5.84 g, 20.0 mmol) in anhydrous THF (60 mL) was added n-BuLi (2.5 M in THF, 10.0 mL, 25.0 mmol) at −78° C. under nitrogen and the solution was stirred for 40 minutes. Then, 2,2,2-trifluoro-N-methoxy-N-methyl-acetamide (3.93 g, 25.0 mmol) was added slowly at this temperature and the solution was warmed to rt and stirred overnight. The resulting mixture was quenched with aqueous NH$_4$Cl and extracted with EtOAc (×2). The combined organic layers were washed with water and brine, dried over anhydrous Na$_2$SO$_4$, filtered, concentrated to dryness and the residue was purified by FCC (PE) and then prep-HPLC to give the title compound as a yellow oil.

Intermediate 5

2-(3-Bromo-5-(tert-butyl)phenyl)-1,1,1,3,3,3-hexafluoropropan-2-ol

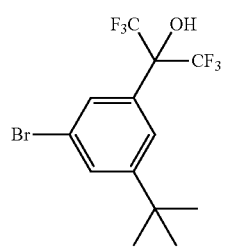 [SMILES: CC(C)(C)c1cc(Br)cc(C(O)(C(F)(F)F)C(F)(F)F)c1]

To a solution of 1-(3-bromo-5-(tert-butyl)phenyl)-2,2,2-trifluoroethanone (3.77 g, 12.2 mmol; Intermediate 5, step a) and (trifluoromethyl)trimethylsilane (2.33 mL, 15.0 mmol) in dry DME (50 mL) was added anhydrous CsF (60.8 mg, 0.40 mmol) at rt under nitrogen and the mixture was stirred for 3 h at rt. Then an additional portion of TMSCF$_3$ (1.00 mL, 6.44 mmol) was added and the mixture stirred for another 2 h, diluted with 2 N aqueous HCl, stirred for 18 h at rt and extracted with EtOAc (×2). The combined organic layers were washed with water and brine, dried over anhydrous Na$_2$SO$_4$, filtered, concentrated to dryness and the residue was purified by FCC (PE/EtOAc=10/1) and then preparative-HPLC to give the title compound as a colorless oil.

Intermediate 6

Step a

Ethyl 4-(diethylcarbamoyl)thiazole-2-carboxylate

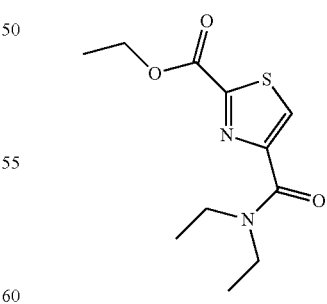

A solution of 2-(ethoxycarbonyl)thiazole-4-carboxylic acid (3.60 g, 1.79 mmol), diethylamine (5.6 mL, 54.0 mmol) and HATU (8.17 g, 2.15 mmol) in DMF (20.0 mL) was stirred overnight at rt. The resulting solution was concentrated to dryness and purified by FCC on silica gel (PE/EtOAc=10/1) to give the title compound as a brown oil.

Intermediate 6

Step b

Potassium 4-(diethylcarbamoyl)thiazole-2-carboxylate

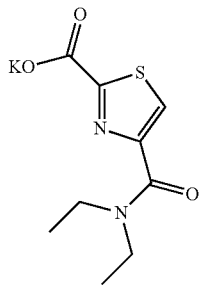

To a solution of ethyl 4-(diethylcarbamoyl)thiazole-2-carboxylate (2.56 g, 10.0 mmol, Intermediate 6, step a) in a mixture of EtOH (25 mL) and H$_2$O (5 mL) was added KOH (1.12 g, 20.0 mmol), and the mixture was stirred for 3 h at rt. The solution was concentrated to dryness, and the residue was triturated with Et$_2$O, filtered and dried under vacuum to give the crude title compound as a yellow solid.

Intermediate 6

N$^4$,N$^4$-Diethyl-N$^2$-(2-hydroxy-2-methylpropyl)thiazole-2,4-dicarboxamide

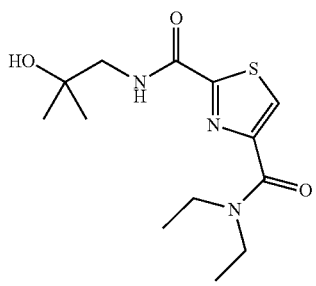 [SMILES: CCN(CC)C(=O)c1csc(C(=O)NCC(C)(C)O)n1]

A mixture of potassium 4-(diethylcarbamoyl)thiazole-2-carboxylate (2.71 g, 10.0 mmol, Intermediate 6, step b), 1-amino-2-methyl-propan-2-ol (981 mg, 11.0 mmol), HATU (4.20 g, 11.0 mmol) and DIPEA (2.58 g, 20.0 mmol) in DCM (50 mL) was stirred at rt for 3 h. The mixture was poured into water and extracted with DCM. The organic layer was washed with water and brine, dried over anhydrous Na$_2$SO$_4$, filtered, concentrated to dryness and the residue was purified by FCC on silica gel (PE/EtOAc=3/1) to give the title compound as a white solid.

Intermediate 6/1

4-(4-Fluoropiperidine-1-carbonyl)-N-(2-hydroxy-2-methylpropyl)thiazole-2-carboxamide

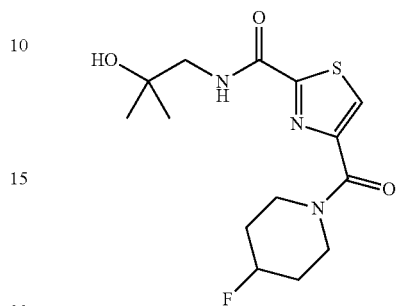

The title compound was prepared as described for Intermediate 6, using in step a 4-fluoropiperidine in place of diethylamine.

Intermediate 7

Step a

Ethyl 5-(2,3-dichloro-4-(1,1,1,3,3,3-hexafluoro-2-hydroxypropan-2-yl)phenyl)-4-(diethylcarbamoyl)thiazole-2-carboxylate

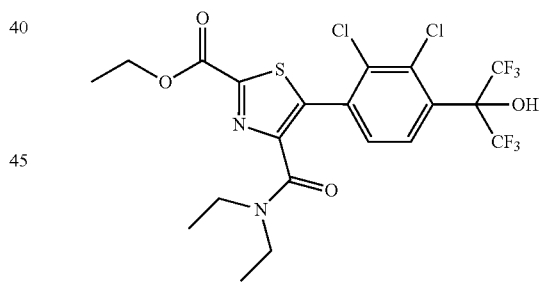

A solution of ethyl 4-(diethylcarbamoyl)thiazole-2-carboxylate (720 mg, 2.80 mmol, Intermediate 6, step a), 2-(4-bromo-2,3-dichlorophenyl)-1,1,1,3,3,3-hexafluoropropan-2-ol (1.0 g, 2.6 mmol, Intermediate 2), KOAc (501 mg, 5.10 mmol), Pd(OAc)$_2$ (115 mg, 0.512 mmol) and PPh$_3$ (267 mg, 1.02 mmol) in DMF (10.0 mL) was heated under argon at 115° C. (internal temperature) overnight and then cooled to rt. The solution was partitioned between EtOAc and H$_2$O, and the layers were separated. The organic phase was washed with H$_2$O and brine, dried over anhydrous Na$_2$SO$_4$, filtered, concentrated to dryness and purified by FCC on silica gel (PE/EtOAc=4/1) to give the title compound as a light yellow oil.

Intermediate 7

Lithium 5-(2,3-dichloro-4-(1,1,1,3,3,3-hexafluoro-2-hydroxypropan-2-yl)phenyl)-4-(diethylcarbamoyl)thiazole-2-carboxylate

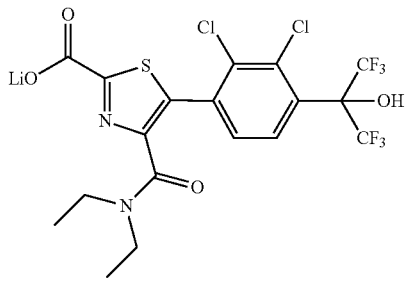

To a solution of ethyl 5-(2,3-dichloro-4-(1,1,1,3,3,3-hexafluoro-2-hydroxypropan-2-yl)phenyl)-4-(diethylcarbamoyl)thiazole-2-carboxylate (1.14 g, 2.01 mmol, Intermediate 7, step a) in a mixture of MeOH (2 mL), THF (10 mL) and $H_2O$ (2 mL) was added $LiOH.H_2O$ (186 mg, 4.42 mmol), and the mixture was stirred at rt for 16 h. The resulting solution was concentrated to dryness, triturated with $Et_2O$ and dried under vacuum to give the title compound as a yellow solid.

Intermediate 8

Step a

Ethyl 4-(4-fluoropiperidine-1-carbonyl)thiazole-2-carboxylate

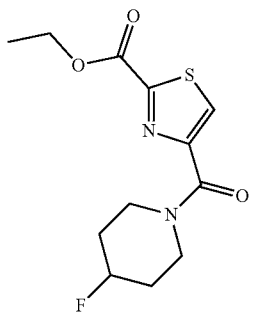 [SMILES: CCOC(=O)c1nc(C(=O)N2CCC(F)CC2)cs1]

A solution of 2-(ethoxycarbonyl)thiazole-4-carboxylic acid (2.01 g, 10.0 mmol), 4-fluoropiperidine hydrochloride (1.54 g, 11.0 mmol), HATU (4.18 g, 11.0 mmol) and DIPEA (3.87 g, 30.0 mmol) in DMF (30 mL) was stirred at rt overnight. The resulting solution was diluted with $H_2O$ and extracted with EtOAc (×3). The combined organic layer was washed with $H_2O$ (×3) and brine consecutively, dried over anhydrous $Na_2SO_4$, filtered, concentrated to dryness and the residue was purified by FCC on silica gel (PE/EtOAc=8/1) to give the title compound as a white solid.

Intermediate 8

Step b

Ethyl 5-(2,3-dichloro-4-(1,1,1,3,3,3-hexafluoro-2-hydroxypropan-2-yl)phenyl)-4-(4-fluoropiperidine-1-carbonyl)thiazole-2-carboxylate

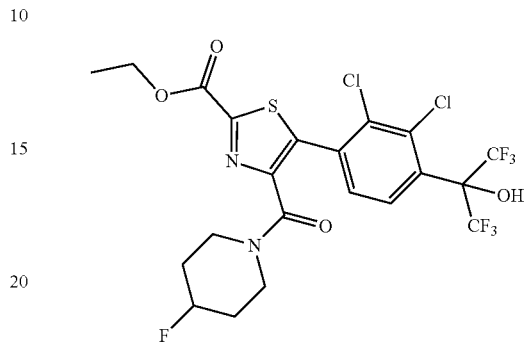

A solution of ethyl 4-(4-fluoropiperidine-1-carbonyl)thiazole-2-carboxylate (286 mg, 1.00 mmol, Intermediate 8, step a), 2-(4-bromo-2,3-dichlorophenyl)-1,1,1,3,3,3-hexafluoropropan-2-ol (392 mg, 1.00 mmol, Intermediate 2), $PPh_3$ (300 mg, 1.14 mmol) and $Pd(dppf)Cl_2$ (30 mg, 0.041 mmol) in DMF (5 mL) was heated at 90° C. overnight before cooling to rt. The resulting solution was partitioned between EtOAc and $H_2O$, and the layers were separated. The organic phase was washed with $H_2O$ and brine, dried over anhydrous $Na_2SO_4$, filtered, concentrated to dryness and the residue was purified by FCC on silica gel (PE/EtOAc=5/1) to give the title compound as a white solid.

Intermediate 8

Lithium 5-(2,3-dichloro-4-(1,1,1,3,3,3-hexafluoro-2-hydroxypropan-2-yl)phenyl)-4-(4-fluoropiperidine-1-carbonyl)thiazole-2-carboxylate

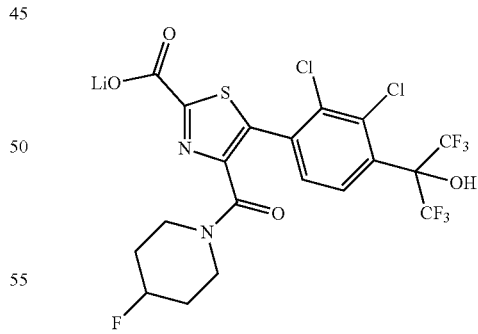

To a solution of ethyl 5-(2,3-dichloro-4-(1,1,1,3,3,3-hexafluoro-2-hydroxypropan-2-yl)phenyl)-4-(4-fluoropiperidine-1-carbonyl)thiazole-2-carboxylate (1.2 g, 2.0 mmol, Intermediate 8, step b) in $MeOH/H_2O$ (10 mL/1 mL) was added LiOH (169 mg, 4.02 mmol) at 0° C. The resulting solution was stirred at rt for 3 h, concentrated to dryness and suspended in $Et_2O$. The mixture was stirred at rt for 1 h, filtered, washed with $Et_2O$ and dried under vacuum to give the title compound as a brown solid.

Intermediate 9

Step a

4-Bromo-N-(2-hydroxy-2-methylpropyl)thiazole-2-carboxamide

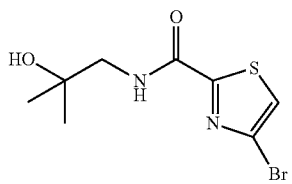

To a solution of 4-bromothiazole-2-carboxylic acid (50 g, 240 mmol) in DMF (350 mL) was added HOBt (38.9 g, 288 mmol) at rt followed by the addition of 1-amino-2-methylpropan-2-ol (23.5 g, 270 mmol). The mixture was cooled to 0° C. and EDCI (69.0 g, 360 mmol) and TEA (72.8 g, 720 mmol) were added. The mixture was stirred at rt for 15 h, and then concentrated to dryness. The residue was diluted with EtOAc and washed with saturated aqueous NaHCO$_3$ followed by brine. The organic layer was dried over anhydrous Na$_2$SO$_4$, filtered, concentrated to dryness and purified by FCC over silica gel (PE/EtOAc=4/1) to give the title compound as a pale yellow solid.

Intermediate 9

Step b

Methyl 2-((2-hydroxy-2-methylpropyl)carbamoyl)thiazole-4-carboxylate

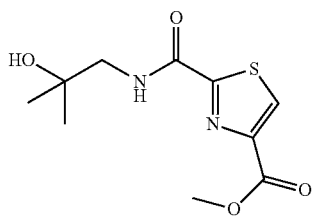 [SMILES: COC(=O)c1csc(C(=O)NCC(C)(C)O)n1]

To a solution of 4-bromo-N-(2-hydroxy-2-methylpropyl)thiazole-2-carboxamide (46.0 g, 165 mmol, Intermediate 9, step a) and TEA (49.9 g, 494 mmol) in MeOH (1000 mL) was added Pd(dppf)Cl$_2$ (5.0 g, 6.8 mmol). The mixture was heated at reflux under an atmosphere of carbon monoxide (5 MPa) overnight. After cooling to rt, the mixture was partitioned between DCM and saturated aqueous NaHCO$_3$. The organic layer was dried over anhydrous Na$_2$SO$_4$, filtered, concentrated to dryness and purified by FCC on silica gel (PE/EtOAc=4/1) to give the title compound as a white solid.

Intermediate 9

Step c

Methyl 5-(2,3-dichloro-4-(1,1,1,3,3,3-hexafluoro-2-hydroxypropan-2-yl)phenyl)-2-((2-hydroxy-2-methylpropyl)carbamoyl)thiazole-4-carboxylate

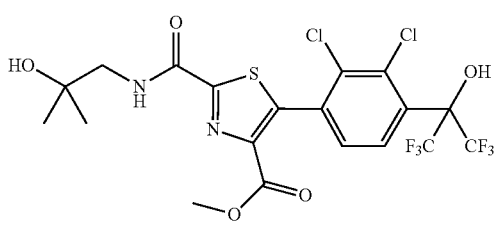 [SMILES: COC(=O)c1nc(C(=O)NCC(C)(C)O)sc1-c1ccc(C(O)(C(F)(F)F)C(F)(F)F)c(Cl)c1Cl]

A solution of 2-(4-bromo-2,3-dichlorophenyl)-1,1,1,3,3,3-hexafluoropropan-2-ol (2.71 g, 6.96 mmol, Intermediate 2), methyl 2-((2-hydroxy-2-methylpropyl)carbamoyl)thiazole-4-carboxylate (1.0 g, 3.9 mmol, Intermediate 9, step b), KOAc (760 mg, 7.74 mmol), Pd(OAc)$_2$ (87 mg, 0.39 mmol) and PPh$_3$ (1.11 g, 4.26 mmol) in DMF (15 mL) was purged with nitrogen for 5 minutes and then stirred at 115° C. overnight. The resulting solution was cooled to rt, concentrated to dryness and purified by FCC on silica gel (PE/EtOAc=10/1 to 4/1) to give the title compound as a yellow solid.

Intermediate 9

5-(2,3-Dichloro-4-(1,1,1,3,3,3-hexafluoro-2-hydroxypropan-2-yl)phenyl)-2-((2-hydroxy-2-methylpropyl)carbamoyl)thiazole-4-carboxylic acid

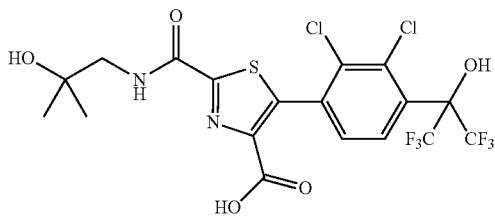 [SMILES: CC(C)(O)CNC(=O)c1nc(C(=O)O)c(-c2ccc(C(O)(C(F)(F)F)C(F)(F)F)c(Cl)c2Cl)s1]

To a solution of methyl 5-(2,3-dichloro-4-(1,1,1,3,3,3-hexafluoro-2-hydroxypropan-2-yl)phenyl)-2-(2-hydroxy-2-methylpropyl)carbamoyl)thiazole-4-carboxylate (31.0 g, 54.7 mmol, Intermediate 9, step c) in MeOH/H$_2$O (300 mL/30 mL) was added KOH (6.10 g, 109 mmol) at 0° C. The resulting solution was stirred at rt overnight and concentrated to dryness. Water (100 mL) was added, the pH was adjusted to 1-2 with 1 N aqueous HCl at 0° C., and the mixture extracted with EtOAc. The organic layer was separated, washed with brine, dried over anhydrous Na$_2$SO$_4$, filtered, and concentrated to dryness. The residue was purified by prep-HPLC to give the title compound as a white solid.

Intermediate 10

Step a

4-Tert-butyl 2-ethyl thiazole-2,4-dicarboxylate

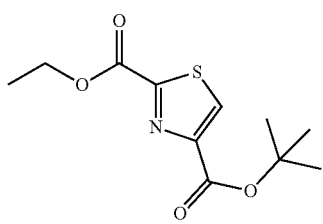 [SMILES: CCOC(=O)c1nc(C(=O)OC(C)(C)C)cs1]

A solution of 2-(ethoxycarbonyl)thiazole-4-carboxylic acid (14.4 g, 70.0 mmol) in tert-butyl alcohol (127 mL, 1.33 mol) and pyridine (38.9 mL, 481 mmol) was cooled to 0° C. in an ice-water bath. p-Toluenesulfonyl chloride (31.3 g, 164 mmol) was added in one portion, and the reaction was stirred for about 7 days at rt. The resulting solution was diluted with water and saturated aqueous $K_2CO_3$ solution and stirred for 30 minutes, resulting in a dark brown biphasic mixture. The aqueous layer was extracted with $Et_2O$ (×3). The combined organic layers were washed with saturated aqueous $K_2CO_3$ (×2) and brine consecutively, dried over anhydrous $Na_2SO_4$, filtered, concentrated to dryness and purified by FCC on silica gel (PE/EtOAc=10/1 to 4/1) to give the title compound as a light brown solid.

Intermediate 10

Step b

Sodium 4-(tert-butoxycarbonyl)thiazole-2-carboxylate

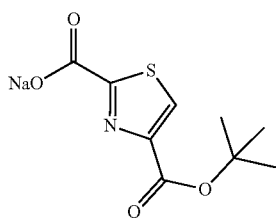

A solution of 4-tert-butyl 2-ethyl thiazole-2,4-dicarboxylate (13.7 g, 53.2 mmol, Intermediate 10, step a) in tetrahydrofuran (200 mL) was treated with 2 M aqueous sodium hydroxide (50 mL), and the resulting dark red brown solution was heated at 50° C., for 2 h. The resulting mixture was cooled to rt and concentrated to dryness to give the crude title compound as an off-white solid.

Intermediate 10 tert-Butyl 2-((2-hydroxy-2-methylpropyl)carbamoyl)thiazole-4-carboxylate

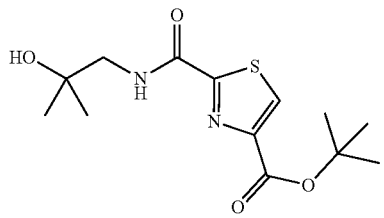 [SMILES: CC(C)(O)CNC(=O)c1nc(C(=O)OC(C)(C)C)cs1]

A solution of sodium 4-(tert-butoxycarbonyl)thiazole-2-carboxylate (13.7 g, 53.2 mmol, Intermediate 10, step b), 1-amino-2-methyl-propan-2-ol (6.24 g, 70.0 mmol), DIPEA (20.6 g, 160 mmol) and HATU (28.0 g, 76.0 mmol) in DMF (500 mL) was stirred overnight at rt. The resulting solution was concentrated to dryness and purified by FCC on silica gel (PE/EtOAc=6/1) to give the title compound as a yellow solid.

Intermediate 11

Step a

1-Benzhydryl-3-hydroxyazetidine-3-carbonitrile

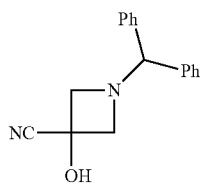

To a solution of 1-benzhydrylazetidin-3-one (1.2 g, 5.0 mmol) in a mixture of THF (10 mL) and water (10 mL) were added $NaHCO_3$ (0.84 g, 10.0 mmol) and KCN (0.4 g, 5 mmol) at rt. The mixture was stirred at rt for 2 h, then poured into water (30 mL) and extracted with EtOAc (30 mL×2). The combined organic layers were washed with brine (20 mL), dried over anhydrous $Na_2SO_4$ and concentrated to dryness. The residue was purified by FCC on silica gel (PE/EtOAc=20/1) to afford the title compound as a colorless oil.

Intermediate 11

Step b

Methyl 1-benzhydryl-3-hydroxyazetidine-3-carboxylate

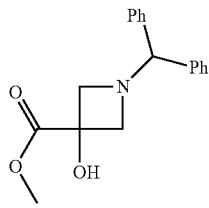 [SMILES: COC(=O)C1(O)CN(C(c2ccccc2)c2ccccc2)C1]

To a solution of 1-benzhydryl-3-hydroxyazetidine-3-carbonitrile (1.0 g, 4.2 mmol, Intermediate 11, step a) in MeOH (25 mL) was added conc. HCl (10 mL) dropwise at 0° C. The mixture was stirred at 80° C. for 3 h and concentrated to dryness to afford the title compound as a white solid.

Intermediate 11

Step c

1-Benzhydryl-3-(2-hydroxypropan-2-yl)azetidin-3-ol

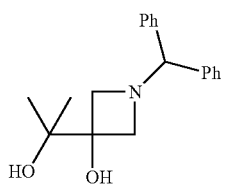

To a solution of methyl 1-benzhydryl-3-hydroxyazetidine-3-carboxylate (0.80 g, 2.7 mmol, Intermediate 11, step b) in THF (8 mL) was added CH$_3$MgCl (3.6 mL, 11 mmol, 3 M in ether) dropwise at 0° C. After addition, the reaction mixture was stirred at rt overnight. The mixture was quenched with saturated aqueous NH$_4$Cl (30 mL) and extracted with EtOAc (30 mL×2). The combined organic layers were dried over anhydrous Na$_2$SO$_4$ and concentrated to dryness. The residue was purified by FCC on silica gel (PE/EtOAc=1/1) to afford the title compound as a yellow solid.

Intermediate 11

3-(2-Hydroxypropan-2-yl)azetidin-3-ol

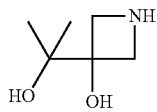

To a solution of 1-benzhydryl-3-(2-hydroxypropan-2-yl)azetidin-3-ol (0.3 g, 1 mmol, Intermediate 11, step c) in MeOH (30 mL) was added Pd/C (0.2 g, 0.19 mmol). The resulting mixture was stirred under 50 Psi of hydrogen at rt overnight. The mixture was filtered through a Celite® pad and the solids were washed with methanol. The combined filtrates were concentrated to dryness to provide the title compound as a yellow oil.

Intermediate 12

Step a (S)-tert-Butyl 4,4-difluoro-2-methylpyrrolidine-1-carboxylate

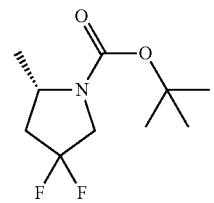

Under a nitrogen atmosphere, DAST (0.60 mL, 4.4 mmol) was added to a stirred solution of (S)-tert-butyl 2-methyl-4-oxopyrrolidine-1-carboxylate (420 mg, 2.10 mmol) in DCM (5.0 mL) under ice cooling. The resultant mixture was stirred for 16 h at rt and quenched with saturated aqueous NaHCO$_3$. The separated organic layer was dried over anhydrous Na$_2$SO$_4$, filtered, and concentrated to dryness. The residue was purified by FCC on silica gel (PE/EtOAc=70/1) to give the title compound as a yellow oil.

Intermediate 12

(S)-4,4-Difluoro-2-methylpyrrolidine hydrochloride

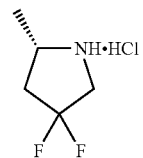

To a solution of (S)-tert-butyl 4,4-difluoro-2-methylpyrrolidine-1-carboxylate (250 mg, 1.13 mmol, Intermediate 12, step a) in 1,4-dioxane (2 mL) was added a solution of HCl in 1,4-dioxane (4 M, 5.0 mL, 20.0 mmol) at 0° C. and the mixture was stirred at rt for 1 h and concentrated to dryness to give the title compound as a red solid.

Intermediate 13

Step a (2S,4S)-tert-Butyl 4-hydroxy-2-methylpiperidine-1-carboxylate and (2S,4R)-tert-butyl 4-hydroxy-2-methylpiperidine-1-carboxylate

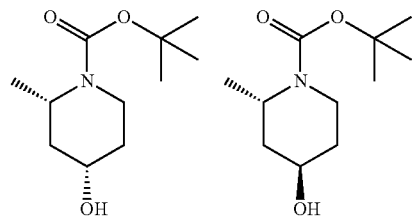

To a solution of (S)-tert-butyl 2-methyl-4-oxopiperidine-1-carboxylate (4.0 g, 19 mmol) in EtOH (40 mL) was added NaBH$_4$ (1.04 g, 28.1 mmol) at 0° C. and the mixture was stirred at rt for 1.5 h, concentrated to dryness and purified by FCC on silica gel (PE/EtOAc=4/1) to give the (2S,4S) isomer as a colorless oil and the (2S,4R) isomer as a colorless oil.

Intermediate 13

Step b (2S,4S)-tert-Butyl 4-fluoro-2-methylpiperidine-1-carboxylate

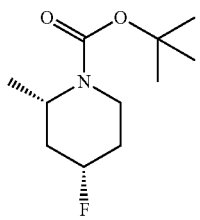

To a solution of (2S,4R)-tert-butyl 4-hydroxy-2-methylpiperidine-1-carboxylate (200 mg, 0.930 mmol, Intermediate 13, step a) in DCM (5 mL) was slowly added DAST (225 mg, 1.40 mmol) at −78° C. and the solution was stirred at −78° C. for 1 h, then slowly warmed to rt and stirred at rt overnight, quenched with saturated aqueous NaHCO$_3$ at 0° C., and extracted with DCM. The organic layer was washed with brine, dried over anhydrous Na$_2$SO$_4$, filtered, concentrated to dryness and the residue was purified by FCC on silica gel (PE/EtOAc=20/1) to give the title compound as a colorless oil.

Intermediate 13

(2S,4S)-4-Fluoro-2-methylpiperidine hydrochloride

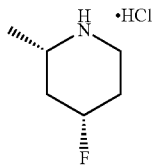

To a solution of (2S,4S)-tert-butyl 4-fluoro-2-methylpiperidine-1-carboxylate (70 mg, 0.32 mmol, Intermediate 13, step b) in Et$_2$O (5 mL) was added HCl/Et$_2$O (15 mL, 2 M) at 0° C. The mixture was stirred at rt for 3 h and concentrated to dryness to give the title compound as an off-white solid.

Intermediate 14

Step a

Ethyl 4-(hydroxymethyl)thiazole-2-carboxylate

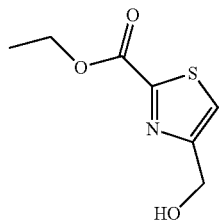

A mixture of 1-bromo-3-hydroxypropan-2-one (3.0 g, 20 mmol) in anhydrous dioxane (100 mL) was treated with ethyl 2-amino-2-thioxoacetate (2.7 g, 20 mmol) for 2 h at 50° C., and then concentrated to dryness at 50° C. to yield a dry yellow solid. The crude product was dissolved in saturated aqueous Na$_2$CO$_3$ (150 mL) and water (150 mL). The aqueous layer was extracted with EtOAc (6×50 mL). The aqueous layer was then acidified to pH=2 with concentrated aqueous HCl, resulting in the formation of a precipitate. This suspension was extracted with EtOAc (3×50 mL). The extracts were pooled, dried over anhydrous Na$_2$SO$_4$, filtered and concentrated to dryness to give the title compound as a red-brown solid.

Intermediate 14

Step b

Ethyl 5-(2,3-dichloro-4-(1,1,1,3,3,3-hexafluoro-2-hydroxypropan-2-yl)phenyl)-4-(hydroxymethyl)thiazole-2-carboxylate

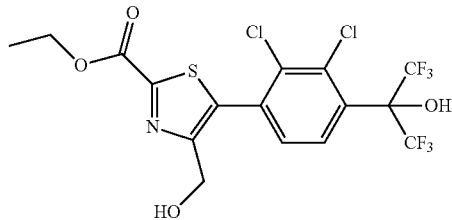 [SMILES: CCOC(=O)c1nc(CO)c(-c2ccc(C(O)(C(F)(F)F)C(F)(F)F)c(Cl)c2Cl)s1]

To a solution of ethyl 4-(hydroxymethyl)thiazole-2-carboxylate (200 mg, 0.78 mmol, Intermediate 14, step a) in DMF (10 mL) were added 2-(4-bromo-2,3-dichlorophenyl)-1,1,1,3,3,3-hexafluoropropan-2-ol (335 mg, 0.86 mmol, Intermediate 2), KOAc (153 mg, 1.56 mmol), PPh$_3$ (225 mg, 0.86 mmol) and Pd(OAc)$_2$ (35 mg, 0.16 mmol) and the mixture was stirred at 110° C. under N$_2$ overnight. Once cooled to rt, the mixture was poured into water (50 mL) and extracted with EtOAc (20 mL×3). The combined organic layers were washed with water and brine, dried over anhydrous Na$_2$SO$_4$, concentrated to dryness and the residue was purified by FCC on silica gel (PE/EtOAc=5/1) to give the title compound as a white solid.

Intermediate 14

Step c 5-(2,3-Dichloro-4-(1,1,1,3,3,3-hexafluoro-2-hydroxypropan-2-yl)phenyl)-2-(ethoxycarbonyl)thiazole-4-carboxylic acid

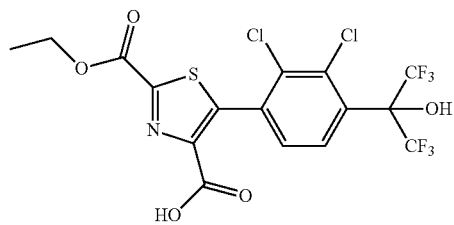 [SMILES: CCOC(=O)c1nc(C(=O)O)c(-c2ccc(C(O)(C(F)(F)F)C(F)(F)F)c(Cl)c2Cl)s1]

To a solution of ethyl 5-(2,3-dichloro-4-(1,1,1,3,3,3-hexafluoro-2-hydroxypropan-2-yl)phenyl)-4-(hydroxymethyl)thiazole-2-carboxylate (150 mg, 0.30 mmol; Intermediate 14, step b) in $CH_3CN$ (3 mL) and $H_2O$ (1.5 mL) were added iodobenzene diacetate (339 mg, 1.05 mmol) and TEMPO (47 mg, 0.30 mmol) and the mixture was stirred at rt for 5 h, concentrated to dryness and extracted with EtOAc (10 mL×2). The combined organic layers were washed with brine, dried over anhydrous $Na_2SO_4$, concentrated to dryness and the residue was purified by FCC on silica gel (DCM/MeOH=20/1) to give the title compound as a white solid.

Intermediate 14

(S)-Ethyl 5-(2,3-dichloro-4-(1,1,1,3,3,3-hexafluoro-2-hydroxypropan-2-yl)phenyl)-4-(4,4-difluoro-2-methylpyrrolidine-1-carbonyl)thiazole-2-carboxylate

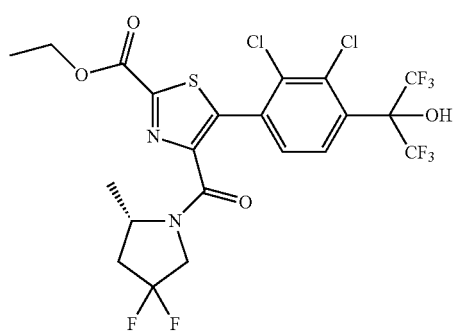 [SMILES: CCOC(=O)c1nc(C(=O)N2CC(F)(F)C[C@@H]2C)c(-c2ccc(C(O)(C(F)(F)F)C(F)(F)F)c(Cl)c2Cl)s1]

To a solution of 5-(2,3-dichloro-4-(1,1,1,3,3,3-hexafluoro-2-hydroxypropan-2-yl)phenyl)-2-(ethoxycarbonyl)thiazole-4-carboxylic acid (100 mg, 0.19 mmol; Intermediate 14, step c) in DMF (5 mL) were added (S)-4,4-difluoro-2-methylpyrrolidine hydrochloride (31 mg, 0.19 mmol; Intermediate 12), TEA (30 mg, 0.29 mmol) and HATU (148 mg, 0.473 mmol) and the mixture was stirred at rt overnight. The mixture was poured into water (25 mL) and extracted with EtOAc (10 mL×3). The combined organic layers were washed with brine, dried over anhydrous $Na_2SO_4$, concentrated to dryness and the residue was purified by FCC on silica gel (PE/EtOAc=5/1) to give the title compound as a white solid.

Intermediate 15

Step a (S)-Ethyl 4-(4,4-difluoro-2-methylpyrrolidine-1-carbonyl)thiazole-2-carboxylate

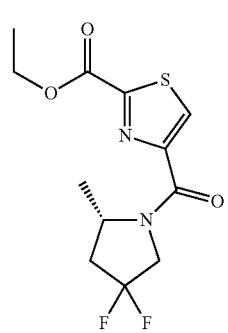 [SMILES: CCOC(=O)c1nc(C(=O)N2CC(F)(F)C[C@@H]2C)cs1]

To a solution of 2-(ethoxycarbonyl)thiazole-4-carboxylic acid (689 mg, 3.43 mmol) and (S)-4,4-difluoro-2-methylpyrrolidine hydrochloride (540 mg, 3.43 mmol, Intermediate 12) in DMF (10 mL) were added TEA (693 mg, 6.86 mmol) and HATU (2.6 g, 6.9 mmol). The mixture was stirred at rt overnight. The reaction mixture was poured into water (60 mL) and extracted with EtOAc (20 mL×3). The combined organic layers were washed with brine, dried over anhydrous $Na_2SO_4$ and concentrated to dryness. The residue was purified by FCC on silica gel (PE/EtOAc=5/1) to afford the title compound as a yellow oil.

Intermediate 15

Step b

Lithium (S)-4-(4,4-difluoro-2-methylpyrrolidine-1-carbonyl)thiazole-2-carboxylate

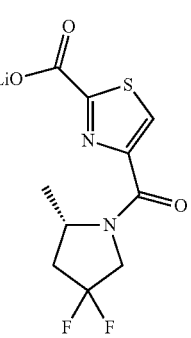

To a solution of (S)-ethyl 4-(4,4-difluoro-2-methylpyrrolidine-1-carbonyl)thiazole-2-carboxylate (500 mg, 1.6 mmol, Intermediate 15, step a) in MeOH (4 mL) and water (2 mL) was added $LiOH.H_2O$ (36 mg, 0.86 mmol). The mixture was stirred at rt for 3 h. The reaction mixture was concentrated to dryness to give the title compound, which was used directly in the next step without further purification.

Intermediate 15

((S)-4,4-Difluoro-2-methylpyrrolidin-1-yl)(2-((3R,5S)-3,5-dihydroxypiperidine-1-carbonyl)thiazol-4-yl)methanone

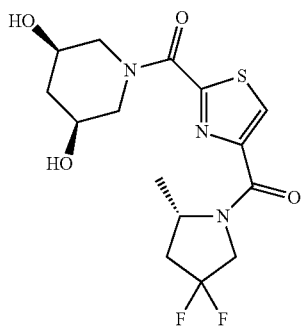 [SMILES: C[C@H]1CC(F)(F)CN1C(=O)c1csc(C(=O)N2C[C@H](O)C[C@H](O)C2)n1]

To a solution of lithium (S)-4-(4,4-difluoro-2-methylpyrrolidine-1-carbonyl)thiazole-2-carboxylate (400 mg, crude Intermediate 15, step b) and (3R,5S)-piperidine-3,5-diol hydrochloride (215 mg, 1.4 mmol) in DMF (6 mL) were added TEA (212 mg, 2.10 mmol) and HATU (1.0 g, 2.8 mmol). The mixture was stirred at rt overnight. The reaction mixture was poured into water (50 mL) and extracted with EtOAc (20 mL×3). The combined organic layers were washed with brine, dried over anhydrous $Na_2SO_4$ and concentrated to dryness. The residue was purified by FCC on silica gel (PE/EtOAc=50/1) to afford the title compound as a yellow oil.

Intermediate 15/1

(S)—N-(2-Hydroxy-2-methylpropyl)-4-(2-methylpyrrolidine-1-carbonyl)thiazole-2-carboxamide

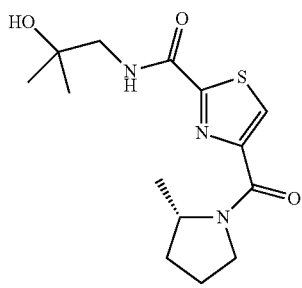 [SMILES: C[C@H]1CCCN1C(=O)c1csc(C(=O)NCC(C)(C)O)n1]

The title compound was prepared as described for Intermediate 15 using in step a (S)-2-methylpyrrolidine in place of (S)-4,4-difluoro-2-methylpyrrolidine hydrochloride and in the final step 1-amino-2-methylpropan-2-ol in place of (3R,5S)-piperidine-3,5-diol hydrochloride.

Alternate Synthesis of Intermediate 15/1

Step a (S)-Ethyl 4-(2-methylpyrrolidine-1-carbonyl)thiazole-2-carboxylate

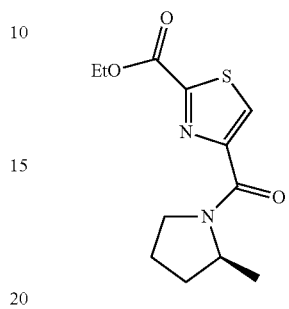

(S)-2-Methylpyrrolidine (14.0 g, 164 mmol) in 2-methyl tetrahydrofuran (10 mL) was added to a mixture of 2-(ethoxycarbonyl)thiazole-4-carboxylic acid (38.7 g, 192 mmol) in 2-methyl tetrahydrofuran (320 mL) at 0° C. Then, 2,4,6-tripropyl-1,3,5,2,4,6-trioxatriphosphinane 2,4,6-trioxide (140 mL, 220 mmol) was added followed by addition of DIPEA (57.0 mL, 331 mmol). After 2 h of stirring, the mixture was poured into 300 mL of aqueous saturated sodium bicarbonate solution. The layers were separated and the aqueous layer was extracted with EtOAc. The combined organic layers were washed with brine, dried over anhydrous $MgSO_4$ and concentrated to provide the title compound as a brownish yellow solid.

Alternate Synthesis of Intermediate 15/1

Step b (S)—N-(2-Hydroxy-2-methylpropyl)-4-(2-methylpyrrolidine-1-carbonyl)thiazole-2-carboxamide

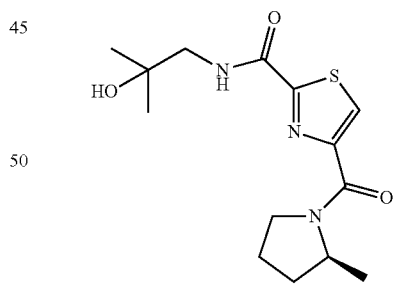

EtOH (440 mL) was added to a mixture of (S)-ethyl 4-(2-methylpyrrolidine-1-carbonyl)thiazole-2-carboxylate (40.0 g, 149 mmol, intermediate 15/1, step a) and 1-amino-2-methyl-propan-2-ol (42.4 g, 475 mmol), The mixture was stirred at rt for 16 h, and then concentrated to dryness. The residue was diluted with EtOAc and washed with water. The aqueous layer was extracted with EtOAc (5×) and the combined organics were washed with aqueous saturated NaCl solution, dried over anhydrous $MgSO_4$, filtered through Celite®, concentrated to dryness and purified by FCC on silica gel (0 to 10% MeOH in DCM) to give the title

Intermediate 15/2

(R)—N-(2-Hydroxy-2-methylpropyl)-4-(2-methyl-pyrrolidine-1-carbonyl)thiazole-2-carboxamide

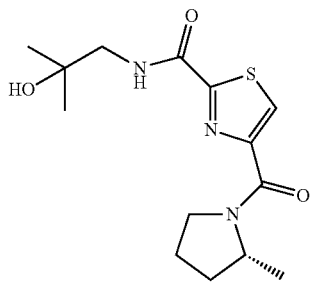 [SMILES: C[C@@H]1CCCN1C(=O)c1csc(C(=O)NCC(C)(C)O)n1]

The title compound was prepared as described in the alternate synthesis of Intermediate 15/1, using in step a (R)-2-methylpyrrolidine in place of (S)-2-methylpyrrolidine.

Intermediate 15/3

(S)—N-(2-Hydroxy-2-methylpropyl)-4-(2-methylpiperidine-1-carbonyl)thiazole-2-carboxamide

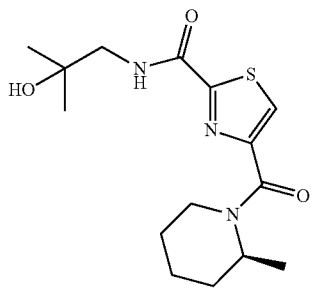 [SMILES: C[C@H]1CCCCN1C(=O)c1csc(C(=O)NCC(C)(C)O)n1]

The title compound was prepared as described in the alternate synthesis of Intermediate 15/1, using in step a (S)-2-methylpiperidine in place of (S)-2-methylpyrrolidine. Trituration of the product with diethyl ether furnished the title compound as a white solid.

Intermediate 15/4

4-(7-Azabicyclo[2.2.1]heptane-7-carbonyl)-N-(2-hydroxy-2-methylpropyl)thiazole-2-carboxamide

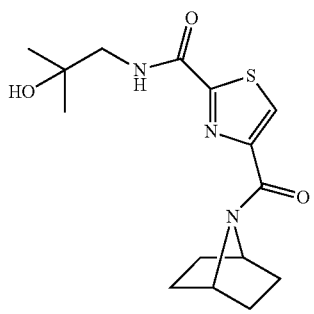 [SMILES: CC(C)(O)CNC(=O)c1nc(C(=O)N2C3CCC2CC3)cs1]

The title compound was prepared as described in the alternate synthesis of Intermediate 15/1, using in step a 7-azabicyclo[2.2.1]heptane in place of (S)-2-methylpyrrolidine.

Intermediate 15/5

(S)-4-(4,4-Difluoro-2-methylpyrrolidine-1-carbonyl)-N-(2-hydroxy-2-methylpropyl)thiazole-2-carboxamide

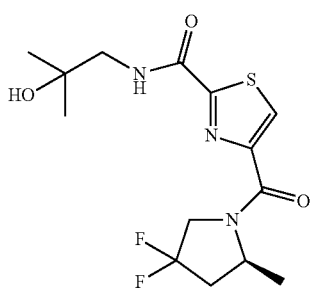 [SMILES: C[C@H]1CC(F)(F)CN1C(=O)c1csc(C(=O)NCC(C)(C)O)n1]

The title compound was prepared as described in the alternate synthesis of Intermediate 15/1, using in step a (S)-4,4-difluoro-2-methylpyrrolidine hydrochloride (Intermediate 12) in place of (S)-2-methylpyrrolidine.

Intermediate 16

Step a

Ethyl 4-(7-azabicyclo[2.2.1]heptane-7-carbonyl)thiazole-2-carboxylate

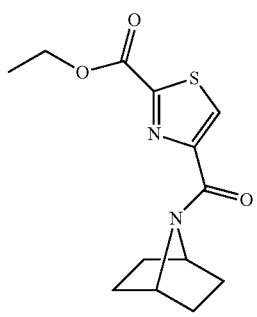 [SMILES: CCOC(=O)c1nc(C(=O)N2C3CCC2CC3)cs1]

To a solution of 2-(ethoxycarbonyl)thiazole-4-carboxylic acid (500 mg, 2.48 mmol) in DMF (5 mL) were added 7-azabicyclo[2.2.1]heptane hydrochloride (365 mg, 4.73 mmol), TEA (376 mg, 3.73 mmol) and HATU (1.9 g, 4.97 mmol) and the mixture was stirred at rt overnight, poured into water (25 mL) and extracted with EtOAc (10 mL×3). The combined organic layers were washed with brine, dried over anhydrous $Na_2SO_4$, concentrated to dryness and the residue was purified by FCC on silica gel (PE/EtOAc=5/1) to give the title compound as a pale yellow solid.

Intermediate 16

Ethyl 4-(7-azabicyclo[2.2.1]heptane-7-carbonyl)-5-(2,3-dichloro-4-(1,1,1,3,3,3-hexafluoro-2-hydroxypropan-2-yl)phenyl)thiazole-2-carboxylate

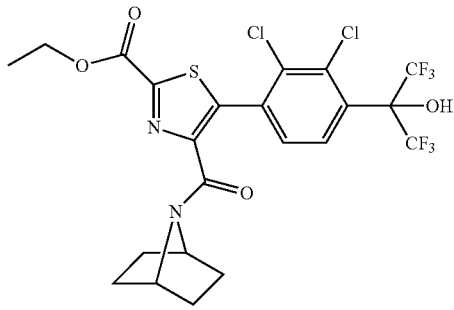 [SMILES: CCOC(=O)c1nc(C(=O)N2C3CCC2CC3)c(-c2ccc(C(O)(C(F)(F)F)C(F)(F)F)c(Cl)c2Cl)s1]

To a solution of ethyl 4-(7-azabicyclo[2.2.1]heptane-7-carbonyl)thiazole-2-carboxylate (500 mg, 1.78 mmol; Intermediate 16, step a) in DMF (10 mL) were added 2-(4-bromo-2,3-dichlorophenyl)-1,1,1,3,3,3-hexafluoropropan-2-ol (770 mg, 1.96 mmol; Intermediate 2), KOAc (350 mg, 3.57 mmol), PPh$_3$ (510 mg, 1.96 mmol), and Pd(OAc)$_2$ (80 mg, 0.36 mmol) and the mixture was stirred at 110° C. under N$_2$ overnight. After cooling to rt, the mixture was poured into water (50 mL) and extracted with EtOAc (20 mL×3). The combined organic layers were washed with water and brine, dried over anhydrous Na$_2$SO$_4$, concentrated to dryness, and purified by FCC on silica gel (PE/EtOAc=5/1) and then by prep-HPLC to give the title compound as a yellow oil.

Intermediate 16/1

(S)-Ethyl 5-(2-chloro-4-(1,1,1,3,3,3-hexafluoro-2-hydroxypropan-2-yl)phenyl)-4-(2-methylpyrrolidine-1-carbonyl)thiazole-2-carboxylate

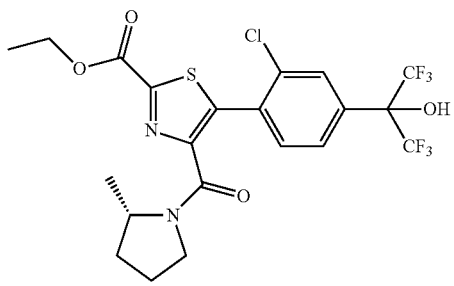 [SMILES: CCOC(=O)c1nc(C(=O)N2CCC[C@@H]2C)c(-c2ccc(C(O)(C(F)(F)F)C(F)(F)F)cc2Cl)s1]

The title compound was prepared as described for Intermediate 16 using in step a (S)-2-methylpyrrolidine in place of 7-azabicyclo[2.2.1]heptane hydrochloride and in the final step 2-(4-bromo-3-chlorophenyl)-1,1,1,3,3,3-hexafluoropropan-2-ol (Intermediate 4/3) in place of 2-(4-bromo-2,3-dichlorophenyl)-1,1,1,3,3,3-hexafluoropropan-2-ol.

Intermediate 16/2

(S)-Ethyl 5-(4-(1,1,1,3,3,3-hexafluoro-2-hydroxypropan-2-yl)-2-(trifluoromethyl)phenyl)-4-(2-methylpyrrolidine-1-carbonyl)thiazole-2-carboxylate

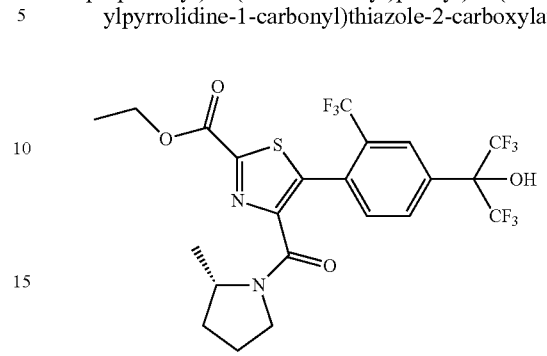

The title compound was prepared as described for Intermediate 16 using in step a (S)-2-methylpyrrolidine in place of 7-azabicyclo[2.2.1]heptane hydrochloride and in the final step 2-(4-bromo-3-(trifluoromethyl)phenyl)-1,1,1,3,3,3-hexafluoropropan-2-ol (Intermediate 4) in place of 2-(4-bromo-2,3-dichlorophenyl)-1,1,1,3,3,3-hexafluoropropan-2-ol.

Intermediate 17

2-(5-Bromoquinolin-8-yl)-1,1,1,3,3,3-hexafluoropropan-2-ol

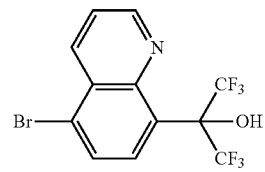

To a mixture of methyl 8-bromoquinoline-5-carboxylate (212 mg, 0.800 mmol) and trimethyl(trifluoromethyl)silane (0.35 mL, 2.4 mmol) in THF (4 mL) at 4° C. was added CsF (28 mg, 0.18 mmol). The mixture was stirred at 4° C. and allowed to warm to room temperature. After stirring for 2.5 days, 1.0 N HCl aqueous solution was added and the aqueous layer was extracted with dichloromethane. The combined organic phases were dried over anhydrous Na$_2$SO$_4$, filtered, and concentrated to dryness. The residue was purified by flash column chromatography (silica gel, 10-40% EtOAc in heptanes) to give the title compound.

Intermediate 18

Step a

1-Bromo-2-(difluoromethyl)-4-iodobenzene

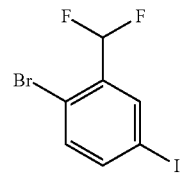 [SMILES: FC(F)c1cc(I)ccc1Br]

DAST (77.8 g, 482 mmol) was added to a solution of 2-bromo-5-iodobenzaldehyde (100 g, 322 mmol) and DCM (1 L) at 0° C. The resultant mixture was stirred at room temperature for 2 h before quenching with ice/water (1 L) and extracting with DCM (800 mL×3). The combined organic extracts were washed with brine, dried over anhydrous Na₂SO₄, filtered and concentrated to dryness to give the crude product, which was purified by FCC on silica gel (PE/EtOAc=50/1) to afford the title compound.

Intermediate 18

Step b 1-(4-Bromo-3-(difluoromethyl)phenyl)-2,2,2-trifluoroethanone

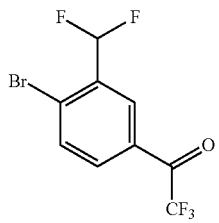

i-PrMgCl.LiCl (194 mL, 1.3 M in THF, 252 mmol) was added drop-wise to a solution of 1-bromo-2-(difluoromethyl)-4-iodobenzene (70.0 g, 210 mmol, Intermediate 18, step a) and anhydrous THF (200 mL) at −78° C. The resultant mixture was stirred at −78° C. for 30 minutes and then treated with 2,2,2-trifluoro-N-methoxy-N-methylacetamide (49.5 g, 315 mmol). The resultant mixture was stirred at −78° C. under N₂ for 1 h before quenching with saturated aqueous NH₄Cl (600 mL) solution and extracting with EtOAc (800 mL×3). The combined organic extracts were dried over anhydrous Na₂SO₄, filtered, and concentrated to dryness to give the crude product, which was purified by FCC on silica gel (PE/EtOAc=10/1 to 4/1) to afford the title compound.

Intermediate 18

2-(4-Bromo-3-(difluoromethyl)phenyl)-1,1,1,3,3,3-hexafluoropropan-2-ol

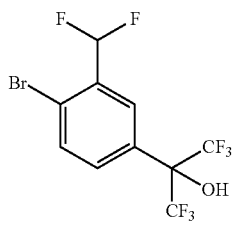 [SMILES: OC(c1ccc(Br)c(C(F)F)c1)(C(F)(F)F)C(F)(F)F]

Tetrabutylammonium fluoride (470 mL, 1 M in THF, 470 mmol) was added drop-wise to a solution of 1-(4-bromo-3-(difluoromethyl)phenyl)-2,2,2-trifluoroethanone (95.0 g, 313 mmol, Intermediate 18, step b), trimethyl(trifluoromethyl)silane (223 g, 1.6 mol), and anhydrous THF (100 mL) at −15° C. The resultant mixture was stirred at −15° C. to −10° C. for 30 minutes and for 2 h with gradual warming to room temperature before quenching with 2 N aqueous HCl (400 mL) and extracting with EtOAc (800 mL×3). The combined organic extracts were dried over anhydrous Na₂SO₄, filtered, and concentrated to dryness to give the crude product, which was purified by FCC on silica gel (PE/EtOAc=100/1 to 20/1) to afford the title compound.

Intermediate 19

Lithium 4-(7-azabicyclo[2.2.1]heptane-7-carbonyl)-5-(2,3-dichloro-4-(1,1,1,3,3,3-hexafluoro-2-hydroxypropan-2-yl)phenyl)thiazole-2-carboxylate

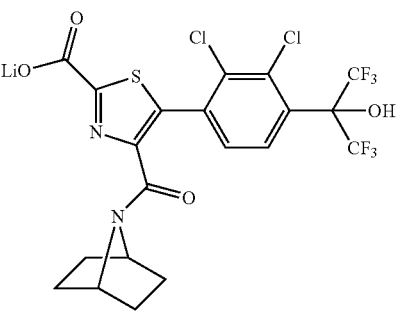

To a solution of ethyl 4-(7-azabicyclo[2.2.1]heptane-7-carbonyl)-5-(2,3-dichloro-4-(1,1,1,3,3,3-hexafluoro-2-hydroxypropan-2-yl)phenyl)thiazole-2-carboxylate (100 mg, 0.17 mmol, Intermediate 16) in MeOH (2 mL) was added LiOH.H₂O (11 mg, 0.26 mmol) and H₂O (2 mL). After addition, the reaction mixture was stirred at rt for 2 h. The reaction mixture was concentrated to afford the title compound as a yellow solid which was used in the next step without further purification.

Intermediate 20

Step a 4-(tert-Butoxycarbonyl)thiazole-2-carboxylic acid

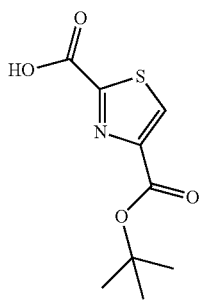

To a solution of 4-tert-butyl 2-ethyl thiazole-2,4-dicarboxylate (165 mg, 0.64 mmol, Intermediate 10, step a) in EtOH (5 mL) was added aqueous LiOH (1 mL, 0.5 N) and the solution was stirred at rt overnight. Then the solvent was removed, the residue adjusted to pH<2 with 2 N aqueous HCl and extracted with EtOAc (3×). The combined organic layers were washed with brine, dried over anhydrous Na₂SO₄, filtered and concentrated to dryness to give the title compound as a yellow solid.

Intermediate 20

Step b tert-Butyl 2-(thiomorpholine-4-carbonyl)thiazole-4-carboxylate

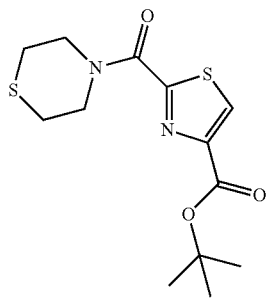 [SMILES: CC(C)(C)OC(=O)c1csc(C(=O)N2CCSCC2)n1]

A solution of 4-(tert-butoxycarbonyl)thiazole-2-carboxylic acid (127 mg, 0.55 mmol, Intermediate 20, step a), HATU (314 mg, 0.83 mmol) and DIPEA (177 mg, 1.38 mmol) in DMF (8 mL) was stirred at rt for 1 h, then thiomorpholine (68 mg, 0.66 mmol) was added and the mixture was stirred overnight, diluted with water and extracted with EtOAc (×3). The combined organic layers were washed with brine, dried over anhydrous Na₂SO₄, filtered and concentrated to dryness. The residue was purified by FCC on silica gel (PE/EtOAc=7/1) to give the title compound as a yellow solid.

Intermediate 20

Step c tert-Butyl 5-(2,3-dichloro-4-(1,1,1,3,3,3-hexafluoro-2-hydroxypropan-2-yl)phenyl)-2-(thiomorpholine-4-carbonyl)thiazole-4-carboxylate

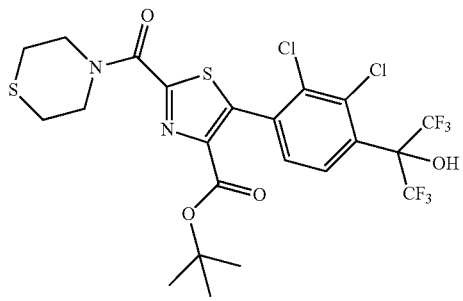 [SMILES: CC(C)(C)OC(=O)c1nc(C(=O)N2CCSCC2)sc1-c1ccc(C(O)(C(F)(F)F)C(F)(F)F)c(Cl)c1Cl]

To a solution of tert-butyl 2-(thiomorpholine-4-carbonyl)thiazole-4-carboxylate (139 mg, 0.44 mmol, Intermediate 20, step b), 2-(4-bromo-2,3-dichlorophenyl)-1,1,1,3,3,3-hexafluoropropan-2-ol (189 mg, 0.48 mmol, Intermediate 2) and Na₂CO₃ (117 mg, 1.10 mmol) in DMF (5 mL) were added PPh₃ (115 mg, 0.438 mmol) and Pd(OAc)₂ (14 mg, 0.06 mmol) under Ar and the solution was stirred at 120° C. overnight. After cooling to rt the mixture was diluted with water and extracted with EtOAc. The combined organic layers were washed with water and brine, dried over anhydrous Na₂SO₄, filtered and concentrated to dryness. The residue was purified by FCC on silica gel (PE/EtOAc=8/1) to give the title compound as a white solid.

Intermediate 20

5-(2,3-Dichloro-4-(1,1,1,3,3,3-hexafluoro-2-hydroxypropan-2-yl)phenyl)-2-(thiomorpholine-4-carbonyl)thiazole-4-carboxylic acid

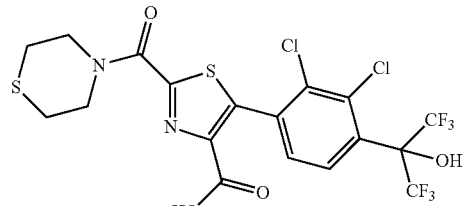

A solution of tert-butyl 5-(2,3-dichloro-4-(1,1,1,3,3,3-hexafluoro-2-hydroxypropan-2-yl)phenyl)-2-(thiomorpholine-4-carbonyl)thiazole-4-carboxylate (185 mg, 0.296 mmol, Intermediate 20, step c) in HCl (3 mL, 4 N in 1,4-dioxane) was stirred at rt for 1 h and concentrated to dryness to give the title compound as a brown solid.

Intermediate 20/1

Step a tert-Butyl 2-(2-thia-6-azaspiro[3.3]heptane-6-carbonyl)thiazole-4-carboxylate

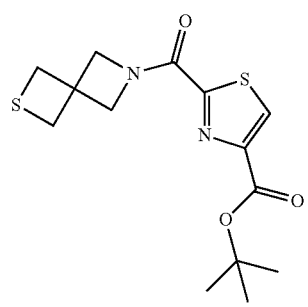 [SMILES: CC(C)(C)OC(=O)c1csc(C(=O)N2CC3(CSC3)C2)n1]

The title compound was prepared as described for Intermediate 20, steps a and b, using in step b 2-thia-6-azaspiro[3.3]heptane in place of thiomorpholine.

Intermediate 20/1

Step b tert-Butyl 2-(2-oxido-2-thia-6-azaspiro[3.3]heptane-6-carbonyl)thiazole-4-carboxylate

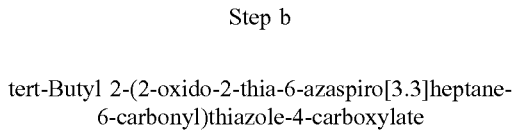

To a solution of tert-butyl 2-(2-thia-6-azaspiro[3.3]heptane-6-carbonyl)thiazole-4-carboxylate (471 mg, 1.45 mmol, Intermediate 20/1, step a) in DCM (20 mL) was added m-CPBA (249 mg, 1.45 mmol, 85%) at 0° C. and the mixture was stirred at rt overnight. The mixture was quenched with NaHSO$_3$, washed with aqueous NaHCO$_3$ and extracted with EtOAc three times. The combined organic layers were washed with brine, dried over anhydrous Na$_2$SO$_4$, filtered and concentrated to dryness to give the title compound as a yellow solid.

Intermediate 20/1

5-(2,3-Dichloro-4-(1,1,1,3,3,3-hexafluoro-2-hydroxypropan-2-yl)phenyl)-2-(2-oxido-2-thia-6-azaspiro[3.3]heptane-6-carbonyl)thiazole-4-carboxylic acid

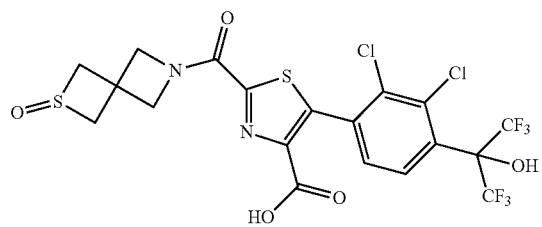 [SMILES: O=C(O)c1nc(C(=O)N2CC3(C2)CS(=O)C3)sc1-c1ccc(C(O)(C(F)(F)F)C(F)(F)F)c(Cl)c1Cl]

The title compound was prepared as described for Intermediate 20, steps c and final step, using in step c tert-butyl 2-(2-oxido-2-thia-6-azaspiro[3.3]heptane-6-carbonyl)thiazole-4-carboxylate (Intermediate 20/1, step b) in place of tert-butyl 2-(thiomorpholine-4-carbonyl)thiazole-4-carboxylate.

Intermediate 21

Step a

N-(2-Hydroxy-2-methylpropyl)-4-(hydroxymethyl)thiazole-2-carboxamide

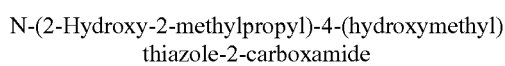

The title compound was prepared as described for Intermediate 10, step b and the final step, using ethyl 4-(hydroxymethyl)thiazole-2-carboxylate in place of 4-tert-butyl 2-ethyl thiazole-2,4-dicarboxylate.

Intermediate 21

Step b 5-(2-(Difluoromethyl)-4-(1,1,1,3,3,3-hexafluoro-2-hydroxypropan-2-yl)phenyl)-N-(2-hydroxy-2-methylpropyl)-4-(hydroxymethyl)thiazole-2-carboxamide

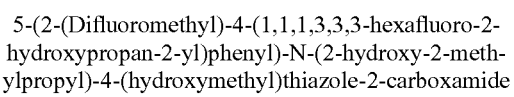

A solution of 2-(4-bromo-3-(difluoromethyl)phenyl)-1,1,1,3,3,3-hexafluoropropan-2-ol (373 mg, 1.00 mmol, Intermediate 18), N-(2-hydroxy-2-methylpropyl)-4-(hydroxymethyl)thiazole-2-carboxamide (401 mg, 1.00 mmol, Intermediate 21, step a), K$_2$CO$_3$ (276 mg, 2.00 mmol), Pd(OAc)$_2$ (45 mg, 0.20 mmol), PCy$_3$.HBF$_4$ (73 mg, 0.20 mmol) and PivOH (13 mg, 0.13 mmol) in DMA (5.0 mL) was heated under argon at 105° C. overnight. The mixture was cooled to rt, partitioned between EtOAc and water, and the layers were separated. The organic layer was washed with water and brine, dried over Na$_2$SO$_4$, filtered and concentrated to dryness. The residue was purified by FCC on silica gel (PE/EtOAc=2/1) followed by prep-HPLC to give the title compound as a white solid.

Intermediate 21

5-(2-(Difluoromethyl)-4-(1,1,1,3,3,3-hexafluoro-2-hydroxypropan-2-yl)phenyl)-2-((2-hydroxy-2-methylpropyl)carbamoyl)thiazole-4-carboxylic acid

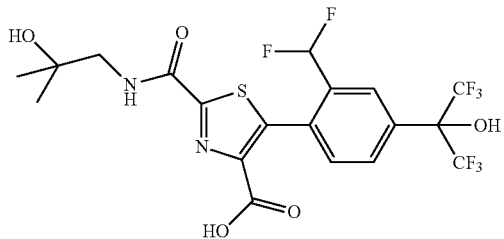 [SMILES: CC(C)(O)CNC(=O)c1nc(C(=O)O)c(-c2ccc(C(O)(C(F)(F)F)C(F)(F)F)cc2C(F)F)s1]

The title compound was prepared as described for Intermediate 14, step c using 5-(2-(difluoromethyl)-4-(1,1,1,3,3,3-hexafluoro-2-hydroxypropan-2-yl)phenyl)-N-(2-hydroxy-2-methylpropyl)-4-(hydroxymethyl)thiazole-2-carboxamide (Intermediate 21, step b) in place of ethyl 5-(2,3-dichloro-4-(1,1,1,3,3,3-hexafluoro-2-hydroxypropan-2-yl)phenyl)-4-(hydroxymethyl)thiazole-2-carboxylate.

Intermediate 22

Step a tert-Butyl 2-((3-amino-2,2-dimethyl-3-oxopropyl)carbamoyl)thiazole-4-carboxylate

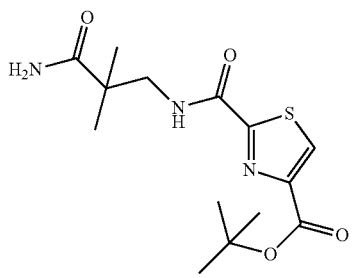 [SMILES: CC(C)(C)OC(=O)c1csc(C(=O)NCC(C)(C)C(N)=O)n1]

The title compound was prepared as described for Intermediate 20 step b, using 3-amino-2,2-dimethylpropanamide in place of thiomorpholine.

Intermediate 22

Step b tert-Butyl 2-((3-amino-2,2-dimethyl-3-oxopropyl)carbamoyl)-5-(2,3-dichloro-4-(1,1,1,3,3,3-hexafluoro-2-hydroxypropan-2-yl)phenyl)thiazole-4-carboxylate

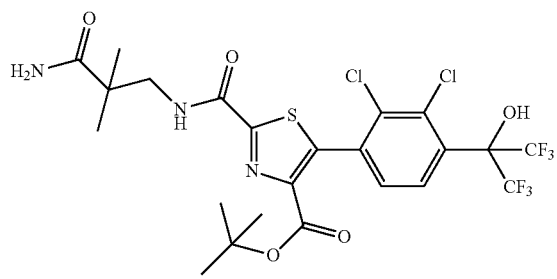 [SMILES: CC(C)(C)OC(=O)c1nc(C(=O)NCC(C)(C)C(N)=O)sc1-c1ccc(C(O)(C(F)(F)F)C(F)(F)F)c(Cl)c1Cl]

The title compound was prepared as described for Intermediate 20, step c using tert-butyl 2-((3-amino-2,2-dimethyl-3-oxopropyl)carbamoyl)thiazole-4-carboxylate (Intermediate 22, step a) in place of tert-butyl 2-(thiomorpholine-4-carbonyl)thiazole-4-carboxylate.

Intermediate 22

2-((3-Amino-2,2-dimethyl-3-oxopropyl)carbamoyl)-5-(2,3-dichloro-4-(1,1,1,3,3,3-hexafluoro-2-hydroxypropan-2-yl)phenyl)thiazole-4-carboxylic acid

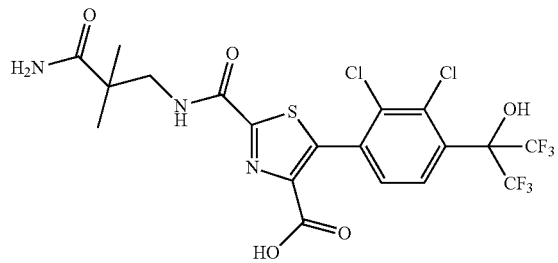 [SMILES: CC(C)(CNC(=O)c1nc(C(=O)O)c(-c2ccc(C(O)(C(F)(F)F)C(F)(F)F)c(Cl)c2Cl)s1)C(N)=O]

The title compound was prepared as described for the synthesis of Intermediate 20 using tert-butyl 2-((3-amino-2,2-dimethyl-3-oxopropyl)carbamoyl)-5-(2,3-dichloro-4-(1,1,1,3,3,3-hexafluoro-2-hydroxypropan-2-yl)phenyl)thiazole-4-carboxylate (Intermediate 22, step b) in place of tert-butyl 5-(2,3-dichloro-4-(1,1,1,3,3,3-hexafluoro-2-hydroxypropan-2-yl)phenyl)-2-(thiomorpholine-4-carbonyl)thiazole-4-carboxylate.

Intermediate 23

Step a 1-(5-Bromo-4-(trifluoromethyl)pyridin-2-yl)-2,2,2-trifluoroethanone

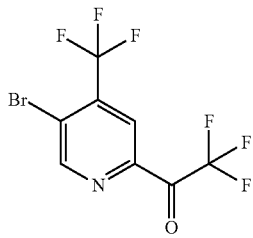 [SMILES: O=C(c1cc(C(F)(F)F)c(Br)cn1)C(F)(F)F]

A solution of 5-bromo-2-iodo-4-(trifluoromethyl)pyridine (3.5 g, 9.95 mmol) in toluene (30 mL) was cooled to −78° C. Then, n-BuLi (4.14 mL, 9.95 mmol, 2.5 M in THF) was added and the resulting mixture was stirred at −78° C. for 30 minutes. Then ethyl 2,2,2-trifluoroacetate (1.7 g, 11.94 mmol) was added and the mixture was stirred at −78° C. for 1 h. The mixture was quenched by the addition of saturated aqueous $NH_4Cl$ (5 mL), diluted with brine and extracted with EtOAc (2×30 mL). The organic layers were combined, washed with brine, dried over anhydrous $MgSO_4$, filtered and concentrated to dryness. The residue was purified by FCC on silica gel (EtOAc/PE=1/50 to 1/20) to provide the title compound as a yellow oil.

Intermediate 23

2-(5-Bromo-4-(trifluoromethyl)pyridin-2-yl)-1,1,1,3,3,3-hexafluoropropan-2-ol

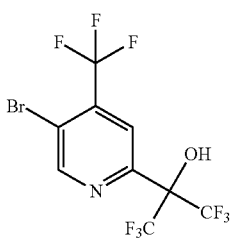

A solution of 1-(5-bromo-4-(trifluoromethyl)pyridin-2-yl)-2,2,2-trifluoroethanone (1.2 g, 3.73 mmol, Intermediate 23, step a) and TMSCF₃ (2.65 g, 18.64 mmol) in anhydrous THF (20 mL) was cooled to −10° C. Then, a solution of TBAF (974 mg, 3.73 mmol) in THF (10 mL) was added followed immediately by the addition of 1 N aqueous HCl (6 mL). The resulting mixture was stirred at rt for 10 minutes. The mixture was then partitioned between saturated aqueous NaHCO₃ (10 mL) and EtOAc (20 mL). The aqueous layer was further extracted with EtOAc (20 mL), then the organic layers were combined, washed with brine, dried over anhydrous Na₂SO₄, filtered and concentrated to dryness. The residue was purified by FCC on silica gel (PE) to afford the title compound as a white solid.

Intermediate 23/1

2-(5-Bromo-4-methylpyridin-2-yl)-1,1,1,3,3,3-hexafluoropropan-2-ol

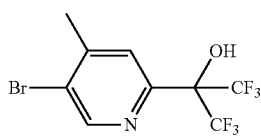

The title compound was prepared as described for Intermediate 23, using in step a 5-bromo-2-iodo-4-methylpyridine in place of 5-bromo-2-iodo-4-(trifluoromethyl)pyridine.

Intermediate 24

Step a

2-Bromo-5-iodophenol

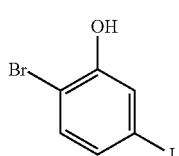

A solution consisting of tribromoborane (52.8 g, 211 mmol) and DCM (200 mL) was added drop-wise to a solution of 1-bromo-4-iodo-2-methoxybenzene (33.0 g, 105 mmol) and DCM (200 mL) at 0° C. The resultant mixture was stirred with gradual warming to rt for 16 h before pouring it into water (500 mL) and extracting with DCM (450 mL×3). The combined organic extracts were washed with brine, dried over anhydrous Na₂SO₄, filtered, and concentrated to dryness to afford the crude title product, which was purified by FCC on silica gel (PE/EtOAc=10/1 to 2/1) to afford the title compound.

Intermediate 24

Step b

1-Bromo-2-(difluoromethoxy)-4-iodobenzene

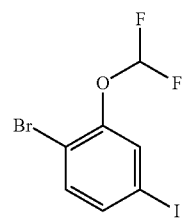 [SMILES: FC(F)Oc1cc(I)ccc1Br]

Difluoromethyl trifluoromethanesulfonate (40 g, 200 mmol) was added drop-wise to a solution of 2-bromo-5-iodophenol (29.0 g, 97.0 mmol, Intermediate 24, step a), aqueous KOH (228 mL, 8 M, 1.82 mol), and MeCN (250 mL). The resultant mixture was stirred at room temperature for 1 h before pouring it into water (1 L) and extracting with DCM (800 mL×3). The combined organic extracts were dried over anhydrous Na₂SO₄, filtered, and concentrated to dryness to afford the title compound.

Intermediate 24

Step c 1-(4-Bromo-3-(difluoromethoxy)phenyl)-2,2,2-trifluoroethanone

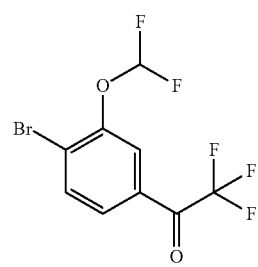 [SMILES: O=C(c1ccc(Br)c(OC(F)F)c1)C(F)(F)F]

i-PrMgCl.LiCl (62 mL, 1.3 M in THF, 81 mmol) was added drop-wise to a solution of 1-bromo-2-(difluoromethoxy)-4-iodobenzene (24 g, 67 mmol, Intermediate 24, step b) and anhydrous THF (200 mL) at −78° C. The resultant mixture was stirred at −78° C. for 10 minutes and then was treated with 2,2,2-trifluoro-N-methoxy-N-methylacetamide (13 g, 81 mmol). The resultant mixture was stirred at −78° C. for 4 h before quenching with MeOH (5 mL) at −10° C. to 5° C. Then the resultant mixture was stirred at 20° C. for 5 minutes before pouring it into saturated aqueous NH₄Cl (200 mL) solution and extracting with EtOAc (250 mL×3). The combined organic extracts were dried over anhydrous Na₂SO₄, filtered, and concentrated to dryness to afford the crude product, which was used in the next step without further purification.

Intermediate 24

2-(4-Bromo-3-(difluoromethoxy)phenyl)-1,1,1,3,3,3-hexafluoropropan-2-ol

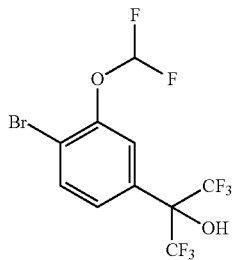

Tetrabutylammonium fluoride (94 mL, 1 M in THF, 94 mmol) was added drop-wise to a solution of 1-(4-bromo-3-(difluoromethoxy)phenyl)-2,2,2-trifluoroethanone (20 g, 63 mmol, Intermediate 24, step c), trimethyl(trifluoromethyl)silane (44.6 g, 314 mmol), and anhydrous THF (100 mL) at −15° C. The resultant mixture was stirred at −15° C. to −10° C. for 30 minutes and for 1 h with gradual warming to room temperature before quenching with 2 N aqueous HCl (160 mL) and extracting with EtOAc (250 mL×3). The combined organic extracts were dried over anhydrous Na₂SO₄, filtered, and concentrated to dryness to give the crude product, which was purified by preparative HPLC with a Phenomenex Synergi Max-RP 250×50 mm×10 μm column (eluent: CH₃CN and H₂O with 0.05% NH₃ from 40% to 80%, v/v). The pure fractions were collected and the volatiles were removed under vacuum. The residue was suspended in water (10 mL), the mixture frozen, and then lyophilized to dryness to afford the title compound.

Intermediate 25

Step a 1-(4-Bromo-3-methoxyphenyl)-2,2,2-trifluoroethanone

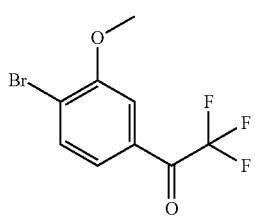

i-PrMgCl.LiCl (74 mL, 1.3 M in THF, 96 mmol) was added drop-wise to a solution of 1-bromo-4-iodo-2-methoxybenzene (25 g, 80 mmol) and anhydrous THF (200 mL) at −65° C. The resultant mixture was stirred at −65° C. for 30 minutes and then treated with 2,2,2-trifluoro-N-methoxy-N-methylacetamide (25.1 g, 160 mmol). The resultant mixture was stirred for 18 h with gradual warming to room temperature under N₂ before pouring into saturated aqueous NH₄Cl (200 mL) solution and extracting with EtOAc (100 mL×3). The combined organic extracts were dried over anhydrous Na₂SO₄, filtered and concentrated to dryness to give the crude product, which was triturated with PE (50 mL). The suspension was isolated via vacuum filtration and the filter cake washed with PE (10 mL). Further drying of the solid under reduced pressure afforded the title compound.

Intermediate 25

2-(4-Bromo-3-methoxyphenyl)-1,1,1,3,3,3-hexafluoropropan-2-ol

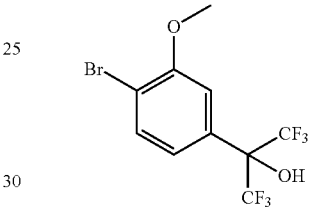

Tetrabutylammonium fluoride (37 mL, 1 M in THF, 37 mmol) was added drop-wise to a solution of 1-(4-bromo-3-methoxyphenyl)-2,2,2-trifluoroethanone (7.0 g, 25 mmol, Intermediate 25, step a), trimethyl(trifluoromethyl)silane (17.6 g, 124 mmol), and anhydrous THF (100 mL) at −15° C. The resultant mixture was stirred for 1.5 h with gradual warming to room temperature before quenching with 2 N aqueous HCl (150 mL) and extracting with EtOAc (150 mL×3). The combined organic extracts were dried over anhydrous Na₂SO₄, filtered and concentrated to dryness to give the crude product, which was purified by FCC on silica gel (PE/EtOAc=10/1 to 2/1) to afford the title compound.

Intermediate 26

Step a

4-Bromo-2-chloro-3-fluoroaniline

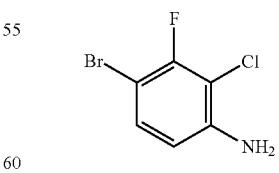

NBS (42.8 g, 240 mmol) was added to a solution of 2-chloro-3-fluoroaniline (35.0 g, 240 mmol) in DMF (200 mL). The resultant mixture was stirred at room temperature for 16 h before pouring it into water (300 mL) and extracting with EtOAc (500 mL×3). The combined organic extracts were dried over anhydrous Na₂SO₄, filtered, and concen- Intermediate 26

Step b

1-Bromo-3-chloro-2-fluoro-4-iodobenzene

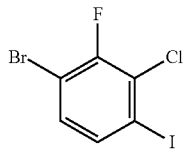

A solution consisting of NaNO₂ (24.6 g, 357 mmol), KI (71.0 g, 428 mmol), and H₂O (300 mL) was added drop-wise to a solution of 4-bromo-2-chloro-3-fluoroaniline (32.0 g, 143 mmol, Intermediate 26, step a), p-toluenesulfonic acid monohydrate (86.0 g, 499 mmol), and acetonitrile (400 mL) at 0° C. The resultant mixture was stirred at room temperature for 16 h before pouring it into water (500 mL) and extracting with EtOAc (500 mL×3). The combined extracts were dried over anhydrous Na₂SO₄, filtered, and concentrated to dryness to give the crude product, which was purified by FCC on silica gel (PE/EtOAc=10/1 to 5/1) to afford the title compound.

Intermediate 26

Step c 1-(4-Bromo-2-chloro-3-fluorophenyl)-2,2,2-trifluoroethanone

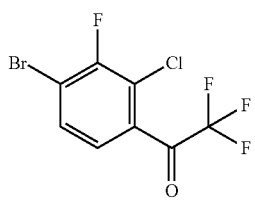 [SMILES: O=C(c1ccc(Br)c(F)c1Cl)C(F)(F)F]

i-PrMgCl.LiCl (41 mL, 1.3 M in THF, 45 mmol) was added drop-wise to a solution of 1-bromo-3-chloro-2-fluoro-4-iodobenzene (15 g, 45 mmol, Intermediate 26, step b) and anhydrous THF (150 mL) at −78° C. The resultant mixture was stirred at −78° C. for 10 minutes and then treated with 2,2,2-trifluoro-N-methoxy-N-methylacetamide (14 g, 89 mmol). The resultant mixture was stirred for 4 h with gradual warming to room temperature under N₂ before pouring it into water (250 mL) and extracting with EtOAc (300 mL×2). The combined organic extracts were dried over anhydrous Na₂SO₄, filtered, and concentrated to dryness to give the crude product, which was purified by FCC on silica gel (PE/EtOAc=50/1 to 5/1) to afford the title compound.

Intermediate 26

2-(4-Bromo-2-chloro-3-fluorophenyl)-1,1,1,3,3,3-hexafluoropropan-2-ol

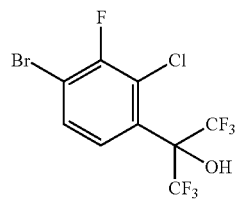

Tetrabutylammonium fluoride (83.5 mL, 1 M in THF, 83.5 mmol) was added drop-wise to a solution of 1-(4-bromo-2-chloro-3-fluorophenyl)-2,2,2-trifluoroethanone (17 g, 56 mmol, Intermediate 26, step c), trimethyl(trifluoromethyl)silane (39.6 g, 278 mmol), and anhydrous THF (100 mL) at −15° C. The resultant mixture was stirred at −15° C. for 0.5 h and for 16 h with gradual warming to room temperature before pouring it into water (150 mL) and extracting with EtOAc (200 mL×2). The combined organic extracts were dried over anhydrous Na₂SO₄, filtered, and concentrated to dryness to give the crude product, which was purified by FCC on silica gel (PE/EtOAc=100/1 to 50/1) to give impure product that was further purified by preparative HPLC with a Phenomenex Synergi Max-RP 250×80 mm×10 μm column (eluent: 44% to 74% (v/v) CH₃CN and H₂O with 0.1% TFA). The pure fractions were combined and the volatiles were removed under vacuum. The residue was re-dissolved in H₂O (100 mL), the resultant solution was adjusted to pH=8 using solid NaHCO₃ and extracted with DCM (100 mL×3). The combined organic extracts were dried over anhydrous Na₂SO₄, filtered, and concentrated to dryness to afford the title compound.

Intermediate 27

Step a 1-(Difluoromethyl)-2-fluoro-3-nitrobenzene

DAST (40.0 g, 248 mmol) was added to a solution of 2-fluoro-3-nitrobenzaldehyde (30.0 g, 177 mmol) and DCM (300 mL) at 0° C. The resultant mixture was stirred at room temperature for 16 h before quenching with ice/water (500 mL) and extracting with DCM (500 mL×3). The combined organic extracts were washed with brine, dried over anhydrous Na₂SO₄, filtered and concentrated to dryness to afford the title product.

Intermediate 27

Step b 3-(Difluoromethyl)-2-fluoroaniline

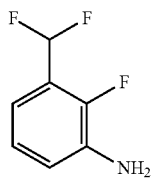

Fe (62 g, 1.1 mol) was added to a solution of 1-(difluoromethyl)-2-fluoro-3-nitrobenzene (33.0 g, 105 mmol, Intermediate 27, step a), NH$_4$Cl (5.90 g, 110 mmol), EtOH (400 mL), and H$_2$O (100 mL). The resultant mixture was stirred at room temperature for 6 h. The suspension was filtered through a pad of Celite® and the pad washed with EtOH (50 mL). The filtrate was concentrated to dryness to afford the title compound.

Intermediate 27

Step c

4-Bromo-3-(difluoromethyl)-2-fluoroaniline

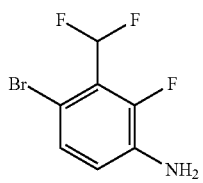

NBS (32.0 g, 180 mmol) was added to a solution of 3-(difluoromethyl)-2-fluoroaniline (30.5 g, 155 mmol, Intermediate 27, step b) and DMF (150 mL) at 0° C. The resultant mixture was stirred at room temperature for 16 h before pouring it into water (300 mL) and extracting with DCM (300 mL×4). The combined organic extracts were dried over anhydrous Na$_2$SO$_4$, filtered, and concentrated to dryness to afford the crude product, which was purified by FCC on silica gel (PE/EtOAc=10/1 to 5/1) to afford the title compound.

Intermediate 27

Step d

1-Bromo-2-(difluoromethyl)-3-fluoro-4-iodobenzene

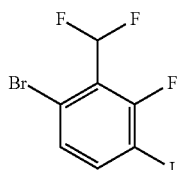

A solution of NaNO$_2$ (8.60 g, 125 mmol), KI (20.8 g, 125 mmol), and H$_2$O (75 mL) was added drop-wise to a solution of 4-bromo-3-(difluoromethyl)-2-fluoroaniline (10 g, 42 mmol, Intermediate 27, step c), p-toluenesulfonic acid monohydrate (18.0 g, 105 mmol), and acetonitrile (200 mL) at 0° C. The resultant mixture was stirred at room temperature for 4 h before pouring it into water (100 mL) and extracting with EtOAc (200 mL×3). The combined extracts were washed with saturated aqueous Na$_2$S$_2$O$_3$ solution (200 mL×3) and brine (200 mL), dried over anhydrous Na$_2$SO$_4$, filtered, and concentrated to dryness to give the crude product, which was purified by FCC on silica gel (PE/EtOAc=10/1 to 5/1) to afford the title compound.

Intermediate 27

Step e 1-(4-Bromo-3-(difluoromethyl)-2-fluorophenyl)-2,2,2-trifluoroethanone

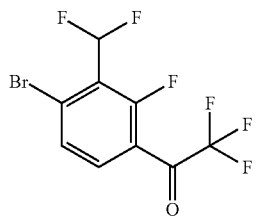 [SMILES: O=C(c1ccc(Br)c(C(F)F)c1F)C(F)(F)F]

i-PrMgCl.LiCl (6.0 mL, 1.3 M in THF, 7.8 mmol) was added drop-wise to a solution of 1-bromo-2-(difluoromethyl)-3-fluoro-4-iodobenzene (2.0 g, 5.7 mmol, Intermediate 27, step d) and anhydrous THF (20 mL) −78° C. The resultant mixture was stirred at −78° C. for 10 minutes and then treated with 2,2,2-trifluoro-N-methoxy-N-methylacetamide (1.4 g, 8.9 mmol). The resultant mixture was stirred at −78° C. for 1 h and for 2 h with gradual warming to room temperature under N$_2$ before quenching with saturated aqueous NH$_4$Cl solution (50 mL) and extracting with EtOAc (60 mL×3). The combined organic extracts were dried over anhydrous Na$_2$SO$_4$, filtered, and concentrated to dryness to give the crude product, which was purified by FCC on silica gel (PE/EtOAc=10/1 to 4/1) to afford the title compound.

Intermediate 27

2-(4-bromo-3-(difluoromethyl)-2-fluorophenyl)-1,1,1,3,3,3-hexafluoropropan-2-ol

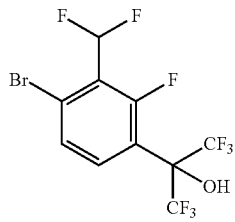

Tetrabutylammonium fluoride (7 mL, 1 M in THF, 7 mmol) was added drop-wise to a solution of 1-(4-bromo-3-(difluoromethyl)-2-fluorophenyl)-2,2,2-trifluoroethanone (1.5 g, 4.7 mmol, Intermediate 27, step e), trimethyl(trifluoromethyl)silane (3.4 g, 24 mmol), and anhydrous THF (20 mL) at −15° C. The resultant mixture was stirred at −15° C. to −10° C. for 30 minutes and for 1 h with gradual warming to room temperature before quenching with 2 N aqueous HCl (16 mL) and extracting with EtOAc (50 mL×3). The combined organic extracts were dried over anhydrous Na₂SO₄, filtered, and concentrated to dryness to give the crude product, which was purified by FCC on silica gel (PE/EtOAc=10/1 to 6/1) to afford the title compound.

Intermediate 28

Step a

Potassium (S)-4-(2-methylpyrrolidine-1-carbonyl)thiazole-2-carboxylate

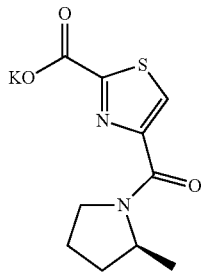

t-BuOK (13.8 g, 123 mmol) was added to a solution consisting of (S)-ethyl 4-(2-methylpyrrolidine-1-carbonyl)thiazole-2-carboxylate (30.0 g, 112 mmol, Intermediate 15/1, step a), THF (160 mL) and H₂O (40 mL). The resultant mixture was stirred at 60° C. for 2 h. THF was removed under reduced pressure and the residue was diluted with H₂O (100 mL) and extracted with dichloromethane (50 mL×2). The aqueous layer was frozen using dry ice/acetone and then lyophilized to dryness to afford the title compound.

Intermediate 28

(S)—N-((1-Hydroxycyclobutyl)methyl)-4-(2-methylpyrrolidine-1-carbonyl)thiazole-2-carboxamide

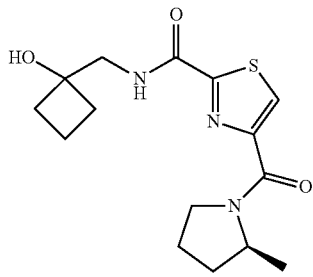 [SMILES: C[C@H]1CCCN1C(=O)c1csc(C(=O)NCC2(O)CCC2)n1]

EDCI (4.9 g, 26 mmol) was added to a solution consisting of 1-(aminomethyl)cyclobutanol (1.3 g, 13 mmol), potassium (S)-4-(2-methylpyrrolidine-1-carbonyl)thiazole-2-carboxylate (3.6 g, 13 mmol, Intermediate 28, step a), HOBt (3.5 g, 26 mmol), DIPEA (6.9 mL, 39 mmol), and THF (100 mL). The resultant mixture was stirred at room temperature for 16 h before diluting with ethyl acetate (200 mL). The mixture was washed with H₂O (50 mL) and brine (30 mL), dried over anhydrous Na₂SO₄, filtered, and concentrated to dryness. The residue was purified by preparative HPLC with a Phenomenex Synergi Max-RP 250 mm×50 mm×10 μm column (eluent: 5% to 45% (v/v) CH₃CN and H₂O with 0.225% HCOOH) and the pure fractions were collected and concentrated to dryness. The residue was suspended in water (10 mL), the mixture frozen using dry ice/acetone, and then lyophilized to dryness to afford the title compound as a white solid.

Example 1

Step a tert-Butyl 5-(4-(1,1,1,3,3,3-hexafluoro-2-hydroxypropan-2-yl)naphthalen-1-yl)-2-((2-hydroxy-2-methylpropyl)carbamoyl)thiazole-4-carboxylate

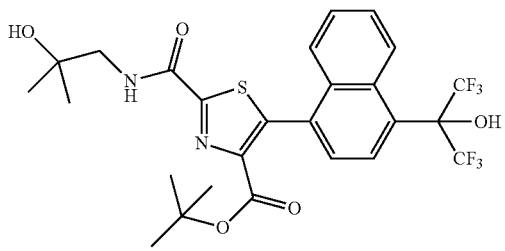 [SMILES: CC(C)(O)CNC(=O)c1nc(C(=O)OC(C)(C)C)c(-c2ccc(C(O)(C(F)(F)F)C(F)(F)F)c3ccccc23)s1]

A solution of 2-(4-bromonaphthalen-1-yl)-1,1,1,3,3,3-hexafluoropropan-2-ol (600 mg, 2.00 mmol, Intermediate 1), tert-butyl 2-((2-hydroxy-2-methylpropyl)carbamoyl)thiazole-4-carboxylate (746 g, 2.00 mmol, Intermediate 10), KOAc (392 mg, 4.00 mmol), Pd(OAc)₂ (100 mg, 0.445 mmol) and PPh₃ (524 mg, 2.00 mmol) in DMF (10 mL) was purged with nitrogen for 5 minutes and then stirred at 120° C. overnight. The resulting solution was cooled to rt, concentrated to dryness and the residue was purified by prep-HPLC to give the title compound as a yellow solid.

Example 1

Step b 5-(4-(1,1,1,3,3,3-Hexafluoro-2-hydroxypropan-2-yl)naphthalen-1-yl)-2-((2-hydroxy-2-methylpropyl)carbamoyl)thiazole-4-carboxylic acid

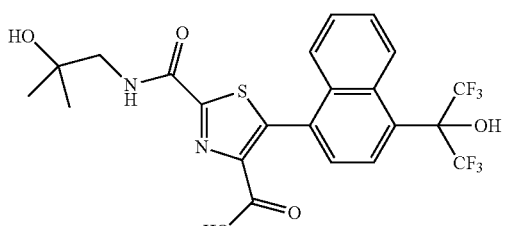

To a solution of tert-butyl 5-(4-(1,1,1,3,3,3-hexafluoro-2-hydroxypropan-2-yl)naphthalen-1-yl)-2-(2-hydroxy-2-methylpropyl)carbamoyl)thiazole-4-carboxylate (200 mg, 0.338 mmol, Example 1, step a) in MeOH (2 mL) was added a solution of HCl in MeOH (3 M, 2 mL, 6.00 mmol), and the solution was stirred at rt for 1 h. The resulting solution was concentrated to dryness. The residue was triturated with hexane and dried under vacuum to give the title compound as a white solid.

Example 1

5-(4-(1,1,1,3,3,3-Hexafluoro-2-hydroxypropan-2-yl)naphthalen-1-yl)-N-(2-hydroxy-2-methylpropyl)-4-(4-methylpiperidine-1-carbonyl)thiazole-2-carboxamide

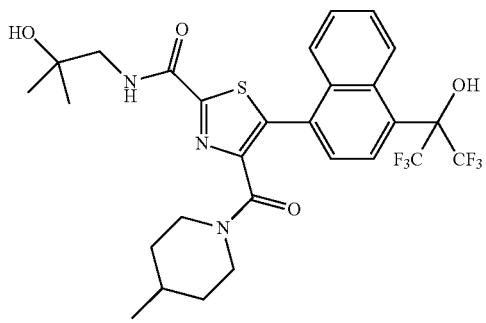 [SMILES: CC1CCN(C(=O)c2nc(C(=O)NCC(C)(C)O)sc2-c2ccc(C(O)(C(F)(F)F)C(F)(F)F)c3ccccc23)CC1]

A solution of 5-(4-(1,1,1,3,3,3-hexafluoro-2-hydroxypropan-2-yl)naphthalen-1-yl)-2-((2-hydroxy-2-methylpropyl)carbamoyl)thiazole-4-carboxylic acid (179 mg, 0.337 mmol, Example 1, step b), 4-methyl-piperidine (45 mg, 0.45 mmol), DIPEA (129 mg, 1.00 mmol) and HATU (122 mg, 0.321 mmol) in DMF (3.0 mL) was stirred overnight at rt. The resulting solution was diluted with water and extracted with EtOAc (×3). The combined organic layers were washed with water (×3) and brine consecutively, dried over anhydrous $Na_2SO_4$, filtered and concentrated to dryness. The residue was purified by prep-HPLC to give the title compound as a white solid. $^1$H NMR (300 MHz, $CDCl_3$): δ ppm 9.13-9.10 (m, 1H), 7.92-7.85 (m, 2H), 7.75-7.71 (m, 1H), 7.60-7.49 (m, 3H), 5.25 (s, 1H), 4.33 (d, J=13.2 Hz, 1H), 3.47 (d, J=6.3 Hz, 2H), 3.39 (d, J=12.3 Hz, 1H), 2.64-2.57 (m, 1H), 2.45-2.37 (m, 1H), 2.13 (br s, 1H), 1.44-1.40 (m, 1H), 1.32 (s, 6H), 1.29-1.28 (m, 1H), 1.01-0.97 (m, 1H), 0.60 (d, J=6.9 Hz, 3H), 0.47-0.44 (m, 1H), −0.22-0.26 (m, 1H). MS (ESI): m/z 618.1 $[M+H]^+$.

Example 2

4-(7-Azabicyclo[2.2.1]heptane-7-carbonyl)-5-(2,3-dichloro-4-(1,1,1,3,3,3-hexafluoro-2-hydroxypropan-2-yl)phenyl)-N-(2-hydroxy-2-methylpropyl)thiazole-2-carboxamide

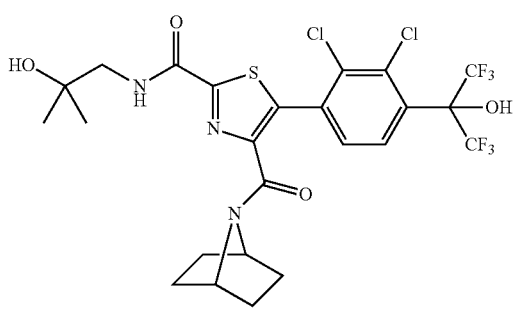 [SMILES: CC(C)(O)CNC(=O)c1nc(C(=O)N2C3CCC2CC3)c(-c2ccc(C(O)(C(F)(F)F)C(F)(F)F)c(Cl)c2Cl)s1]

A solution of 5-(2,3-dichloro-4-(1,1,1,3,3,3-hexafluoro-2-hydroxypropan-2-yl)phenyl)-2-((2-hydroxy-2-methylpropyl)carbamoyl)thiazole-4-carboxylic acid (200 mg, 0.36 mmol, Intermediate 9), 7-aza-bicyclo[2.2.1]heptane hydrochloride (54 mg, 0.40 mmol), DIPEA (139 mg, 1.08 mmol) and HATU (164 mg, 0.43 mmol) in DMF (5 mL) was stirred overnight at rt and concentrated to dryness. The residue was purified by prep-HPLC to give the title compound as a white solid. $^1$H NMR ($CDCl_3$, 300 MHz): δ ppm 7.80-7.64 (m, 1H), 7.50 (d, J=8.4 Hz, 1H), 4.67 (br s, 1H), 4.13 (s, 1H), 3.48 (d, J=6.3 Hz, 2H), 1.97-1.40 (m, 8H), 1.32 (s, 6H). MS(ESI): m/z 634.1 $[M+H]^+$.

Example 2/1

5-(2,3-Dichloro-4-(1,1,1,3,3,3-hexafluoro-2-hydroxypropan-2-yl)phenyl)-4-((2S,4S)-4-fluoro-2-methylpiperidine-1-carbonyl)-N-(2-hydroxy-2-methylpropyl)thiazole-2-carboxamide

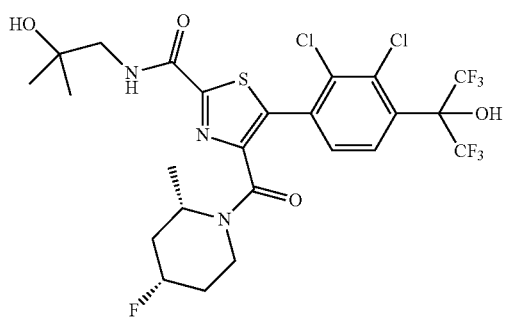 [SMILES: C[C@H]1C[C@@H](F)CCN1C(=O)c1nc(C(=O)NCC(C)(C)O)sc1-c1ccc(C(O)(C(F)(F)F)C(F)(F)F)c(Cl)c1Cl]

The title compound was prepared as described in Example 2 using (2S,4S)-4-fluoro-2-methylpiperidine hydrochloride (Intermediate 13) in place of 7-aza-bicyclo[2.2.1]heptane hydrochloride. $^1$H NMR ($CDCl_3$, 300 MHz, mixture of rotamers): δ ppm 7.73-7.52 (m, 2H), 5.34-3.94 (m, 2H), 3.48 (d, J=6.6 Hz, 2H), 3.38-3.21 (m, 1H), 2.22-1.42 (m, 4H), 1.32 (s, 6H), 1.29-0.88 (m, 5H). MS (ESI): m/z 654.1 $[M+H]^+$.

Example 2/2

(S)-5-(2,3-Dichloro-4-(1,1,1,3,3,3-hexafluoro-2-hydroxypropan-2-yl)phenyl)-4-(4,4-difluoro-2-methylpyrrolidine-1-carbonyl)-N-(2-hydroxy-2-methylpropyl)thiazole-2-carboxamide

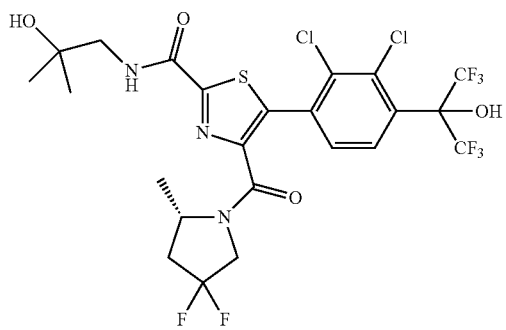 [SMILES: C[C@H]1CC(F)(F)CN1C(=O)c1nc(C(=O)NCC(C)(C)O)sc1-c1ccc(C(O)(C(F)(F)F)C(F)(F)F)c(Cl)c1Cl]

The title compound was prepared as described in Example 2 using (S)-4,4-difluoro-2-methylpyrrolidine hydrochloride (Intermediate 12) in place of 7-aza-bicyclo[2.2.1]heptane hydrochloride. $^1$H NMR (CDCl$_3$, 300 MHz, mixture of rotamers): δ ppm 7.73 (br s, 1H), 7.56-7.45 (m, 2H), 5.49-3.42 (m, 5H), 2.63-1.93 (m, 3H), 1.38-1.25 (m, 10H). MS (ESI): m/z 658.0 [M+H]$^+$.

Example 2/3a, Example 2/3b and Example 2/3c 5-(2,3-Dichloro-4-(1,1,1,3,3,3-hexafluoro-2-hydroxypropan-2-yl)phenyl)-4-(3-fluoro-3-methylpyrrolidine-1-carbonyl)-N-(2-hydroxy-2-methylpropyl)thiazole-2-carboxamide

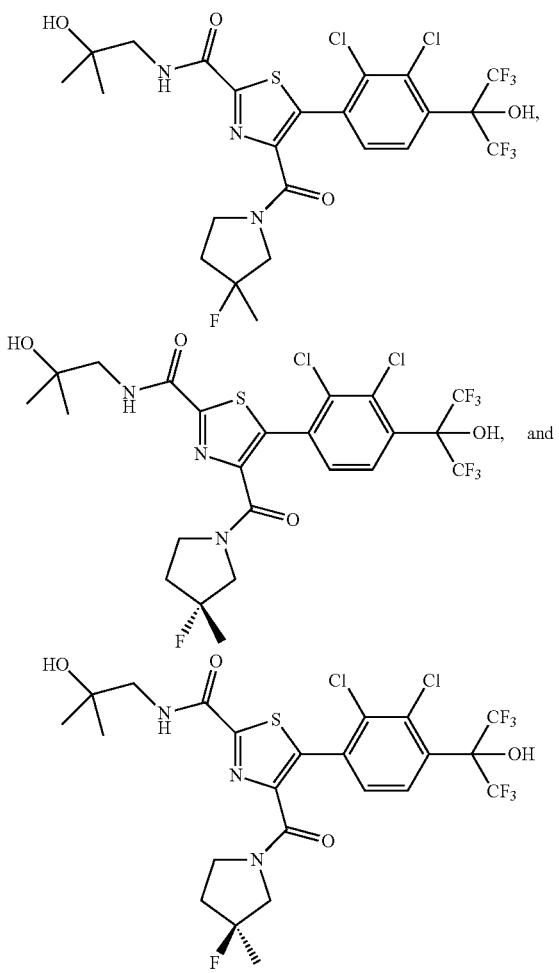

The title compound, Example 2/3a, was prepared as described in Example 2 using 3-fluoro-3-methylpyrrolidine in place of 7-aza-bicyclo[2.2.1]heptane hydrochloride. The racemate Example 2/3a was separated by chiral HPLC (Chiralpak ID 4.6×150 mm column; phase: hexane/IPA=9:1; flow: 1.0 mL/minute; w=254 nM; T=35° C.) to give the two enantiomers. The first eluting isomer was Example 2/3b: $^1$H NMR (CDCl$_3$, 300 MHz, mixture of rotamers): δ ppm 7.74-7.47 (m, 3H), 3.82-3.41 (m, 6H), 2.33-2.21 (m, 1H), 2.05-1.51 (m, 5H), 1.32 (s, 6H). MS: m/z 640.1 [M+H]$^+$. The second eluting isomer was Example 2/3c: $^1$H NMR (CDCl$_3$, 300 MHz, mixture of rotamers): δ ppm 7.74-7.47 (m, 3H), 3.82-3.41 (m, 6H), 2.33-2.21 (m, 1H), 2.05-1.51 (m, 5H), 1.32 (s, 6H). MS (ESI): m/z 640.0 [M+H]$^+$.

Example 2/4

4-(2-Azabicyclo[2.1.1]hexane-2-carbonyl)-5-(2,3-dichloro-4-(1,1,1,3,3,3-hexafluoro-2-hydroxypropan-2-yl)phenyl)-N-(2-hydroxy-2-methylpropyl)thiazole-2-carboxamide

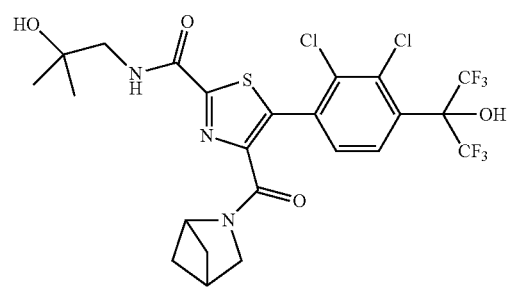 [SMILES: CC(C)(O)CNC(=O)c1nc(C(=O)N2CC3CC2C3)c(-c2ccc(C(O)(C(F)(F)F)C(F)(F)F)c(Cl)c2Cl)s1]

The title compound was prepared as described in Example 2 using 2-azabicyclo[2.1.1]hexane in place of 7-aza-bicyclo[2.2.1]heptane hydrochloride. $^1$H NMR (CDCl$_3$, 300 MHz, mixture of rotamers): δ ppm 7.76 (br s, 1H), 7.65-7.51 (m, 1H), 7.49 (d, J=8.4 Hz, 1H), 5.52-3.45 (m, 6H), 2.93-2.85 (m, 1H), 2.03-1.84 (m, 3H), 1.38-1.31 (m, 7H), 1.08-1.06 (m, 1H). MS (ESI): m/z 620.0 [M+H]$^+$.

Example 2/5

5-(2,3-Dichloro-4-(1,1,1,3,3,3-hexafluoro-2-hydroxypropan-2-yl)phenyl)-N$^4$-ethyl-N$^2$-(2-hydroxy-2-methylpropyl)-N$^4$-(2,2,2-trifluoroethyl)thiazole-2,4-dicarboxamide

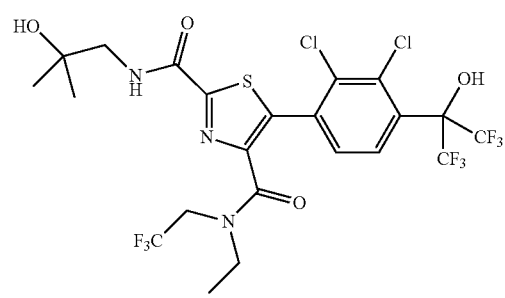 [SMILES: CCN(CC(F)(F)F)C(=O)c1nc(C(=O)NCC(C)(C)O)sc1-c1ccc(C(O)(C(F)(F)F)C(F)(F)F)c(Cl)c1Cl]

The title compound was prepared as described in Example 2 using N-ethyl-2,2,2-trifluoroethanamine in place of 7-aza-bicyclo[2.2.1]heptane hydrochloride. $^1$H NMR (CDCl$_3$, 300 MHz): δ ppm 7.74-7.47 (m, 3H), 5.51 (br s, 1H), 4.24-3.38 (m, 6H), 1.89 (br s, 1H), 1.32 (s, 6H), 1.18-1.13 (m, 3H). MS (ESI): m/z 664.0 [M+H]$^+$.

Example 2/6

5-(2,3-Dichloro-4-(1,1,1,3,3,3-hexafluoro-2-hydroxypropan-2-yl)phenyl)-N$^2$-(2-hydroxy-2-methylpropyl)-N$^4$-methyl-N$^4$-propylthiazole-2,4-dicarboxamide

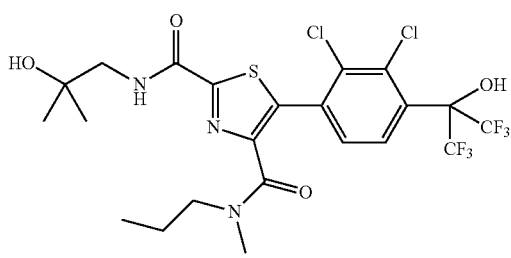 [SMILES: CCCN(C)C(=O)c1nc(C(=O)NCC(C)(C)O)sc1-c1ccc(C(O)(C(F)(F)F)C(F)(F)F)c(Cl)c1Cl]

The title compound was prepared as described in Example 2 using N-methylpropan-1-amine in place of 7-aza-bicyclo[2.2.1]heptane hydrochloride. $^1$H NMR (CDCl$_3$, 300 MHz): δ ppm 7.62-7.51 (m, 3H), 5.53 (br s, 1H), 3.48 (d, J=6.6 Hz, 2H), 3.42-3.36 (m, 1H), 3.18-3.12 (m, 1H), 2.97-2.85 (m, 3H), 2.01-1.94 (m, 1H), 1.52-1.46 (m, 2H), 1.32 (s, 6H), 0.83-0.74 (m, 3H). MS (ESI): m/z 610.1 [M+H]$^+$.

Example 2/7

5-(2,3-Dichloro-4-(1,1,1,3,3,3-hexafluoro-2-hydroxypropan-2-yl)phenyl)-N$^2$-(2-hydroxy-2-methylpropyl)-N$^4$-isobutyl-N$^4$-methylthiazole-2,4-dicarboxamide

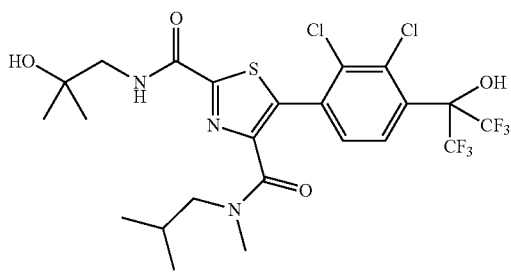 [SMILES: CC(C)CN(C)C(=O)c1nc(C(=O)NCC(C)(C)O)sc1-c1ccc(C(O)(C(F)(F)F)C(F)(F)F)c(Cl)c1Cl]

The title compound was prepared as described in Example 2 using N,2-dimethylpropan-1-amine in place of 7-aza-bicyclo[2.2.1]heptane hydrochloride. $^1$H NMR (CDCl$_3$, 300 MHz): δ ppm 7.78-7.53 (m, 3H), 5.70 (br s, 1H), 3.48 (d, J=6.6 Hz, 2H), 3.25 (d, J=7.5 Hz, 1.3H), 2.96 (d, J=6.9 Hz, 0.7H), 2.93 (s, 1H), 2.84 (s, 2H), 1.93-1.65 (m, 1H), 1.31 (s, 6H), 0.77-0.71 (m, 6H). MS (ESI): m/z 624.1 [M+H]$^+$.

Example 2/8

(S)-5-(2,3-Dichloro-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

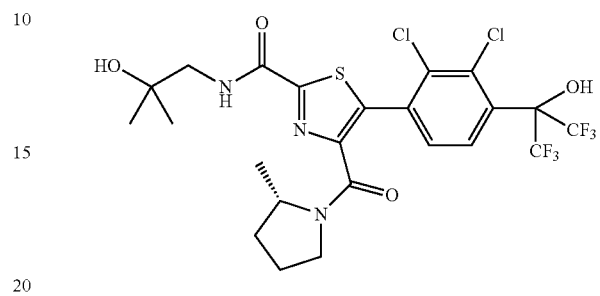

The title compound was prepared as described in Example 2 using (S)-2-methylpyrrolidine in place of 7-aza-bicyclo [2.2.1]heptane hydrochloride. $^1$H NMR (CDCl$_3$, 300 MHz): δ ppm 7.73-7.50 (m, 3H), 5.49 (br s, 1H), 4.29-4.20 (m, 1H), 3.60-3.39 (m, 5H), 2.10-1.50 (m, 4H), 1.32 (s, 6H), 1.20 (d, J=6.6 Hz, 2H), 1.09 (d, J=6.0 Hz, 1H). MS (ESI): m/z 622.1 [M+H]$^+$.

Alternative Synthesis of Example 2/8

The title compound was prepared as described in Example 15 using 2-(4-bromo-2,3-dichlorophenyl)-1,1,1,3,3,3-hexafluoropropan-2-ol (Intermediate 2) in place of 2-(4-bromo-3-(difluoromethyl)phenyl)-1,1,1,3,3,3-hexafluoropropan-2-ol.

Example 2/9

5-(2,3-Dichloro-4-(1,1,1,3,3,3-hexafluoro-2-hydroxypropan-2-yl)phenyl)-N-(2-hydroxy-2-methylpropyl)-4-(3-(trifluoromethyl)azetidine-1-carbonyl)thiazole-2-carboxamide

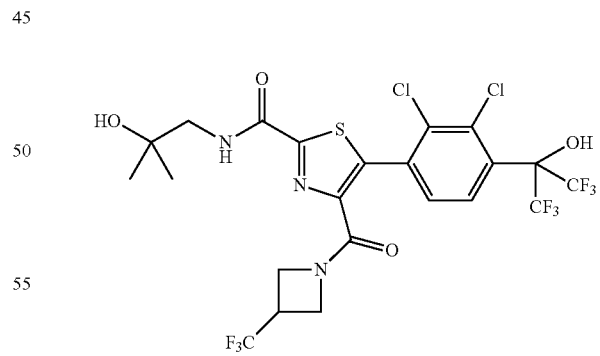

The title compound was prepared as described in Example 2 using 3-(trifluoromethyl)azetidine in place of 7-aza-bicyclo[2.2.1]heptane hydrochloride. $^1$H NMR (CDCl$_3$, 300 MHz): δ ppm 7.85-7.60 (m, 1H), 7.51-7.45 (m, 1H), 7.40 (d, J=8.7 Hz, 1H), 5.56 (br s, 1H), 4.80-4.70 (m, 1H), 4.67-4.59 (m, 1H), 4.27-4.19 (m, 2H), 3.50-3.47 (m, 2H), 3.38-3.29 (m, 1H), 1.84 (s, 1H), 1.32 (s, 6H). MS (ESI): m/z 662.0 [M+H]$^+$.

Example 2/10

5-(2,3-Dichloro-4-(1,1,1,3,3,3-hexafluoro-2-hydroxypropan-2-yl)phenyl)-4-(4-fluoropiperidine-1-carbonyl)-N-(2-hydroxy-2-methylpropyl)thiazole-2-carboxamide

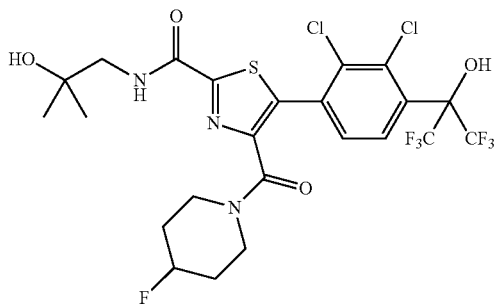 [SMILES: CC(C)(O)CNC(=O)c1nc(C(=O)N2CCC(F)CC2)c(-c2ccc(C(O)(C(F)(F)F)C(F)(F)F)c(Cl)c2Cl)s1]

The title compound was prepared as described in Example 2 using 4-fluoropiperidine in place of 7-aza-bicyclo[2.2.1]heptane hydrochloride. $^1$H NMR (DMSO-$d_6$, 300 MHz): δ ppm 9.17 (s, 1H), 8.46-8.42 (m, 1H), 7.89 (br s, 1H), 7.66 (d, J=8.4 Hz, 1H), 4.93-4.76 (m, 1H), 4.68 (s, 1H), 3.70-3.40 (m, 4H), 3.33-3.30 (m, 2H), 1.74-1.40 (m, 4H), 1.13 (s, 6H). MS (ESI): m/z 640.0 [M+H]$^+$.

Example 2/11

5-(2,3-Dichloro-4-(1,1,1,3,3,3-hexafluoro-2-hydroxypropan-2-yl)phenyl)-N$^2$-(2-hydroxy-2-methylpropyl)-N$^4$-isopropyl-N$^4$-methylthiazole-2,4-dicarboxamide

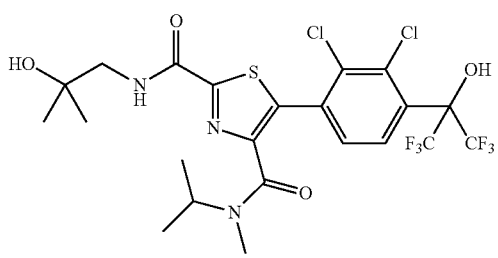 [SMILES: CC(C)N(C)C(=O)c1nc(C(=O)NCC(C)(C)O)sc1-c1ccc(C(O)(C(F)(F)F)C(F)(F)F)c(Cl)c1Cl]

The title compound was prepared as described in Example 2 using N-methylpropan-2-amine in place of 7-aza-bicyclo[2.2.1]heptane hydrochloride. $^1$H NMR (CDCl$_3$, 300 MHz): δ ppm 7.80-7.50 (m, 3H), 5.49 (br s, 1H), 4.80-4.65 (m, 0.46H), 3.90-3.80 (m, 0.54H), 3.48-3.46 (m, 2H), 2.84 (s, 1.62H), 2.65 (s, 1.38H), 1.31 (s, 6H), 1.06-1.04 (d, J=6.6 Hz, 6H). MS (ESI): m/z 610.1 [M+H]$^+$.

Example 2/12

5-(2,3-Dichloro-4-(1,1,1,3,3,3-hexafluoro-2-hydroxypropan-2-yl)phenyl)-4-(3,3-difluoropyrrolidine-1-carbonyl)-N-(2-hydroxy-2-methylpropyl)thiazole-2-carboxamide

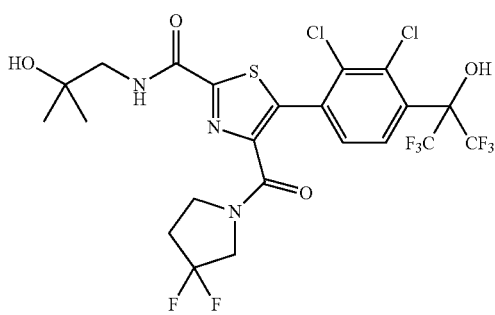 [SMILES: CC(C)(O)CNC(=O)c1nc(C(=O)N2CCC(F)(F)C2)c(-c2ccc(C(O)(C(F)(F)F)C(F)(F)F)c(Cl)c2Cl)s1]

The title compound was prepared as described in Example 2 using 3,3-difluoropyrrolidine in place of 7-aza-bicyclo[2.2.1]heptane hydrochloride. $^1$H NMR (CDCl$_3$, 300 MHz): δ ppm 7.79-7.61 (m, 1H), 7.60-7.56 (m, 1H), 7.48-7.44 (m, 1H), 5.92 (br s, 1H), 4.14-4.04 (m, 1H), 3.95-3.78 (m, 2H), 3.49 (d, J=6.0 Hz, 2H), 2.47-2.40 (m, 2H), 1.32 (s, 6H). MS (ESI): m/z 644.0 [M+H]$^+$.

Example 2/13

N$^4$-Cyclobutyl-5-(2,3-dichloro-4-(1,1,1,3,3,3-hexafluoro-2-hydroxypropan-2-yl)phenyl)-N$^2$-(2-hydroxy-2-methylpropyl)-N$^4$-methylthiazole-2,4-dicarboxamide

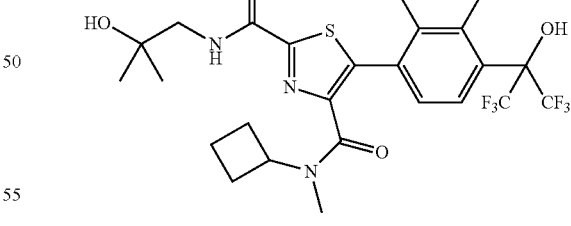

The title compound was prepared as described in Example 2 using N-methylcyclobutanamine in place of 7-aza-bicyclo[2.2.1]heptane hydrochloride. $^1$H NMR (CDCl$_3$, 300 MHz): δ ppm 7.72-7.63 (m, 2H), 7.52-7.49 (m, 1H), 5.60 (br s, 1H), 4.84-4.75 (m, 0.25H), 4.21-4.15 (m, 0.75H), 3.48-3.46 (d, J=6.3 Hz, 2H), 2.97 (s, 2.25H), 2.79 (s, 0.75H), 2.20-1.98 (m, 3H), 1.89-1.81 (m, 1H), 1.70-1.49 (m, 3H), 1.31 (s, 6H). MS (ESI): m/z 622.0 [M+H]$^+$.

Example 2/14

5-(2,3-Dichloro-4-(1,1,1,3,3,3-hexafluoro-2-hydroxypropan-2-yl)phenyl)-$N^4$-ethyl-$N^2$-(2-hydroxy-2-methylpropyl)-$N^4$-(2-methoxyethyl)thiazole-2,4-dicarboxamide

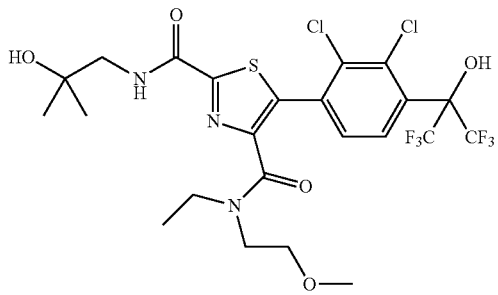 [SMILES: CCN(CCOC)C(=O)c1nc(C(=O)NCC(C)(C)O)sc1-c1ccc(C(O)(C(F)(F)F)C(F)(F)F)c(Cl)c1Cl]

The title compound was prepared as described in Example 2 using N-ethyl-2-methoxyethanamine in place of 7-aza-bicyclo[2.2.1]heptane hydrochloride. $^1$H NMR (CDCl$_3$, 300 MHz): δ ppm 7.74-7.54 (m, 3H), 5.40 (br s, 1H), 3.60-3.45 (m, 7H), 3.37-3.35 (m, 1H), 3.25 (s, 3H), 1.32 (s, 6H), 1.23-1.06 (m, 3H). MS (ESI): m/z 640.1 [M+H]$^+$.

Example 2/15

$N^4$-Cyclobutyl-5-(2,3-dichloro-4-(1,1,1,3,3,3-hexafluoro-2-hydroxypropan-2-yl)phenyl)-$N^4$-ethyl-$N^2$-(2-hydroxy-2-methylpropyl)thiazole-2,4-dicarboxamide

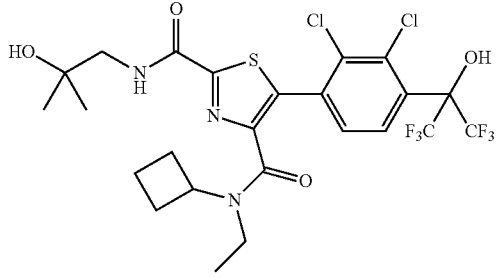 [SMILES: CCN(C(=O)c1nc(C(=O)NCC(C)(C)O)sc1-c1ccc(C(O)(C(F)(F)F)C(F)(F)F)c(Cl)c1Cl)C1CCC1]

The title compound was prepared as described in Example 2 using N-ethylcyclobutanamine in place of 7-aza-bicyclo[2.2.1]heptane hydrochloride. $^1$H NMR (CDCl$_3$, 300 MHz): δ ppm 7.66-7.50 (m, 3H), 4.07-3.21 (m, 4H), 2.09-1.48 (m, 7H), 1.34 (s, 6H), 1.26-1.15 (m, 1H), 1.08-1.01 (m, 3H). MS (ESI): m/z 636.1 [M+H]$^+$.

Example 2/16

(R)-5-(2,3-dichloro-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

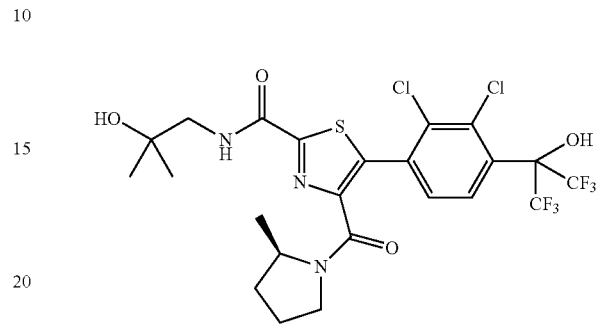

The title compound was prepared as described in Example 2 using (R)-2-methylpyrrolidine in place of 7-aza-bicyclo[2.2.1]heptane hydrochloride. $^1$H NMR (CDCl$_3$, 400 MHz): δ ppm 7.74-7.50 (m, 3H), 5.51 (br s, 1H), 4.29-4.20 (m, 1H), 3.60-3.38 (m, 5H), 2.11-1.50 (m, 4H), 1.32 (s, 6H), 1.20 (d, J=6.4 Hz, 2H), 1.09 (d, J=6.4 Hz, 1H). MS (ESI): m/z 622.1 [M+H]$^+$.

Example 3

5-(2,3-Dichloro-4-(1,1,1,3,3,3-hexafluoro-2-hydroxypropan-2-yl)phenyl)-$N^4$,$N^4$-diethyl-$N^2$-(2-hydroxy-2-methylpropyl)thiazole-2,4-dicarboxamide

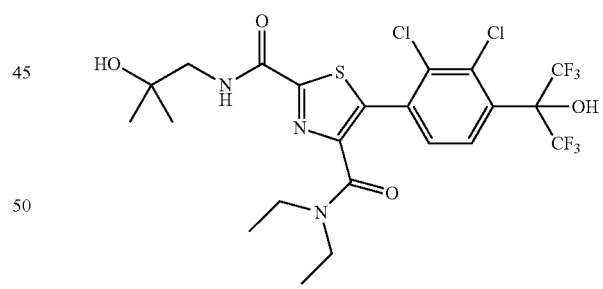

A solution of lithium 5-(2,3-dichloro-4-(1,1,1,3,3,3-hexafluoro-2-hydroxypropan-2-yl)phenyl)-4-(diethylcarbamoyl)thiazole-2-carboxylate (142 mg, 0.26 mmol, Intermediate 7), 1-amino-2-methyl-propan-2-ol (27.6 mg, 0.310 mmol), DIPEA (101 mg, 0.783 mmol) and HATU (118 mg, 0.310 mmol) in DMF (5.0 mL) was stirred overnight at rt. The resulting solution was concentrated to dryness and the residue was purified by prep-HPLC to give the title compound as a white solid. $^1$H NMR (CDCl$_3$, 300 MHz): δ ppm 7.75 (br s, 1H), 7.60-7.55 (m, 2H), 3.50-3.41 (m, 4H), 3.25-3.22 (m, 2H), 1.32 (s, 6H), 1.12-1.05 (m, 6H). MS (ESI): m/z 610.0 [M+H]$^+$.

Example 3/1

N²-(2-Cyano-2-methylpropyl)-5-(2,3-dichloro-4-(1,1,1,3,3,3-hexafluoro-2-hydroxypropan-2-yl)phenyl)-N⁴,N⁴-diethylthiazole-2,4-dicarboxamide

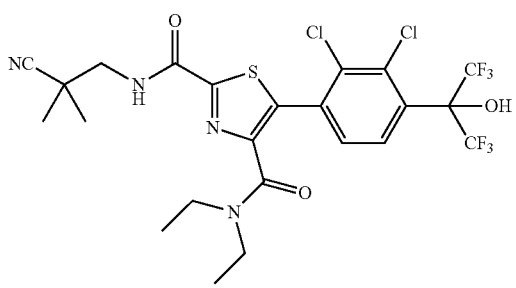 [SMILES: CCN(CC)C(=O)c1nc(C(=O)NCC(C)(C)C#N)sc1-c1ccc(C(O)(C(F)(F)F)C(F)(F)F)c(Cl)c1Cl]

The title compound was prepared as described in Example 3 using 3-amino-2,2-dimethylpropanenitrile in place of 1-amino-2-methyl-propan-2-ol. $^1$H NMR (DMSO-d$_6$, 300 MHz): δ ppm 9.23-9.15 (m, 2H), 7.84 (br s, 1H), 7.63 (d, J=8.1 Hz, 1H), 3.48 (d, J=6.3 Hz, 2H), 3.35-3.18 (m, 4H), 1.33 (s, 6H), 1.03 (t, J=7.2 Hz, 3H), 0.94 (t, J=7.2 Hz, 3H). MS (ESI): m/z 619.0 [M+H]⁺.

Example 3/2

N²-(3-Amino-2,2-dimethyl-3-oxopropyl)-5-(2,3-dichloro-4-(1,1,1,3,3,3-hexafluoro-2-hydroxypropan-2-yl)phenyl)-N⁴,N⁴-diethylthiazole-2,4-dicarboxamide

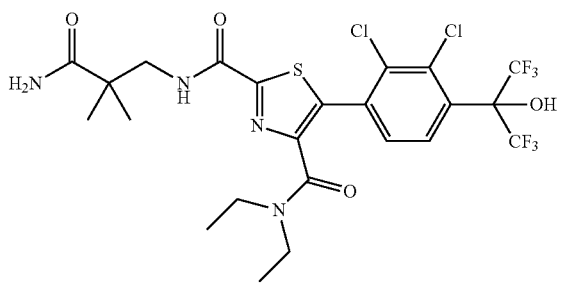 [SMILES: CCN(CC)C(=O)c1nc(C(=O)NCC(C)(C)C(N)=O)sc1-c1ccc(C(O)(C(F)(F)F)C(F)(F)F)c(Cl)c1Cl]

The title compound was prepared as described in Example 3 using 3-amino-2,2-dimethylpropanamide in place of 1-amino-2-methyl-propan-2-ol. $^1$H NMR (CDCl$_3$, 300 MHz): δ ppm 7.91-7.90 (m, 1H), 7.76-7.65 (m, 1H), 7.56-7.26 (m, 1H), 5.80 (br s, 1H), 5.32 (br s, 1H), 3.63-3.56 (m, 2H), 3.49-3.38 (m, 2H), 3.32-3.24 (m, 2H), 1.31 (s, 6H), 1.18-1.07 (m, 6H). MS (ESI): m/z 637.0 [M+H]⁺.

Example 3/3a and Example 3/3b 5-(2,3-Dichloro-4-(1,1,1,3,3,3-hexafluoro-2-hydroxypropan-2-yl)phenyl)-N⁴,N⁴-diethyl-N²-(6-oxaspiro[2.5]octan-1-yl)thiazole-2,4-dicarboxamide

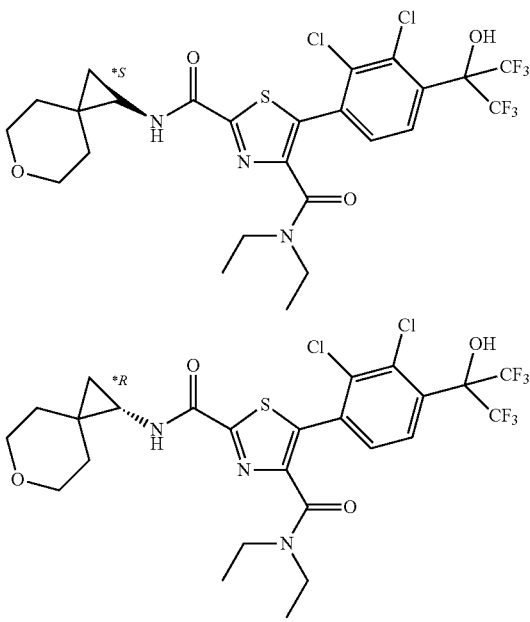

The racemic title compound was prepared as described in Example 3 using 6-oxaspiro[2.5]octan-1-amine in place of 1-amino-2-methyl-propan-2-ol. The racemate was separated by chiral HPLC (Chiralpak AD-H column, hexane:EtOH:diethylamine=90/10/0.2) to give the two separated enantiomers. The first eluting enantiomer was Example 3/3a: $^1$H NMR (300 MHz, CDCl$_3$): δ ppm 7.75-7.65 (m, 1H), 7.56 (d, J=8.7 Hz, 1H), 7.19-7.18 (m, 1H), 3.88-3.69 (m, 4H), 3.46-3.39 (m, 2H), 3.22-3.15 (m, 2H), 2.85-2.81 (m, 1H), 1.62-1.42 (m, 3H), 1.08-0.95 (m, 6H), 0.88-0.82 (m, 2H), 0.64-0.60 (m, 1H). MS (ESI): 648.0 [M+H]⁺. The second eluting enantiomer was Example 3/3b: $^1$H NMR (300 MHz, CDCl$_3$): δ ppm 7.80-7.62 (m, 1H), 7.56 (d, J=8.7 Hz, 1H), 7.19-7.18 (m, 1H), 3.88-3.69 (m, 4H), 3.46-3.39 (m, 2H), 3.22-3.15 (m, 2H), 2.85-2.81 (m, 1H), 1.62-1.42 (m, 3H), 1.08-0.95 (m, 6H), 0.88-0.82 (m, 2H), 0.64-0.60 (m, 1H). MS (ESI): 648.0 m/z [M+H]⁺.

Example 3/4

5-(2,3-Dichloro-4-(1,1,1,3,3,3-hexafluoro-2-hydroxypropan-2-yl)phenyl)-2-((3R,5S)-3,5-dihydroxypiperidine-1-carbonyl)-N,N-diethylthiazole-4-carboxamide

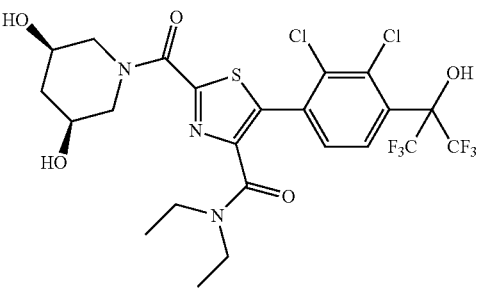 [SMILES: CCN(CC)C(=O)c1nc(C(=O)N2C[C@H](O)C[C@H](O)C2)sc1-c1ccc(C(O)(C(F)(F)F)C(F)(F)F)c(Cl)c1Cl]

The title compound was prepared as described in Example 3 using (3R,5S)-piperidine-3,5-diol in place of 1-amino-2-methyl-propan-2-ol. $^1$H NMR (CDCl$_3$, 300 MHz): δ ppm 7.74 (m, 1H), 7.55 (d, J=8.4 Hz, 1H), 5.52 (br s, 1H), 5.26-5.22 (m, 1H), 4.80-4.76 (m, 1H), 4.18 (m, 3H), 3.66-3.63 (m, 1H), 3.50-3.39 (m, 3H), 3.29-3.22 (m, 2H), 3.17-3.13 (m, 1H), 2.28-2.23 (m, 1H), 1.89-1.85 (m, 1H), 1.12-1.05 (m, 6H). MS (ESI): m/z 638.0 [M+H]$^+$.

Example 3/5

5-(2,3-Dichloro-4-(1,1,1,3,3,3-hexafluoro-2-hydroxypropan-2-yl)phenyl)-N$^4$,N$^4$-diethyl-N$^2$-((3-hydroxyoxetan-3-yl)methyl)thiazole-2,4-dicarboxamide

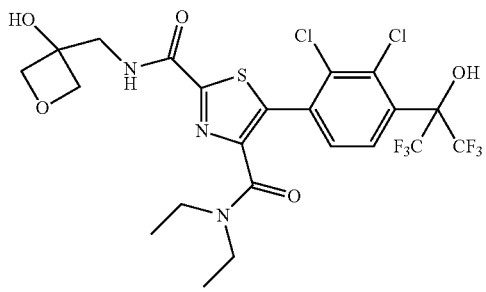 [SMILES: CCN(CC)C(=O)c1nc(C(=O)NCC2(O)COC2)sc1-c1ccc(C(O)(C(F)(F)F)C(F)(F)F)c(Cl)c1Cl]

The title compound was prepared as described in Example 3 using 3-(aminomethyl)oxetan-3-ol in place of 1-amino-2-methyl-propan-2-ol. $^1$H NMR (CDCl$_3$, 300 MHz): δ ppm 7.80-7.74 (m, 2H), 7.53 (d, J=8.7 Hz, 1H), 5.52 (br s, 1H), 4.60-4.58 (m, 2H), 4.51-4.48 (m, 2H), 3.92-3.90 (m, 2H), 3.45-3.41 (m, 2H), 3.21-3.19 (m, 2H), 1.08-1.04 (m, 6H). MS (ESI): m/z 624.0 [M+H]$^+$.

Example 3/6

(S)-5-(2,3-Dichloro-4-(1,1,1,3,3,3-hexafluoro-2-hydroxypropan-2-yl)phenyl)-N$^4$,N$^4$-diethyl-N$^2$-(2-hydroxypropyl)thiazole-2,4-dicarboxamide

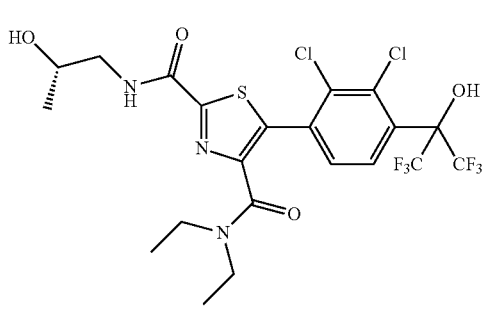 [SMILES: CCN(CC)C(=O)c1nc(C(=O)NC[C@H](C)O)sc1-c1ccc(C(O)(C(F)(F)F)C(F)(F)F)c(Cl)c1Cl]

The title compound was prepared as described in Example 3 using (S)-1-aminopropan-2-ol in place of 1-amino-2-methyl-propan-2-ol. $^1$H NMR (CDCl$_3$, 300 MHz): δ ppm 7.76-7.54 (m, 3H), 5.49 (br s, 1H), 4.08-4.02 (m, 1H), 3.70-3.62 (m, 1H), 3.46-3.18 (m, 5H), 2.20 (br s, 1H), 1.28 (d, J=6.3 Hz, 3H), 1.10-1.04 (m, 6H). MS (ESI): 596.1 m/z [M+H]$^+$.

Example 3/7

(R)-5-(2,3-Dichloro-4-(1,1,1,3,3,3-hexafluoro-2-hydroxypropan-2-yl)phenyl)-N$^4$,N$^4$-diethyl-N$^2$-(2-hydroxypropyl)thiazole-2,4-dicarboxamide

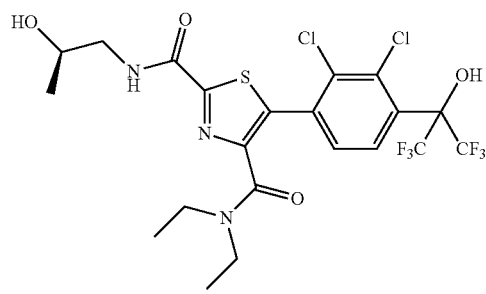 [SMILES: CCN(CC)C(=O)c1nc(C(=O)NC[C@@H](C)O)sc1-c1ccc(C(O)(C(F)(F)F)C(F)(F)F)c(Cl)c1Cl]

The title compound was prepared as described in Example 3 using (R)-1-aminopropan-2-ol in place of 1-amino-2-methyl-propan-2-ol. $^1$H NMR (CDCl$_3$, 300 MHz): δ ppm 7.76-7.54 (m, 3H), 5.49 (br s, 1H), 4.08-4.02 (m, 1H), 3.70-3.62 (m, 1H), 3.46-3.18 (m, 5H), 2.20 (br s, 1H), 1.28 (d, J=6.3 Hz, 3H), 1.10-1.04 (m, 6H). MS (ESI): 596.0 m/z [M+H]$^+$.

Example 3/8

5-(2,3-Dichloro-4-(1,1,1,3,3,3-hexafluoro-2-hydroxypropan-2-yl)phenyl)-N$^4$,N$^4$-diethyl-N$^2$-(oxetan-3-yl)thiazole-2,4-dicarboxamide

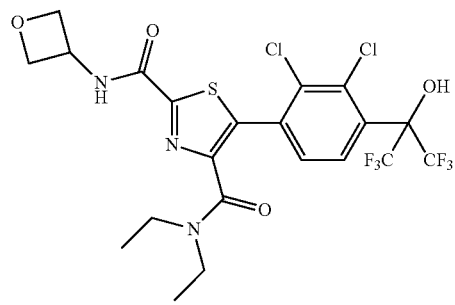 [SMILES: CCN(CC)C(=O)c1nc(C(=O)NC2COC2)sc1-c1ccc(C(O)(C(F)(F)F)C(F)(F)F)c(Cl)c1Cl]

The title compound was prepared as described in Example 3 using oxetan-3-amine in place of 1-amino-2-methyl-propan-2-ol. $^1$H NMR (CDCl$_3$, 300 MHz): δ ppm 7.75-7.72 (m, 2H), 7.57 (d, J=8.4 Hz, 1H), 5.32 (t, J=6.9 Hz, 2H), 5.30-5.22 (m, 1H), 4.66 (t, J=6.9 Hz, 2H), 3.49-3.42 (m, 2H), 3.24-3.17 (m, 2H), 1.09-1.03 (m, 6H). MS (ESI): m/z 594.0 [M+H]$^+$.

Example 3/9

5-(2,3-Dichloro-4-(1,1,1,3,3,3-hexafluoro-2-hydroxypropan-2-yl)phenyl)-$N^4,N^4$-diethyl-$N^2$-((1-hydroxycyclopropyl)methyl)thiazole-2,4-dicarboxamide

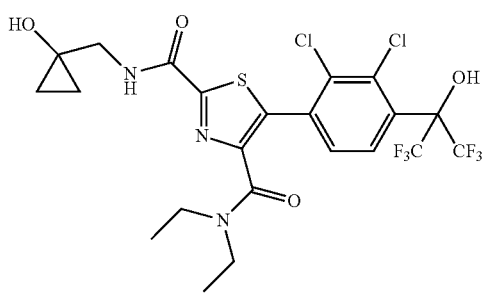 [SMILES: CCN(CC)C(=O)c1nc(C(=O)NCC2(O)CC2)sc1-c1ccc(C(O)(C(F)(F)F)C(F)(F)F)c(Cl)c1Cl]

The title compound was prepared as described in Example 3 using 1-(aminomethyl)cyclopropanol in place of 1-amino-2-methyl-propan-2-ol. $^1$H NMR (CDCl$_3$, 300 MHz): δ ppm 7.75-7.66 (m, 2H), 7.56 (d, J=8.7 Hz, 1H), 3.60 (d, J=6.0 Hz, 2H), 3.43 (q, J=7.2 Hz, 2H), 3.20 (q, J=7.2 Hz, 2H), 1.60 (br s, 1H), 1.06 (m, 6H), 0.91-0.87 (m, 2H), 0.72-0.68 (m, 2H). MS (ESI): m/z 608.1 [M+H]$^+$.

Example 3/10

4-(4-(7-Azabicyclo[2.2.1]heptane-7-carbonyl)-5-(2,3-dichloro-4-(1,1,1,3,3,3-hexafluoro-2-hydroxypropan-2-yl)phenyl)thiazole-2-carbonyl)piperazin-2-one

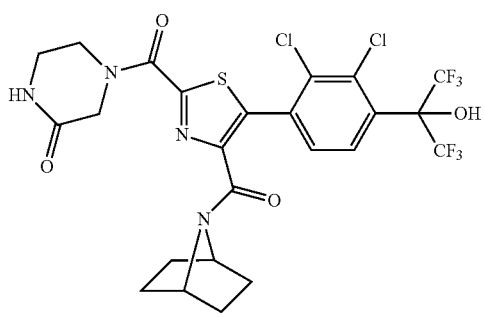 [SMILES: O=C1CN(C(=O)c2nc(C(=O)N3C4CCC3CC4)c(-c3ccc(C(O)(C(F)(F)F)C(F)(F)F)c(Cl)c3Cl)s2)CCN1]

The title compound was prepared from lithium 4-(7-azabicyclo[2.2.1]heptane-7-carbonyl)-5-(2,3-dichloro-4-(1,1,1,3,3,3-hexafluoro-2-hydroxypropan-2-yl)phenyl)thiazole-2-carboxylate (Intermediate 19) using a procedure as described for Example 3, using piperazin-2-one in place of 1-amino-2-methyl-propan-2-ol. $^1$H NMR (DMSO-d$_6$, 400 MHz): δ ppm 9.18 (br s, 1H), 8.25-8.19 (m, 1H), 8.00-7.71 (m, 1H), 7.65 (d, J=8.4 Hz, 1H), 4.89 (s, 1H), 4.61-4.40 (m, 3H), 4.17 (s, 1H), 3.85 (t, J=4.8 Hz, 1H), 3.41-3.38 (m, 1H), 3.29 (s, 1H), 1.67-1.40 (m, 8H). MS (ESI): m/z 645.5 [M+H]$^+$.

Example 3/11

4-(4-(7-Azabicyclo[2.2.1]heptane-7-carbonyl)-5-(2,3-dichloro-4-(1,1,1,3,3,3-hexafluoro-2-hydroxypropan-2-yl)phenyl)thiazole-2-carbonyl)piperazine-2,6-dione

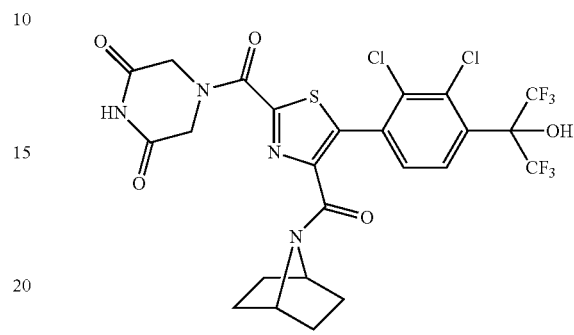

The title compound was prepared from lithium 4-(7-azabicyclo[2.2.1]heptane-7-carbonyl)-5-(2,3-dichloro-4-(1,1,1,3,3,3-hexafluoro-2-hydroxypropan-2-yl)phenyl)thiazole-2-carboxylate (Intermediate 19) using a procedure as described for Example 3, using piperazine-2,6-dione in place of 1-amino-2-methyl-propan-2-ol. $^1$H NMR (DMSO-d$_6$, 400 MHz): δ ppm 11.52 (br s, 1H), 9.18 (br s, 1H), 7.91-7.60 (m, 2H), 5.27 (s, 2H), 4.51 (s, 4H), 1.69-1.55 (m, 4H), 1.55-1.42 (m, 4H). MS (ESI): m/z 658.9 [M+H]$^+$.

Example 4

5-(2,3-Dichloro-4-(1,1,1,3,3,3-hexafluoro-2-hydroxypropan-2-yl)phenyl)-$N^4,N^4$-diethylthiazole-2,4-dicarboxamide

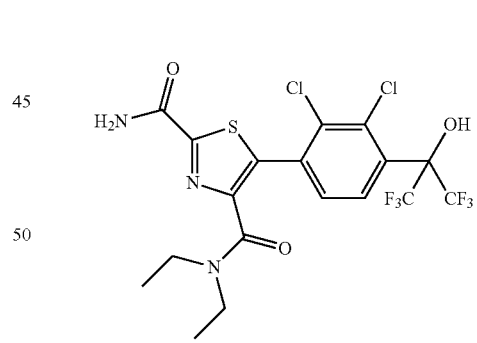

A mixture of ethyl 5-(2,3-dichloro-4-(1,1,1,3,3,3-hexafluoro-2-hydroxypropan-2-yl)phenyl)-4-(diethylcarbamoyl)thiazole-2-carboxylate (200 mg, 0.35 mmol, Intermediate 7, step a) in a solution of NH$_3$ in ethanol (4 M, 5.0 mL, 20.0 mmol) was stirred overnight at 80° C. in an autoclave. The resulting solution was cooled to rt, concentrated to dryness and the residue was purified by prep-HPLC to give the title compound as a white solid. $^1$H NMR (CD$_3$OD, 300 MHz): δ ppm 8.20-7.65 (br s, 1H), 7.57 (d, J=8.4 Hz, 1H), 3.31-3.47 (m, 4H), 1.04-1.17 (m, 6H). MS (ESI): m/z 538.0 [M+H]$^+$.

Example 5

5-(2,3-Dichloro-4-(1,1,1,3,3,3-hexafluoro-2-hydroxypropan-2-yl)phenyl)-N,N-diethyl-2-(3-hydroxy-3-(2-hydroxypropan-2-yl)azetidine-1-carbonyl)thiazole-4-carboxamide

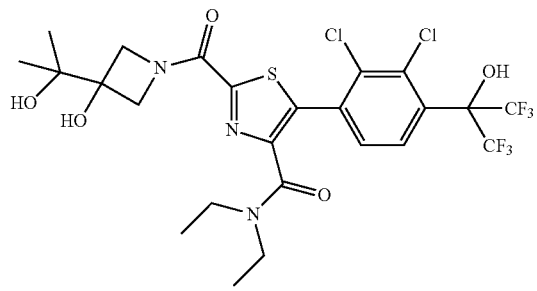 [SMILES: CCN(CC)C(=O)c1nc(C(=O)N2CC(O)(C(C)(C)O)C2)sc1-c1ccc(C(O)(C(F)(F)F)C(F)(F)F)c(Cl)c1Cl]

To a solution of 3-(2-hydroxypropan-2-yl)azetidin-3-ol (50 mg, 0.38 mmol, Intermediate 11) in MeOH (10 mL) were added ethyl 5-(2,3-dichloro-4-(1,1,1,3,3,3-hexafluoro-2-hydroxypropan-2-yl)phenyl)-4-(diethylcarbamoyl)thiazole-2-carboxylate (216 mg, 0.381 mmol, Intermediate 7, step a) and $K_2CO_3$ (105 mg, 0.761 mmol). After addition, the mixture was stirred at rt for 12 h. The mixture was poured into water (30 mL) and extracted with EtOAc (20 mL×3). The combined organic layers were washed with brine (20 mL), dried over anhydrous $Na_2SO_4$ and concentrated to dryness. The residue was purified by FCC on silica gel (PE/EtOAc=5/1) followed by prep-HPLC (0.05% TFA as additive) to afford the title compound as a white solid. $^1$H NMR (400 MHz, $CD_3OD$): δ ppm 8.11-7.49 (m, 2H), 5.02-4.98 (m, 1H), 4.54-4.50 (m, 1H), 4.44-4.40 (m, 1H), 3.93-3.89 (m, 1H), 3.56-3.38 (m, 4H), 1.30-1.18 (m, 9H), 1.09 (m, 3H). MS (ESI): m/z 651.7 $[M+H]^+$.

Example 6

(5-(2,3-Dichloro-4-(1,1,1,3,3,3-hexafluoro-2-hydroxypropan-2-yl)phenyl)-2-(2,2-dioxido-2-thia-6-azaspiro[3.3]heptane-6-carbonyl)thiazol-4-yl)(4-fluoropiperidin-1-yl)methanone

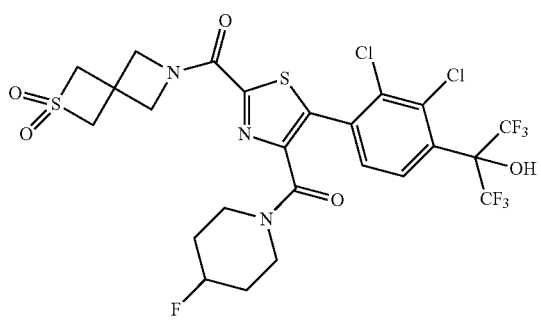 [SMILES: O=C(c1nc(C(=O)N2CCC(F)CC2)c(-c2ccc(C(O)(C(F)(F)F)C(F)(F)F)c(Cl)c2Cl)s1)N1CC2(C1)CS(=O)(=O)C2]

To a solution of lithium 5-(2,3-dichloro-4-(1,1,1,3,3,3-hexafluoro-2-hydroxypropan-2-yl)phenyl)-4-(4-fluoropiperidine-1-carbonyl)thiazole-2-carboxylate (339 mg, 0.61 mmol, Intermediate 8) in DCM (10 mL) were added DIPEA (314 mg, 2.44 mmol) and HOAt (331 mg, 2.44 mmol). The mixture was stirred at rt for 30 minutes, then 2-thia-6-aza-spiro[3.3]heptane 2,2-dioxide oxalate (117 mg, 0.61 mmol) was added and the mixture was stirred at rt for 30 minutes. Then HATU (466 mg, 1.22 mmol) was added and the mixture was stirred at rt overnight, diluted with $H_2O$ and extracted with DCM. The organic layer was washed with brine, dried over anhydrous $Na_2SO_4$, filtered, and concentrated to dryness. The residue was purified by FCC on silica gel (PE/EtOAc=5/1) and then prep-HPLC to give the title compound as a white solid. $^1$H NMR ($CD_3OD$, 300 MHz): δ ppm 7.93 (br s, 1H), 7.57-7.54 (m, 1H), 4.97-4.75 (m, 1H), 4.47-4.45 (m, 6H), 3.84-3.79 (m, 1H), 3.60-3.55 (m, 3H), 3.34 (s, 2H), 1.86-1.74 (m, 4H). MS (ESI): m/z 698.0 $[M+H]^+$.

Example 6/1

5-(2,3-Dichloro-4-(1,1,1,3,3,3-hexafluoro-2-hydroxypropan-2-yl)phenyl)-N-(1,1-dioxidothietan-3-yl)-4-(4-fluoropiperidine-1-carbonyl)thiazole-2-carboxamide

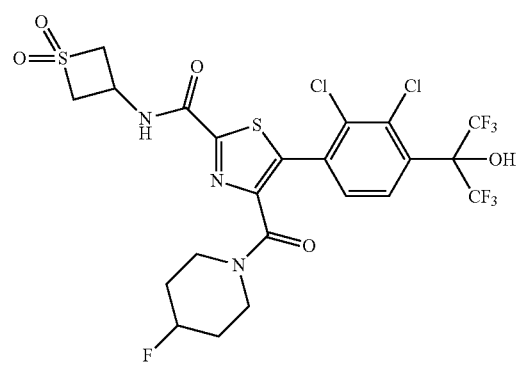 [SMILES: O=C(NC1CS(=O)(=O)C1)c1nc(C(=O)N2CCC(F)CC2)c(-c2ccc(C(O)(C(F)(F)F)C(F)(F)F)c(Cl)c2Cl)s1]

The title compound was prepared as described in Example 6 using 3-aminothietane 1,1-dioxide in place of 2-thia-6-aza-spiro[3.3]heptane 2,2-dioxide oxalate. $^1$H NMR ($CD_3OD$, 300 MHz): δ ppm 7.91 (s, 1H), 7.59-7.56 (m, 1H), 4.74-4.71 (m, 1H), 4.60-4.52 (m, 2H), 4.41-4.34 (m, 2H), 3.82-3.77 (m, 1H), 3.58-3.44 (m, 3H), 3.34 (s, 2H), 1.83-1.63 (m, 4H). MS (ESI): m/z 672.0 $[M+H]^+$.

Example 6/2

5-(2,3-Dichloro-4-(1,1,1,3,3,3-hexafluoro-2-hydroxypropan-2-yl)phenyl)-4-(4-fluoropiperidine-1-carbonyl)-N-(3-hydroxy-3-methylbutyl)thiazole-2-carboxamide

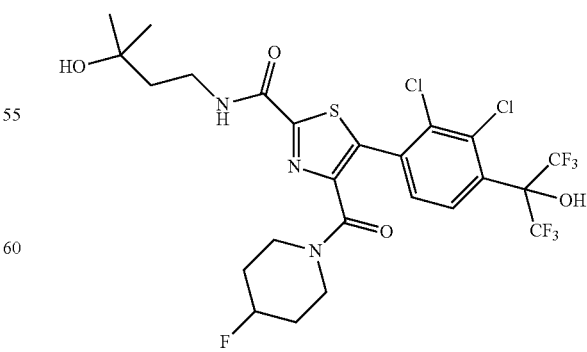

The title compound was prepared as described in Example 6 using 4-amino-2-methylbutan-2-ol in place of 2-thia-6- aza-spiro[3.3]heptane 2,2-dioxide oxalate. $^1$H NMR (CDCl$_3$, 300 MHz): δ ppm 8.08-8.03 (m, 1H), 7.76 (br s, 1H), 7.50 (d, J=8.4 Hz, 1H), 5.99-5.70 (br s, 1H), 4.81 (d, J=47.4 Hz, 1H), 3.97-3.91 (m, 1H), 3.64 (q, J=6.3 Hz, 2H), 3.51-3.43 (m, 4H), 1.83-1.64 (m, 6H), 1.33 (s, 6H). MS (ESI): m/z 654.0 [M+H]$^+$.

Example 7

5-(3-(tert-Butyl)-5-(1,1,1,3,3,3-hexafluoro-2-hydroxypropan-2-yl)phenyl)-4-(4-fluoropiperidine-1-carbonyl)-N-(2-hydroxy-2-methylpropyl)thiazole-2-carboxamide

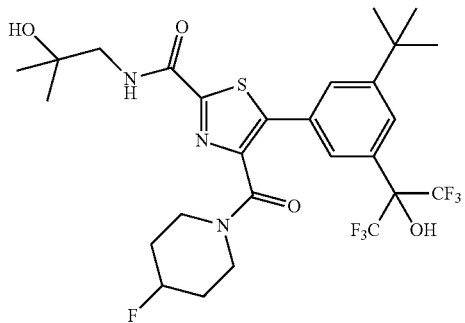 [SMILES: CC(C)(O)CNC(=O)c1nc(C(=O)N2CCC(F)CC2)c(-c2cc(C(C)(C)C)cc(C(O)(C(F)(F)F)C(F)(F)F)c2)s1]

To a solution of 4-(4-fluoropiperidine-1-carbonyl)-N-(2-hydroxy-2-methylpropyl)thiazole-2-carboxamide (263 mg, 0.8 mmol, Intermediate 6/1), 2-(3-bromo-5-(tert-butyl)phenyl)-1,1,1,3,3,3-hexafluoropropan-2-ol (335 mg, 0.87 mmol; Intermediate 5), PPh$_3$ (230 mg, 0.87 mmol) and KOAc (157 mg, 1.6 mmol) in DMF (15 mL) was added Pd(OAc)$_2$ (37 mg, 0.16 mmol) at rt under nitrogen. Then the mixture was heated at 110° C. overnight, cooled to rt and filtered. The filter cake was washed with EtOAc. The organic layer was washed with water, brine, dried over anhydrous Na$_2$SO$_4$, filtered, concentrated to dryness and the residue was purified by prep-HPLC and then by prep-TLC (DCM/MeOH=1/1) to give the title compound as a white solid. $^1$H NMR (CDCl$_3$, 300 MHz): δ ppm 7.85-7.81 (m, 1H), 7.75 (s, 1H), 7.71 (s, 1H), 7.61 (s, 1H), 5.80 (br s, 1H), 4.84-4.67 (m, 1H), 4.13-4.08 (m, 1H), 3.52-3.42 (m, 3H), 3.27-3.12 (m, 2H), 2.94-2.90 (m, 1H), 1.92-1.54 (m, 4H), 1.34 (s, 9H), 1.29-1.25 (m, 6H). MS (ESI): m/z 628.2 [M+H]$^+$.

Example 8

(5-(2,3-Dichloro-4-(1,1,1,3,3,3-hexafluoro-2-hydroxypropan-2-yl)phenyl)-2-((3R,5S)-3,5-dihydroxypiperidine-1-carbonyl)thiazol-4-yl)((S)-4,4-difluoro-2-methylpyrrolidin-1-yl)methanone

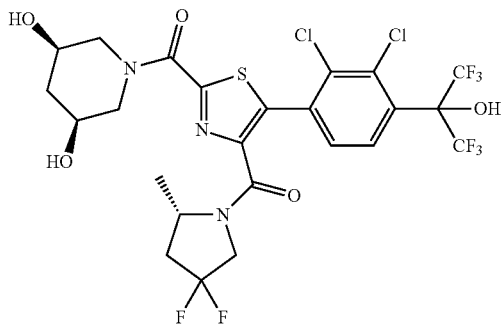 [SMILES: C[C@H]1CC(F)(F)CN1C(=O)c1nc(C(=O)N2C[C@H](O)C[C@H](O)C2)sc1-c1ccc(C(O)(C(F)(F)F)C(F)(F)F)c(Cl)c1Cl]

A solution of (9-ethyl 5-(2,3-dichloro-4-(1,1,1,3,3,3-hexafluoro-2-hydroxypropan-2-yl)phenyl)-4-(4,4-difluoro-2-methylpyrrolidine-1-carbonyl)thiazole-2-carboxylate (100 mg, 0.16 mmol, Intermediate 14), (3R,5S)-piperidine-3,5-diol hydrochloride (25 mg, 0.16 mmol) and K$_2$CO$_3$ (49 mg, 0.36 mmol) in MeOH (5 mL) was stirred at rt overnight, poured into water (50 mL) and extracted with EtOAc (20 mL×3). The combined organic layers were washed with brine, dried over anhydrous Na$_2$SO$_4$, concentrated to dryness and the residue was purified by prep-HPLC to give the title compound as a white solid. $^1$H NMR (DMSO-d$_6$, 400 MHz): δ ppm 9.17 (br s, 1H), 7.87-7.65 (m, 2H), 5.19-4.87 (m, 3H), 4.40-3.54 (m, 6H), 3.01-2.96 (m, 1H), 2.73-2.45 (m, 2H), 2.23-2.15 (m, 2H), 1.35 (q, J=10.8 Hz, 1H), 1.29-1.21 (m, 3H). MS (ESI): m/z 685.7 [M+H]$^+$.

Example 9

((S)-4,4-Difluoro-2-methylpyrrolidin-1-yl)(2-((3R,5S)-3,5-dihydroxypiperidine-1-carbonyl)-5-(4-(1,1,1,3,3,3-hexafluoro-2-hydroxypropan-2-yl)-2-(trifluoromethoxy)phenyl)thiazol-4-yl)methanone

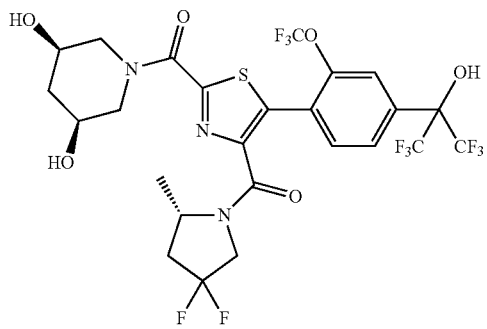 [SMILES: C[C@H]1CC(F)(F)CN1C(=O)c1nc(C(=O)N2C[C@H](O)C[C@H](O)C2)sc1-c1ccc(C(O)(C(F)(F)F)C(F)(F)F)cc1OC(F)(F)F]

To a solution of 2-(4-bromo-3-(trifluoromethoxy)phenyl)-1,1,1,3,3,3-hexafluoropropan-2-ol (200 mg, 0.49 mmol, Intermediate 4/1) and ((S)-4,4-difluoro-2-methylpyrrolidin-1-yl)(2-((3R,5S)-3,5-dihydroxypiperidine-1-carbonyl)thiazol-4-yl)methanone (148 mg, 0.38 mmol, Intermediate 15) in DMF (6 mL) were added KOAc (74 mg, 0.76 mmol), PPh$_3$ (199 mg, 0.759 mmol) and Pd(OAc)$_2$ (85 mg, 0.38 mmol). After addition, the reaction mixture was stirred at 110° C. under N$_2$ overnight. The reaction mixture was poured into water (20 mL) and extracted with EtOAc (10 mL×3). The combined organic phase was washed with brine, dried over anhydrous Na$_2$SO$_4$, filtered and concentrated to dryness. The residue was purified by prep-HPLC to afford the title compound as a white solid. $^1$H NMR (DMSO-d$_6$, 400 MHz): δ ppm 9.29 (s, 1H), 7.88-7.76 (m, 2H), 7.71-7.69 (m, 1H), 5.21-5.18 (m, 1H), 5.13-4.89 (m, 2H), 4.46-4.31 (m, 2H), 4.12-3.84 (m, 2H), 3.68-3.48 (m, 2H), 3.04-2.92 (m, 1H), 2.72-2.57 (m, 2H), 2.30-2.11 (m, 2H), 1.41-1.14 (m, 4H). MS (ESI): m/z 701.7 [M+H]$^+$.

Example 9/1

((S)-4,4-Difluoro-2-methylpyrrolidin-1-yl)(2-((3R,5S)-3,5-dihydroxypiperidine-1-carbonyl)-5-(4-(1,1,1,3,3,3-hexafluoro-2-hydroxypropan-2-yl)-2-(trifluoromethyl)phenyl)thiazol-4-yl)methanone

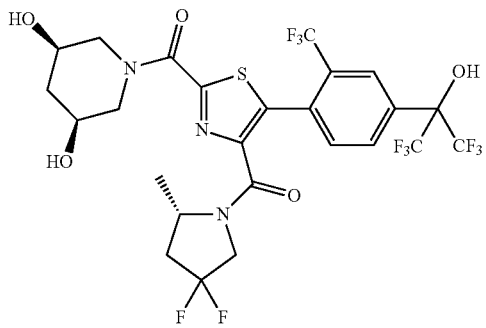 [SMILES: C[C@H]1CC(F)(F)CN1C(=O)c1nc(C(=O)N2C[C@H](O)C[C@H](O)C2)sc1-c1ccc(C(O)(C(F)(F)F)C(F)(F)F)cc1C(F)(F)F]

The title compound was prepared as described in Example 9, using 2-(4-bromo-3-(trifluoromethyl)phenyl)-1,1,1,3,3,3-hexafluoropropan-2-ol (Intermediate 4) in place of 2-(4-bromo-3-(trifluoromethoxy)phenyl)-1,1,1,3,3,3-hexafluoropropan-2-ol. $^1$H NMR (DMSO-$d_6$, 400 MHz): δ ppm 9.33 (s, 1H), 8.10-7.98 (m, 2H), 7.80-7.77 (m, 1H), 5.23-5.16 (m, 1H), 5.15-4.91 (m, 2H), 4.44-4.34 (m, 1H), 4.30-4.02 (m, 2H), 3.68-3.48 (m, 2H), 3.06-2.94 (m, 1H), 2.70-2.57 (m, 2H), 2.35-2.05 (m, 3H), 1.41-1.30 (m, 2H), 1.26-1.15 (m, 3H). MS (ESI): m/z 685.7 [M+H]$^+$.

Example 9/2

((S)-4,4-Difluoro-2-methylpyrrolidin-1-yl)(2-((3R,5S)-3,5-dihydroxypiperidine-1-carbonyl)-5-(4-(1,1,1,3,3,3-hexafluoro-2-hydroxypropan-2-yl)-2-isopropoxyphenyl)thiazol-4-yl)methanone

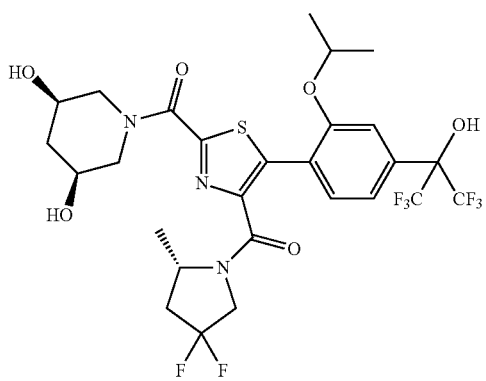 [SMILES: CC(C)Oc1cc(C(O)(C(F)(F)F)C(F)(F)F)ccc1-c1sc(C(=O)N2C[C@H](O)C[C@H](O)C2)nc1C(=O)N1CC(F)(F)C[C@@H]1C]

The title compound was prepared as described in Example 9, using 2-(4-bromo-3-isopropoxyphenyl)-1,1,1,3,3,3-hexafluoropropan-2-ol (Intermediate 4/2) in place of 2-(4-bromo-3-(trifluoromethoxy)phenyl)-1,1,1,3,3,3-hexafluoropropan-2-ol. $^1$H NMR (DMSO-$d_6$, 400 MHz): δ ppm 8.92 (s, 1H), 7.52-7.44 (m, 1H), 7.41-7.34 (m, 1H), 7.29-7.27 (m, 1H), 5.21-5.13 (m, 1H), 5.12-4.93 (m, 2H), 4.79-4.64 (m, 1H), 4.45-4.34 (m, 2H), 3.95-3.75 (m, 2H), 3.64-3.48 (m, 2H), 2.99-2.87 (m, 1H), 2.36-2.05 (m, 3H), 1.46-1.17 (m, 10H), 1.06-1.04 (m, 1H). MS (ESI): m/z 675.8 [M+H]$^+$.

Example 9/3

N$^4$,N$^4$-Diethyl-5-(2-ethyl-4-(1,1,1,3,3,3-hexafluoro-2-hydroxypropan-2-yl)phenyl)-N$^2$-(2-hydroxy-2-methylpropyl)thiazole-2,4-dicarboxamide

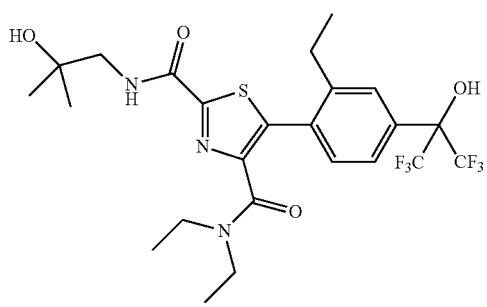 [SMILES: CCc1cc(C(O)(C(F)(F)F)C(F)(F)F)ccc1-c1sc(C(=O)NCC(C)(C)O)nc1C(=O)N(CC)CC]

The title compound was prepared as described in Example 9, starting from N$^4$,N$^4$-diethyl-N$^2$-(2-hydroxy-2-methylpropyl)thiazole-2,4-dicarboxamide (Intermediate 6) and 2-(4-bromo-3-ethylphenyl)-1,1,1,3,3,3-hexafluoropropan-2-ol (Intermediate 3). $^1$H NMR (CDCl$_3$, 300 MHz): δ ppm 7.69-7.64 (m, 2H), 7.57-7.54 (m, 1H), 7.41-7.38 (m, 1H), 4.58 (s, 1H), 3.48-3.46 (m, 2H), 3.43-3.35 (m, 2H), 3.12-3.05 (m, 2H), 2.72-2.65 (m, 2H), 2.20 (s, 1H), 1.31 (s, 6H), 1.21-1.16 (m, 3H), 0.99-0.91 (m, 6H). MS (ESI): m/z 570.1 [M+H]$^+$.

Example 9/4

N$^4$,N$^4$-Diethyl-5-(4-(1,1,1,3,3,3-hexafluoro-2-hydroxypropan-2-yl)-2-(trifluoromethoxy)phenyl)-N$^2$-(2-hydroxy-2-methylpropyl)thiazole-2,4-dicarboxamide

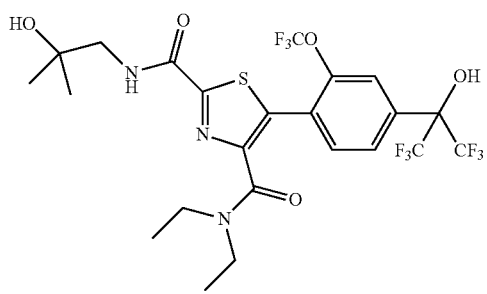 [SMILES: CCN(CC)C(=O)c1nc(C(=O)NCC(C)(C)O)sc1-c1ccc(C(O)(C(F)(F)F)C(F)(F)F)cc1OC(F)(F)F]

The title compound was prepared as described in Example 9, starting from N$^4$,N$^4$-diethyl-N$^2$-(2-hydroxy-2-methylpropyl)thiazole-2,4-dicarboxamide (Intermediate 6) and 2-(4-bromo-3-trifluoromethoxyphenyl)-1,1,1,3,3,3-hexafluoropropan-2-ol (Intermediate 4/1). $^1$H NMR (CDCl$_3$, 300 MHz): δ ppm 7.76-7.58 (m, 4H), 4.66 (s, 1H), 3.55-3.44 (m, 4H), 3.22-3.11 (m, 2H), 1.97 (s, 1H), 1.60 (s, 6H), 1.18-1.03 (m, 6H). MS (ESI): m/z 626.1 [M+H]$^+$.

Example 9/5

5-(2-Chloro-3-fluoro-4-(1,1,1,3,3,3-hexafluoro-2-hydroxypropan-2-yl)phenyl)-$N^4$,$N^4$-diethyl-$N^2$-(2-hydroxy-2-methylpropyl)thiazole-2,4-dicarboxamide

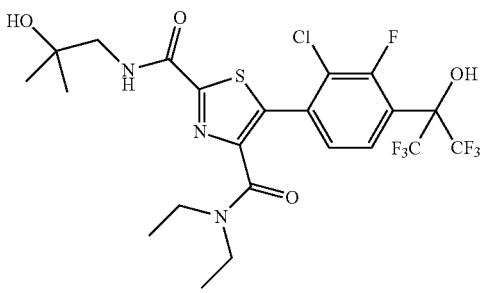 [SMILES: CCN(CC)C(=O)c1nc(C(=O)NCC(C)(C)O)sc1-c1ccc(C(O)(C(F)(F)F)C(F)(F)F)c(F)c1Cl]

The title compound was prepared as described in Example 9, starting from $N^4$,$N^4$-diethyl-$N^2$-(2-hydroxy-2-methylpropyl)thiazole-2,4-dicarboxamide (Intermediate 6) and 2-(4-bromo-3-chloro-2-fluorophenyl)-1,1,1,3,3,3-hexafluoropropan-2-ol (Intermediate 3/1). $^1$H NMR (CDCl$_3$, 300 MHz): δ ppm 7.76-7.72 (m, 1H), 7.65-7.61 (m, 1H), 7.46-7.40 (m, 1H), 5.39 (s, 1H), 3.50-3.38 (m, 4H), 3.23-3.17 (m, 2H), 2.10 (s, 1H), 1.31 (s, 6H), 1.11-1.00 (m, 6H). MS (ESI): m/z 594.1 [M+H]$^+$.

Example 10

(4-(7-Azabicyclo[2.2.1]heptane-7-carbonyl)-5-(2,3-dichloro-4-(1,1,1,3,3,3-hexafluoro-2-hydroxypropan-2-yl)phenyl)thiazol-2-yl)((3R,5S)-3,5-dihydroxypiperidin-1-yl)methanone

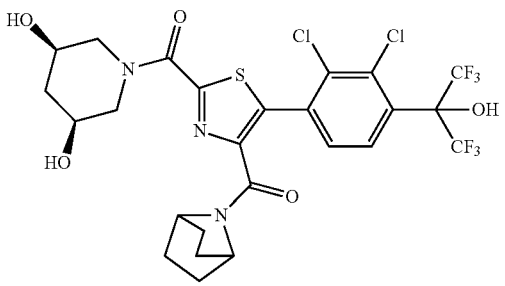 [SMILES: O=C(c1nc(C(=O)N2C3CCC2CC3)c(-c2ccc(C(O)(C(F)(F)F)C(F)(F)F)c(Cl)c2Cl)s1)N1C[C@H](O)C[C@H](O)C1]

A solution of ethyl 4-(7-azabicyclo[2.2.1]heptane-7-carbonyl)-5-(2,3-dichloro-4-(1,1,1,3,3,3-hexafluoro-2-hydroxypropan-2-yl)phenyl)thiazole-2-carboxylate (200 mg, 338 µmol; Intermediate 16), (3R,5S)-piperidine-3,5-diol hydrochloride (50 mg, 0.33 mmol) and K$_2$CO$_3$ (102 mg, 744 µmol) in MeOH (10 mL) was stirred at rt overnight, poured into water (50 mL) and extracted with EtOAc (20 mL×3). The combined organic layers were washed with brine, dried over anhydrous Na$_2$SO$_4$, concentrated to dryness and purified by prep-HPLC to give the title compound as a yellow solid. $^1$H NMR (DMSO-d$_6$, 400 MHz): δ ppm 9.18 (br s, 1H), 8.02-7.70 (m, 1H), 7.65 (d, J=8.4 Hz, 1H), 5.25-5.14 (m, 2H), 5.07 (d, J=5.2 Hz, 1H), 4.54-4.39 (m, 3H), 3.62-3.53 (m, 2H), 2.98 (t, J=11.2 Hz, 1H), 2.60 (t, J=11.2 Hz, 1H), 2.27-2.20 (m, 1H), 1.61-1.45 (m, 8H), 1.39-1.31 (m, 1H). MS (ESI): m/z 661.7 [M+H]$^+$.

Example 10/1

(4-(7-Azabicyclo[2.2.1]heptane-7-carbonyl)-5-(2,3-dichloro-4-(1,1,1,3,3,3-hexafluoro-2-hydroxypropan-2-yl)phenyl)thiazol-2-yl)((3S,4R)-3,4-dihydroxypyrrolidin-1-yl)methanone

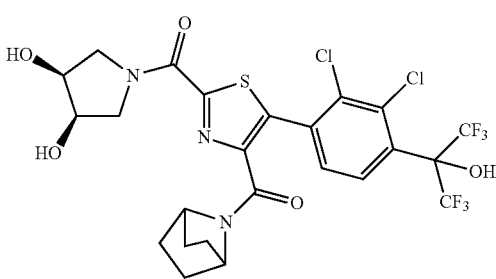 [SMILES: O=C(c1nc(C(=O)N2C3CCC2CC3)c(-c2ccc(C(O)(C(F)(F)F)C(F)(F)F)c(Cl)c2Cl)s1)N1C[C@@H](O)[C@@H](O)C1]

The title compound was prepared using a procedure as described for Example 10, using (3S,4R)-pyrrolidine-3,4-diol hydrochloride in place of (3R,5S)-piperidine-3,5-diol hydrochloride. $^1$H NMR (DMSO-d$_6$, 400 MHz): δ ppm 9.20 (br s, 1H), 8.03-7.83 (m, 1H), 7.65 (d, J=8.0 Hz, 1H), 5.12-5.04 (m, 2H), 4.57-4.48 (m, 2H), 4.25-4.10 (m, 3H), 3.91-3.87 (m, 1H), 3.68-3.64 (m, 1H), 3.48-3.41 (m, 1H), 1.67-1.43 (m, 8H). MS (ESI): m/z 647.7 [M+H]$^+$.

Example 10/2

4-(7-Azabicyclo[2.2.1]heptane-7-carbonyl)-5-(2,3-dichloro-4-(1,1,1,3,3,3-hexafluoro-2-hydroxypropan-2-yl)phenyl)-N-(2,3-dihydroxy-3-methylbutyl)thiazole-2-carboxamide

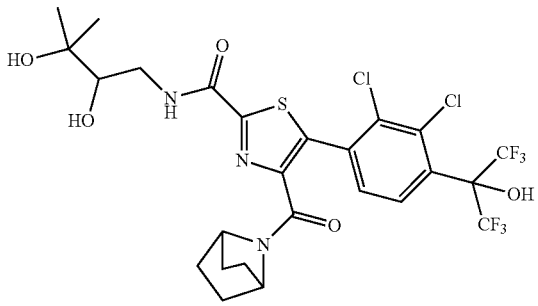 [SMILES: CC(C)(O)C(O)CNC(=O)c1nc(C(=O)N2C3CCC2CC3)c(-c2ccc(C(O)(C(F)(F)F)C(F)(F)F)c(Cl)c2Cl)s1]

The title compound was prepared using a procedure as described for Example 10, using 1-amino-3-methylbutane-2,3-diol in place of (3R,5S)-piperidine-3,5-diol hydrochloride. $^1$H NMR (DMSO-d$_6$, 400 MHz): δ ppm 9.18 (br s, 1H), 8.59-8.56 (m, 1H), 7.98-7.62 (m, 2H), 4.95 (d, J=5.2 Hz, 1H), 4.47-4.34 (m, 3H), 3.66-3.61 (m, 1H), 3.45-3.40 (m, 1H), 3.30-3.19 (m, 1H), 1.52-1.36 (m, 8H), 1.13 (s, 3H), 1.09 (s, 3H). MS (ESI): m/z 663.7 [M+H]$^+$.

Example 10/3

(S)-(5-(2-Chloro-4-(1,1,1,3,3,3-hexafluoro-2-hydroxypropan-2-yl)phenyl)-2-(3-hydroxy-3-(2-hydroxypropan-2-yl)azetidine-1-carbonyl)thiazol-4-yl)(2-methylpyrrolidin-1-yl)methanone

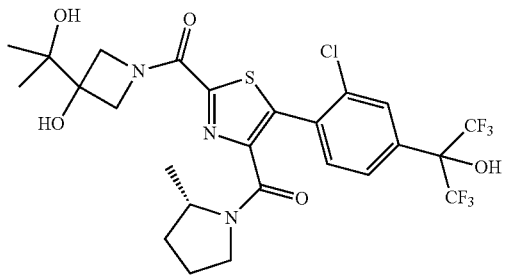 [SMILES: C[C@H]1CCCN1C(=O)c1nc(C(=O)N2CC(O)(C(C)(C)O)C2)sc1-c1ccc(C(O)(C(F)(F)F)C(F)(F)F)cc1Cl]

The title compound was prepared using a procedure as described for Example 10, starting from (S)-ethyl 5-(2-chloro-4-(1,1,1,3,3,3-hexafluoro-2-hydroxypropan-2-yl)phenyl)-4-(2-methylpyrrolidine-1-carbonyl)thiazole-2-carboxylate (Intermediate 16/1), using 3-(2-hydroxypropan-2-yl)azetidin-3-ol (Intermediate 11) in place of (3R,5S)-piperidine-3,5-diol hydrochloride. $^1$H NMR (CD$_3$OD, 300 MHz): δ ppm 7.88 (s, 1H), 7.76-7.73 (m, 1H), 7.63-7.59 (m, 1H), 4.99-4.86 (m, 1H), 4.51-4.38 (m, 2H), 4.18-4.16 (m, 1H), 3.90-3.87 (m, 1H), 3.59-3.51 (m, 2H), 2.14-1.57 (m, 4H), 1.23-1.09 (m, 9H). MS (ESI): m/z 630.1 [M+H]$^+$.

Example 10/4

(S)-5-(4-(1,1,1,3,3,3-Hexafluoro-2-hydroxypropan-2-yl)-2-(trifluoromethyl)phenyl)-N-(2-hydroxy-2-methylpropyl)-4-(2-methylpyrrolidine-1-carbonyl)thiazole-2-carboxamide

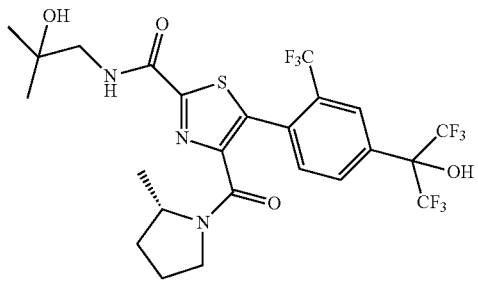 [SMILES: C[C@H]1CCCN1C(=O)c1nc(C(=O)NCC(C)(C)O)sc1-c1ccc(C(O)(C(F)(F)F)C(F)(F)F)cc1C(F)(F)F]

The title compound was prepared using a procedure as described for Example 10, starting from (S)-ethyl 5-(4-(1,1,1,3,3,3-hexafluoro-2-hydroxypropan-2-yl)-2-(trifluoromethyl)phenyl)-4-(2-methylpyrrolidine-1-carbonyl)thiazole-2-carboxylate (Intermediate 16/2), using 1-amino-2-methylpropan-2-ol in place of (3R,5S)-piperidine-3,5-diol hydrochloride. $^1$H NMR (CDCl$_3$, 400 MHz): δ ppm 8.11 (s, 1H), 7.92-7.90 (m, 1H), 7.65-7.59 (m, 2H), 4.44-4.12 (m, 1H), 3.55-3.48 (m, 4H), 2.08-1.53 (m, 4H), 1.32 (s, 6H), 1.19-1.15 (m, 3H). MS (ESI): m/z 622.2 [M+H]$^+$.

Example 10/5

((3R,5S)-3,5-Dihydroxypiperidin-1-yl)(5-(4-(1,1,1,3,3,3-hexafluoro-2-hydroxypropan-2-yl)-2-(trifluoromethyl)phenyl)-4-((S)-2-methylpyrrolidine-1-carbonyl)thiazol-2-yl)methanone

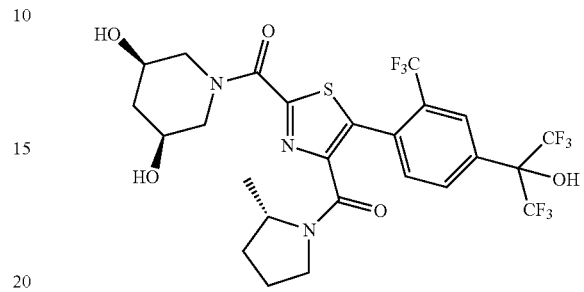

The title compound was prepared using a procedure as described for Example 10, starting from (S)-ethyl 5-(4-(1,1,1,3,3,3-hexafluoro-2-hydroxypropan-2-yl)-2-(trifluoromethyl)phenyl)-4-(2-methylpyrrolidine-1-carbonyl)thiazole-2-carboxylate (Intermediate 16/2). $^1$H NMR (400 MHz, CDCl$_3$): δ ppm 8.09-8.04 (m, 1H), 7.98-7.89 (m, 1H), 7.59-7.46 (m, 1H), 5.53-5.17 (m, 1H), 4.82-4.72 (m, 1H), 4.17-4.15 (m, 2H), 3.69-3.45 (m, 3H), 3.15-3.12 (m, 2H), 2.20-1.74 (m, 4H), 1.53-1.43 (m, 3H), 1.15-1.12 (m, 2H). MS (ESI): m/z 650.1 [M+H]$^+$.

Example 10/6

(S)-(5-(4-(1,1,1,3,3,3-Hexafluoro-2-hydroxypropan-2-yl)-2-(trifluoromethyl)phenyl)-2-(3-hydroxy-3-(2-hydroxypropan-2-yl)azetidine-1-carbonyl)thiazol-4-yl)(2-methylpyrrolidin-1-yl)methanone

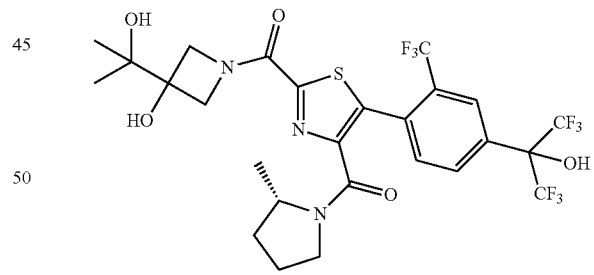

The title compound was prepared using a procedure as described for Example 10, starting from (S)-ethyl 5-(4-(1,1,1,3,3,3-hexafluoro-2-hydroxypropan-2-yl)-2-(trifluoromethyl)phenyl)-4-(2-methylpyrrolidine-1-carbonyl)thiazole-2-carboxylate (Intermediate 16/2), using 3-(2-hydroxypropan-2-yl)azetidin-3-ol (Intermediate 11) in place of (3R,5S)-piperidine-3,5-diol hydrochloride. $^1$H NMR (DMSO-d$_6$, 400 MHz): δ ppm 8.06-8.00 (m, 2H), 7.77-7.31 (m, 1H), 5.94-5.89 (m, 1H), 4.86-4.78 (m, 2H), 4.39-4.35 (m, 1H), 4.31-4.26 (m, 1H), 3.98-3.97 (m, 1H), 3.77-3.58 (m, 3H), 2.00-1.88 (m, 2H), 1.76-1.74 (m, 1H), 1.51-1.49 (m, 1H), 1.11-1.04 (m, 9H). MS (ESI): m/z 664.2 [M+H]$^+$.

Example 11

Step a 2-(4-Bromo-2,3-dichlorophenyl)-1,1,1-trifluorobutan-2-ol

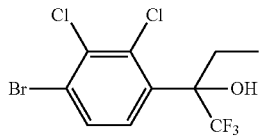

To a solution of 1-(4-bromo-2,3-dichlorophenyl)-2,2,2-trifluoroethanone (2.0 g, 6.2 mmol, Intermediate 2, step a) in THF (20 mL) was added ethylmagnesium chloride (4.50 mL, 2.8 M in THF, 12.6 mmol) dropwise at −30° C. under a $N_2$ atmosphere and the mixture was stirred at rt for 5 h. The solution was diluted with aqueous $NH_4Cl$ at 0° C. and extracted with EtOAc (×2). The combined organic layers were washed with $H_2O$ and brine, dried over anhydrous $Na_2SO_4$, filtered, concentrated to dryness and the residue was purified by FCC on silica gel (PE/EtOAc=30/1) to give the title compound as a yellow solid.

Example 11

Step b

Ethyl 5-(2,3-dichloro-4-(1,1,1-trifluoro-2-hydroxybutan-2-yl)phenyl)-4-(diethylcarbamoyl)thiazole-2-carboxylate

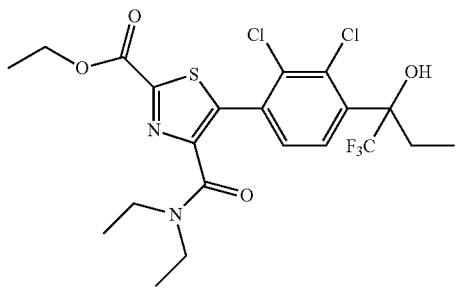 [SMILES: CCOC(=O)c1nc(C(=O)N(CC)CC)c(-c2ccc(C(O)(CC)C(F)(F)F)c(Cl)c2Cl)s1]

A solution of 2-(4-bromo-2,3-dichlorophenyl)-1,1,1-trifluorobutan-2-ol (2.0 g, 5.7 mmol, Example 11, step a), ethyl 4-(diethylcarbamoyl)thiazole-2-carboxylate (1.4 g, 5.7 mmol, Intermediate 6, step a), KOAc (1.1 g, 11.4 mmol), Pd(OAc)$_2$ (650 mg, 2.9 mmol), and PPh$_3$ (760 mg, 2.9 mmol) in DMF (10 mL) was purged with $N_2$ for 5 minutes and then stirred at 110° C. overnight. The resulting solution was cooled to rt, diluted with $H_2O$, and extracted with EtOAc (×3). The combined organic layers were washed with brine, dried over anhydrous $Na_2SO_4$, filtered, concentrated to dryness and the residue was purified by FCC on silica gel (PE/EtOAc=5/1) to give the title compound as a white solid.

Example 11

Step c 5-(2,3-Dichloro-4-(1,1,1-trifluoro-2-hydroxybutan-2-yl)phenyl)-4-(diethylcarbamoyl)thiazole-2-carboxylic acid

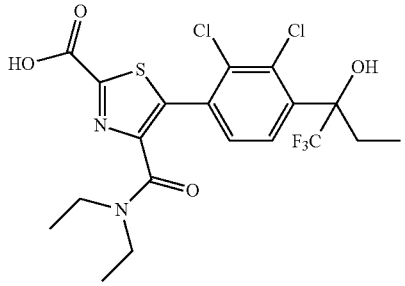 [SMILES: CCN(CC)C(=O)c1nc(C(=O)O)sc1-c1ccc(C(O)(CC)C(F)(F)F)c(Cl)c1Cl]

To a solution of ethyl 5-(2,3-dichloro-4-(1,1,1-trifluoro-2-hydroxybutan-2-yl)phenyl)-4-(diethylcarbamoyl)thiazole-2-carboxylate (1.0 g, 2.0 mmol, Example 11, step b) in a mixture of EtOH (5 mL) and $H_2O$ (1 mL) was added KOH (213 mg, 3.80 mmol) and the mixture was stirred for 3 h at rt. The solution was concentrated to dryness and the residue was dissolved in $H_2O$. The pH was adjusted to ~5 with 2 N aqueous HCl under cooling with an ice bath. The mixture was then extracted with EtOAc (2×20 mL). The combined organic layers were washed with $H_2O$ and brine, dried over anhydrous $Na_2SO_4$, filtered and concentrated to dryness to give the title compound as a yellow solid.

Example 11a 5-(2,3-Dichloro-4-(1,1,1-trifluoro-2-hydroxybutan-2-yl)phenyl)-$N^4$,$N^4$-diethyl-$N^2$-(2-hydroxy-2-methylpropyl)thiazole-2,4-dicarboxamide (Racemate)

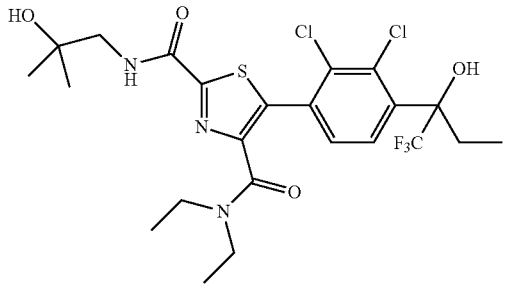 [SMILES: CCN(CC)C(=O)c1nc(C(=O)NCC(C)(C)O)sc1-c1ccc(C(O)(CC)C(F)(F)F)c(Cl)c1Cl]

A mixture of 5-(2,3-dichloro-4-(1,1,1-trifluoro-2-hydroxybutan-2-yl)phenyl)-4-(diethylcarbamoyl)thiazole-2-carboxylic acid (600 mg, 1.2 mmol, Example 11, step c), 1-amino-2-methyl-propan-2-ol (118 mg, 1.33 mmol), HATU (916 mg, 2.41 mmol) and DIPEA (311 mg, 2.41 mmol) in DCM (5 mL) was stirred at rt for 3 h. The mixture was poured into $H_2O$ and extracted with DCM (2×20 mL). The combined organic layers were washed with water and brine, dried over anhydrous $Na_2SO_4$, filtered, and concentrated to dryness. The residue was purified by FCC on silica gel (PE/EtOAc=3/1) to give the title compound as a white solid.

Example 11b and Example 11c 5-(2,3-Dichloro-4-(1,1,1-trifluoro-2-hydroxybutan-2-yl)phenyl)-N⁴,N⁴-diethyl-N²-(2-hydroxy-2-methylpropyl)thiazole-2,4-dicarboxamide (separated single enantiomers)

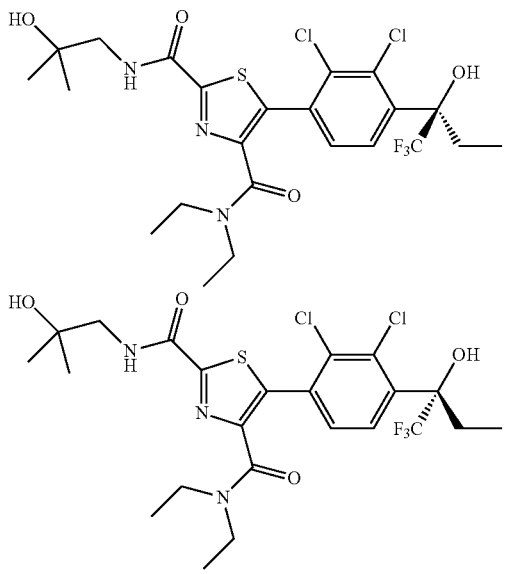

5-(2,3-Dichloro-4-(1,1,1-trifluoro-2-hydroxybutan-2-yl)phenyl)-N⁴,N⁴-diethyl-N²-(2-hydroxy-2-methylpropyl)thiazole-2,4-dicarboxamide (racemate, Example 11a) was separated by chiral SFC (column: Chiralpak IE, 5 µM 4.6×250 mm, Eluent: CO$_2$/MeOH 80:20, (0.2% DEA), column temperature 40.1° C.) to give two separated enantiomers. The first eluting enantiomer was Example 11b: ¹H NMR (CDCl$_3$, 300 MHz): δ ppm 7.78 (d, J=8.4 Hz, 1H), 7.64-7.60 (m, 1H), 7.51 (d, J=8.4 Hz, 1H), 3.50-3.39 (m, 4H), 3.22-3.13 (m, 2H), 2.96-2.84 (m, 1H), 2.09-2.01 (m, 1H), 1.31 (s, 6H), 1.07-1.00 (m, 6H), 0.92-0.87 (m, 3H). MS (ESI): m/z 570.1 [M+H]⁺. The second eluting enantiomer was Example 11c: ¹H NMR (CDCl$_3$, 300 MHz): δ ppm 7.78 (d, J=8.4 Hz, 1H), 7.64-7.60 (m, 1H), 7.51 (d, J=8.4 Hz, 1H), 3.50-3.39 (m, 4H), 3.22-3.13 (m, 2H), 2.96-2.84 (m, 1H), 2.09-2.01 (m, 1H), 1.31 (s, 6H), 1.07-1.00 (m, 6H), 0.92-0.87 (m, 3H). MS (ESI): m/z 570.1 [M+H]⁺.

Example 12

Step a

Potassium 5-(2,3-dichloro-4-(1,1,1,3,3,3-hexafluoro-2-hydroxypropan-2-yl)phenyl)-4-(hydroxymethyl)thiazole-2-carboxylate

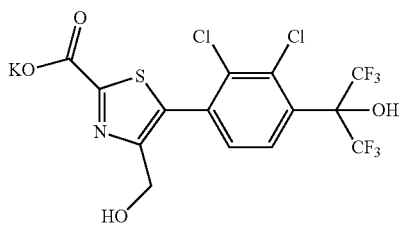

A solution of ethyl 5-(2,3-dichloro-4-(1,1,1,3,3,3-hexafluoro-2-hydroxypropan-2-yl)phenyl)-4-(hydroxymethyl)thiazole-2-carboxylate (2.08 g, 4.17 mmol, Intermediate 14, step b) and KOH (468 mg, 8.35 mmol) in a mixture of MeOH (25 mL) and H$_2$O (5.0 mL) was stirred at rt overnight, concentrated to dryness, suspended in Et$_2$O, filtered, and dried under vacuum to give the title compound as a white solid.

Example 12

Step b trans-Methyl 3-(5-(2,3-dichloro-4-(1,1,1,3,3,3-hexafluoro-2-hydroxypropan-2-yl)phenyl)-4-(hydroxymethyl)thiazole-2-carboxamido)cyclobutanecarboxylate

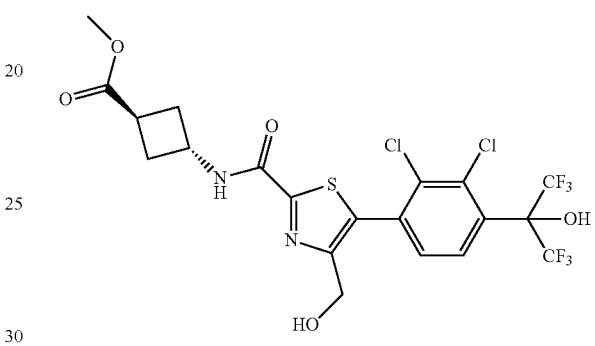

A solution of potassium 5-(2,3-dichloro-4-(1,1,1,3,3,3-hexafluoro-2-hydroxypropan-2-yl)phenyl)-4-(hydroxymethyl)thiazole-2-carboxylate (1.16 g, 2.00 mmol, Example 12, step a), trans-methyl 3-amino-cyclobutane carboxylate hydrochloride (398 mg, 2.40 mmol), DIPEA (645 mg, 5.00 mmol) and HATU (736 mg, 2.00 mmol) in DMF (15 mL) was stirred overnight at rt, concentrated to dryness, diluted with water and extracted with EtOAc three times. The combined organic layers were washed with water three times and brine consecutively, dried over anhydrous Na$_2$SO$_4$, filtered, concentrated to dryness and purified by FCC on silica gel (PE/EtOAc=2/1 to 1/2) to give the title compound as a white solid.

Example 12

Step c 5-(2,3-Dichloro-4-(1,1,1,3,3,3-hexafluoro-2-hydroxypropan-2-yl)phenyl)-2-((trans-3-(methoxycarbonyl)cyclobutyl)carbamoyl)thiazole-4-carboxylic acid

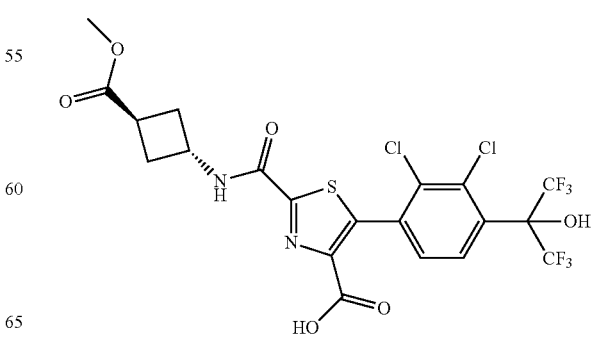

To a solution of trans-methyl 3-(5-(2,3-dichloro-4-(1,1,1,3,3,3-hexafluoro-2-hydroxypropan-2-yl)phenyl)-4-(hydroxymethyl)thiazole-2-carboxamido)cyclobutanecarboxylate (558 mg, 0.960 mmol, Example 12, step b) in MeCN (10 mL) and H$_2$O (5.0 mL) were added iodobenzene diacetate (1.28 g, 4.0 mmol) and TEMPO (151 mg, 0.966 mmol) and the mixture was stirred for 5 h at rt, concentrated to dryness, and extracted with EtOAc (×3). The combined organic layers were washed with brine, dried over anhydrous Na$_2$SO$_4$, filtered, concentrated to dryness, and purified by FCC on silica gel (PE/EtOAc=1/2) to give the title compound as a white solid.

Example 12

Step d trans-Methyl 3-(5-(2,3-dichloro-4-(1,1,1,3,3,3-hexafluoro-2-hydroxypropan-2-yl)phenyl)-4-(ethyl(2,2,2-trifluoroethyl)carbamoyl)thiazole-2-carboxamido)cyclobutanecarboxylate

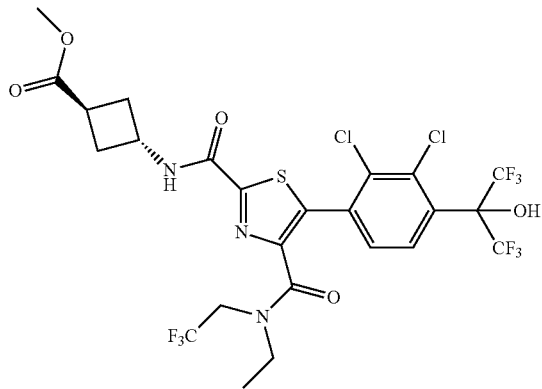 [SMILES: CCN(CC(F)(F)F)C(=O)c1nc(C(=O)N[C@H]2C[C@H](C(=O)OC)C2)sc1-c1ccc(C(O)(C(F)(F)F)C(F)(F)F)c(Cl)c1Cl]

A solution of 5-(2,3-dichloro-4-(1,1,1,3,3,3-hexafluoro-2-hydroxypropan-2-yl)phenyl)-2-((trans-3-(methoxycarbonyl)cyclobutyl)carbamoyl)thiazole-4-carboxylic acid (249 mg, 0.418 mmol, Example 12, step c), ethyl-(2,2,2-trifluoroethyl)-amine hydrochloride (81.8 mg, 0.500 mmol), DIPEA (258 mg, 2.00 mmol) and HATU (160 mg, 0.42 mmol) in DMF (3.0 mL) was stirred overnight at rt, concentrated to dryness and purified by prep-HPLC to give the title compound as a white solid.

Example 12 trans-3-(5-(2,3-Dichloro-4-(1,1,1,3,3,3-hexafluoro-2-hydroxypropan-2-yl)phenyl)-4-(ethyl(2,2,2-trifluoroethyl)carbamoyl)thiazole-2-carboxamido)cyclobutanecarboxylic acid

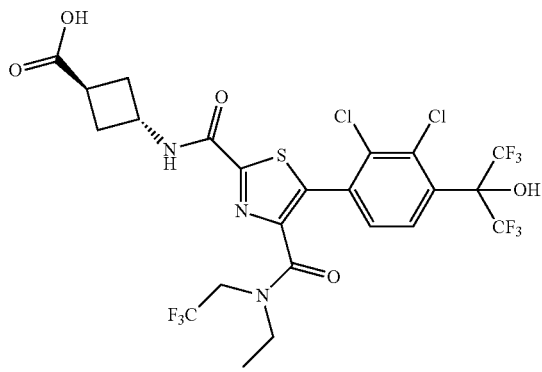 [SMILES: CCN(CC(F)(F)F)C(=O)c1nc(C(=O)N[C@H]2C[C@H](C(=O)O)C2)sc1-c1ccc(C(O)(C(F)(F)F)C(F)(F)F)c(Cl)c1Cl]

To a solution of trans-methyl 3-(5-(2,3-dichloro-4-(1,1,1,3,3,3-hexafluoro-2-hydroxypropan-2-yl)phenyl)-4-(ethyl(2,2,2-trifluoroethyl)carbamoyl)thiazole-2-carboxamido)cyclobutane-carboxylate (141 mg, 0.200 mmol, Example 12, step d) in mixed solvents (THF/MeOH/H$_2$O, 1/1/1, 10 mL) was added LiOH.H$_2$O (33.6 mg, 0.802 mmol) and the mixture was stirred at rt overnight, adjusted to pH=2 with 1 N aqueous HCl and then diluted with EtOAc. The resulting mixture was washed with water and brine, dried over anhydrous Na$_2$SO$_4$, filtered, concentrated to dryness, and purified by prep-HPLC to give the title compound as a white solid. $^1$H NMR (CDCl$_3$, 300 MHz): δ ppm 7.70 (br s, 1H), 7.51-7.36 (m, 2H), 4.84-4.76 (m, 1H), 4.15-4.03 (m, 2H), 3.61-3.37 (m, 2H), 3.21-3.16 (m, 1H), 2.87-2.78 (m, 2H), 2.53-2.42 (m, 2H), 1.33-1.24 (m, 2H), 1.18-1.09 (m, 3H). MS (ESI): m/z 690.0 [M+H]$^+$.

Example 13

4-(4-Fluoropiperidine-1-carbonyl)-5-(8-(1,1,1,3,3,3-hexafluoro-2-hydroxypropan-2-yl)quinolin-5-yl)-N-(2-hydroxy-2-methylpropyl)thiazole-2-carboxamide

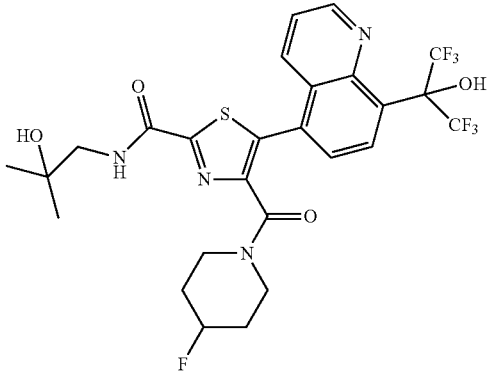 [SMILES: CC(C)(O)CNC(=O)c1nc(C(=O)N2CCC(F)CC2)c(-c2ccc(C(O)(C(F)(F)F)C(F)(F)F)c3ncccc23)s1]

A mixture of 2-(5-bromoquinolin-8-yl)-1,1,1,3,3,3-hexafluoropropan-2-ol (30 mg, 0.080 mmol, Intermediate 17), 4-(4-fluoropiperidine-1-carbonyl)-N-(2-hydroxy-2-methylpropyl)thiazole-2-carboxamide (26 mg, 0.079 mmol, Intermediate 6/1), Pd(OAc)$_2$ (6.0 mg, 0.027 mmol), RuPhos (14 mg, 0.030 mmol), KOAc (16 mg, 0.16 mmol), and pivalic acid (3.0 mg, 0.029 mmol) in butyronitrile (1 mL) was degassed by bubbling N$_2$ through the solution for 5 minutes. The container was then sealed and heated at 115° C. for 15 h. After cooling the reaction to room temperature, the mixture was concentrated and purified by FCC on silica gel (0-100% EtOAc in heptanes) and then prep-HPLC (10-95% CH$_3$CN in H$_2$O, 0.1% TFA) to give the title compound. $^1$H NMR (CDCl$_3$, 400 MHz) δ ppm 8.90 (d, J=3.0 Hz, 1H), 8.43 (d, J=7.6 Hz, 1H), 8.16 (d, J=7.6 Hz, 1H), 7.75 (d, J=8.1 Hz, 1H), 7.73 (br s, 1H), 7.63 (dd, J=4.6, 8.6 Hz, 1H), 4.66 (d, J=47.5 Hz, 1H), 3.84-3.95 (m, 1H), 3.53 (d, J=5.1 Hz, 2H), 3.19-3.33 (m, 3H), 1.68-1.80 (m, 1H), 1.37-1.57 (m, 2H), 1.35 (s, 6H), 0.84-1.08 (m, 1H). MS (ESI): m/z 623.2 [M+H]$^+$.

Example 14

Step a 5-(2,3-Dichloro-4-(1,1,1,3,3,3-hexafluoro-2-hydroxypropan-2-yl)phenyl)-N,N-diethyl-2-(thiomorpholine-4-carbonyl)thiazole-4-carboxamide

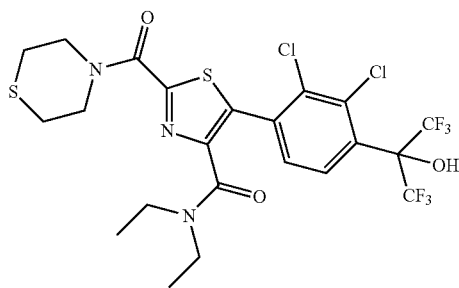 [SMILES: CCN(CC)C(=O)c1nc(C(=O)N2CCSCC2)sc1-c1ccc(C(O)(C(F)(F)F)C(F)(F)F)c(Cl)c1Cl]

A solution of 5-(2,3-dichloro-4-(1,1,1,3,3,3-hexafluoro-2-hydroxypropan-2-yl)phenyl)-2-(thiomorpholine-4-carbonyl)thiazole-4-carboxylic acid (147 mg, 0.258 mmol, Intermediate 20), HATU (148 mg, 0.389 mmol), and DIPEA (84 mg, 0.65 mmol) in DMF (3 mL) was stirred at rt for 1 h, then diethylamine (23 mg, 0.31 mmol) was added and the mixture was stirred overnight. The mixture was diluted with water and extracted with EtOAc (×3). The combined organic layers were washed with brine, dried over anhydrous Na₂SO₄, filtered, concentrated to dryness and the residue was purified by FCC on silica gel (PE/EtOAc=3/1) to give the title compound as a white solid.

Example 14

Step b 5-(2,3-Dichloro-4-(1,1,1,3,3,3-hexafluoro-2-hydroxypropan-2-yl)phenyl)-N,N-diethyl-2-(1-oxidothiomorpholine-4-carbonyl)thiazole-4-carboxamide

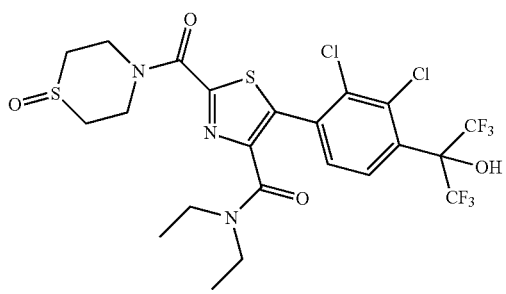 [SMILES: CCN(CC)C(=O)c1nc(C(=O)N2CCS(=O)CC2)sc1-c1ccc(C(O)(C(F)(F)F)C(F)(F)F)c(Cl)c1Cl]

To a solution of 5-(2,3-dichloro-4-(1,1,1,3,3,3-hexafluoro-2-hydroxypropan-2-yl)phenyl)-N, N-diethyl-2-(thiomorpholine-4-carbonyl)thiazole-4-carboxamide (122 mg, 0.195 mmol, Example 14, step a) in DCM (10 mL) was added m-CPBA (39 mg, 0.20 mmol, 85%) at 0° C. and the mixture was stirred at rt overnight. The mixture was quenched with aqueous NaHSO₃, diluted with an aqueous NaHCO₃ solution and extracted with EtOAc (×3). The combined organic layers were washed with brine, dried over anhydrous Na₂SO₄, filtered, and concentrated to dryness to give the title compound as a yellow solid.

Example 14

Step c 5-(2,3-Dichloro-4-(1,1,1,3,3,3-hexafluoro-2-hydroxypropan-2-yl)phenyl)-N,N-diethyl-2-(1-oxido-1-((2,2,2-trifluoroacetyl)imino)thiomorpholine-4-carbonyl)thiazole-4-carboxamide

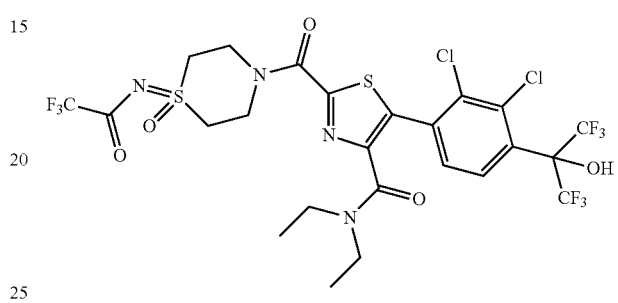

To a solution of 5-(2,3-dichloro-4-(1,1,1,3,3,3-hexafluoro-2-hydroxypropan-2-yl)phenyl)-N, N-diethyl-2-(1-oxidothiomorpholine-4-carbonyl)thiazole-4-carboxamide (108 mg, 0.169 mmol, Example 14, step b), 2,2,2-trifluoroacetamide (38 mg, 0.34 mmol), MgO (27 mg, 0.68 mmol) and Rh₂(OAc)₄ (8 mg, 20 μmol) in DCM (8 mL) was added PhI(OAc)₂ (82 mg, 0.26 mmol) and the mixture was stirred at 40° C. for 6 h. The resulting mixture was diluted with water and extracted with EtOAc three times. The combined organic layers were washed with brine, dried over anhydrous Na₂SO₄, filtered, concentrated to dryness and the residue was purified by FCC on silica gel (PE/EtOAc=5/1) to give the title compound as a white solid.

Example 14

5-(2,3-Dichloro-4-(1,1,1,3,3,3-hexafluoro-2-hydroxypropan-2-yl)phenyl)-N,N-diethyl-2-(1-imino-1-oxidothiomorpholine-4-carbonyl)thiazole-4-carboxamide

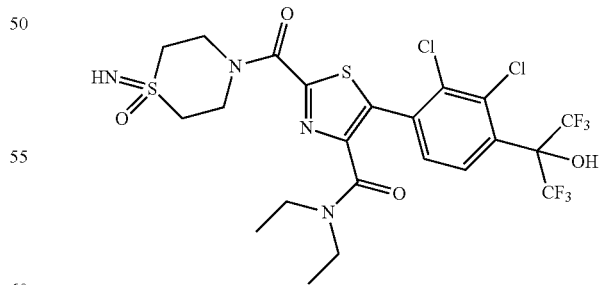

To a solution of 5-(2,3-dichloro-4-(1,1,1,3,3,3-hexafluoro-2-hydroxypropan-2-yl)phenyl)-N, N-diethyl-2-(1-oxido-1-((2,2,2-trifluoroacetyl)imino)thiomorpholine-4-carbonyl)thiazole-4-carboxamide (82 mg, 0.11 mmol, Example 14, step c) in MeOH (4 mL) was added K₂CO₃ (38 mg, 0.28 mmol) and the mixture was stirred at rt for 2 h, diluted with water, and extracted with EtOAc (×3). The combined organic layers were washed with brine, dried over anhydrous Na₂SO₄, filtered, concentrated to dryness and the residue was purified by prep-HPLC to give the title compound as a white solid. ¹H NMR (CDCl₃, 400 MHz): δ ppm 7.71 (br s, 1H), 7.55 (d, J=8.8 Hz, 1H), 5.02-4.99 (m, 1H), 4.80-4.77 (m, 1H), 4.40-4.36 (m, 1H), 4.23-4.22 (m, 1H), 3.47-3.42 (m, 2H), 3.25-3.21 (m, 6H), 3.70 (s, 1H), 1.12-1.04 (m, 6H). MS (ESI): m/z 655.0 [M+H]⁺.

Example 14/1

(S)-(5-(2,3-Dichloro-4-(1,1,1,3,3,3-hexafluoro-2-hydroxypropan-2-yl)phenyl)-2-(2-imino-2-oxido-2-thia-6-azaspiro[3.3]heptane-6-carbonyl)thiazol-4-yl)(4,4-difluoro-2-methylpyrrolidin-1-yl)methanone

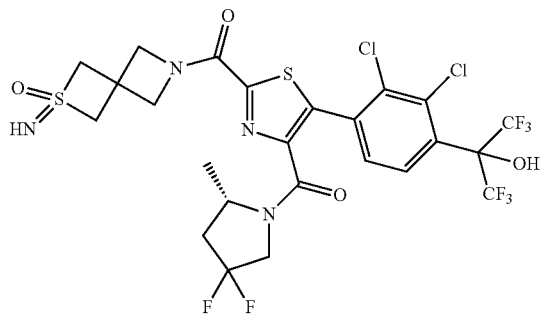 [SMILES: C[C@H]1CC(F)(F)CN1C(=O)c1nc(C(=O)N2CC3(C2)CS(=N)(=O)C3)sc1-c1ccc(C(O)(C(F)(F)F)C(F)(F)F)c(Cl)c1Cl]

The title compound was prepared as described in Example 14, steps a, c and final step using in step a 5-(2,3-dichloro-4-(1,1,1,3,3,3-hexafluoro-2-hydroxypropan-2-yl)phenyl)-2-(2-oxido-2-thia-6-azaspiro[3.3]heptane-6-carbonyl)thiazole-4-carboxylic acid (Intermediate 20/1) in place of 5-(2,3-dichloro-4-(1,1,1,3,3,3-hexafluoro-2-hydroxypropan-2-yl)phenyl)-2-(thiomorpholine-4-carbonyl)thiazole-4-carboxylic acid and (S)-4,4-difluoro-2-methylpyrrolidine hydrochloride (Intermediate 12) in place of diethylamine. ¹H NMR (CD₃OD, 500 MHz): δ ppm 7.95-7.87 (m, 1H), 7.59-7.55 (m, 1H), 5.06-5.00 (m, 2H), 4.51-4.31 (m, 8H), 4.22-4.12 (m, 1H), 2.71-2.66 (m, 1H), 2.22-2.18 (m, 1H), 1.38-1.28 (m, 3H). MS (ESI): m/z 715.0 [M+H]⁺.

Example 14/2

(S)-(5-(2,3-Dichloro-4-(1,1,1,3,3,3-hexafluoro-2-hydroxypropan-2-yl)phenyl)-2-(2-(methylimino)-2-oxido-2-thia-6-azaspiro[3.3]heptane-6-carbonyl)thiazol-4-yl)(4,4-difluoro-2-methylpyrrolidin-1-yl)methanone

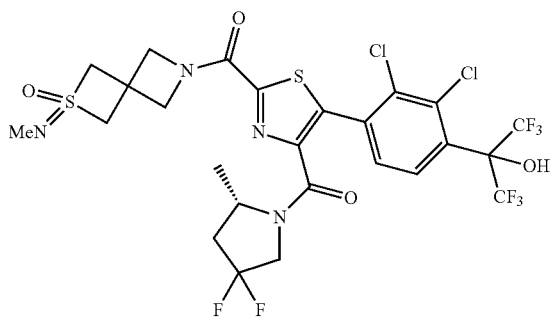

To a solution of (S)-(5-(2,3-dichloro-4-(1,1,1,3,3,3-hexafluoro-2-hydroxypropan-2-yl)phenyl)-2-(2-imino-2-oxido-2-thia-6-azaspiro[3.3]heptane-6-carbonyl)thiazol-4-yl)(4,4-difluoro-2-methylpyrrolidin-1-yl)methanone (81 mg, 0.11 mmol, Example 14/1) in DMF (4 mL) was added K₂CO₃ (23 mg, 0.17 mmol) and MeI (26 mg, 0.17 mmol) and the mixture was stirred at rt overnight, then diluted with water and extracted with EtOAc three times. The combined organic layers were washed with brine, dried over anhydrous Na₂SO₄, filtered and concentrated to dryness. The residue was purified by prep-HPLC to give the title compound as white solid. ¹H NMR (CDCl₃, 500 MHz): δ ppm 7.62 (d, J=8.5 Hz, 1H), 7.45 (d, J=8.5 Hz, 1H), 5.01-4.90 (m, 2H), 4.54-4.27 (m, 6H), 4.04-3.95 (m, 2H), 3.54 (s, 3H), 3.25-3.17 (m, 1H), 2.65-2.57 (m, 1H), 2.18-2.11 (m, 1H), 1.39-1.22 (m, 3H). MS (ESI): m/z 729.0 [M+H]⁺.

Example 15

(S)-5-(2-(Difluoromethyl)-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

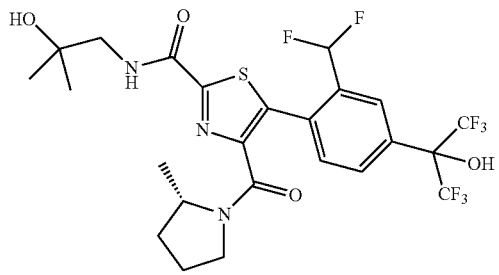 [SMILES: C[C@H]1CCCN1C(=O)c1nc(C(=O)NCC(C)(C)O)sc1-c1ccc(C(O)(C(F)(F)F)C(F)(F)F)cc1C(F)F]

A flask under nitrogen, was charged with (S)—N-(2-hydroxy-2-methylpropyl)-4-(2-methylpyrrolidine-1-carbonyl)thiazole-2-carboxamide (2.0 g, 6.42 mmol, Intermediate 15/1), 2-(4-bromo-3-(difluoromethyl)phenyl)-1,1,1,3,3,3-hexafluoropropan-2-ol (2.63 g, 7.06 mmol, Intermediate 18), K₂CO₃ (1.78 g, 12.84 mmol), pivalic acid (0.26 g, 2.57 mmol), Pd₂(dba)₃·CHCl₃ (0.50 g, 0.48 mmol), cataCXium® A (0.35 g, 0.96 mmol) and n-butyronitrile (30 mL). The resulting solution was stirred for 16.5 h at 100-105° C. The reaction mixture was then cooled to room temperature, diluted with H₂O (30 mL), and the aqueous phase was extracted with EtOAc (30 mL). The combined organic layers were concentrated under vacuum, and the crude product was purified by FCC on silica gel (EtOAc/heptane=1/2 to 2/1) to give the title compound as an off-white solid. ¹H NMR (CD₃OD, 400 MHz) δ 8.14 (d, J=1.8 Hz, 1H), 7.97 (d, J=7.9 Hz, 1H), 7.63 (dd, J=14.4, 8.2 Hz, 1H), 7.07-6.76 (m, 1H), 4.55-4.11 (m, 1H), 3.70-3.41 (m, 4H), 2.16-1.89 (m, 2H), 1.87-1.78 (m, 1H), 1.63-1.55 (m, 1H), 1.28 (s, 6H), 1.18-1.12 (dd, J=16.1, 6.4 Hz, 3H). MS (ESI): m/z 604.1 [M+H]⁺.

Example 15/1

(R)-5-(2-(Difluoromethyl)-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

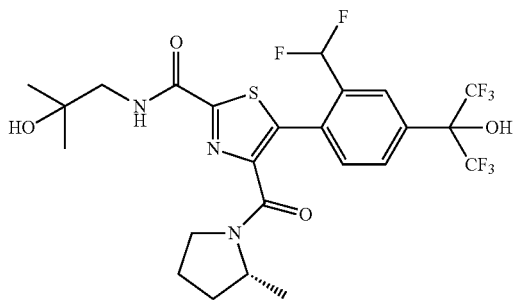 [SMILES: C[C@@H]1CCCN1C(=O)c1nc(C(=O)NCC(C)(C)O)sc1-c1ccc(C(O)(C(F)(F)F)C(F)(F)F)cc1C(F)F]

n-Butyronitrile (2 mL) that had been sparged with argon for 45 minutes was added to a mixture of (R)—N-(2-hydroxy-2-methylpropyl)-4-(2-methylpyrrolidine-1-carbonyl)thiazole-2-carboxamide (150 mg, 0.482 mmol, Intermediate 15/2), 2-(4-bromo-3-(difluoromethyl)phenyl)-1,1,1,3,3,3-hexafluoropropan-2-ol (0.17 g, 0.46 mmol, Intermediate 18), K₂CO₃ (0.27 g, 1.95 mmol) and pivalic acid (0.025 g, 0.241 mmol). The resulting mixture was further sparged with nitrogen for 25 minutes. Then Pd((t-Bu)₃P)₂ (0.025 g, 0.048 mmol) was added at rt under nitrogen and the mixture was sparged with nitrogen for 2 minutes. The mixture was then heated at 100° C. for 19 h, cooled to rt and filtered through Celite®. The filter cake was washed with EtOAc and the organic layer was washed with aqueous saturated NaHCO₃ solution, water and brine. The organic layer was dried over anhydrous MgSO₄, filtered, concentrated to dryness, and the residue was purified by FCC on silica gel (0 to 60% EtOAc in DCM) to afford the title compound. ¹H NMR (CDCl₃, 400 MHz): δ ppm 8.08 (s, 1H), 7.83 (t, J=9.1 Hz, 1H), 7.64-7.43 (m, 2H), 6.97-6.64 (m, 1H), 4.93 (s, 0.3H), 4.89 (s, 0.7H), 4.31-4.1 (m, 1H), 3.58-3.33 (m, 4H), 2.07-1.49 (m, 5H), 1.32 (s, 6H), 1.15 (d, J=6.3 Hz, 2H), 1.07 (d, J=6.4 Hz, 1H). MS (ESI): m/z 604.1 [M+H]⁺.

Example 15/2

(S)-5-(2-(Difluoromethyl)-4-(1,1,1,3,3,3-hexafluoro-2-hydroxypropan-2-yl)phenyl)-N-(2-hydroxy-2-methylpropyl)-4-(2-methylpiperidine-1-carbonyl)thiazole-2-carboxamide

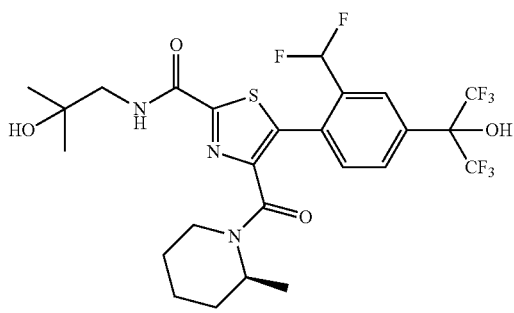 [SMILES: C[C@H]1CCCCN1C(=O)c1nc(C(=O)NCC(C)(C)O)sc1-c1ccc(C(O)(C(F)(F)F)C(F)(F)F)cc1C(F)F]

n-Butyronitrile (2 mL) that had been sparged with argon for 1 h was added to a mixture of (S)—N-(2-hydroxy-2-methylpropyl)-4-(2-methylpiperidine-1-carbonyl)thiazole-2-carboxamide (63 mg, 0.19 mmol, Intermediate 15/3), 2-(4-bromo-3-(difluoromethyl)phenyl)-1,1,1,3,3,3-hexafluoropropan-2-ol (100 mg, 0.268 mmol, Intermediate 18), K₂CO₃ (0.12 g, 0.87 mmol) and pivalic acid (0.009 g, 0.088 mmol). The mixture was sparged with nitrogen for 20 minutes. Then Pd(OAc)₂ (9.7 mg, 0.04 mmol) and di-(1-adamantyl)-N-butyphosphine (14.8 mg, 0.041 mmol) were added at rt under nitrogen and the mixture was sparged with nitrogen for 1 minute. The mixture was heated at 100° C. for 3 days, cooled to rt and filtered through Celite®. The filter cake was washed with EtOAc and the organic layer was washed with aqueous saturated NaHCO₃ solution and brine, dried over anhydrous MgSO₄, filtered, concentrated to dryness and the residue was purified by FCC on silica gel (0 to 60% EtOAc in DCM) to provide the title compound. ¹H NMR (CDCl₃, 600 MHz): δ ppm 8.13 (s, 1H), 7.88 (d, J=8.2 Hz, 1H), 7.64 (s, 1H), 7.56 (d, J=7.7 Hz, 1H), 6.95-6.73 (m, 1H), 4.82 (s, 0.5H), 4.54 (s, 1H), 4.39 (d, J=13.5 Hz, 0.5H), 3.83 (s, 0.5H), 3.48 (dd, J=6.4, 1.7 Hz, 2H), 3.28 (d, J=13.4 Hz, 0.5H), 2.88 (t, J=13.3 Hz, 0.5H), 2.77 (d, J=13.5 Hz, 0.5H), 2.04-1.98 (m, 1H), 1.49-1.41 (m, 4H), 1.32 (s, 6H), 1.28-1.18 (m, 1H), 1.11 (d, J=6.8 Hz, 1.5H), 1.01 (d, J=7.0 Hz, 1.5H) 0.86-0.78 (m, 1H). MS (ESI): m/z 617.7 [M+H]⁺.

Example 15/3

4-(7-Azabicyclo[2.2.1]heptane-7-carbonyl)-5-(2-(difluoromethyl)-4-(1,1,1,3,3,3-hexafluoro-2-hydroxypropan-2-yl)phenyl)-N-(2-hydroxy-2-methylpropyl)thiazole-2-carboxamide

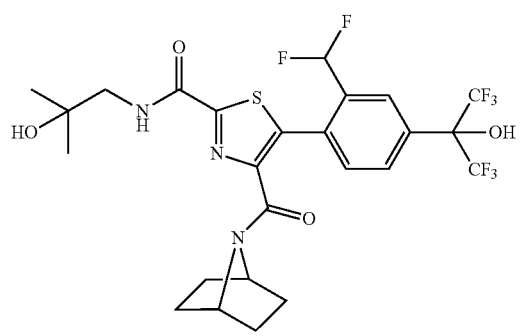 [SMILES: CC(C)(O)CNC(=O)c1nc(C(=O)N2C3CCC2CC3)c(-c2ccc(C(O)(C(F)(F)F)C(F)(F)F)cc2C(F)F)s1]

The title compound was prepared as described in Example 15/1, using 4-(7-azabicyclo[2.2.1]heptane-7-carbonyl)-N-(2-hydroxy-2-methylpropyl)thiazole-2-carboxamide (Intermediate 15/4) in place of (R)—N-(2-hydroxy-2-methylpropyl)-4-(2-methylpyrrolidine-1-carbonyl)thiazole-2-carboxamide. ¹H NMR (CDCl₃, 600 MHz): δ ppm 8.13-8.07 (m, 1H), 7.88-7.82 (d, J=8.0 Hz, 1H), 7.62 (t, J=6.3 Hz, 1H), 7.51 (d, J=8.2 Hz, 1H), 6.81 (t, J=54.9 Hz, 1H), 4.72 (s, 1H), 4.66 (s, 1H), 4.20 (s, 1H), 3.49 (d, J=6.3 Hz, 2H), 1.97 (s, 1H), 1.73-1.66 (m, 2H), 1.46-1.36 (m, 6H), 1.33 (s, 6H). MS (ESI): m/z 615.6 [M+H]⁺.

Example 15/4

(S)-5-(2-(Difluoromethyl)-3-fluoro-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

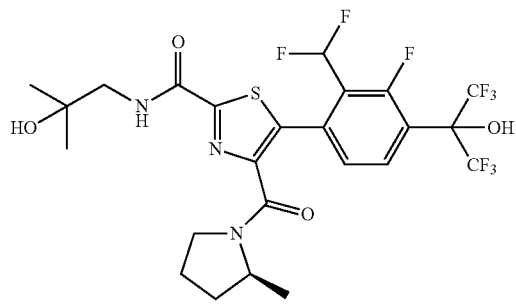 [SMILES: C[C@H]1CCCN1C(=O)c1nc(C(=O)NCC(C)(C)O)sc1-c1ccc(C(O)(C(F)(F)F)C(F)(F)F)c(F)c1C(F)F]

The title compound was prepared as described in Example 15/1, using (S)—N-(2-hydroxy-2-methylpropyl)-4-(2-methylpyrrolidine-1-carbonyl)thiazole-2-carboxamide (Intermediate 15/1) in place of (R)—N-(2-hydroxy-2-methylpropyl)-4-(2-methylpyrrolidine-1-carbonyl)thiazole-2-carboxamide and 2-(4-bromo-3-(difluoromethyl)-2-fluorophenyl)-1,1,1,3,3,3-hexafluoropropan-2-ol (Intermediate 27) in place of 2-(4-bromo-3-(difluoromethyl)phenyl)-1,1,1,3,3,3-hexafluoropropan-2-ol. $^1$H NMR (CDCl$_3$, 500 MHz): δ ppm 8.00-7.91 (m, 1H), 7.60-7.55 (m, 1H), 7.38 (dd, J=18.2, 8.4 Hz, 1H), 6.97-6.74 (m, 1H), 4.86 (s, 1H), 4.41-4.32 (m, 0.3H), 4.24-4.15 (m, 0.7H), 3.62-3.41 (m, 4H), 2.12-1.84 (m, 4H), 1.78-1.75 (m, 1H), 1.33 (s, 6H), 1.20 (d, J=6.3 Hz, 2H), 1.13 (d, J=6.4 Hz, 1H). MS (ESI): m/z 621.6 [M+H]$^+$.

Example 15/5

(S)-5-(3-Chloro-2-fluoro-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

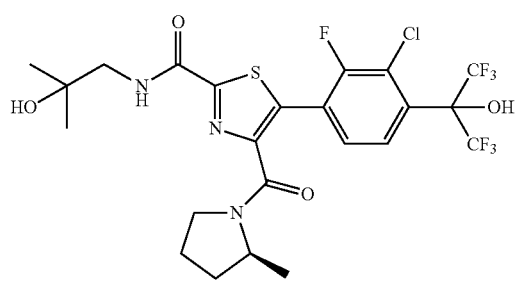 [SMILES: C[C@H]1CCCN1C(=O)c1nc(C(=O)NCC(C)(C)O)sc1-c1ccc(C(O)(C(F)(F)F)C(F)(F)F)c(Cl)c1F]

The title compound was prepared as described in Example 15/1, using (S)—N-(2-hydroxy-2-methylpropyl)-4-(2-methylpyrrolidine-1-carbonyl)thiazole-2-carboxamide (Intermediate 15/1) in place of (R)—N-(2-hydroxy-2-methylpropyl)-4-(2-methylpyrrolidine-1-carbonyl)thiazole-2-carboxamide and 2-(4-bromo-2-chloro-3-fluorophenyl)-1,1,1,3,3,3-hexafluoropropan-2-ol (Intermediate 26) in place of 2-(4-bromo-3-(difluoromethyl)phenyl)-1,1,1,3,3,3-hexafluoropropan-2-ol. $^1$H NMR (CDCl$_3$, 500 MHz): δ ppm 7.60-7.56 (m, 3H), 4.37-4.27 (m, 0.8H), 4.17-4.11 (m, 0.2H), 3.74-3.35 (m, 4H), 2.16-1.89 (m, 4H), 1.88-1.75 (m, 1H), 1.32 (s, 6H), 1.29 (d, J=6.3 Hz, 2H), 1.03 (d, J=6.4 Hz, 1H). MS (ESI): m/z 605.5 [M+H]$^+$.

Example 15/6

(S)-5-(2-(Difluoromethoxy)-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

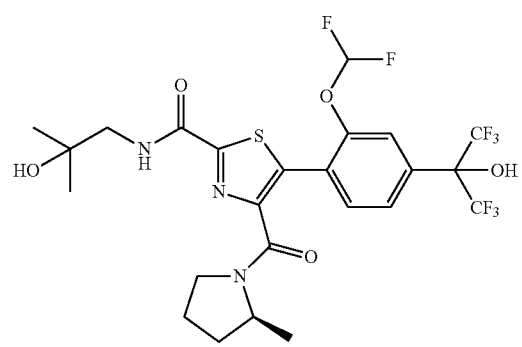 [SMILES: C[C@H]1CCCN1C(=O)c1nc(C(=O)NCC(C)(C)O)sc1-c1ccc(C(O)(C(F)(F)F)C(F)(F)F)cc1OC(F)F]

The title compound was prepared as described in Example 15/2, using (S)—N-(2-hydroxy-2-methylpropyl)-4-(2-methylpyrrolidine-1-carbonyl)thiazole-2-carboxamide (Intermediate 15/1) in place of (S)—N-(2-hydroxy-2-methylpropyl)-4-(2-methylpiperidine-1-carbonyl)thiazole-2-carboxamide and 2-(4-bromo-3-(difluoromethoxy)phenyl)-1,1,1,3,3,3-hexafluoropropan-2-ol (Intermediate 24) in place of 2-(4-bromo-3-(difluoromethyl)phenyl)-1,1,1,3,3,3-hexafluoropropan-2-ol. $^1$H NMR (CDCl$_3$, 600 MHz): δ ppm 7.64-7.53 (m, 4H), 6.70-6.42 (m, 1H), 4.76-4.74 (m, 1H), 4.29-4.25 (m, 0.7H), 4.12-4.09 (m, 0.3H), 3.64-3.58 (m, 0.7H), 3.55-3.35 (m, 3.3H), 2.12-2.05 (m, 0.7H), 2.04 (s, 0.7H), 1.99-1.92 (m, 0.6H), 1.94-1.81 (m, 2H), 1.80-1.74 (m, 1H), 1.31 (s, 6H), 1.26 (d, J=6.3 Hz, 2H), 1.01 (d, J=6.4 Hz, 1H). MS (ESI): m/z 619.6 [M+H]$^+$.

Example 15/7

(S)-5-(4-(1,1,1,3,3,3-Hexafluoro-2-hydroxypropan-2-yl)-2-methoxyphenyl)-N-(2-hydroxy-2-methylpropyl)-4-(2-methylpyrrolidine-1-carbonyl)thiazole-2-carboxamide

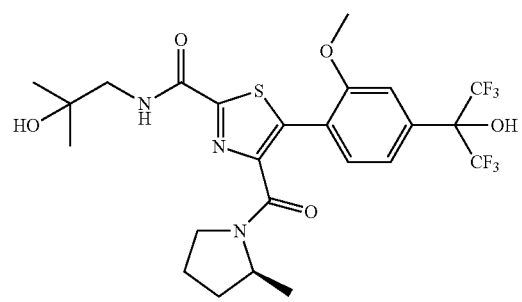 [SMILES: COc1cc(C(O)(C(F)(F)F)C(F)(F)F)ccc1-c1sc(C(=O)NCC(C)(C)O)nc1C(=O)N1CCC[C@@H]1C]

The title compound was prepared as described in Example 15/2, using (S)—N-(2-hydroxy-2-methylpropyl)-4-(2-methylpyrrolidine-1-carbonyl)thiazole-2-carboxamide (Intermediate 15/1) in place of (S)—N-(2-hydroxy-2-methylpropyl)-4-(2-methylpiperidine-1-carbonyl)thiazole-2-carboxamide and 2-(4-bromo-3-methoxyphenyl)-1,1,1,3,3,3-hexafluoropropan-2-ol (Intermediate 25) in place of 2-(4-bromo-3-(difluoromethyl)phenyl)-1,1,1,3,3,3-hexafluoropropan-2-ol. $^1$H NMR (CDCl$_3$, 500 MHz): δ ppm 7.69-7.65 (m, 1H), 7.54 (d, J=8.2 Hz, 1H), 7.36 (s, 1H), 7.32-7.28 (m, 1H), 4.49 (br s, 1H), 4.35-4.26 (m, 1H), 3.91 (s, 1H), 3.90 (s, 2H), 3.76-3.71 (m, 0.3H), 3.65-3.45 (m, 0.7H), 3.52-3.41 (m, 2H), 3.17-3.12 (m, 0.5H), 3.05-3.00 (m, 0.5H), 2.26 (s, 0.7H), 2.21 (s, 0.3H), 2.03-1.97 (m, 1H), 1.85-1.62 (m, 2H), 1.52-1.49 (m, 1H), 1.30 (s, 6H), 1.24 (d, J=6.4 Hz, 2H), 0.87 (d, J=6.5 Hz, 1H). MS (ESI): m/z 583.6 [M+H]$^+$.

Example 15/8

(S)-4-(4,4-Difluoro-2-methylpyrrolidine-1-carbonyl)-5-(2-(difluoromethyl)-4-(1,1,1,3,3,3-hexafluoro-2-hydroxypropan-2-yl)phenyl)-N-(2-hydroxy-2-methylpropyl)thiazole-2-carboxamide

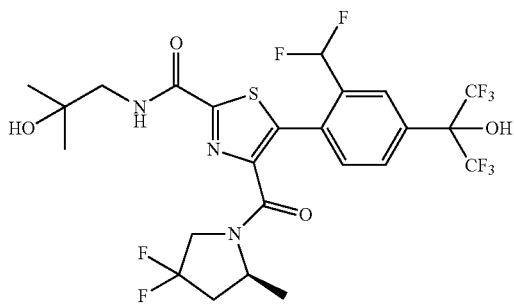 [SMILES: C[C@H]1CC(F)(F)CN1C(=O)c1nc(C(=O)NCC(C)(C)O)sc1-c1ccc(C(O)(C(F)(F)F)C(F)(F)F)cc1C(F)F]

The title compound was prepared as described in Example 15/1, using (S)-4-(4,4-difluoro-2-methylpyrrolidine-1-carbonyl)-N-(2-hydroxy-2-methylpropyl)thiazole-2-carboxamide (Intermediate 15/5) in place of (R)—N-(2-hydroxy-2-methylpropyl)-4-(2-methylpyrrolidine-1-carbonyl)thiazole-2-carboxamide. $^1$H NMR (CDCl$_3$, 600 MHz): δ ppm 8.12-8.04 (m, 1H), 7.91-7.83 (m, 1H), 7.54-7.46 (m, 2H), 6.87-6.63 (m, 1H), 4.71-4.66 (m, 0.3H), 4.5-4.47 (m, 0.7H), 4.27 (s, 1H), 4.05 (q, J=12.7 Hz, 1H), 3.93 (q, J=12.0 Hz, 0.7H), 3.84-3.77 (m, 0.3H), 3.57-3.42 (m, 2H), 2.58-2.50 (m, 1H), 2.21-2.01 (m, 1H), 1.87 (s, 0.7H), 1.78 (s, 0.3H), 1.34 (s, 6H), 1.33-1.29 (m, 2H), 1.28-1.26 (m, 1H). MS (ESI): m/z 639.6 [M+H]$^+$.

Example 15/9

(S)-5-(2-Ethyl-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

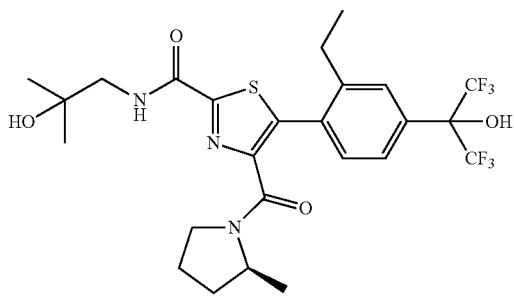 [SMILES: CCc1cc(C(O)(C(F)(F)F)C(F)(F)F)ccc1-c1sc(C(=O)NCC(C)(C)O)nc1C(=O)N1CCC[C@@H]1C]

The title compound was prepared as described in Example 15/2, using (S)—N-(2-hydroxy-2-methylpropyl)-4-(2-methylpyrrolidine-1-carbonyl)thiazole-2-carboxamide (Intermediate 15/1) in place of (S)—N-(2-hydroxy-2-methylpropyl)-4-(2-methylpiperidine-1-carbonyl)thiazole-2-carboxamide and 2-(4-bromo-3-ethylphenyl)-1,1,1,3,3,3-hexafluoropropan-2-ol (Intermediate 3) in place of 2-(4-bromo-3-(difluoromethyl)phenyl)-1,1,1,3,3,3-hexafluoropropan-2-ol. $^1$H NMR (CDCl$_3$, 600 MHz): δ ppm 7.69 (s, 1H), 7.65 (t, J=6.4 Hz, 0.7H), 7.61 (t, J=6.4 Hz, 0.3H), 7.58-7.55 (m, 1H), 7.42-7.39 (m, 1H), 4.22-4.19 (m, 0.7H), 4.06 (s, 0.3H), 4.02 (s, 0.7H), 3.94-3.92 (m, 0.3H), 3.56-3.42 (m, 3H), 3.24-3.21 (m, 0.5H), 3.11-3.06 (m, 0.5H), 2.76-2.62 (m, 2H), 2.09 (s, 0.7H), 2.02 (s, 0.3H), 2.01-1.95 (m, 0.7H), 1.92-1.86 (m, 0.3H), 1.80-1.61 (m, 2H), 1.46 1.40 (m, 1H), 1.32 (s, 6H), 1.21-1.17 (m, 3H), 1.11 (d, J=6.3 Hz, 2H), 0.98 (d, J=6.4 Hz, 1H). MS (ESI): m/z 581.7 [M+H]$^+$.

Example 15/10

(S)-5-(2-Chloro-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

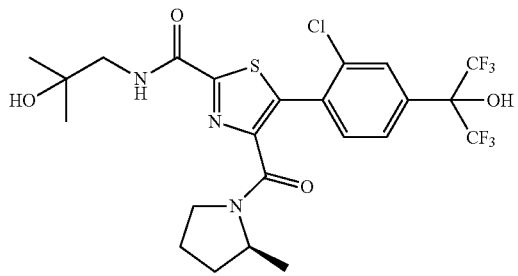 [SMILES: C[C@H]1CCCN1C(=O)c1nc(C(=O)NCC(C)(C)O)sc1-c1ccc(C(O)(C(F)(F)F)C(F)(F)F)cc1Cl]

The title compound was prepared as described in Example 15/2, using (S)—N-(2-hydroxy-2-methylpropyl)-4-(2-methylpyrrolidine-1-carbonyl)thiazole-2-carboxamide (Intermediate 15/1) in place of (S)—N-(2-hydroxy-2-methylpropyl)-4-(2-methylpiperidine-1-carbonyl)thiazole-2-carboxamide and 2-(4-bromo-3-chlorophenyl)-1,1,1,3,3,3-hexafluoropropan-2-ol (Intermediate 4/3) in place of 2-(4-bromo-3-(difluoromethyl)phenyl)-1,1,1,3,3,3-hexafluoropropan-2-ol. $^1$H NMR (CDCl$_3$, 600 MHz): δ ppm 7.88-7.85 (m, 1H), 7.70-7.58 (m, 2H), 7.56-7.53 (m, 1H), 5.86 (s, 1H), 4.30-4.17 (m, 0.7H), 4.10-4.07 (m, 0.3H), 3.60-3.39 (m, 2.7H), 3.40-3.24 (m, 1.3H), 2.34 (s, 0.7H), 2.27 (s, 0.3H), 2.09-1.65 (m, 3H), 1.62-1.57 (m, 0.3H), 1.53-1.46 (m, 0.7H), 1.31 (s, 6H), 1.17 (d, J=6.3 Hz, 2H), 1.03 (d, J=6.4 Hz, 1H). MS (ESI): m/z 587.7 [M+H]$^+$.

Example 15/11

(S)-5-(6-(1,1,1,3,3,3-Hexafluoro-2-hydroxypropan-2-yl)-4-methylpyridin-3-yl)-N-(2-hydroxy-2-methylpropyl)-4-(2-methylpiperidine-1-carbonyl)thiazole-2-carboxamide

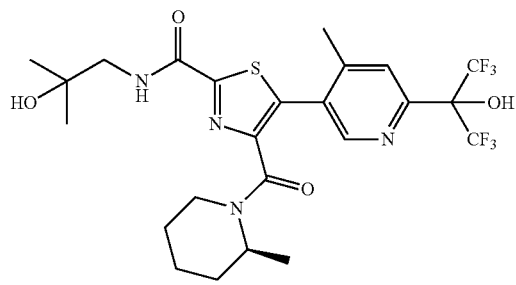 [SMILES: Cc1cc(C(O)(C(F)(F)F)C(F)(F)F)ncc1-c1sc(C(=O)NCC(C)(C)O)nc1C(=O)N1CCCC[C@@H]1C]

The title compound was prepared as described in Example 15, using (S)—N-(2-hydroxy-2-methylpropyl)-4-(2-methylpiperidine-1-carbonyl)thiazole-2-carboxamide (Intermediate 15/3) in place of (S)—N-(2-hydroxy-2-methylpropyl)-4-(2-methylpyrrolidine-1-carbonyl)thiazole-2-carboxamide and 2-(5-bromo-4-methylpyridin-2-yl)-1,1,1,3,3,3-hexafluoropropan-2-ol (Intermediate 23/1) in place of 2-(4-bromo-3-(difluoromethyl)phenyl)-1,1,1,3,3,3-hexafluoropropan-2-ol. $^1$H NMR (CDCl$_3$, 500 MHz) δ ppm 8.67 (d, J=8.6 Hz, 1H), 7.66-7.60 (m, 1H), 7.42-7.34 (m, 1H), 5.47-5.33 (m, 1H), 5.12-4.65 (m, 1H), 3.69-3.12 (m, 3H), 3.04-2.88 (m, 1H), 2.57 (d, J=7.5 Hz, 3H), 2.19-2.12 (m, 1H), 1.84-1.69 (m, 1H), 1.64-1.55 (m, 2H), 1.50-1.43 (m, 1H), 1.40-1.31 (m, 1H), 1.31-1.28 (m, 8H), 1.10 (d, J=6.9 Hz, 1H). MS (ESI): m/z 583.0 [M+H]$^+$.

Example 16

(S)-5-(2-Fluoro-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

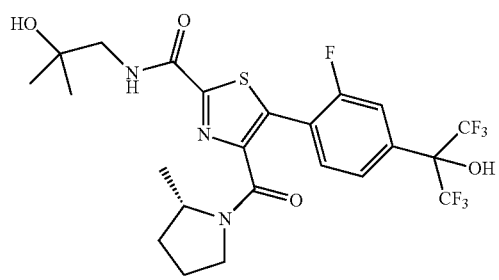 [SMILES: C[C@H]1CCCN1C(=O)c1nc(C(=O)NCC(C)(C)O)sc1-c1ccc(C(O)(C(F)(F)F)C(F)(F)F)cc1F]

The title compound was prepared as described for Intermediate 21, step b using (S)—N-(2-hydroxy-2-methylpropyl)-4-(2-methylpyrrolidine-1-carbonyl)thiazole-2-carboxamide (Intermediate 15/1) in place of N-(2-hydroxy-2-methylpropyl)-4-(hydroxymethyl)thiazole-2-carboxamide and 2-(4-bromo-3-fluorophenyl)-1,1,1,3,3,3-hexafluoropropan-2-ol (Intermediate 4/4) in place of 2-(4-bromo-3-(difluoromethyl)phenyl)-1,1,1,3,3,3-hexafluoropropan-2-ol. $^1$H NMR (CDCl$_3$, 400 MHz, mixture of rotamers): δ ppm 7.94-7.51 (m, 4H), 4.33-3.24 (m, 5H), 1.96-1.78 (m, 4H), 1.31 (m, 6H), 1.28-0.96 (m, 3H). MS (ESI): m/z 572.1 [M+H]$^+$.

Example 17

Step a (S)—N-(3-amino-2,2-dimethyl-3-oxopropyl)-5-(2,3-dichloro-4-(1,1,1,3,3,3-hexafluoro-2-hydroxypropan-2-yl)phenyl)-4-(2-methylpiperidine-1-carbonyl)thiazole-2-carboxamide

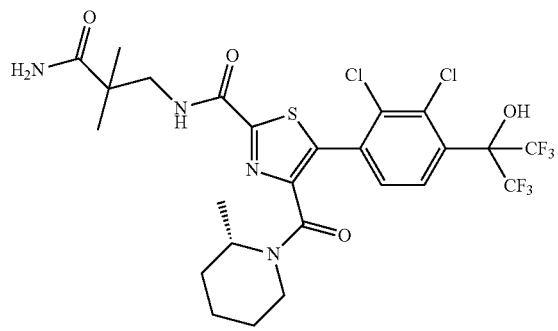 [SMILES: C[C@H]1CCCCN1C(=O)c1nc(C(=O)NCC(C)(C)C(N)=O)sc1-c1ccc(C(O)(C(F)(F)F)C(F)(F)F)c(Cl)c1Cl]

The title compound was prepared as described for Example 1 using 2-((3-amino-2,2-dimethyl-3-oxopropyl)carbamoyl)-5-(2,3-dichloro-4-(1,1,1,3,3,3-hexafluoro-2-hydroxypropan-2-yl)phenyl)thiazole-4-carboxylic acid (Intermediate 22) in place of 2-((3-amino-2,2-dimethyl-3-oxopropyl)carbamoyl)-5-(4-(1,1,1,3,3,3-hexafluoro-2-hydroxypropan-2-yl)naphthalen-1-yl)thiazole-4-carboxylic acid and (S)-2-methylpiperidine in place of 4-methylpiperidine.

Example 17

Step b (S)—N-(2-Cyano-2-methylpropyl)-5-(2,3-dichloro-4-(1,1,1,3,3,3-hexafluoro-2-hydroxypropan-2-yl)phenyl)-4-(2-methylpiperidine-1-carbonyl)thiazole-2-carboxamide

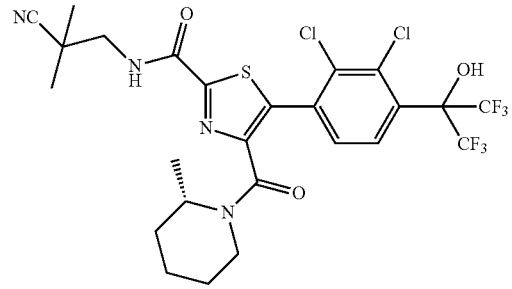 [SMILES: C[C@H]1CCCCN1C(=O)c1nc(C(=O)NCC(C)(C)C#N)sc1-c1ccc(C(O)(C(F)(F)F)C(F)(F)F)c(Cl)c1Cl]

To a solution of (S)—N-(3-amino-2,2-dimethyl-3-oxopropyl)-5-(2,3-dichloro-4-(1,1,1,3,3,3-hexafluoro-2-hydroxypropan-2-yl)phenyl)-4-(2-methylpiperidine-1-carbonyl)thiazole-2-carboxamide (168 mg, 0.253 mmol, Example 17, step a) in dry DCM (10 mL) was added TFAA (106 mg, 0.505 mmol) at 0° C. and the mixture was stirred at this temperature for 1 h. The mixture was quenched with water and extracted with DCM three times. The combined organic layers were washed with brine, dried over anhydrous Na₂SO₄, filtered and concentrated to dryness to give the title compound as yellow solid.

Example 17

Step c (S)—N-(3-Amino-3-(hydroxyimino)-2,2-dimethylpropyl)-5-(2,3-dichloro-4-(1,1,1,3,3,3-hexafluoro-2-hydroxypropan-2-yl)phenyl)-4-(2-methylpiperidine-1-carbonyl)thiazole-2-carboxamide

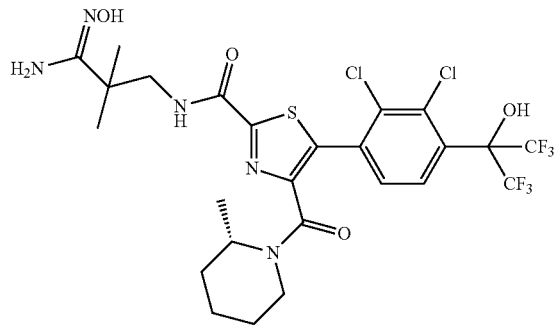

A solution of (S)—N-(2-cyano-2-methylpropyl)-5-(2,3-dichloro-4-(1,1,1,3,3,3-hexafluoro-2-hydroxypropan-2-yl)phenyl)-4-(2-methylpiperidine-1-carbonyl)thiazole-2-carboxamide (152 mg, 0.24 mmol, Example 17, step b), NaOEt (49 mg, 0.72 mmol) and hydroxylamine hydrochloride (25 mg, 0.36 mmol) in EtOH (5 mL) was stirred at 65° C. overnight. Water was added and the mixture was extracted with EtOAc. The combined organic layers were washed with brine, dried over anhydrous Na₂SO₄ and filtered. The filtrate was concentrated to dryness to give the title compound as a white solid.

Example 17

(S)-5-(2,3-Dichloro-4-(1,1,1,3,3,3-hexafluoro-2-hydroxypropan-2-yl)phenyl)-N-(2-methyl-2-(5-oxo-4,5-dihydro-1,2,4-oxadiazol-3-yl)propyl)-4-(2-methylpiperidine-1-carbonyl)thiazole-2-carboxamide

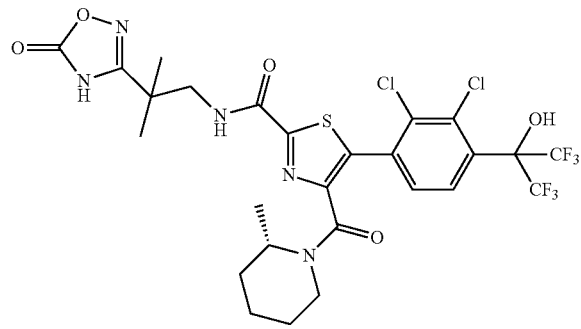 [SMILES: C[C@H]1CCCCN1C(=O)c1nc(C(=O)NCC(C)(C)c2noc(=O)[nH]2)sc1-c1ccc(C(O)(C(F)(F)F)C(F)(F)F)c(Cl)c1Cl]

A solution of (S)—N-(3-amino-3-(hydroxyimino)-2,2-dimethylpropyl)-5-(2,3-dichloro-4-(1,1,1,3,3,3-hexafluoro-2-hydroxypropan-2-yl)phenyl)-4-(2-methylpiperidine-1-carbonyl)thiazole-2-carboxamide (122 mg, 0.18 mmol, Example 17, step c), NaOEt (61 mg, 0.90 mmol), CDI (156 mg, 0.90 mmol) in EtOH (4 mL) was stirred at 70° C. for 72 h. Water was added and the mixture was extracted with EtOAc. The combined organic layers were washed with brine, dried over anhydrous Na₂SO₄, filtered and concentrated. The residue was purified by prep-HPLC to give the title compound as white solid. ¹H NMR (CD₃OD, 400 MHz): δ ppm 8.04-7.84 (m, 1H), 7.60-7.56 (m, 1H), 4.79-3.48 (m, 4H), 3.15-2.88 (m, 1H), 1.70-1.51 (m, 4H), 1.45-1.03 (m, 11H). MS (ESI): m/z 704.0 [M+H]⁺.

Example 18

(S)-5-(6-(1,1,1,3,3,3-Hexafluoro-2-hydroxypropan-2-yl)-4-(trifluoromethyl)pyridin-3-yl)-N-(2-hydroxy-2-methylpropyl)-4-(2-methylpyrrolidine-1-carbonyl)thiazole-2-carboxamide

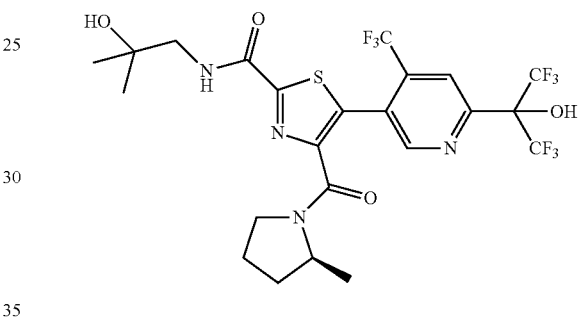

To an oven-dried vial was added (S)—N-(2-hydroxy-2-methylpropyl)-4-(2-methylpyrrolidine-1-carbonyl)thiazole-2-carboxamide (87 mg, 0.28 mmol, Intermediate 15/1), 2-(5-bromo-4-(trifluoromethyl)pyridin-2-yl)-1,1,1,3,3,3-hexafluoropropan-2-ol (100 mg, 0.26 mmol, Intermediate 23), Pd(OAc)₂ (9 mg, 0.038 mmol), 2-dicyclohexylphosphino-2',6'-di-i-propoxy-1,1'-biphenyl (RuPhos, 18 mg, 0.038 mmol), pivalic acid (10.5 mg, 0.1 mmol) and K₂CO₃ (60 mg, 0.43 mmol). The vial was placed under N₂, then butyronitrile (1.6 mL, bubbled with N₂ for 1 hour) was added and the resulting mixture stirred at 120° C. for 17 h. The mixture was cooled to rt, filtered through Celite®, washed with EtOAc and the organics were concentrated to dryness. To the crude residue was added 2-dicyclohexylphosphino-2',6'-di-i-propoxy-1,1'-biphenyl (RuPhos, 18 mg, 0.038 mmol), pivalic acid (10.5 mg, 0.1 mmol), K₂CO₃ (60 mg, 0.43 mmol) and butyronitrile (1.6 mL). The mixture was sparged with N₂ for 30 minutes, then Pd(OAc)₂ (9 mg, 0.038 mmol) was added and the mixture sparged with N₂ for 2 minutes. The mixture was stirred at 120° C. for 16 h then was cooled to rt, quenched with water (15 mL), then extracted with EtOAc (2×20 mL). The organics were combined, washed with brine, dried over Na₂SO₄, filtered and concentrated to dryness. The residue was purified by prep-HPLC to provide the title compound as a cream-colored solid. ¹H NMR (CDCl₃, 400 MHz) δ ppm 8.90-8.84 (m, 1H), 8.03 (s, 1H), 7.61-7.51 (m, 1H), 6.71 (br s, 1H), 4.73-4.14 (m, 1H), 3.76-3.46 (m, 4H), 2.10-1.70 (m, 4H), 1.64-1.50 (m, 1H), 1.34 (s, 6H), 1.20 (d, J=6.3 Hz, 3H). MS (ESI): m/z 623.0 [M+H]⁺.

Example 18/1

(S)-5-(6-(1,1,1,3,3,3-Hexafluoro-2-hydroxypropan-2-yl)-4-(trifluoromethyl)pyridin-3-yl)-N-(2-hydroxy-2-methylpropyl)-4-(2-methylpiperidine-1-carbonyl)thiazole-2-carboxamide

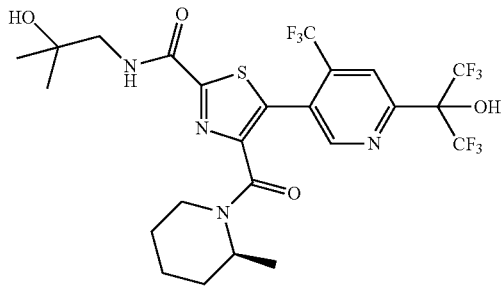 [SMILES: C[C@H]1CCCCN1C(=O)c1nc(C(=O)NCC(C)(C)O)sc1-c1cnc(C(O)(C(F)(F)F)C(F)(F)F)cc1C(F)(F)F]

The title compound was prepared using the procedure described for Example 18, using (S)—N-(2-hydroxy-2-methylpropyl)-4-(2-methylpiperidine-1-carbonyl)thiazole-2-carboxamide (Intermediate 15/3) in place of (S)—N-(2-hydroxy-2-methylpropyl)-4-(2-methylpyrrolidine-1-carbonyl)thiazole-2-carboxamide. $^1$H NMR (CDCl$_3$, 500 MHz) δ ppm 8.98-8.91 (m, 1H), 8.05 (s, 1H), 7.63-7.55 (m, 1H), 4.84-4.33 (m, 1H), 4.12-4.04 (m, 0.5H), 3.51-3.48 (m, 2H), 3.09-2.76 (m, 1H), 2.58-2.48 (m, 0.5H), 1.87-1.43 (m, 7H), 1.33 (s, 6H), 1.31-1.24 (m, 2H), 1.11-1.02 (m, 2H). MS (ESI): m/z 636.9 [M+H]$^+$.

Example 18/2

4-(4-Fluoropiperidine-1-carbonyl)-5-(6-(1,1,1,3,3,3-hexafluoro-2-hydroxypropan-2-yl)-4-(trifluoromethyl)pyridin-3-yl)-N-(2-hydroxy-2-methylpropyl)thiazole-2-carboxamide

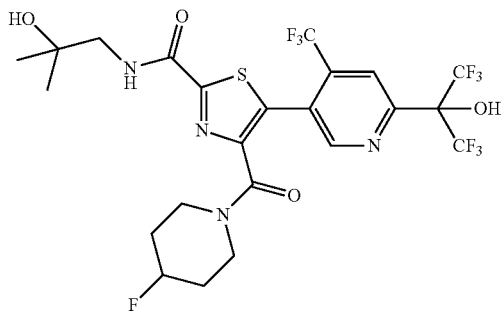 [SMILES: CC(C)(O)CNC(=O)c1nc(C(=O)N2CCC(F)CC2)c(-c2cnc(C(O)(C(F)(F)F)C(F)(F)F)cc2C(F)(F)F)s1]

The title compound was prepared using the procedure described for Example 18, using 4-(4-fluoropiperidine-1-carbonyl)-N-(2-hydroxy-2-methylpropyl)thiazole-2-carboxamide (Intermediate 6/1) in place of (S)—N-(2-hydroxy-2-methylpropyl)-4-(2-methylpyrrolidine-1-carbonyl)thiazole-2-carboxamide. $^1$H NMR (CDCl$_3$, 500 MHz) δ ppm 8.91 (s, 1H), 8.05 (s, 1H), 7.61-7.54 (m, 1H), 6.67 (br s, 1H), 3.9-3.89 (m, 1H), 3.66-3.58 (m, 2H), 3.51 (d, J=6.3 Hz, 2H), 3.50-3.44 (m, 1H), 1.97-1.75 (m, 4H), 1.35 (s, 6H), 4.97-4.82 (m, 1H). MS (ESI): m/z 641.0 [M+H]$^+$.

Example 18/3

(S)-5-(6-(1,1,1,3,3,3-Hexafluoro-2-hydroxypropan-2-yl)-4-methylpyridin-3-yl)-N-(2-hydroxy-2-methylpropyl)-4-(2-methylpyrrolidine-1-carbonyl)thiazole-2-carboxamide

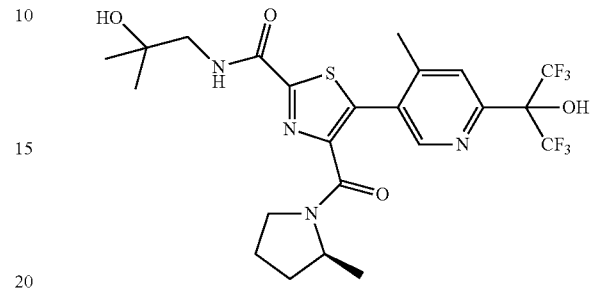

The title compound was prepared using the procedure described for Example 18, using 2-(5-bromo-4-methylpyridin-2-yl)-1,1,1,3,3,3-hexafluoropropan-2-ol (Intermediate 23/1) in place of 2-(5-bromo-4-(trifluoromethyl)pyridin-2-yl)-1,1,1,3,3,3-hexafluoropropan-2-ol. $^1$H NMR (CDCl$_3$, 500 MHz) δ 8.70 (s, 1H), 7.66-7.60 (m, 1H), 7.55-7.47 (m, 1H), 4.47-4.40 (m, 1H), 3.83-3.72 (m, 1H), 3.49-3.45 (m, 2H), 3.30-3.12 (m, 2H), 2.61-2.59 (m, 3H), 2.14-2.10 (m, 2H), 1.93-1.88 (m, 1H), 1.85-1.77 (m, 1H), 1.68-1.62 (m, 1H), 1.41-1.39 (m, 2H), 1.31 (s, 6H), 0.90 (d, J=6.5 Hz, 1H). MS (ESI): m/z 569.0 [M+H]$^+$.

Example 19

(S)-5-(4-(1,1,1,3,3,3-Hexafluoro-2-hydroxypropan-2-yl)-2-methylphenyl)-N-(2-hydroxy-2-methylpropyl)-4-(2-methylpyrrolidine-1-carbonyl)thiazole-2-carboxamide

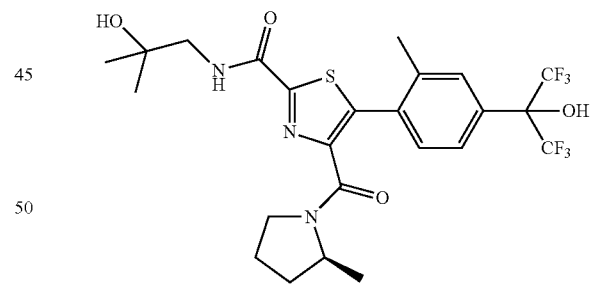

To an oven-dried vial was added (S)—N-(2-hydroxy-2-methylpropyl)-4-(2-methylpyrrolidine-1-carbonyl)thiazole-2-carboxamide (92 mg, 0.3 mmol, Intermediate 15/1), 2-(4-bromo-3-methylphenyl)-1,1,1,3,3,3-hexafluoropropan-2-ol (100 mg, 0.3 mmol, Intermediate 3/2), pivalic acid (12 mg, 0.12 mmol), K$_2$CO$_3$ (164 mg, 1.19 mmol) and butyronitrile (sparged with N$_2$ for 1 hour). The mixture was sparged with N$_2$ for 30 minutes, then bis(tri-tert-butylphosphine)palladium(0) (15 mg, 0.03 mmol) was added and the mixture sparged with N$_2$ for an additional 2 minutes. The resulting mixture was stirred at 100° C. for 16.5 h, cooled to rt and quenched by the addition of water (15 mL). The mixture was extracted with EtOAc (2×20 mL) and the combined organic layers were washed with brine, dried over anhydrous Na₂SO₄, filtered and concentrated to dryness. The residue was purified by prep-HPLC and the product fractions concentrated to dryness. The residue was partitioned between saturated aqueous NaHCO₃ (15 mL) and DCM (15 mL), and the aqueous further extracted with DCM (15 mL). The organic layers were combined, dried over anhydrous Na₂SO₄, filtered and concentrated to dryness to provide the title compound as a yellow foam. ¹H NMR (CDCl₃, 500 MHz) δ 7.67-7.60 (m, 2H), 7.59-7.54 (m, 1H), 7.44-7.40 (m, 1H), 4.25-4.18 (m, 1H), 4.14-3.87 (m, 1H), 3.57-3.03 (m, 4H), 2.40-2.36 (m, 3H), 2.16-1.86 (m, 2H), 1.79-1.72 (m, 1H), 1.67-1.62 (m, 1H), 1.47-1.39 (m, 1H), 1.31 (s, 6H), 1.12 (d, J=6.3 Hz, 2H), 0.97 (d, J=6.4 Hz, 1H). MS (ESI): m/z 568.0 [M+H]⁺.

Example 19/1

(R)-5-(4-(1,1,1,3,3,3-Hexafluoro-2-hydroxypropan-2-yl)-2-methylphenyl)-N-(2-hydroxy-2-methylpropyl)-4-(2-methylpyrrolidine-1-carbonyl)thiazole-2-carboxamide

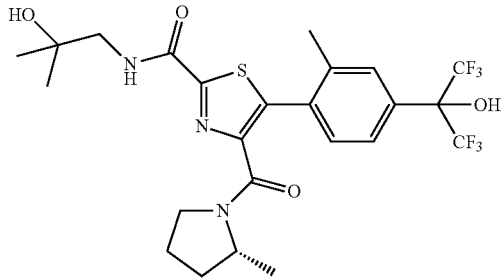 [SMILES: Cc1cc(C(O)(C(F)(F)F)C(F)(F)F)ccc1-c1sc(C(=O)NCC(C)(C)O)nc1C(=O)N1CCC[C@H]1C]

The title compound was prepared using the procedure described for Example 19, using (R)—N-(2-hydroxy-2-methylpropyl)-4-(2-methylpyrrolidine-1-carbonyl)thiazole-2-carboxamide (Intermediate 15/2) in place of (S)—N-(2-hydroxy-2-methylpropyl)-4-(2-methylpyrrolidine-1-carbonyl)thiazole-2-carboxamide. ¹H NMR (CDCl₃, 500 MHz) δ 7.67-7.59 (m, 2H), 7.59-7.54 (m, 1H), 7.46-7.42 (m, 1H), 4.24-3.88 (m, 1H), 3.55-3.06 (m, 4H), 2.41-2.37 (m, 3H), 2.02-1.88 (m, 2H), 1.79-1.71 (m, 1H), 1.68-1.60 (m, 1H), 1.48-1.38 (m, 1H), 1.32 (s, 6H), 1.13 (d, J=6.3 Hz, 2H), 0.98 (d, J=6.5 Hz, 1H). MS (ESI): m/z 568.0 [M+H]⁺.

Example 19/2

(S)-5-(4-(1,1,1,3,3,3-Hexafluoro-2-hydroxypropan-2-yl)-2-methylphenyl)-N-((1-hydroxycyclobutyl)methyl)-4-(2-methylpyrrolidine-1-carbonyl)thiazole-2-carboxamide

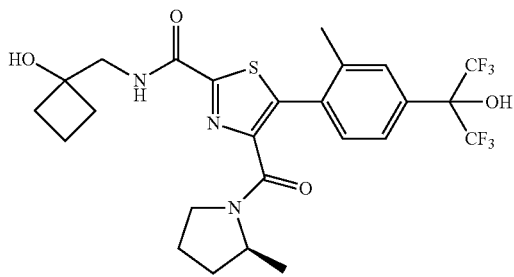

The title compound was prepared using the procedure described for Example 19, using (S)—N-((1-hydroxycyclobutyl)methyl)-4-(2-methylpyrrolidine-1-carbonyl)thiazole-2-carboxamide (Intermediate 28) in place of (S)—N-(2-hydroxy-2-methylpropyl)-4-(2-methylpyrrolidine-1-carbonyl)thiazole-2-carboxamide. ¹H NMR (CDCl₃, 500 MHz) δ 7.74-7.63 (m, 2H), 7.59-7.53 (m, 1H), 7.42-7.37 (m, 1H), 5.04-4.90 (m, 1H), 4.24-4.16 (m, 1H), 3.92-3.47 (m, 3H), 3.23-3.01 (m, 2H), 2.38-2.35 (m, 3H), 2.18-2.06 (m, 4H), 2.00-1.86 (m, 1H), 1.81-1.72 (m, 2H), 1.66-1.51 (m, 2H), 1.46-1.38 (m, 1H), 1.11 (d, J=6.3 Hz, 2H), 0.96 (d, J=6.4 Hz, 1H). MS (ESI): m/z 580.0 [M+H]⁺.

Example 20

(S)-5-(4-(1,1,1,3,3,3-Hexafluoro-2-hydroxypropan-2-yl)-2-(trifluoromethoxy)phenyl)-N-(2-hydroxy-2-methylpropyl)-4-(2-methylpyrrolidine-1-carbonyl)thiazole-2-carboxamide

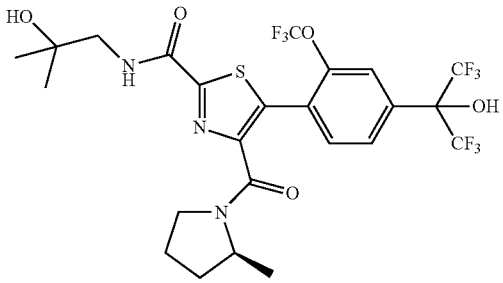 [SMILES: C[C@H]1CCCN1C(=O)c1nc(C(=O)NCC(C)(C)O)sc1-c1ccc(C(O)(C(F)(F)F)C(F)(F)F)cc1OC(F)(F)F]

To an oven-dried vial was added (S)—N-(2-hydroxy-2-methylpropyl)-4-(2-methylpyrrolidine-1-carbonyl)thiazole-2-carboxamide (82 mg, 0.26 mmol, Intermediate 15/1), 2-(4-bromo-3-(trifluoromethoxy)phenyl)-1,1,1,3,3,3-hexafluoropropan-2-ol (110 mg, 0.26 mmol, Intermediate 4/1), Pd(OAc)₂ (12 mg, 0.052 mmol), tricyclohexylphosphonium tetrafluoroborate (19 mg, 0.052 mmol), pivalic acid (3.5 mg, 0.034 mmol) and K₂CO₃ (72.5 mg, 0.52 mmol). The vial placed under N₂, then DMA (1.6 mL) was added and the resulting mixture was stirred at 100° C. for 14.5 h. The mixture was cooled to rt, filtered through Celite® and washed with EtOAc and the organics were concentrated to dryness. The residue was resubjected to the reaction conditions. To the residue was added tricyclohexylphosphonium tetrafluoroborate (19 mg, 0.052 mmol), pivalic acid (3.5 mg, 0.034 mmol) and K₂CO₃ (72.5 mg, 0.52 mmol). The vial was palced under N₂, then DMA (1.6 mL) was added and the resulting mixture was stirred at 100° C. for 16 h, then cooled to rt, quenched with water (15 mL), then extracted with EtOAc (2×20 mL). The combined organics were washed with brine, dried over Na₂SO₄, filtered and concentrated to dryness. The residue was purified by prep-HPLC followed by FCC on silica gel (0-5% MeOH/DCM) to provide the title compound as a light yellow oil. ¹H NMR (CDCl₃, 500 MHz) δ ppm 7.74 (s, 1H), 7.68-7.58 (m, 3H), 5.27-5.19 (m, 1H), 4.32-4.01 (m, 1H), 3.63-3.36 (m, 4H), 2.09-2.01 (m, 2H), 1.93-1.75 (m, 2H), 1.59-1.53 (m, 1H), 1.33-1.30 (m, 6H), 1.26 (d, J=6.2 Hz, 2H), 1.02 (d, J=6.4 Hz, 1H). MS (ESI): m/z 638.0 [M+H]⁺.

Example 21

(S)-4-(4,4-Difluoro-2-methylpyrrolidine-1-carbonyl)-5-(4-(1,1,1,3,3,3-hexafluoro-2-hydroxypropan-2-yl)-2-methylphenyl)-N-(2-hydroxy-2-methylpropyl)thiazole-2-carboxamide

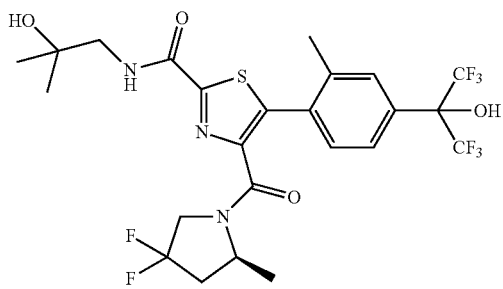 [SMILES: Cc1cc(C(O)(C(F)(F)F)C(F)(F)F)ccc1-c1sc(C(=O)NCC(C)(C)O)nc1C(=O)N1CC(F)(F)C[C@@H]1C]

To an oven-dried vial was added (S)-4-(4,4-difluoro-2-methylpyrrolidine-1-carbonyl)-N-(2-hydroxy-2-methylpropyl)thiazole-2-carboxamide (113 mg, 0.33 mmol, Intermediate 15/5), 2-(4-bromo-3-methylphenyl)-1,1,1,3,3,3-hexafluoropropan-2-ol (100 mg, 0.3 mmol, Intermediate 3/2), Pd(OAc)$_2$ (13 mg, 0.059 mmol), di-(1-adamantyl)-N-butyphosphine (22.4 mg, 0.059 mmol), pivalic acid (12 mg, 0.12 mmol) and K$_2$CO$_3$ (164 mg, 1.19 mmol). The vial was placed under N$_2$, then DMA (1.9 mL) was added and the resulting mixture stirred at 100° C. for 16 h. The mixture was cooled to rt, filtered through Celite® and washed with EtOAc and the organics were concentrated to dryness. The residue was resubjected to the reaction conditions. To the residue was added Pd(OAc)$_2$ (13 mg, 0.059 mmol), di-(1-adamantyl)-N-butyphosphine (22.4 mg, 0.059 mmol), pivalic acid (12 mg, 0.12 mmol) and K$_2$CO$_3$ (164 mg, 1.19 mmol). The vial was placed under N2, then DMA (1.9 mL) was added and the resulting mixture was stirred at 100° C. for 17.5 h. The reaction mixture was cooled to rt, quenched with water, then extracted with EtOAc (15 mL). The aqueous was further extracted with EtOAc (20 mL). The organics were then combined, washed with brine, dried over Na$_2$SO$_4$, filtered and concentrated to dryness. The residue was purified by prep-HPLC followed by FCC on silica gel (EtOAc/DCM 0-70%) to provide the title compound as a clear colorless oil. $^1$H NMR (CDCl$_3$, 500 MHz) δ 7.68-7.64 (m, 1H), 7.61-7.55 (m, 2H), 7.38 (d, J=8.3 Hz, 1H), 4.55-4.34 (m, 1H), 4.07-3.66 (m, 2H), 3.55-3.42 (m, 2H), 2.60-2.45 (m, 1H), 2.35-2.32 (m, 3H), 1.62-1.59 (m, 3H), 1.34-1.31 (m, 6H), 1.29 (d, J=6.5 Hz, 2H), 1.17 (d, J=6.5 Hz, 1H). MS (ESI): m/z 604.0 [M+H]$^+$.

Example 21/1

(S)-5-(2,3-Difluoro-4-(1,1,1,3,3,3-hexafluoro-2-hydroxypropan-2-yl)phenyl)-N-(2-hydroxy-2-methylpropyl)-4-(2-methylpyrrolidine-1-carbonyl)thiazole-2-carboxamide

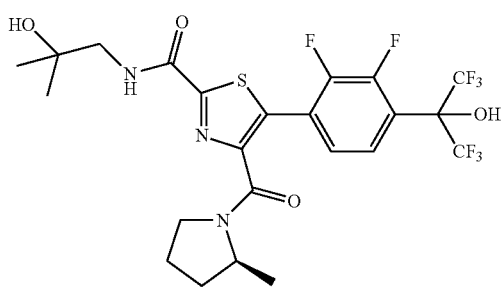 [SMILES: C[C@H]1CCCN1C(=O)c1nc(C(=O)NCC(C)(C)O)sc1-c1ccc(C(O)(C(F)(F)F)C(F)(F)F)c(F)c1F]

The title compound was prepared using the procedure described for Example 21, using (S)—N-(2-hydroxy-2-methylpropyl)-4-(2-methylpyrrolidine-1-carbonyl)thiazole-2-carboxamide (Intermediate 15/1) in place of (S)-4-(4,4-difluoro-2-methylpyrrolidine-1-carbonyl)-N-(2-hydroxy-2-methylpropyl)thiazole-2-carboxamide and 2-(4-bromo-2,3-difluorophenyl)-1,1,1,3,3,3-hexafluoropropan-2-ol (Intermediate 3/3) in place of 2-(4-bromo-3-methylphenyl)-1,1,1,3,3,3-hexafluoropropan-2-ol. $^1$H NMR (CDCl$_3$, 400 MHz) δ ppm 7.65-7.52 (m, 2H), 7.41-7.32 (m, 1H), 5.42 (s, 1H), 4.37-4.09 (m, 1H), 3.71-3.34 (m, 4H), 2.14-1.77 (m, 4H), 1.31 (s, 6H), 1.29 (d, J=6.3 Hz, 2H), 1.02 (d, J=6.5 Hz, 1H). MS (ESI): m/z 590.1 [M+H]$^+$.

Example 21/2

(S)-5-(4-(1,1,1,3,3,3-Hexafluoro-2-hydroxypropan-2-yl)-2-methylphenyl)-N-(2-hydroxy-2-methylpropyl)-4-(2-methylpiperidine-1-carbonyl)thiazole-2-carboxamide

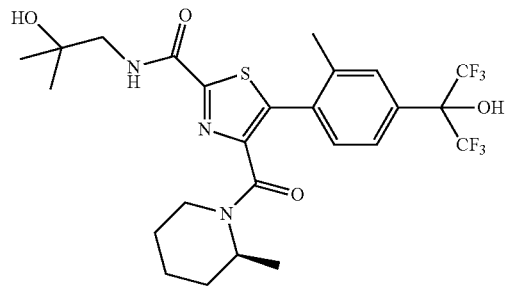 [SMILES: Cc1cc(C(O)(C(F)(F)F)C(F)(F)F)ccc1-c1sc(C(=O)NCC(C)(C)O)nc1C(=O)N1CCCC[C@@H]1C]

The title compound was prepared using the procedure described for Example 21, using (S)—N-(2-hydroxy-2-methylpropyl)-4-(2-methylpiperidine-1-carbonyl)thiazole-2-carboxamide (Intermediate 15/3) in place of (S)-4-(4,4-difluoro-2-methylpyrrolidine-1-carbonyl)-N-(2-hydroxy-2-methylpropyl)thiazole-2-carboxamide. $^1$H NMR (CDCl$_3$, 500 MHz) δ 7.72-7.65 (m, 2H), 7.62-7.57 (m, 1H), 7.46-7.39 (m, 1H), 4.89-4.41 (m, 1H), 4.40 (s, 1H), 3.76-3.15 (m, 3H), 2.82-2.69 (m, 1H), 2.40 (s, 3H), 2.24-2.16 (m, 1H), 1.63-1.61 (m, 3H), 1.49-1.36 (m, 3H), 1.31 (s, 6H), 1.01 (d, J=6.9 Hz, 3H). MS (ESI): m/z 582.0 [M+H]$^+$.

Example 21/3

4-(7-Azabicyclo[2.2.1]heptane-7-carbonyl)-5-(4-(1,1,1,3,3,3-hexafluoro-2-hydroxypropan-2-yl)-2-methylphenyl)-N-(2-hydroxy-2-methylpropyl)thiazole-2-carboxamide

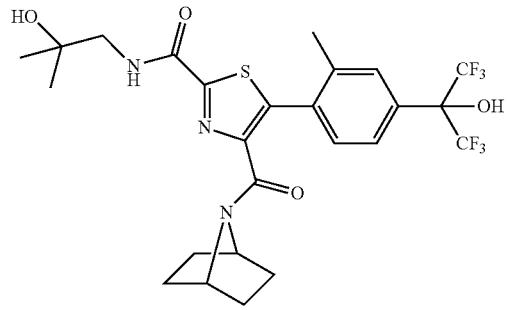 [SMILES: Cc1cc(C(O)(C(F)(F)F)C(F)(F)F)ccc1-c1sc(C(=O)NCC(C)(C)O)nc1C(=O)N1C2CCC1CC2]

The title compound was prepared using the procedure described for Example 21, using 4-(7-azabicyclo[2.2.1]heptane-7-carbonyl)-N-(2-hydroxy-2-methylpropyl)thiazole-2-carboxamide (Intermediate 15/4) in place of (S)-4-(4,4-difluoro-2-methylpyrrolidine-1-carbonyl)-N-(2-hydroxy-2-methylpropyl)thiazole-2-carboxamide. ¹H NMR (CDCl₃, 500 MHz) δ 7.74-7.69 (m, 1H), 7.68-7.65 (m, 1H), 7.62-7.58 (m, 1H), 7.43 (d, J=8.2 Hz, 1H), 4.68-4.61 (m, 2H), 3.81-3.75 (m, 1H), 3.47 (d, J=6.4 Hz, 2H), 2.40 (s, 3H), 2.30 (s, 1H), 1.66-1.65 (m, 3H), 1.40-1.33 (m, 2H), 1.31 (s, 6H), 1.24-1.20 (m, 1H), 1.11-1.00 (m, 2H). MS (ESI): m/z 580.0 [M+H]⁺.

Example 22

4-(4-Cyanopiperidine-1-carbonyl)-5-(2-(difluoromethyl)-4-(1,1,1,3,3,3-hexafluoro-2-hydroxypropan-2-yl)phenyl)-N-(2-hydroxy-2-methylpropyl)thiazole-2-carboxamide

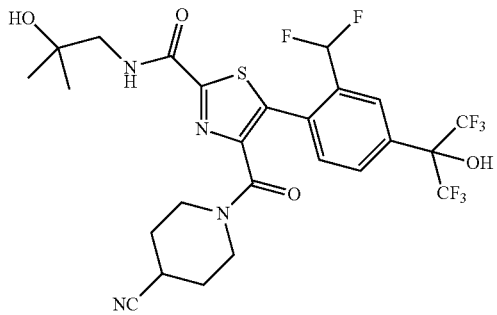 [SMILES: CC(C)(O)CNC(=O)c1nc(C(=O)N2CCC(C#N)CC2)c(-c2ccc(C(O)(C(F)(F)F)C(F)(F)F)cc2C(F)F)s1]

The title compound was prepared as described in Intermediate 14, final step using 5-(2-(difluoromethyl)-4-(1,1,1,3,3,3-hexafluoro-2-hydroxypropan-2-yl)phenyl)-2-(2-hydroxy-2-methylpropyl)carbamoyl)thiazole-4-carboxylic acid (Intermediate 21) in place of 5-(2,3-dichloro-4-(1,1,1,3,3,3-hexafluoro-2-hydroxypropan-2-yl)phenyl)-2-(ethoxycarbonyl)thiazole-4-carboxylic acid and piperidine-4-carbonitrile in place of (S)-4,4-difluoro-2-methylpyrrolidine hydrochloride. ¹H NMR (CDCl₃, 300 MHz): δ ppm 8.10 (s, 1H), 7.90 (d, J=9.6 Hz, 1H), 7.60-7.54 (m, 2H), 6.79 (t, J=54.9 Hz, 1H), 4.42 (s, 1H), 3.76-3.38 (m, 6H), 2.83 (t, J=5.6 Hz, 1H), 1.82-1.60 (m, 4H), 1.33 (s, 6H). MS (ESI): m/z 629.1 [M+H]⁺.

Example 22/1

(R)-5-(2-(Difluoromethyl)-4-(1,1,1,3,3,3-hexafluoro-2-hydroxypropan-2-yl)phenyl)-N-(2-hydroxy-2-methylpropyl)-4-(2-(hydroxymethyl)pyrrolidine-1-carbonyl)thiazole-2-carboxamide

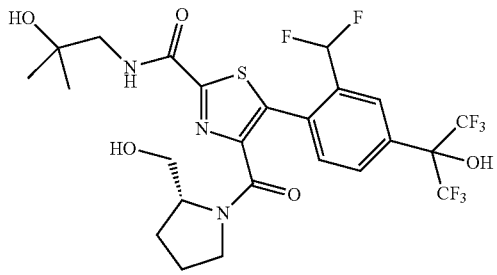 [SMILES: CC(C)(O)CNC(=O)c1nc(C(=O)N2CCC[C@@H]2CO)c(-c2ccc(C(O)(C(F)(F)F)C(F)(F)F)cc2C(F)F)s1]

The title compound was prepared as described in Intermediate 14, final step using 5-(2-(difluoromethyl)-4-(1,1,1,
3,3,3-hexafluoro-2-hydroxypropan-2-yl)phenyl)-2-(2-hydroxy-2-methylpropyl)carbamoyl)thiazole-4-carboxylic acid (Intermediate 21) in place of 5-(2,3-dichloro-4-(1,1,1,3,3,3-hexafluoro-2-hydroxypropan-2-yl)phenyl)-2-(ethoxycarbonyl)thiazole-4-carboxylic acid and (R)-pyrrolidin-2-ylmethanol in place of (S)-4,4-difluoro-2-methylpyrrolidine hydrochloride. ¹H NMR (CDCl₃, 300 MHz, mixture of rotamers): δ ppm 8.07 (s, 1H), 7.92-7.85 (m, 1H), 7.66-7.62 (m, 1H), 7.51-7.42 (m, 1H), 6.72 (t, J=54.9 Hz, 1H), 5.94 (br s, 1H), 4.59-1.58 (m, 13H), 1.31 (s, 6H). MS (ESI): m/z 620.1 [M+H]⁺.

Example 23

(S)-5-(4-(1,1,1,3,3,3-hexafluoro-2-hydroxypropan-2-yl)-2-methoxyphenyl)-N-(2-hydroxy-2-methylpropyl)-4-(2-methylpiperidine-1-carbonyl)thiazole-2-carboxamide

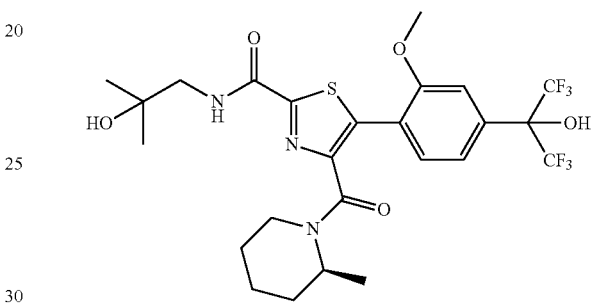

The title compound was prepared as described in Example 15/2, using 2-(4-bromo-3-methoxyphenyl)-1,1,1,3,3,3-hexafluoropropan-2-ol in place of 2-(4-bromo-3-(difluoromethyl)phenyl)-1,1,1,3,3,3-hexafluoropropan-2-ol and 2-(4-bromo-3-methoxyphenyl)-1,1,1,3,3,3-hexafluoropropan-2-ol in place of 2-(4-bromo-3-(difluoromethyl)phenyl)-1,1,1,3,3,3-hexafluoropropan-2-ol. ¹H NMR (400 MHz, CDCl₃) δ 7.72-7.67 (m, 1H), 7.58-7.53 (m, 1H), 7.41-7.37 (m, 1H), 7.34 (d, J=8.3 Hz, 1H), 4.95 (s, 0.5H), 4.66 (s, 1H), 4.54-4.51 (m, 0.5H), 3.91 (s, 3H), 3.71-3.64 (m, 0.5H), 3.46 (d, J=6.4 Hz, 2H), 3.17 (d, J=13.7 Hz, 0.5H), 2.82-2.75 (m, 1H), 2.35 (s, 0.5H), 2.31 (s, 0.5H), 1.68-1.41 (m, 4H), 1.32-1.18 (m, 7H), 1.13 (d, J=7.0 Hz, 1.5H), 1.04-0.90 (m, 1.5H), 0.86-0.74 (m, 0.5H), 0.65-0.53 (m, 0.5H). MS (ESI): m/z 598.2 [M+H]⁺.

Example 24

(S)-4-(4,4-difluoro-2-methylpyrrolidine-1-carbonyl)-5-(4-(1,1,1,3,3,3-hexafluoro-2-hydroxypropan-2-yl)-2-methoxyphenyl)-N-(2-hydroxy-2-methylpropyl)thiazole-2-carboxamide

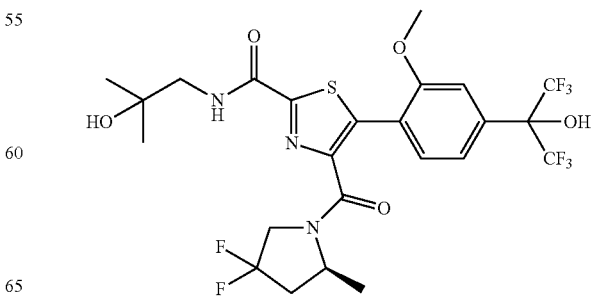

The title compound was prepared as described in Example 15/2, using (S)-4-(4,4-difluoro-2-methylpyrrolidine-1-carbonyl)-N-(2-hydroxy-2-methylpropyl)thiazole-2-carboxamide in place of (S)—N-(2-hydroxy-2-methylpropyl)-4-(2-methylpiperidine-1-carbonyl)thiazole-2-carboxamide and 2-(4-bromo-3-methoxyphenyl)-1,1,1,3,3,3-hexafluoropropan-2-ol in place of 2-(4-bromo-3-(difluoromethyl)phenyl)-1,1,1,3,3,3-hexafluoropropan-2-ol. $^1$H NMR (400 MHz, CDCl$_3$) δ 7.60 (t, J=6.3 Hz, 1H), 7.52-7.47 (m, 1H), 7.39-7.31 (m, 2H), 4.59-4.51 (m, 1H), 4.32 (s, 1H), 3.90-3.88 (m, 3H), 3.77-3.57 (m, 2H), 3.54-3.39 (m, 2H), 2.64-2.47 (m, 1H), 2.14-1.96 (m, 2H), 1.38 (d, J=6.4 Hz, 2H), 1.31 (d, J=2.6 Hz, 6H), 1.07 (d, J=6.6 Hz, 1H). MS (ESI): m/z 620.05 [M+H]$^+$.

The compounds of Example 25-45 can be made according to the procedures described below.

Example 25

Step a

Ethyl 5-(2-(difluoromethyl)-4-(1,1,1,3,3,3-hexafluoro-2-hydroxypropan-2-yl)phenyl)-4-(hydroxymethyl)thiazole-2-carboxylate

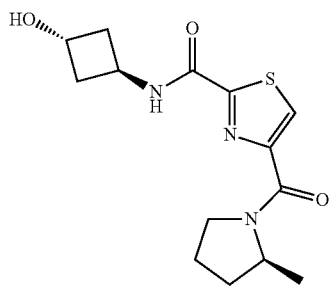

The title compound can be prepared as described in Intermediate 14, step b, using 2-(4-bromo-3-(difluoromethyl)phenyl)-1,1,1,3,3,3-hexafluoropropan-2-ol (Intermediate 18) in place of 2-(4-bromo-2,3-dichlorophenyl)-1,1,1,3,3,3-hexafluoropropan-2-ol.

Example 25 trans-3-(5-(2-(Difluoromethyl)-4-(1,1,1,3,3,3-hexafluoro-2-hydroxypropan-2-yl)phenyl)-4-((S)-2-methylpyrrolidine-1-carbonyl)thiazole-2-carboxamido)cyclobutanecarboxylic acid

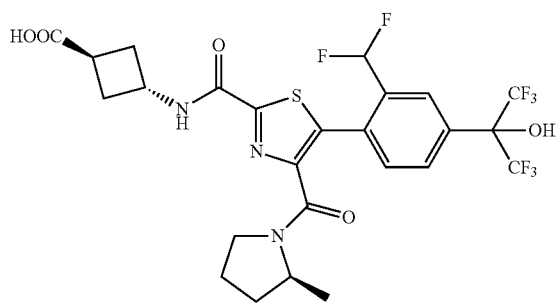

The title compound can be prepared as described in Example 12, using in step a ethyl 5-(2-(difluoromethyl)-4-(1,1,1,3,3,3-hexafluoro-2-hydroxypropan-2-yl)phenyl)-4-(hydroxymethyl)thiazole-2-carboxylate (Example 25, step a) in place of ethyl 5-(2,3-dichloro-4-(1,1,1,3,3,3-hexafluoro-2-hydroxypropan-2-yl)phenyl)-4-(hydroxymethyl)thiazole-2-carboxylate and in step d (S)-2-methylpyrrolidine in place of ethyl-(2,2,2-trifluoro-ethyl)-amine hydrochloride.

Example 26

Step a

N-(trans-3-Hydroxycyclobutyl)-4-((S)-2-methylpyrrolidine-1-carbonyl)thiazole-2-carboxamide

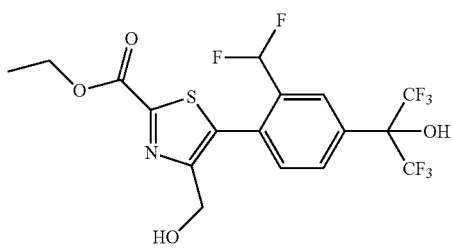 [SMILES: CCOC(=O)c1nc(CO)c(-c2ccc(C(O)(C(F)(F)F)C(F)(F)F)cc2C(F)F)s1]

The title compound can be prepared as described in Intermediate 15, using in step a (S)-2-methylpyrrolidine in place of (S)-4,4-difluoro-2-methylpyrrolidine hydrochloride and in the final step trans-3-aminocyclobutanol in place of (3R,5S)-piperidine-3,5-diol hydrochloride.

Example 26

5-(2-(Difluoromethyl)-4-(1,1,1,3,3,3-hexafluoro-2-hydroxypropan-2-yl)phenyl)-N-(trans-3-hydroxycyclobutyl)-4-((S)-2-methylpyrrolidine-1-carbonyl)thiazole-2-carboxamide

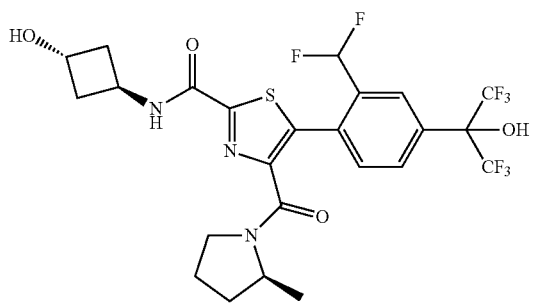 [SMILES: C[C@H]1CCCN1C(=O)c1nc(C(=O)N[C@H]2C[C@H](O)C2)sc1-c1ccc(C(O)(C(F)(F)F)C(F)(F)F)cc1C(F)F]

The title compound can be prepared as described in Example 15, using N-(trans-3-hydroxycyclobutyl)-4-((S)-2-methylpyrrolidine-1-carbonyl)thiazole-2-carboxamide (Example 26, step a) in place of (S)—N-(2-hydroxy-2-methylpropyl)-4-(2-methylpyrrolidine-1-carbonyl)thiazole-2-carboxamide.

Example 27

Step a (S)-Methyl 2,2-dimethyl-3-(4-(2-methylpyrrolidine-1-carbonyl)thiazole-2-carboxamido)propanoate

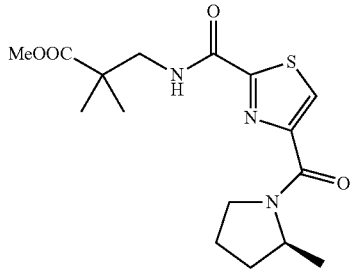 [SMILES: COC(=O)C(C)(C)CNC(=O)c1nc(C(=O)N2CCC[C@@H]2C)cs1]

The title compound can be prepared as described in Intermediate 15, using in step a (S)-2-methylpyrrolidine in place of (S)-4,4-difluoro-2-methylpyrrolidine hydrochloride and in the final step methyl 3-amino-2,2-dimethylpropanoate in place of (3R,5S)-piperidine-3,5-diol hydrochloride.

Example 27

Step b (S)-Methyl 3-(5-(2-(difluoromethyl)-4-(1,1,1,3,3,3-hexafluoro-2-hydroxypropan-2-yl)phenyl)-4-(2-methylpyrrolidine-1-carbonyl)thiazole-2-carboxamido)-2,2-dimethylpropanoate

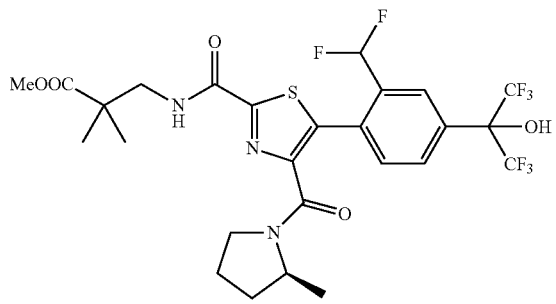 [SMILES: COC(=O)C(C)(C)CNC(=O)c1nc(C(=O)N2CCC[C@@H]2C)c(-c2ccc(C(O)(C(F)(F)F)C(F)(F)F)cc2C(F)F)s1]

The title compound can be prepared as described in Example 15, using (S)-methyl 2,2-dimethyl-3-(4-(2-methylpyrrolidine-1-carbonyl)thiazole-2-carboxamido)propanoate (Example 27, step a) in place of (S)—N-(2-hydroxy-2-methylpropyl)-4-(2-methylpyrrolidine-1-carbonyl)thiazole-2-carboxamide.

(S)-3-(5-(2-(Difluoromethyl)-4-(1,1,1,3,3,3-hexafluoro-2-hydroxypropan-2-yl)phenyl)-4-(2-methylpyrrolidine-1-carbonyl)thiazole-2-carboxamido)-2,2-dimethylpropanoic acid

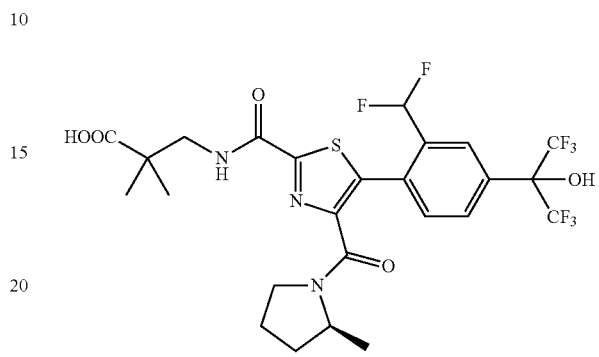

The title compound can be prepared as described in Example 12, using in the final step (S)-methyl 3-(5-(2-(difluoromethyl)-4-(1,1,1,3,3,3-hexafluoro-2-hydroxypropan-2-yl)phenyl)-4-(2-methylpyrrolidine-1-carbonyl)thiazole-2-carboxamido)-2,2-dimethylpropanoate (Example 27, step b) in place of trans-methyl 3-(5-(2,3-dichloro-4-(1,1,1,3,3,3-hexafluoro-2-hydroxypropan-2-yl)phenyl)-4-(ethyl(2,2,2-trifluoroethyl)carbamoyl)thiazole-2-carboxamido)cyclobutane-carboxylate.

Example 28

Step a (S)—N-(1,1-Dioxidothietan-3-yl)-4-(2-methylpyrrolidine-1-carbonyl)thiazole-2-carboxamide

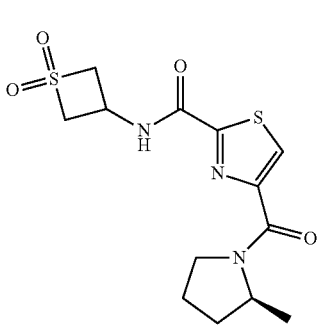 [SMILES: C[C@H]1CCCN1C(=O)c1csc(C(=O)NC2CS(=O)(=O)C2)n1]

The title compound can be prepared as described in Intermediate 15, using in step a (S)-2-methylpyrrolidine in place of (S)-4,4-difluoro-2-methylpyrrolidine hydrochloride and in the final step 3-aminothietane 1,1-dioxide in place of (3R,5S)-piperidine-3,5-diol hydrochloride.

Example 28

(S)-5-(2-(Difluoromethyl)-4-(1,1,1,3,3,3-hexafluoro-2-hydroxypropan-2-yl)phenyl)-N-(1,1-dioxidothietan-3-yl)-4-(2-methylpyrrolidine-1-carbonyl)thiazole-2-carboxamide

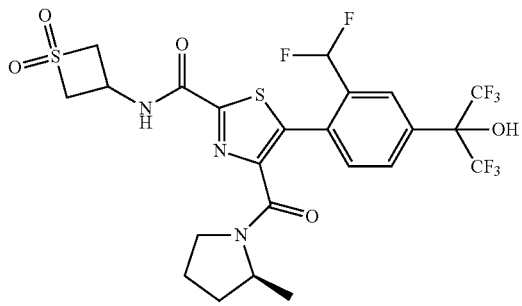 [SMILES: C[C@H]1CCCN1C(=O)c1nc(C(=O)NC2CS(=O)(=O)C2)sc1-c1ccc(C(O)(C(F)(F)F)C(F)(F)F)cc1C(F)F]

The title compound can be prepared as described in Example 15, using (S)—N-(1,1-dioxidothietan-3-yl)-4-(2-methylpyrrolidine-1-carbonyl)thiazole-2-carboxamide (Example 28, step a) in place of (S)—N-(2-hydroxy-2-methylpropyl)-4-(2-methylpyrrolidine-1-carbonyl)thiazole-2-carboxamide.

Example 29

(S)-5-(2-(Difluoromethyl)-4-(1,1,1,3,3,3-hexafluoro-2-hydroxypropan-2-yl)phenyl)-N-((1-hydroxycyclobutyl)methyl)-4-(2-methylpyrrolidine-1-carbonyl)thiazole-2-carboxamide

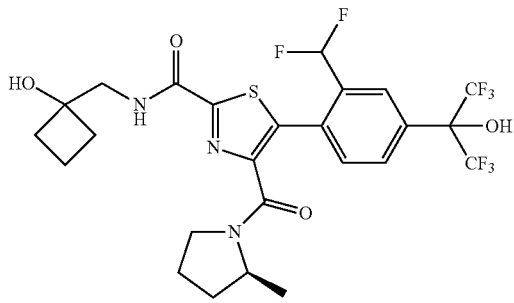 [SMILES: C[C@H]1CCCN1C(=O)c1nc(C(=O)NCC2(O)CCC2)sc1-c1ccc(C(O)(C(F)(F)F)C(F)(F)F)cc1C(F)F]

The title compound can be prepared using the procedure described for Example 19, using (S)—N-((1-hydroxycyclobutyl)methyl)-4-(2-methylpyrrolidine-1-carbonyl)thiazole-2-carboxamide (Intermediate 28) in place of (S)—N-(2-hydroxy-2-methylpropyl)-4-(2-methylpyrrolidine-1-carbonyl)thiazole-2-carboxamide and 2-(4-bromo-3-(difluoromethyl)phenyl)-1,1,1,3,3,3-hexafluoropropan-2-ol (Intermediate 18) in place of 2-(4-bromo-3-methylphenyl)-1,1,1,3,3,3-hexafluoropropan-2-ol.

Example 30

Step a (S)—N-((3-Hydroxyoxetan-3-yl)methyl)-4-(2-methylpyrrolidine-1-carbonyl)thiazole-2-carboxamide

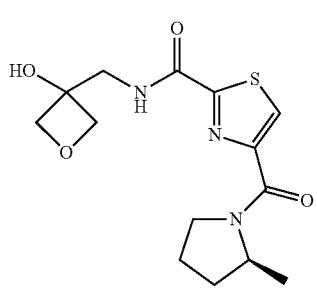

The title compound can be prepared as described in Intermediate 15, using in step a (S)-2-methylpyrrolidine in place of (S)-4,4-difluoro-2-methylpyrrolidine hydrochloride and in the final step 3-(aminomethyl)oxetan-3-ol in place of (3R,5S)-piperidine-3,5-diol hydrochloride.

Example 30

(S)-5-(2-(Difluoromethyl)-4-(1,1,1,3,3,3-hexafluoro-2-hydroxypropan-2-yl)phenyl)-N-((3-hydroxyoxetan-3-yl)methyl)-4-(2-methylpyrrolidine-1-carbonyl)thiazole-2-carboxamide

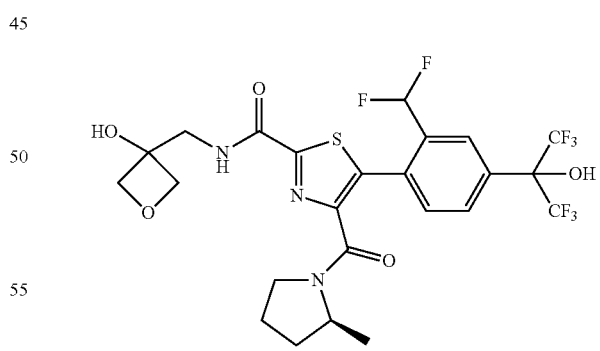

The title compound can be prepared as described in Example 15, using (S)—N-((3-hydroxyoxetan-3-yl)methyl)-4-(2-methylpyrrolidine-1-carbonyl)thiazole-2-carboxamide (Example 30, step a) in place of (S)—N-(2-hydroxy-2-methylpropyl)-4-(2-methylpyrrolidine-1-carbonyl)thiazole-2-carboxamide.

Example 31

Step a (S)-Methyl 1-((4-(2-methylpyrrolidine-1-carbonyl)thiazole-2-carboxamido)methyl)cyclopropanecarboxylate

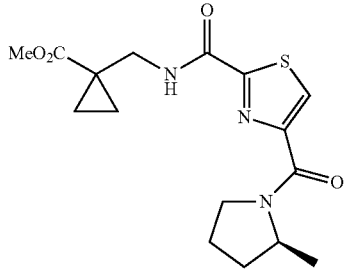 [SMILES: COC(=O)C1(CNC(=O)c2nc(C(=O)N3CCC[C@@H]3C)cs2)CC1]

The title compound can be prepared as described in Intermediate 15, using in step a (S)-2-methylpyrrolidine in place of (S)-4,4-difluoro-2-methylpyrrolidine hydrochloride and in the final step methyl 1-(aminomethyl)cyclopropanecarboxylate in place of (3R,5S)-piperidine-3,5-diol hydrochloride.

Example 31

Step b (S)-Methyl 1-((5-(2-(difluoromethyl)-4-(1,1,1,3,3,3-hexafluoro-2-hydroxypropan-2-yl)phenyl)-4-(2-methylpyrrolidine-1-carbonyl)thiazole-2-carboxamido)methyl)cyclopropanecarboxylate

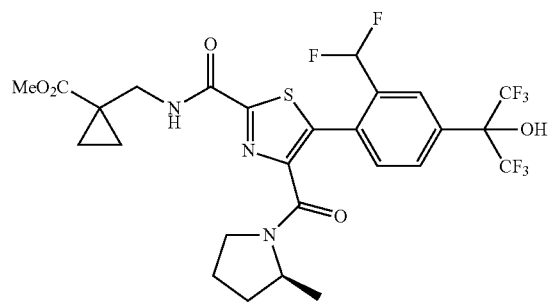 [SMILES: COC(=O)C1(CNC(=O)c2nc(C(=O)N3CCC[C@@H]3C)c(-c3ccc(C(O)(C(F)(F)F)C(F)(F)F)cc3C(F)F)s2)CC1]

The title compound can be prepared as described in Example 15, using (S)-methyl 1-((4-(2-methylpyrrolidine-1-carbonyl)thiazole-2-carboxamido)methyl)cyclopropanecarboxylate (Example 31, step a) in place of (S)—N-(2-hydroxy-2-methylpropyl)-4-(2-methylpyrrolidine-1-carbonyl)thiazole-2-carboxamide.

Example 31

(S)-1-((5-(2-(Difluoromethyl)-4-(1,1,1,3,3,3-hexafluoro-2-hydroxypropan-2-yl)phenyl)-4-(2-methylpyrrolidine-1-carbonyl)thiazole-2-carboxamido)methyl)cyclopropanecarboxylic acid

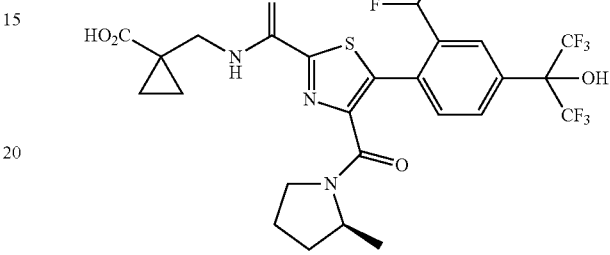

The title compound can be prepared as described in Example 12, using in the final step (S)-methyl 1-((5-(2-(difluoromethyl)-4-(1,1,1,3,3,3-hexafluoro-2-hydroxypropan-2-yl)phenyl)-4-(2-methylpyrrolidine-1-carbonyl)thiazole-2-carboxamido)methyl)cyclopropanecarboxylate (Example 31, step b) in place of trans-methyl 3-(5-(2,3-dichloro-4-(1,1,1,3,3,3-hexafluoro-2-hydroxypropan-2-yl)phenyl)-4-(ethyl(2,2,2-trifluoroethyl)carbamoyl)thiazole-2-carboxamido)cyclobutane-carboxylate.

Example 32

Step a (S)—N-((1-Hydroxycyclopropyl)methyl)-4-(2-methylpyrrolidine-1-carbonyl)thiazole-2-carboxamide

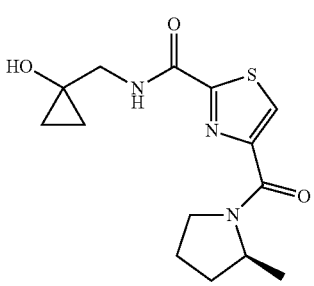 [SMILES: C[C@H]1CCCN1C(=O)c1csc(C(=O)NCC2(O)CC2)n1]

The title compound can be prepared as described in Intermediate 15, using in step a (S)-2-methylpyrrolidine in place of (S)-4,4-difluoro-2-methylpyrrolidine hydrochloride and in the final step 1-(aminomethyl)cyclopropanol in place of (3R,5S)-piperidine-3,5-diol hydrochloride.

Example 32

(S)-5-(2-(Difluoromethyl)-4-(1,1,1,3,3,3-hexafluoro-2-hydroxypropan-2-yl)phenyl)-N-((1-hydroxycyclopropyl)methyl)-4-(2-methylpyrrolidine-1-carbonyl)thiazole-2-carboxamide

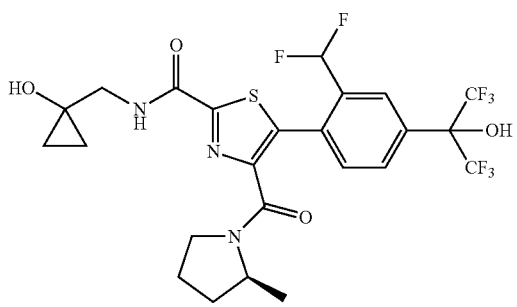 [SMILES: C[C@H]1CCCN1C(=O)c1nc(C(=O)NCC2(O)CC2)sc1-c1ccc(C(O)(C(F)(F)F)C(F)(F)F)cc1C(F)F]

The title compound can be prepared as described in Example 15, using (S)—N-((1-hydroxycyclopropyl)methyl)-4-(2-methylpyrrolidine-1-carbonyl)thiazole-2-carboxamide (Example 32, step a) in place of (S)—N-(2-hydroxy-2-methylpropyl)-4-(2-methylpyrrolidine-1-carbonyl)thiazole-2-carboxamide.

Example 33

Step a 4-((S)-2-Methylpyrrolidine-1-carbonyl)-N-(trans-3-(methylsulfonyl)cyclobutyl)thiazole-2-carboxamide

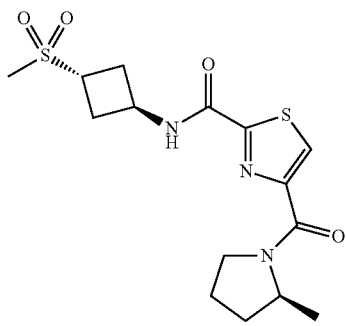 [SMILES: C[C@H]1CCCN1C(=O)c1csc(C(=O)N[C@H]2C[C@H](S(C)(=O)=O)C2)n1]

The title compound can be prepared as described in Intermediate 15, using in step a (S)-2-methylpyrrolidine in place of (S)-4,4-difluoro-2-methylpyrrolidine hydrochloride and in the final step trans-3-(methylsulfonyl)cyclobutanamine in place of (3R,5S)-piperidine-3,5-diol hydrochloride.

Example 33

5-(2-(Difluoromethyl)-4-(1,1,1,3,3,3-hexafluoro-2-hydroxypropan-2-yl)phenyl)-4-((S)-2-methylpyrrolidine-1-carbonyl)-N-(trans-3-(methylsulfonyl)cyclobutyl)thiazole-2-carboxamide

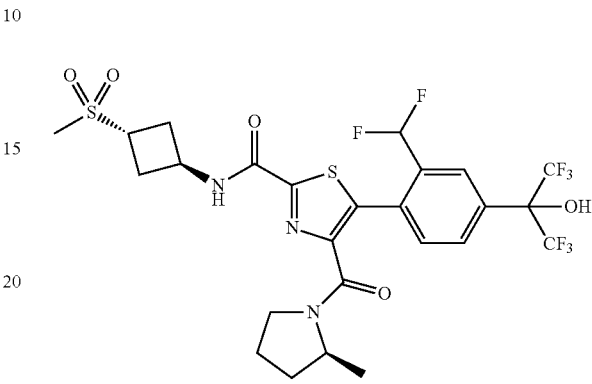

The title compound can be prepared as described in Example 15, using 4-((S)-2-methylpyrrolidine-1-carbonyl)-N-(trans-3-(methylsulfonyl)cyclobutyl)thiazole-2-carboxamide (Example 33, step a) in place of (S)—N-(2-hydroxy-2-methylpropyl)-4-(2-methylpyrrolidine-1-carbonyl)thiazole-2-carboxamide.

Example 34

Step a (S)—N-((4-Hydroxy-1,1-dioxidotetrahydro-2H-thiopyran-4-yl)methyl)-4-(2-methylpyrrolidine-1-carbonyl)thiazole-2-carboxamide

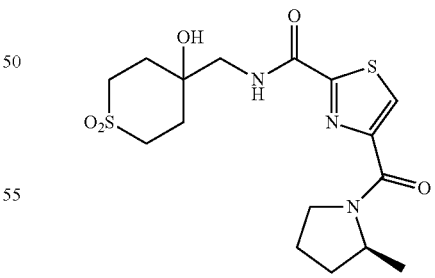

The title compound can be prepared as described in Intermediate 15, using in step a (S)-2-methylpyrrolidine in place of (S)-4,4-difluoro-2-methylpyrrolidine hydrochloride and in the final step 4-(aminomethyl)-4-hydroxytetrahydro-2H-thiopyran 1,1-dioxide in place of (3R,5S)-piperidine-3,5-diol hydrochloride.

Example 34

(S)-5-(2-(Difluoromethyl)-4-(1,1,1,3,3,3-hexafluoro-2-hydroxypropan-2-yl)phenyl)-N-((4-hydroxy-1,1-dioxidotetrahydro-2H-thiopyran-4-yl)methyl)-4-(2-methylpyrrolidine-1-carbonyl)thiazole-2-carboxamide

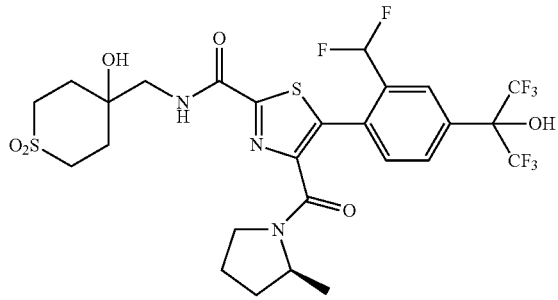 [SMILES: C[C@H]1CCCN1C(=O)c1nc(C(=O)NCC2(O)CCS(=O)(=O)CC2)sc1-c1ccc(C(O)(C(F)(F)F)C(F)(F)F)cc1C(F)F]

The title compound can be prepared as described in Example 15, using (S)—N-((4-hydroxy-1,1-dioxidotetrahydro-2H-thiopyran-4-yl)methyl)-4-(2-methylpyrrolidine-1-carbonyl)thiazole-2-carboxamide (Example 34, step a) in place of (S)—N-(2-hydroxy-2-methylpropyl)-4-(2-methylpyrrolidine-1-carbonyl)thiazole-2-carboxamide.

Example 35

Step a

Ethyl 5-(4-(1,1,1,3,3,3-hexafluoro-2-hydroxypropan-2-yl)-2-methylphenyl)-4-(hydroxymethyl)thiazole-2-carboxylate

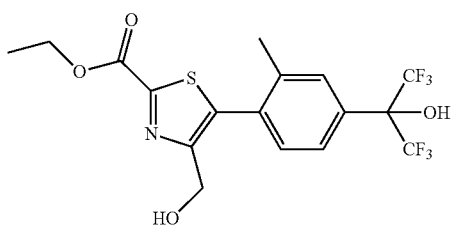 [SMILES: CCOC(=O)c1nc(CO)c(-c2ccc(C(O)(C(F)(F)F)C(F)(F)F)cc2C)s1]

The title compound can be prepared as described in Intermediate 14, step b, using 2-(4-bromo-3-methylphenyl)-1,1,1,3,3,3-hexafluoropropan-2-ol (Intermediate 3/2) in place of 2-(4-bromo-2,3-dichlorophenyl)-1,1,1,3,3,3-hexafluoropropan-2-ol.

Example 35 trans-3-(5-(4-(1,1,1,3,3,3-Hexafluoro-2-hydroxypropan-2-yl)-2-methylphenyl)-4-((S)-2-methylpyrrolidine-1-carbonyl)thiazole-2-carboxamido)cyclobutanecarboxylic acid

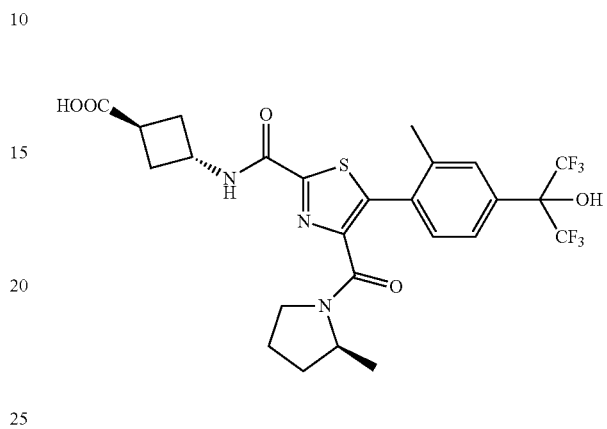

The title compound can be prepared as described in Example 12, using in step a ethyl 5-(4-(1,1,1,3,3,3-hexafluoro-2-hydroxypropan-2-yl)-2-methylphenyl)-4-(hydroxymethyl)thiazole-2-carboxylate (Example 35, step a) in place of ethyl 5-(2,3-dichloro-4-(1,1,1,3,3,3-hexafluoro-2-hydroxypropan-2-yl)phenyl)-4-(hydroxymethyl)thiazole-2-carboxylate and in step d (S)-2-methylpyrrolidine in place of ethyl-(2,2,2-trifluoro-ethyl)-amine hydrochloride.

Example 36

5-(4-(1,1,1,3,3,3-Hexafluoro-2-hydroxypropan-2-yl)-2-methylphenyl)-N-((1r,3S)-3-hydroxycyclobutyl)-4-((S)-2-methylpyrrolidine-1-carbonyl)thiazole-2-carboxamide

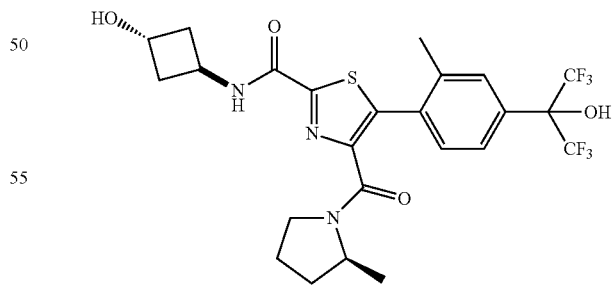

The title compound can be prepared as described in Example 26, using 2-(4-bromo-3-methylphenyl)-1,1,1,3,3,3-hexafluoropropan-2-ol (Intermediate 3/2) in place of 2-(4-bromo-3-(difluoromethyl)phenyl)-1,1,1,3,3,3-hexafluoropropan-2-ol.

Example 37

Step a (S)-Methyl 3-(5-(4-(1,1,1,3,3,3-hexafluoro-2-hydroxypropan-2-yl)-2-methylphenyl)-4-(2-methylpyrrolidine-1-carbonyl)thiazole-2-carboxamido)-2,2-dimethylpropanoate

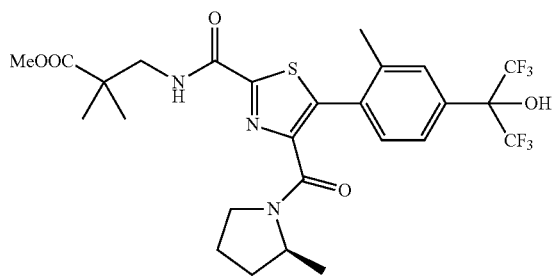 [SMILES: COC(=O)C(C)(C)CNC(=O)c1nc(C(=O)N2CCC[C@@H]2C)c(-c2ccc(C(O)(C(F)(F)F)C(F)(F)F)cc2C)s1]

The title compound can be prepared as described in Example 15, using (S)-methyl 2,2-dimethyl-3-(4-(2-methylpyrrolidine-1-carbonyl)thiazole-2-carboxamido)propanoate (Example 27, step a) in place of (S)—N-(2-hydroxy-2-methylpropyl)-4-(2-methylpyrrolidine-1-carbonyl)thiazole-2-carboxamide and 2-(4-bromo-3-methylphenyl)-1,1,1,3,3,3-hexafluoropropan-2-ol (Intermediate 3/2) in place of 2-(4-bromo-3-(difluoromethyl)phenyl)-1,1,1,3,3,3-hexafluoropropan-2-ol.

Example 37

(S)-3-(5-(4-(1,1,1,3,3,3-Hexafluoro-2-hydroxypropan-2-yl)-2-methylphenyl)-4-(2-methylpyrrolidine-1-carbonyl)thiazole-2-carboxamido)-2,2-dimethylpropanoic acid

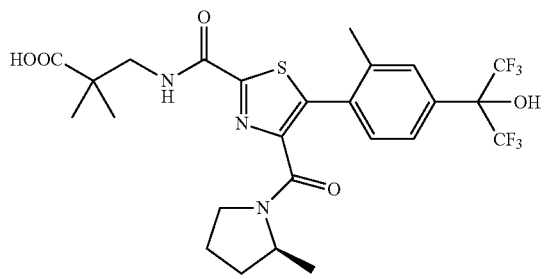 [SMILES: Cc1cc(C(O)(C(F)(F)F)C(F)(F)F)ccc1-c1sc(C(=O)NCC(C)(C)C(=O)O)nc1C(=O)N1CCC[C@@H]1C]

The title compound can be prepared as described in Example 12, using in the final step (S)-methyl 3-(5-(2-(difluoromethyl)-4-(1,1,1,3,3,3-hexafluoro-2-hydroxypropan-2-yl)phenyl)-4-(2-methylpyrrolidine-1-carbonyl)thiazole-2-carboxamido)-2,2-dimethylpropanoate (Example 37, step a) in place of trans-methyl 3-(5-(2,3-dichloro-4-(1,1,1,3,3,3-hexafluoro-2-hydroxypropan-2-yl)phenyl)-4-(ethyl(2,2,2-trifluoroethyl)carbamoyl)thiazole-2-carboxamido)cyclobutane-carboxylate.

Example 38

(S)—N-(1,1-Dioxidothietan-3-yl)-5-(4-(1,1,1,3,3,3-hexafluoro-2-hydroxypropan-2-yl)-2-methylphenyl)-4-(2-methylpyrrolidine-1-carbonyl)thiazole-2-carboxamide

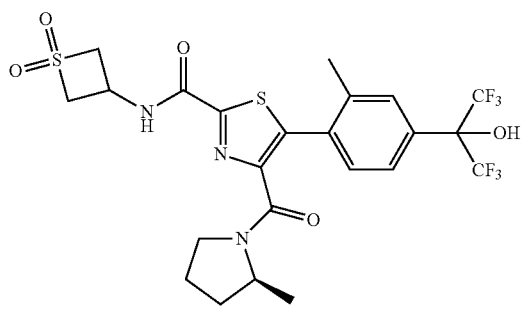 [SMILES: Cc1cc(C(O)(C(F)(F)F)C(F)(F)F)ccc1-c1sc(C(=O)NC2CS(=O)(=O)C2)nc1C(=O)N1CCC[C@@H]1C]

The title compound can be prepared as described in Example 15, using (S)—N-(1,1-dioxidothietan-3-yl)-4-(2-methylpyrrolidine-1-carbonyl)thiazole-2-carboxamide (Example 28, step a) in place of (S)—N-(2-hydroxy-2-methylpropyl)-4-(2-methylpyrrolidine-1-carbonyl)thiazole-2-carboxamide and 2-(4-bromo-3-methylphenyl)-1,1,1,3,3,3-hexafluoropropan-2-ol (Intermediate 3/2) in place of 2-(4-bromo-3-(difluoromethyl)phenyl)-1,1,1,3,3,3-hexafluoropropan-2-ol.

Example 39

(S)-5-(4-(1,1,1,3,3,3-Hexafluoro-2-hydroxypropan-2-yl)-2-methylphenyl)-N-((3-hydroxyoxetan-3-yl)methyl)-4-(2-methylpyrrolidine-1-carbonyl)thiazole-2-carboxamide

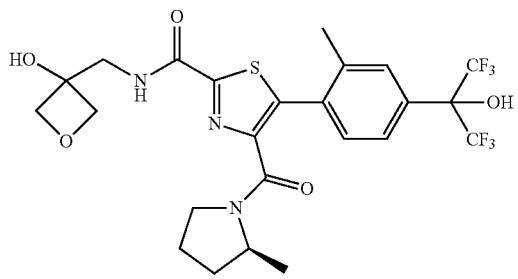 [SMILES: Cc1cc(C(O)(C(F)(F)F)C(F)(F)F)ccc1-c1sc(C(=O)NCC2(O)COC2)nc1C(=O)N1CCC[C@@H]1C]

The title compound can be prepared as described in Example 15, using (S)—N-((3-hydroxyoxetan-3-yl)methyl)-4-(2-methylpyrrolidine-1-carbonyl)thiazole-2-carboxamide (Example 30, step a) in place of (S)—N-(2-hydroxy-2-methylpropyl)-4-(2-methylpyrrolidine-1-carbonyl)thiazole-2-carboxamide and 2-(4-bromo-3-methylphenyl)-1,1,1,3,3,3-hexafluoropropan-2-ol (Intermediate 3/2) in place of 2-(4-bromo-3-(difluoromethyl)phenyl)-1,1,1,3,3,3-hexafluoropropan-2-ol.

Example 40

Step a (S)-Methyl 1-((5-(4-(1,1,1,3,3,3-hexafluoro-2-hydroxypropan-2-yl)-2-methylphenyl)-4-(2-methylpyrrolidine-1-carbonyl)thiazole-2-carboxamido)methyl)cyclopropanecarboxylate

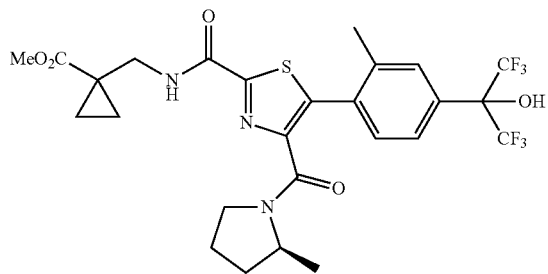 [SMILES: COC(=O)C1(CNC(=O)c2nc(C(=O)N3CCC[C@@H]3C)c(-c3ccc(C(O)(C(F)(F)F)C(F)(F)F)cc3C)s2)CC1]

The title compound can be prepared as described in Example 15, using (S)-methyl 1-((4-(2-methylpyrrolidine-1-carbonyl)thiazole-2-carboxamido)methyl)cyclopropanecarboxylate (Example 31, step a) in place of (S)—N-(2-hydroxy-2-methylpropyl)-4-(2-methylpyrrolidine-1-carbonyl)thiazole-2-carboxamide and 2-(4-bromo-3-methylphenyl)-1,1,1,3,3,3-hexafluoropropan-2-ol (Intermediate 3/2) in place of 2-(4-bromo-3-(difluoromethyl)phenyl)-1,1,1,3,3,3-hexafluoropropan-2-ol.

Example 40

(S)-1-((5-(4-(1,1,1,3,3,3-Hexafluoro-2-hydroxypropan-2-yl)-2-methylphenyl)-4-(2-methylpyrrolidine-1-carbonyl)thiazole-2-carboxamido)methyl)cyclopropanecarboxylic acid

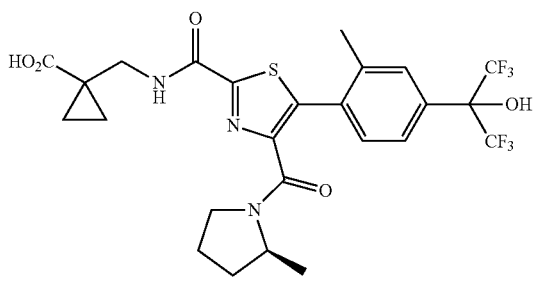 [SMILES: Cc1cc(C(O)(C(F)(F)F)C(F)(F)F)ccc1-c1sc(C(=O)NCC2(C(=O)O)CC2)nc1C(=O)N1CCC[C@@H]1C]

The title compound can be prepared as described in Example 12, using in the final step (S)-methyl 1-((5-(4-(1,1,1,3,3,3-hexafluoro-2-hydroxypropan-2-yl)-2-methylphenyl)-4-(2-methylpyrrolidine-1-carbonyl)thiazole-2-carboxamido)methyl)cyclopropanecarboxylate (Example 40, step a) in place of trans-methyl 3-(5-(2,3-dichloro-4-(1,1,1,3,3,3-hexafluoro-2-hydroxypropan-2-yl)phenyl)-4-(ethyl(2,2,2-trifluoroethyl)carbamoyl)thiazole-2-carboxamido)cyclobutane-carboxylate.

Example 41

(S)-5-(4-(1,1,1,3,3,3-Hexafluoro-2-hydroxypropan-2-yl)-2-methylphenyl)-N-((1-hydroxycyclopropyl)methyl)-4-(2-methylpyrrolidine-1-carbonyl)thiazole-2-carboxamide

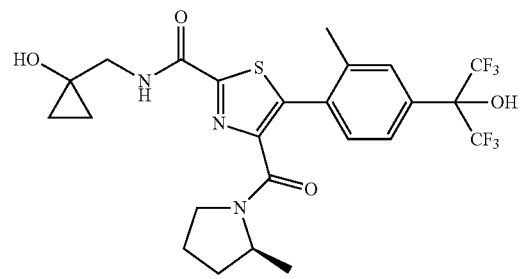 [SMILES: Cc1cc(C(O)(C(F)(F)F)C(F)(F)F)ccc1-c1sc(C(=O)NCC2(O)CC2)nc1C(=O)N1CCC[C@@H]1C]

The title compound can be prepared as described in Example 15, using (S)—N-((1-hydroxycyclopropyl)methyl)-4-(2-methylpyrrolidine-1-carbonyl)thiazole-2-carboxamide (Example 32, step a) in place of (S)—N-(2-hydroxy-2-methylpropyl)-4-(2-methylpyrrolidine-1-carbonyl)thiazole-2-carboxamide and 2-(4-bromo-3-methylphenyl)-1,1,1,3,3,3-hexafluoropropan-2-ol (Intermediate 3/2) in place of 2-(4-bromo-3-(difluoroethyl)phenyl)-1,1,1,3,3,3-hexafluoropropan-2-ol.

Example 42

5-(4-(1,1,1,3,3,3-Hexafluoro-2-hydroxypropan-2-yl)-2-methylphenyl)-4-((S)-2-methylpyrrolidine-1-carbonyl)-N-(trans-3-(methylsulfonyl)cyclobutyl)thiazole-2-carboxamide

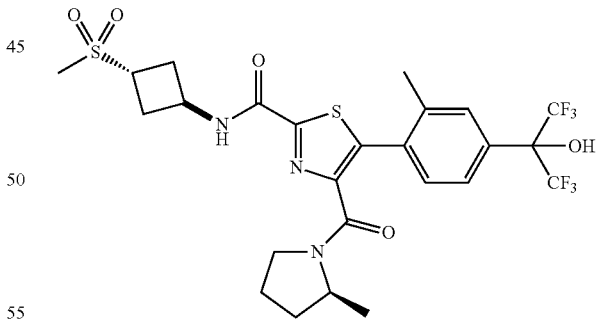

The title compound can be prepared as described in Example 15, using 4-((S)-2-methylpyrrolidine-1-carbonyl)-N-(trans-3-(methylsulfonyl)cyclobutyl)thiazole-2-carboxamide (Example 33, step a) in place of (S)—N-(2-hydroxy-2-methylpropyl)-4-(2-methylpyrrolidine-1-carbonyl)thiazole-2-carboxamide and 2-(4-bromo-3-methylphenyl)-1,1,1,3,3,3-hexafluoropropan-2-ol (Intermediate 3/2) in place of 2-(4-bromo-3-(difluoromethyl)phenyl)-1,1,1,3,3,3-hexafluoropropan-2-ol.

Example 43

(S)-5-(4-(1,1,1,3,3,3-Hexafluoro-2-hydroxypropan-2-yl)-2-methylphenyl)-N-((4-hydroxy-1,1-dioxido-tetrahydro-2H-thiopyran-4-yl)methyl)-4-(2-methyl-pyrrolidine-1-carbonyl)thiazole-2-carboxamide

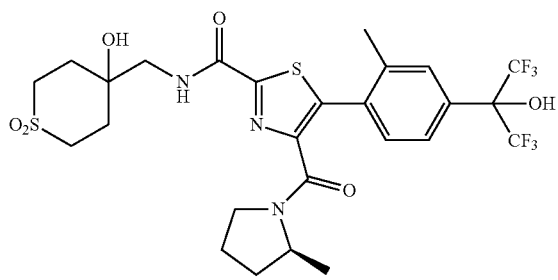 [SMILES: Cc1cc(C(O)(C(F)(F)F)C(F)(F)F)ccc1-c1sc(C(=O)NCC2(O)CCS(=O)(=O)CC2)nc1C(=O)N1CCC[C@@H]1C]

The title compound can be prepared as described in Example 15, using (S)—N-((4-hydroxy-1,1-dioxidotetrahydro-2H-thiopyran-4-yl)methyl)-4-(2-methylpyrrolidine-1-carbonyl)thiazole-2-carboxamide (Example 34, step a) in place of (S)—N-(2-hydroxy-2-methylpropyl)-4-(2-methyl-pyrrolidine-1-carbonyl)thiazole-2-carboxamide and 2-(4-bromo-3-methylphenyl)-1,1,1,3,3,3-hexafluoropropan-2-ol (Intermediate 3/2) in place of 2-(4-bromo-3-(difluoromethyl)phenyl)-1,1,1,3,3,3-hexafluoropropan-2-ol.

Example 44

Step a

2-Bromo-5-(1,1,1,3,3,3-hexafluoro-2-hydroxypropan-2-yl)benzonitrile

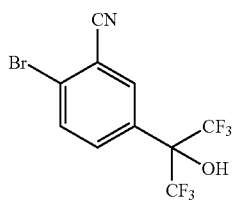

The title compound can be prepared as described in Intermediate 18, using in step b 2-bromo-5-iodobenzonitrile in place of 1-bromo-2-(difluoromethyl)-4-iodobenzene.

Example 44

(S)-5-(2-Cyano-4-(1,1,1,3,3,3-hexafluoro-2-hydroxypropan-2-yl)phenyl)-N-(2-hydroxy-2-methyl-propyl)-4-(2-methylpyrrolidine-1-carbonyl)thiazole-2-carboxamide

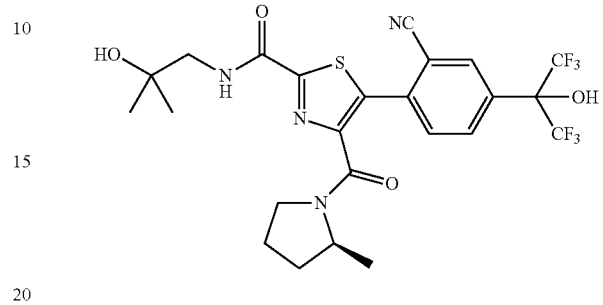

The title compound can be prepared as described in Example 15, using 2-bromo-5-(1,1,1,3,3,3-hexafluoro-2-hydroxypropan-2-yl)benzonitrile (Example 44, step a) in place of 2-(4-bromo-3-(difluoromethyl)phenyl)-1,1,1,3,3,3-hexafluoropropan-2-ol.

Example 45

Step a 2-(5-Bromo-4-methoxypyridin-2-yl)-1,1,1,3,3,3-hexafluoropropan-2-ol

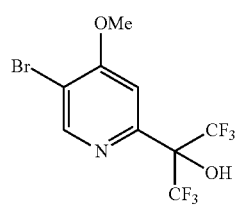

The title compound can be prepared as described in Intermediate 26, using in step b 5-bromo-4-methoxypyridin-2-amine in place of 4-bromo-2-chloro-3-fluoroaniline.

Example 45

(S)-5-(6-(1,1,1,3,3,3-Hexafluoro-2-hydroxypropan-2-yl)-4-methoxypyridin-3-yl)-N-(2-hydroxy-2-methylpropyl)-4-(2-methylpyrrolidine-1-carbonyl)thiazole-2-carboxamide

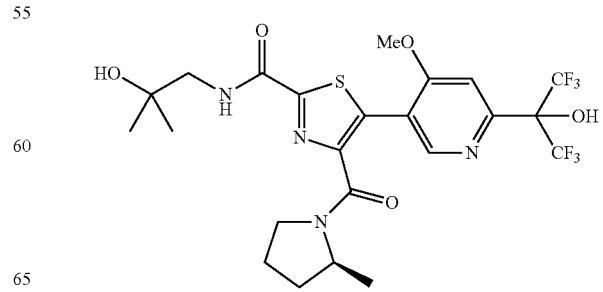

The title compound can be prepared as described in Example 15, using 2-(5-bromo-4-methoxypyridin-2-yl)-1,1,1,3,3,3-hexafluoropropan-2-ol (Example 45, step a) in place of 2-(4-bromo-3-(difluoromethyl)phenyl)-1,1,1,3,3,3-hexafluoropropan-2-ol.

In Vitro Biological Data
ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM 001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor® assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 µL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 µM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 µL, followed by 1 µL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data
RORγt (Full-Length Human) Reporter Assay:

Three similar reporter assay protocols, shown below, have been used to test the functional activity of RORγt modulatory compounds on transcriptional activation driven by full-length human RORγt. All three provide similar data and can be used interchangeably.

Conditions A

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 35000 per well in 96-well plate in medium of MEM with 8.6% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.1% and DMSO 0.1%. After overnight (16 to 20 hours) incubation, media were removed and cells were lysed with 20 µL 1× Passive Lysis Buffer (Promega) for 10-15 minutes. Luminescence was measured using a BMG LUMIstar OPTIMA plate reader, after addition of 75 µL/well firefly luciferase buffer, followed by 75 µL/well Renilla luciferase buffer. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Conditions B

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 35,000 per well in 96-well plate in medium of DMEM with 10% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 50 μL Glo Lysis Buffer (Promega) for 10-15 minutes followed by 10 minute incubation with 50 μL Dual Glo reagent (Promega) at room temperature. Firefly luciferase luminescence was measured using a BMG Pherastar plate reader. To each well, 50 μL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Conditions C

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 8750 cells per well in 384-well plate in medium of DMEM with 10% FBS. After 18-22 hours incubation, the transfection was carried out by using a PEI solution with 42.6 ng total DNA/well (12.5 ng pCMV-BD-ROR plus 5 ng of pFR-Luc reporter and 0.125 ng of pRL-CMV reporter plus 25 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 20 μL Glo Lysis Buffer (Promega) for 10-15 minutes followed by 10 minute incubation with 20 μL Dual Glo reagent (Promega) at room temperature. Firefly luciferase luminescence was measured using a BMG Pherastar plate reader. To each well, 20 μL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total $CD4^+$ T cells were isolated from the peripheral blood mononuclear cells (PBMC) of healthy donors using a $CD4^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5 \times 10^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: $3 \times 10^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL113, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example # | ThermoFluor ® Assay, Kd (μM) | RORγt (FL) Reporter Assay A, $IC_{50}$ (μM) | RORγt (FL) Reporter Assay A, % inhibition @ 6 μM | RORγt (FL) Reporter Assay B or C, $IC_{50}$ (μM) | RORγt (FL) Reporter Assay B or C, % inhibition @ 6 μM | Human Th17 Assay, $IC_{50}$ (μM) |
|---|---|---|---|---|---|---|
| 1 | 0.0056 | 0.0070 | 105** | ND | ND | ND |
| 2 | 0.0057 | 0.014 | 104** | ND | ND | ND |
| 2/1 | 0.00016 | 0.014 | 103** | ND | ND | ND |
| 2/2 | 0.00022 | 0.010 | 101*** | ND | ND | ND |
| 2/3a | 0.0049 | 0.050 | 104** | ND | ND | ND |
| 2/3b | 0.0071 | 0.037 | 96** | ND | ND | ND |
| 2/3c | 0.0055 | 0.038 | 99** | ND | ND | ND |

TABLE 1-continued

| Example # | ThermoFluor ® Assay, Kd (µM) | RORγt (FL) Reporter Assay A, IC$_{50}$ (µM) | RORγt (FL) Reporter Assay A, % inhibition @ 6 µM | RORγt (FL) Reporter Assay B or C, IC$_{50}$ (µM) | RORγt (FL) Reporter Assay B or C, % inhibition @ 6 µM | Human Th17 Assay, IC$_{50}$ (µM) |
|---|---|---|---|---|---|---|
| 2/4 | 0.0037 | 0.024 | 103** | ND | ND | ND |
| 2/5 | 0.00067 | 0.0049 | 107** | ND | ND | ND |
| 2/6 | 0.0031 | 0.016 | 104** | ND | ND | ND |
| 2/7 | 0.00056 | 0.0080 | 104** | ND | ND | ND |
| 2/8 | 0.00030 | 0.012 | 103** | 0.0026 | 108** | 0.017 |
| 2/9 | 0.027 | 0.067 | 103** | ND | ND | ND |
| 2/10 | 0.013 | 0.025 | 105** | ND | ND | ND |
| 2/11 | 0.0061 | 0.020 | 100** | ND | ND | ND |
| 2/12 | 0.018 | 0.026 | 100** | ND | ND | ND |
| 2/13 | 0.00043 | 0.010 | 103*** | ND | ND | ND |
| 2/14 | 0.044 | 0.083 | 106 | ND | ND | ND |
| 2/15 | 0.00018 | 0.0050 | 106*** | ND | ND | ND |
| 2/16 | ND | 0.43 | 86** | ND | ND | ND |
| 3 | 0.0046 | 0.012 | 104** | ND | ND | ND |
| 3/1 | 0.011 | 0.016 | 103*** | ND | ND | ND |
| 3/2 | 0.0097 | 0.020 | 103** | ND | ND | ND |
| 3/3a | 0.017 | 0.018 | 100**** | ND | ND | ND |
| 3/3b | 0.0036 | 0.0090 | 104**** | ND | ND | ND |
| 3/4 | 0.010 | 0.014 | 100** | ND | ND | ND |
| 3/5 | 0.050 | 0.029 | 100** | ND | ND | ND |
| 3/6 | 0.022 | 0.032 | 103** | ND | ND | ND |
| 3/7 | 0.034 | 0.052 | 102** | ND | ND | ND |
| 3/8 | 0.038 | 0.026 | 100** | ND | ND | ND |
| 3/9 | 0.019 | 0.029 | 102** | ND | ND | ND |
| 3/10 | 0.024 | 0.13 | 97** | ND | ND | ND |
| 3/11 | 0.068 | 2.9 | 26 | ND | ND | ND |
| 4 | 0.41 | 0.35 | 87** | ND | ND | ND |
| 5 | 0.0029 | 0.022 | 105** | ND | ND | ND |
| 6 | 0.0038 | 0.032 | 102 | ND | ND | ND |
| 6/1 | 0.0021 | 0.010 | 101** | ND | ND | 0.042 |
| 6/2 | 0.011 | 0.041 | 102** | ND | ND | ND |
| 7 | 0.0027 | 0.017 | 106** | ND | ND | ND |
| 8 | 0.00015 | 0.011 | 102*** | ND | ND | ND |
| 9 | 0.000070 | 0.010 | 102** | ND | ND | ND |
| 9/1 | 0.00011 | 0.014 | 103** | ND | ND | 0.013 |
| 9/2 | 0.00011 | 0.033 | 106** | ND | ND | ND |
| 9/3 | 0.0080 | 0.019 | 104** | ND | ND | ND |
| 9/4 | 0.0031 | 0.012 | 106** | ND | ND | ND |
| 9/5 | 0.033 | 0.078 | 101** | ND | ND | ND |
| 10 | 0.0021 | 0.013 | 103 | ND | ND | ND |
| 10/1 | 0.026 | 0.12 | 107 | ND | ND | ND |
| 10/2 | 0.0032 | 0.018 | 103** | ND | ND | ND |
| 10/3 | 0.0025 | 0.032 | 105 | ND | ND | ND |
| 10/4 | 0.0014 | 0.020 | 103** | ND | ND | ND |
| 10/5 | 0.00083 | 0.014 | 106** | ND | ND | ND |
| 10/6 | 0.0028 | 0.029 | 102** | ND | ND | ND |
| 11a | 0.59 | 0.55 | 78** | ND | ND | ND |
| 11b | 0.40 | 0.33 | 89** | ND | ND | ND |
| 12 | ND | 0.049 | 104 | ND | ND | ND |
| 13 | 0.42 | 1.1 | 88 | ND | ND | ND |
| 14 | 0.047 | 0.28 | 100 | ND | ND | ND |
| 14/1 | 0.00050 | 0.015 | 104** | ND | ND | ND |
| 14/2 | 0.014 | 0.032 | 99** | ND | ND | ND |
| 15 | 0.0011 | 0.027 | 105 | 0.010 | 107* | 0.047 |
| 15/1 | 0.55 | ND | ND | 0.35 | 96 | ND |
| 15/2 | 0.000060 | ND | ND | 0.0022 | 91* | ND |
| 15/3 | 0.0014 | ND | ND | 0.011 | 99* | ND |
| 15/4 | 0.0094 | ND | ND | 0.054 | 105 | ND |
| 15/5 | 0.0011 | ND | ND | 0.015 | 113 | ND |
| 15/6 | 0.00091 | ND | ND | 0.024 | 107* | ND |
| 15/7 | 0.0017 | ND | ND | 0.0097 | 102 | ND |
| 15/8 | 0.00029 | ND | ND | 0.013 | 101* | ND |
| 15/9 | 0.00046 | ND | ND | 0.0082 | 96* | ND |
| 15/10 | 0.00026 | ND | ND | 0.0079 | 97* | ND |
| 15/11 | 0.021 | ND | ND | 0.051 | 121* | ND |
| 16 | 0.0088 | 0.046 | 101** | ND | ND | ND |
| 17 | 0.0000090 | 0.048 | 105 | ND | ND | ND |
| 18 | 0.0023 | ND | ND | 0.012 | 99 | ND |
| 18/1 | 0.000080 | ND | ND | 0.014 | 105 | ND |
| 18/2 | 0.0044 | ND | ND | 0.076 | 104 | ND |
| 18/3 | 0.23 | ND | ND | 0.73 | 68* | ND |
| 19 | 0.0021 | ND | ND | 0.014 | 107 | 0.055 |

TABLE 1-continued

| Example # | ThermoFluor ® Assay, Kd (μM) | RORγt (FL) Reporter Assay A, IC$_{50}$ (μM) | RORγt (FL) Reporter Assay A, % inhibition @ 6 μM | RORγt (FL) Reporter Assay B or C, IC$_{50}$ (μM) | RORγt (FL) Reporter Assay B or C, % inhibition @ 6 μM | Human Th17 Assay, IC$_{50}$ (μM) |
|---|---|---|---|---|---|---|
| 19/1 | 0.49 | ND | ND | 0.56 | 79* | ND |
| 20 | 0.00017 | ND | ND | 0.016 | 102** | ND |
| 21 | 0.00035 | ND | ND | 0.0052 | 109* | ND |
| 21/1 | 0.0087 | ND | ND | 0.053 | 107 | ND |
| 21/2 | 0.00021 | ND | ND | 0.0039 | 101* | ND |
| 21/3 | 0.0021 | ND | ND | 0.015 | 96* | ND |
| 22 | 0.11 | 0.42 | 99 | ND | ND | ND |
| 22/1 | 0.14 | 0.91 | 102 | ND | ND | ND |
| 23 | 0.00029 | ND | ND | 0.0022 | 99* | ND |
| 24 | 0.00084 | ND | ND | 0.0033 | 103* | ND |

All data shown in Table 1 is either the value of one data point or the average of more than one data point. ND: value not determined. *% inhibition is shown at 3 μM compound concentration, % inhibition is shown at 2 μM compound concentration, *% inhibition is shown at 0.67 μM compound concentration, ****% inhibition is shown at 0.22 μM compound concentration.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:

1. A compound of Formula I:

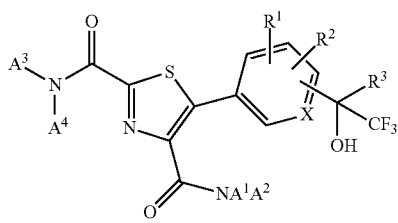

Formula I

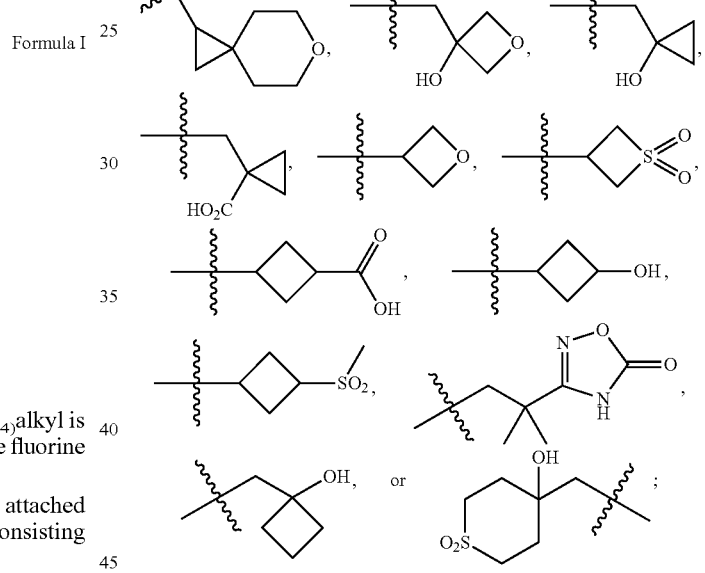

wherein

X is CH, $CR^1$, or N;

$A^1$ is $C_{(1-2)}$alkyl;

$A^2$ is cyclobutyl, or $C_{(1-4)}$alkyl, wherein said $C_{(1-4)}$alkyl is optionally substituted with $OCH_3$ or up to three fluorine atoms;

or $A^1$ and $A^2$ are taken together with their attached nitrogen to form a ring selected the group consisting of azetidinyl, piperidinyl, pyrrolidinyl,

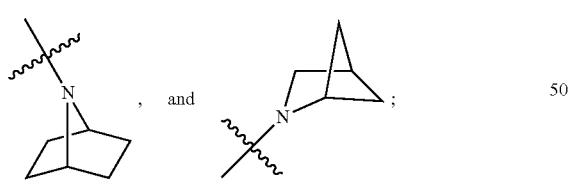

, and

;

wherein said ring is optionally substituted with up to three substituents independently selected from the group consisting of F, $CF_3$, $CH_3$, —CN, and $CH_2OH$;

$R^1$ is Cl, $C(CH_3)_3$, $CH_2CH_3$, $OCF_3$, $CF_3$, $OCH(CH_3)_2$, $CHF_2$, $OCHF_2$, $OCH_3$, F, $CH_3$, or —CN;

$R^2$ is H, F, or Cl;

or $R^1$ and $R^2$ may be taken together with their attached phenyl to form a naphthalenyl, or quinolinyl group;

$R^3$ is $CF_3$, or $CH_2CH_3$;

$A^3$ is H $A^4$ is H, $C_{(1-5)}$alkyl, wherein said $C_{(1-5)}$alkyl is optionally substituted with one to two substituents independently selected from COOH, $CONH_2$, —CN, and OH;

or $A^3$ and $A^4$ may be taken together with their attached nitrogen to make a ring selected from the group consisting of

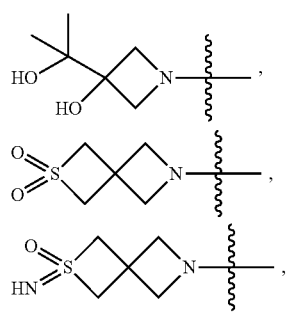

-continued

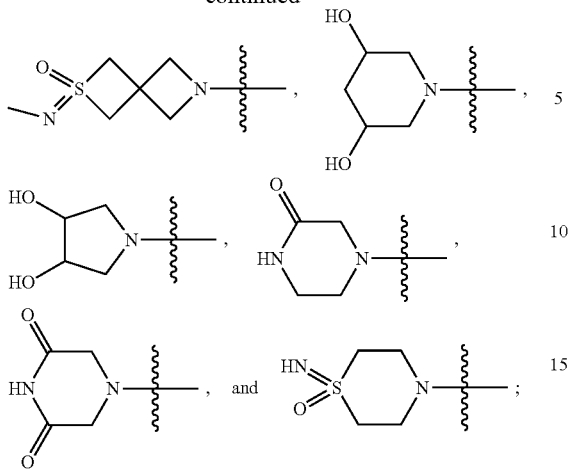

and pharmaceutically acceptable salts thereof.

2. The compound of claim 1 wherein:

$R^1$ is Cl, $C(CH_3)_3$, $CH_2CH_3$, $OCF_3$, $CF_3$, $OCH(CH_3)_2$, $CHF_2$, $OCHF_2$, $OCH_3$, F, or $CH_3$;

$A^4$ is H, $C_{(1-5)}$alkyl,

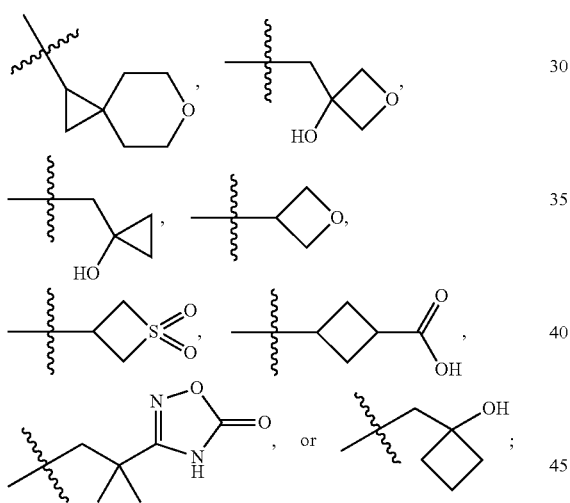

wherein said $C_{(1-5)}$alkyl is optionally substituted with one to two substituents independently selected from $CONH_2$, —CN, and OH;

and pharmaceutically acceptable salts thereof.

3. The compound of claim 2, of Formula II:

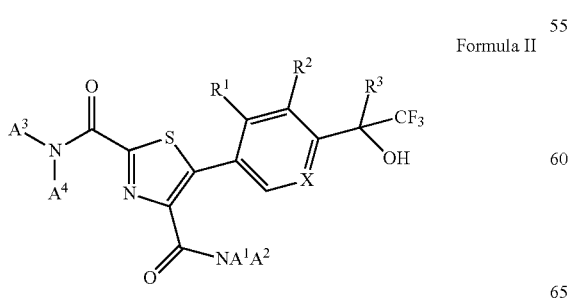

Formula II and pharmaceutically acceptable salts thereof.

4. The compound of claim 2 selected from the group consisting of:

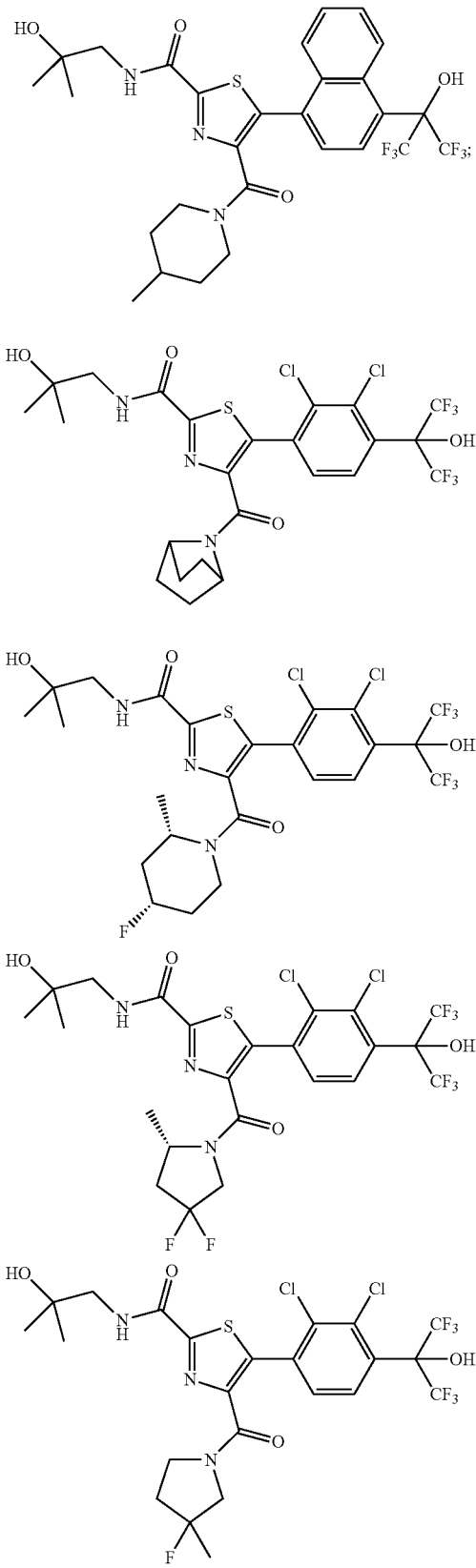

201
-continued
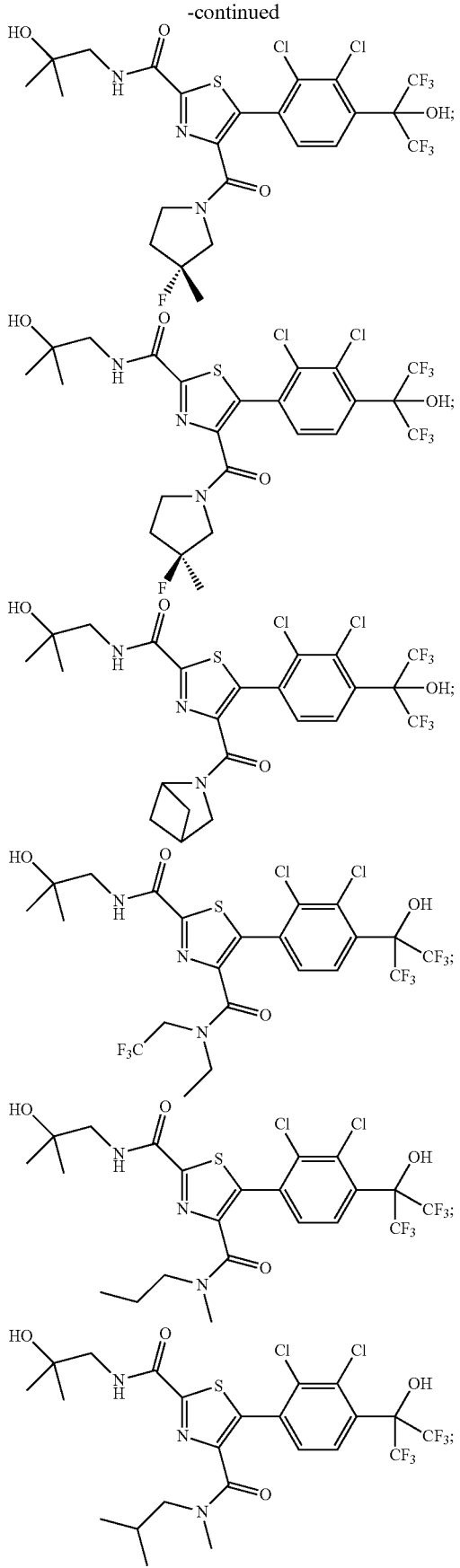
202
-continued
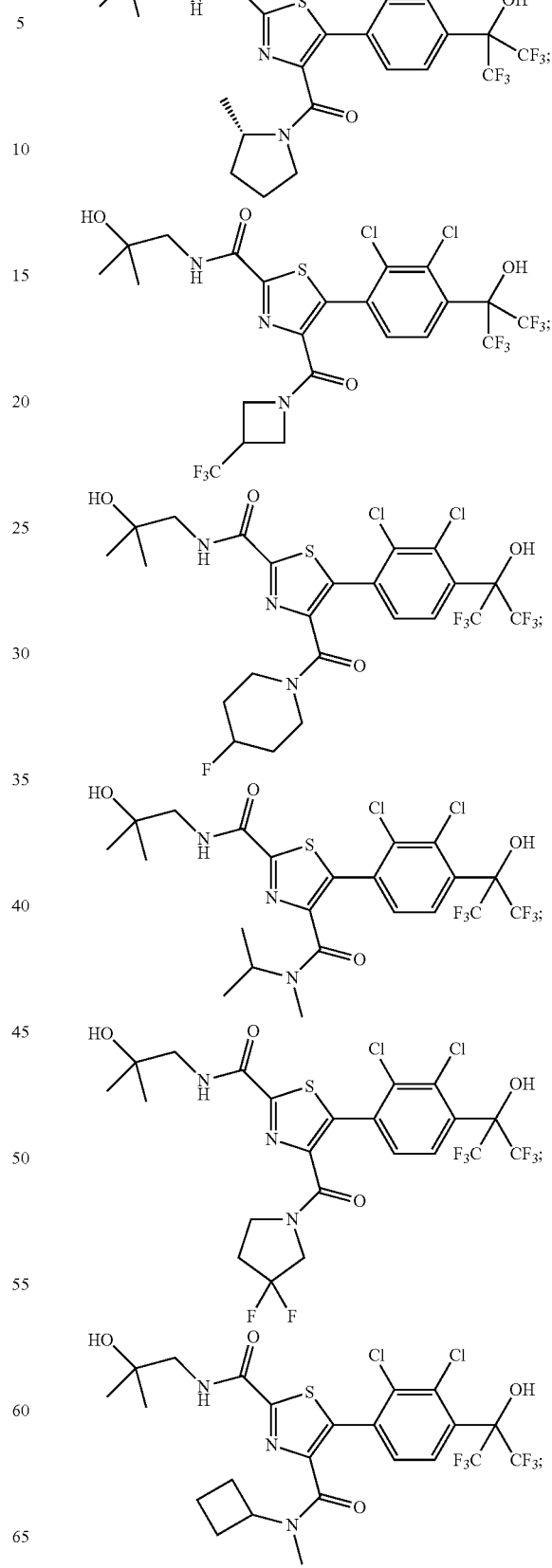

203
-continued
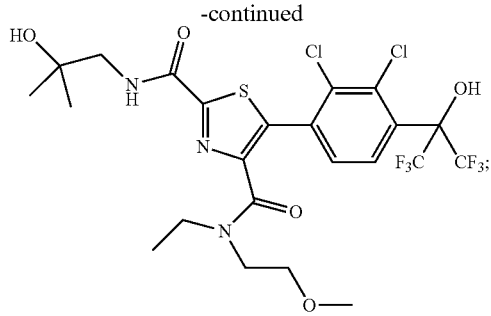
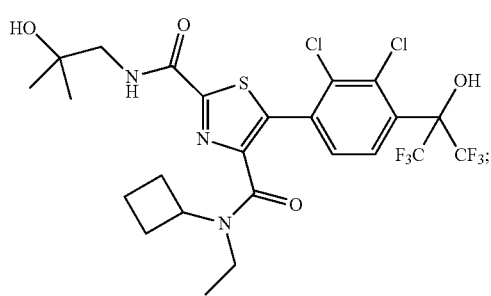
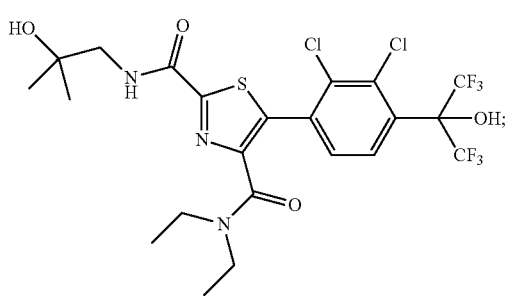
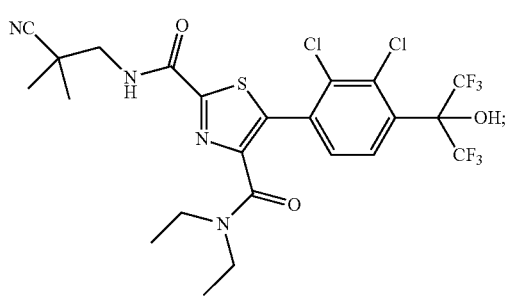
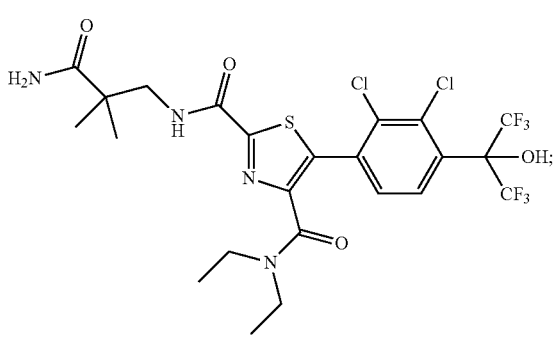
204
-continued
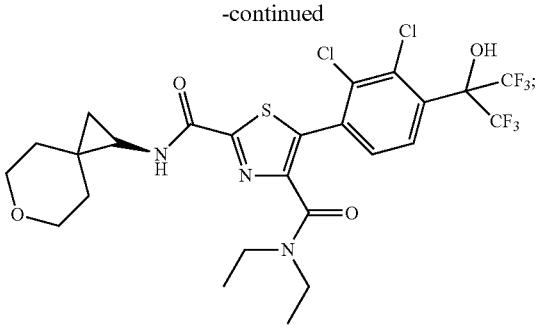
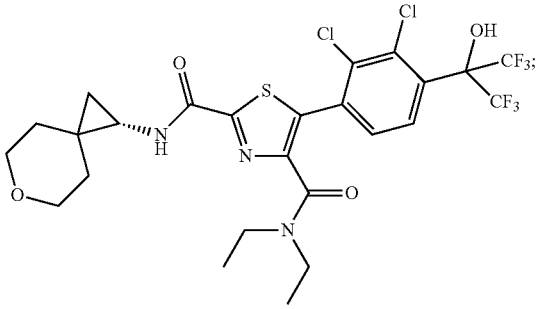
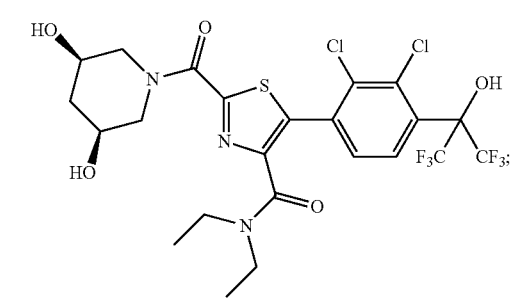
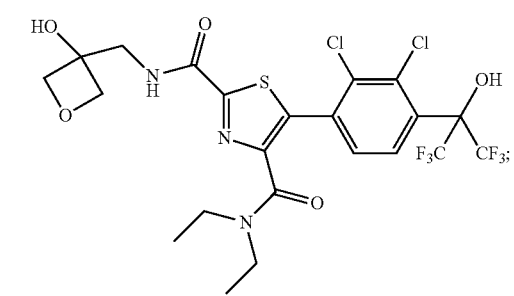
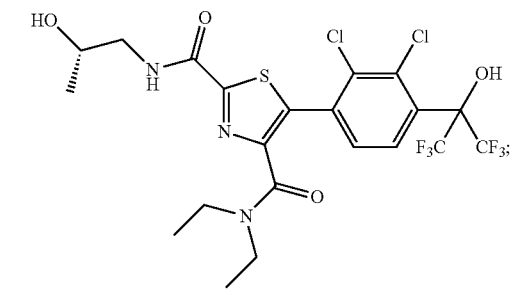

205
-continued
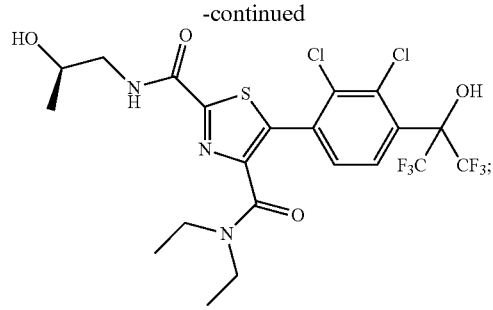
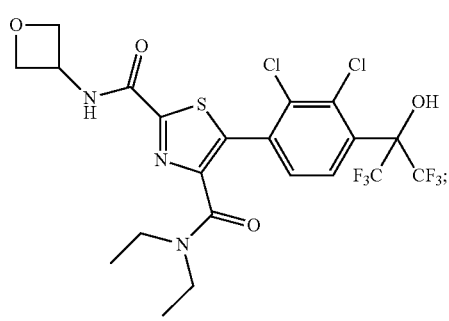
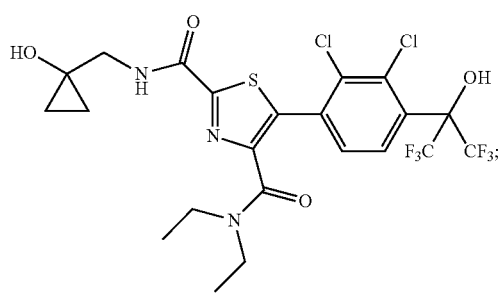
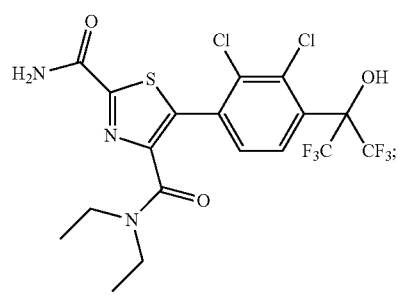
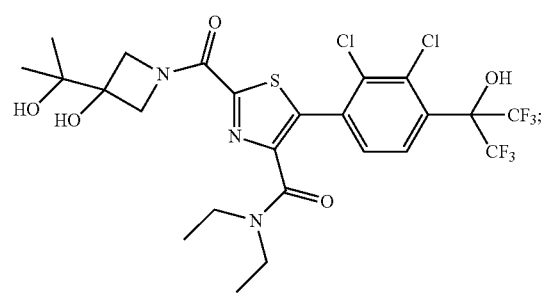
206
-continued
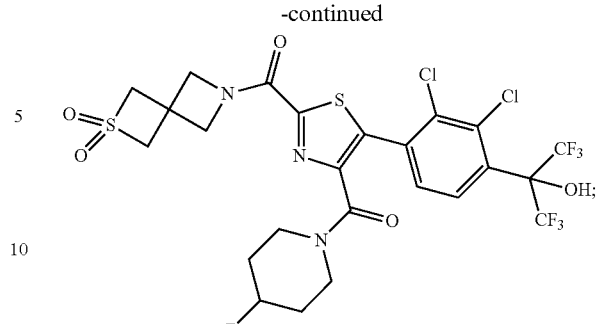
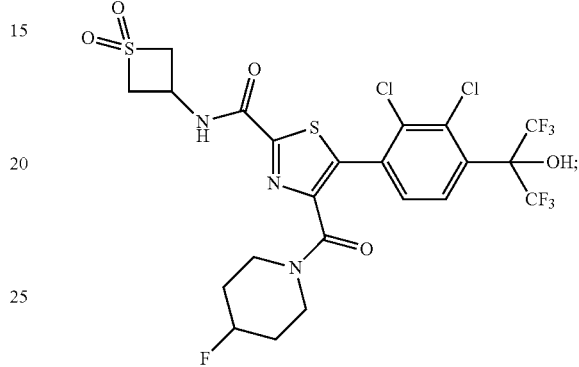
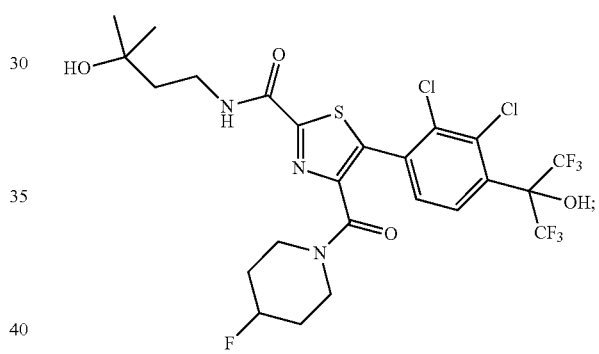
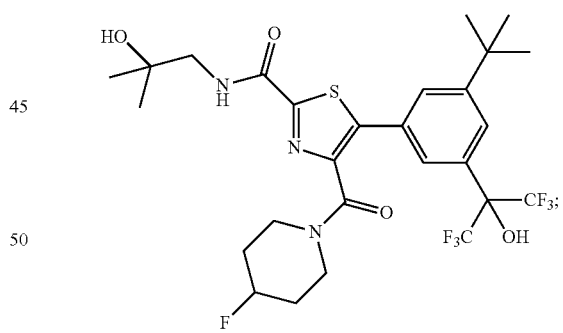
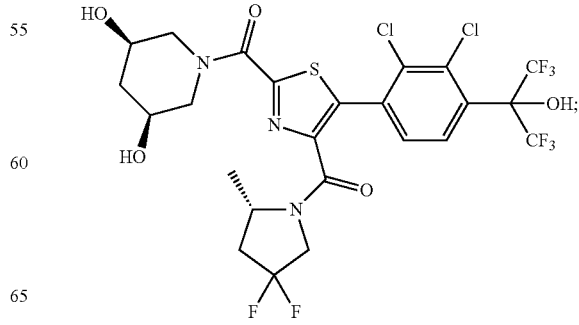

207
-continued
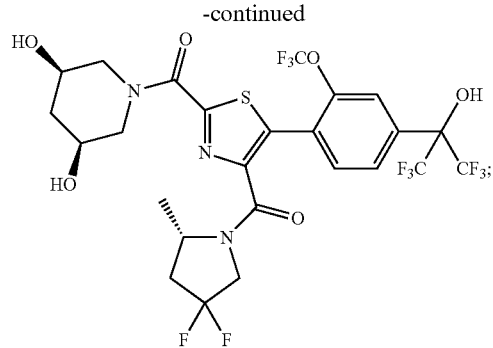
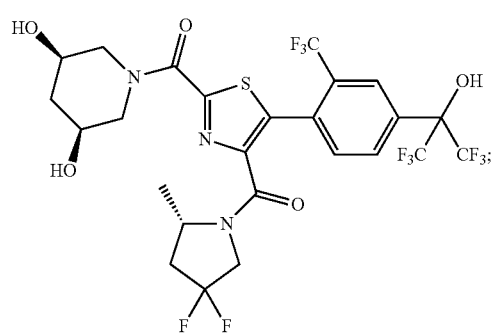
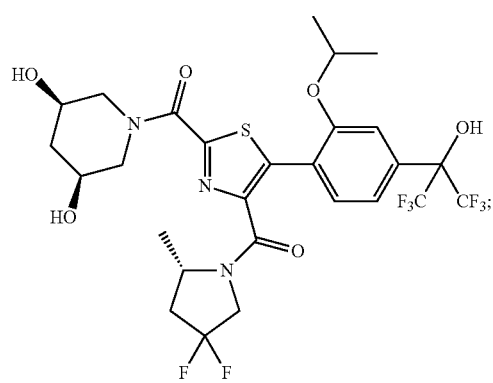
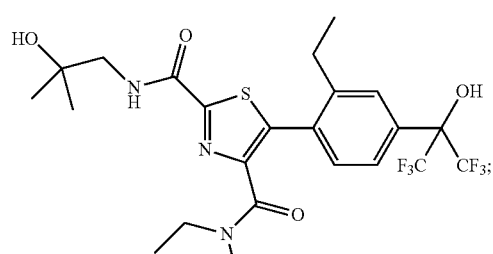
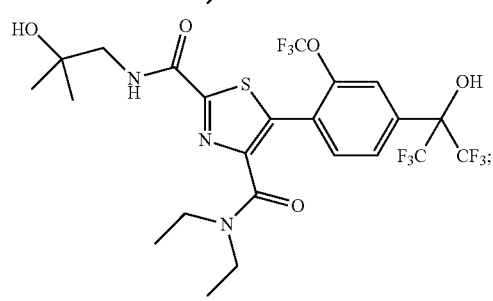
208
-continued
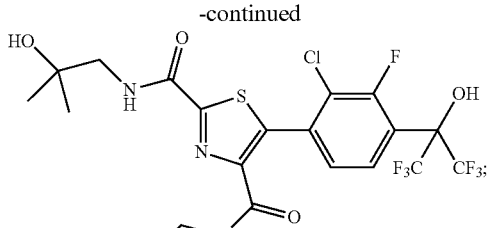
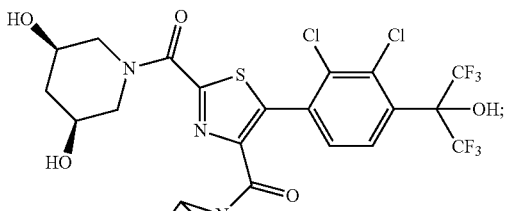
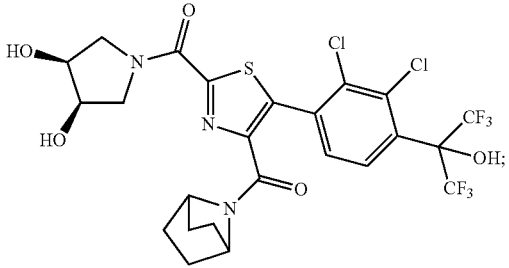
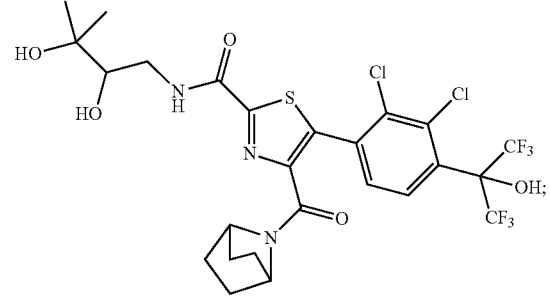
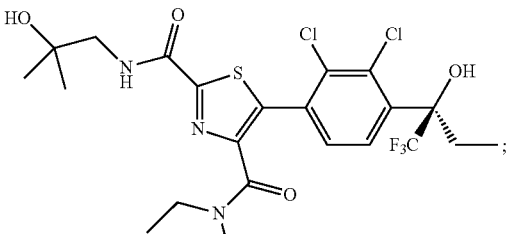
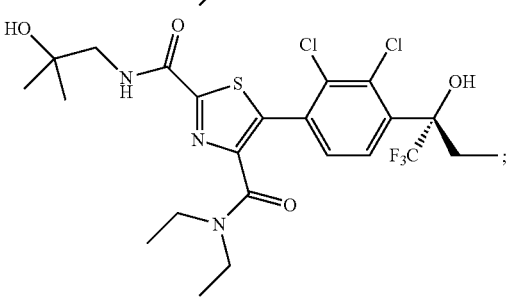

209
-continued
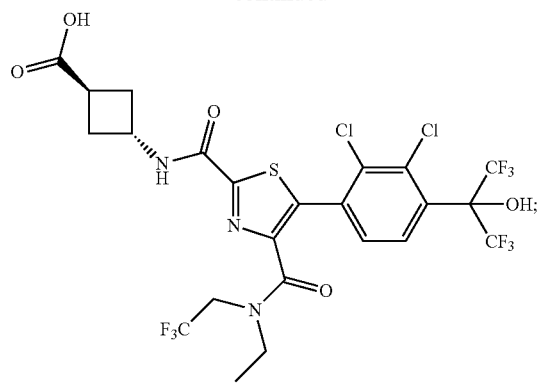
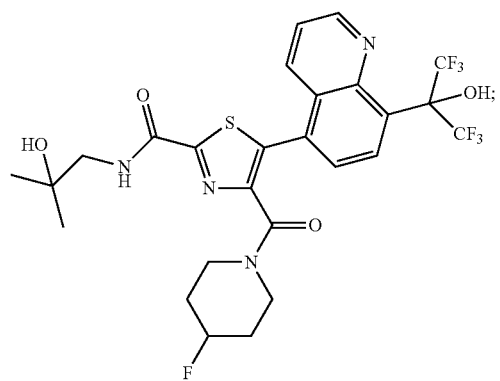
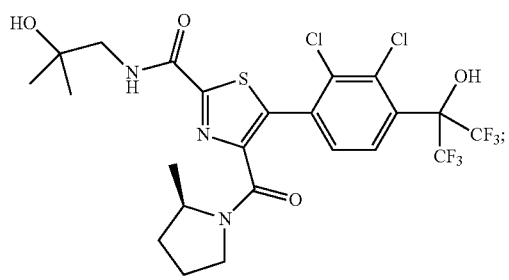
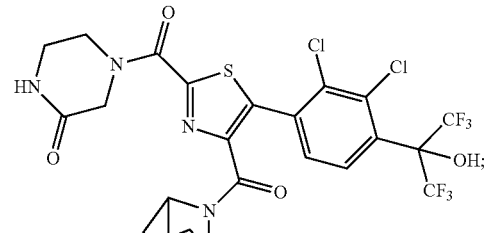
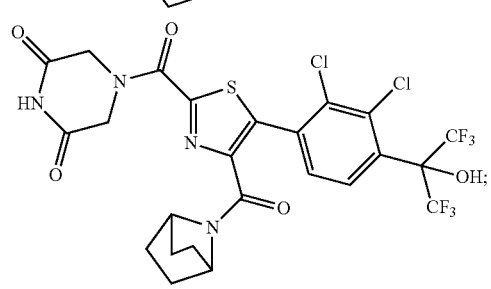
210
-continued
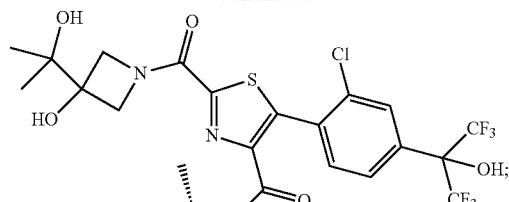
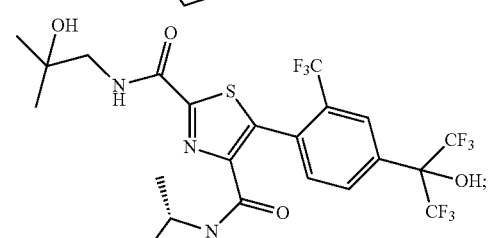
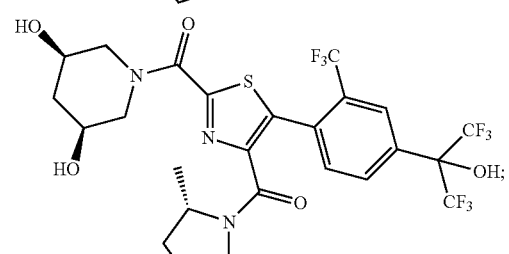
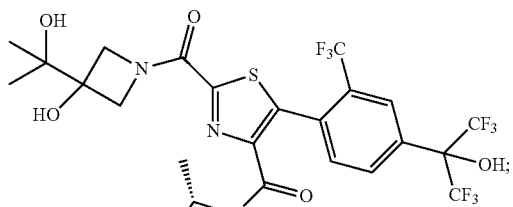
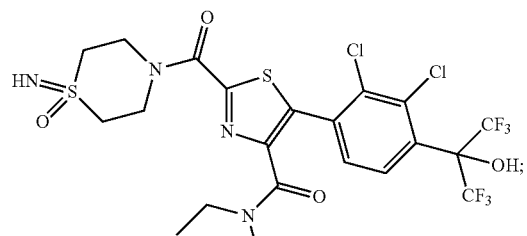
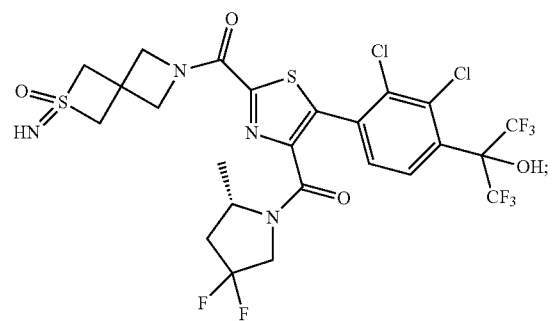

211
-continued
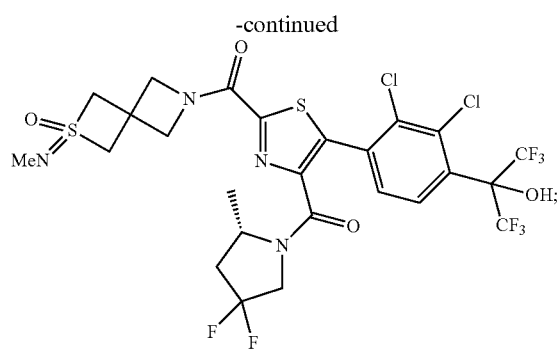
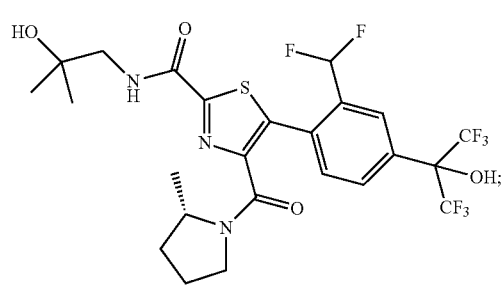
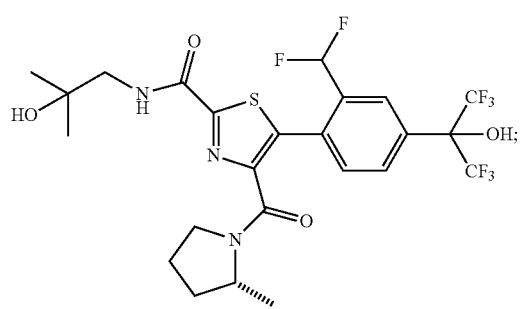
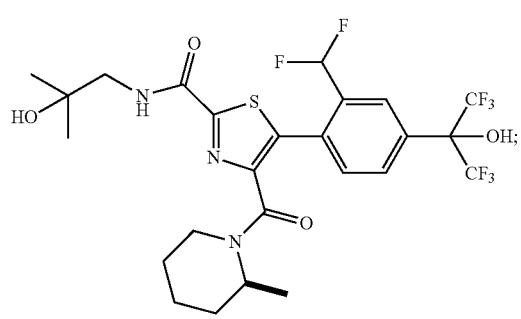
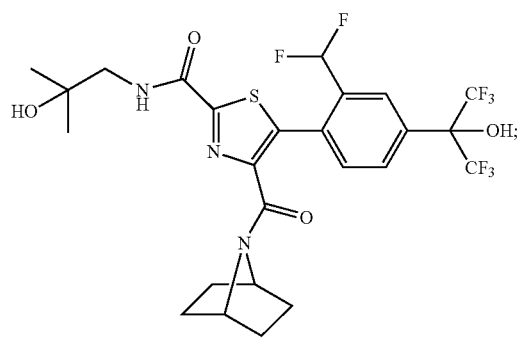
212
-continued
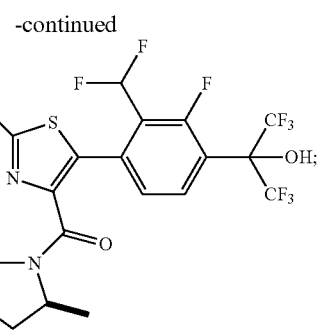
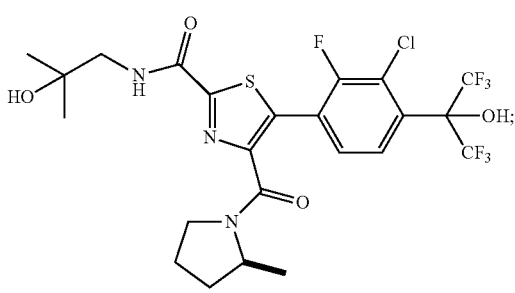
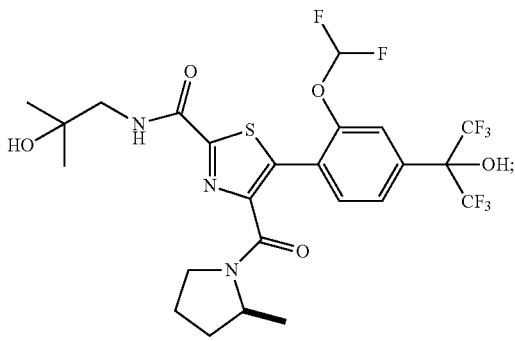
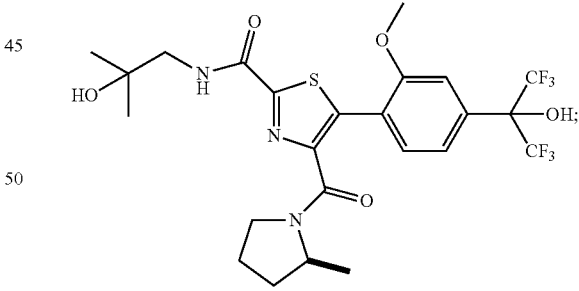
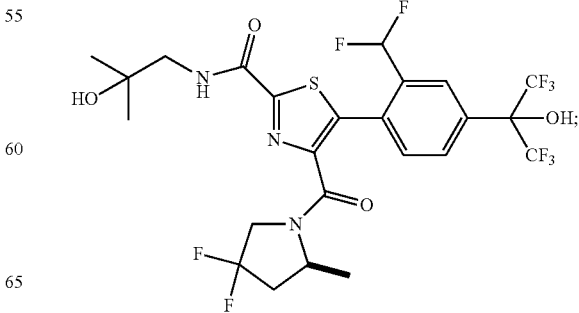

213
-continued
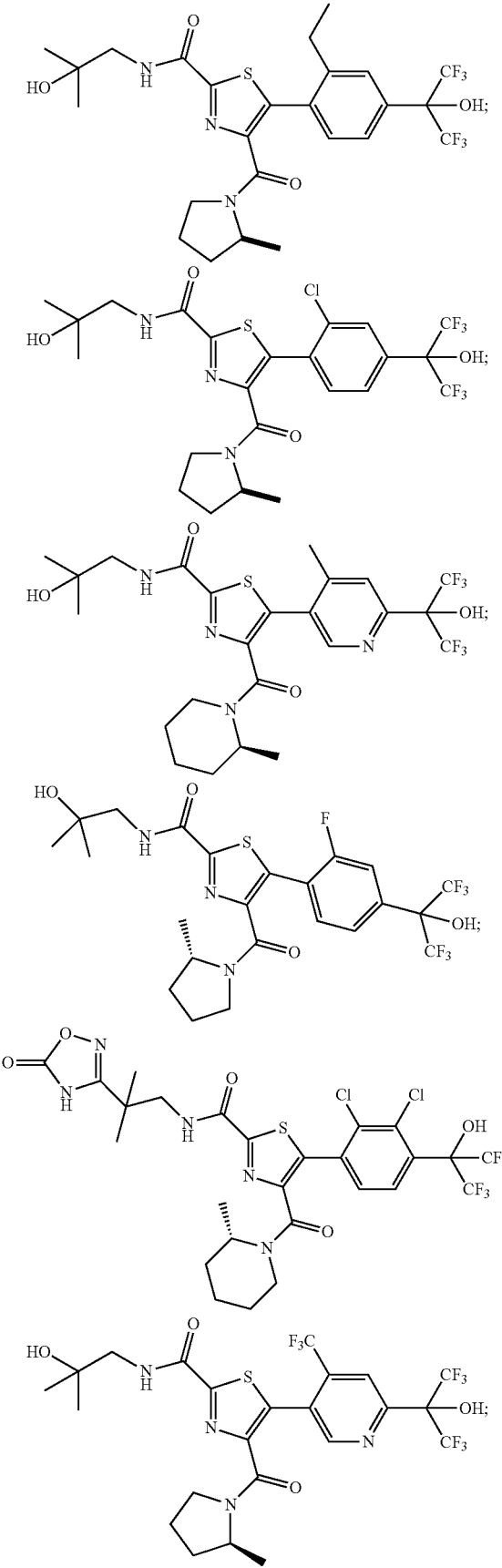
214
-continued
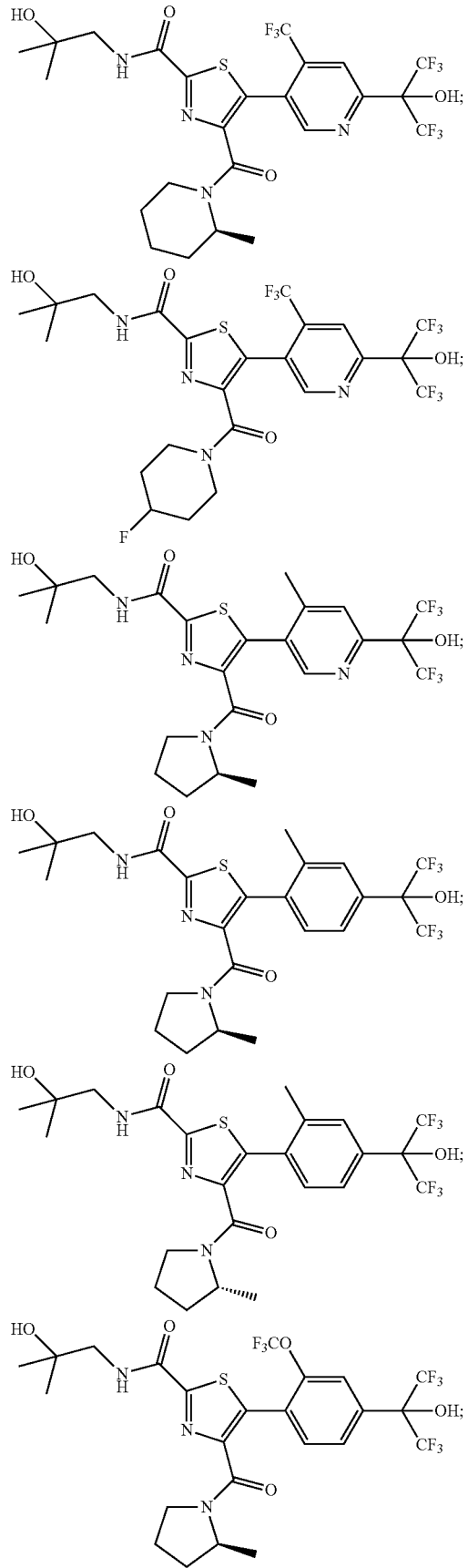

215
-continued
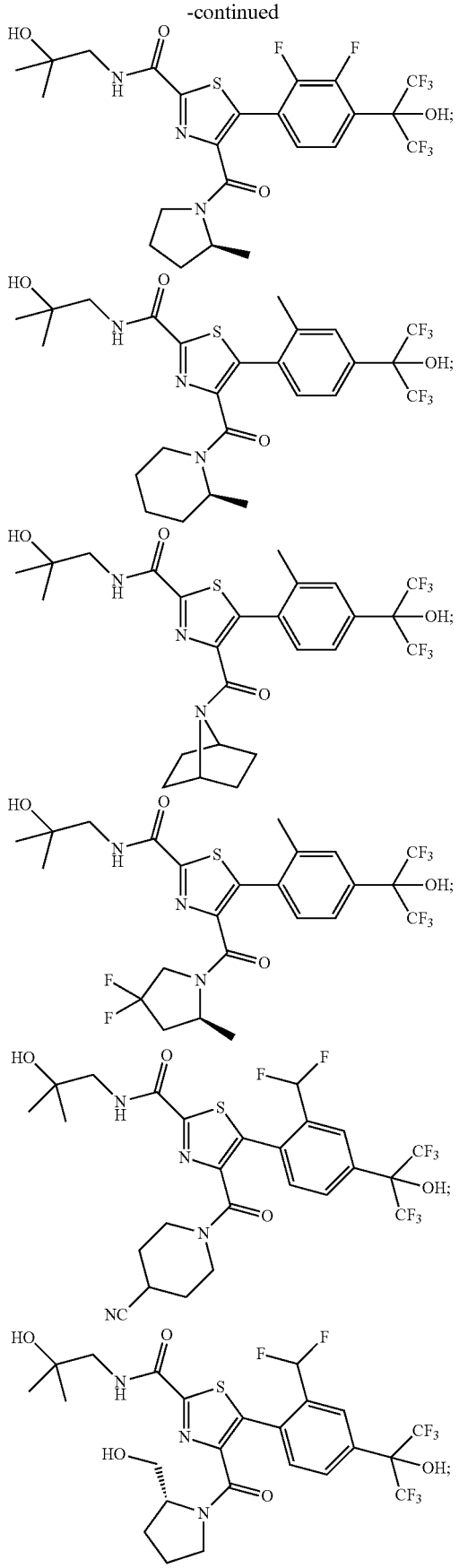
216
-continued
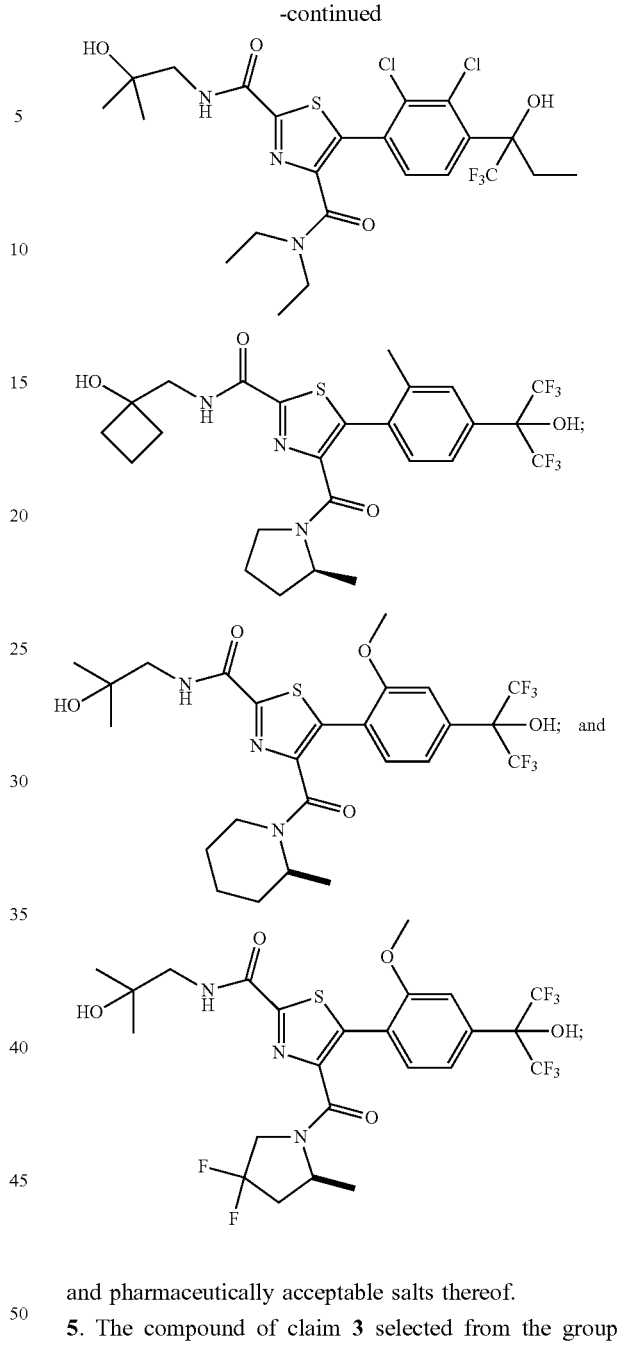
and pharmaceutically acceptable salts thereof.
5. The compound of claim 3 selected from the group consisting of:
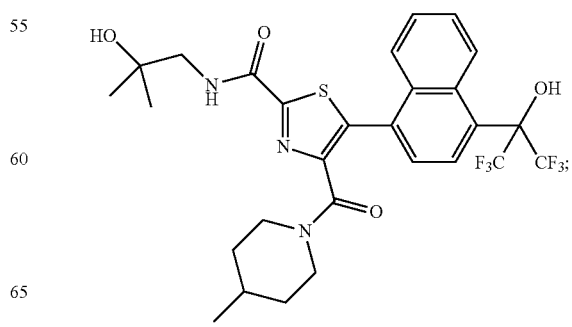

-continued
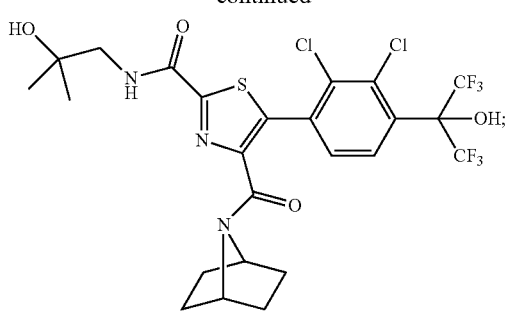
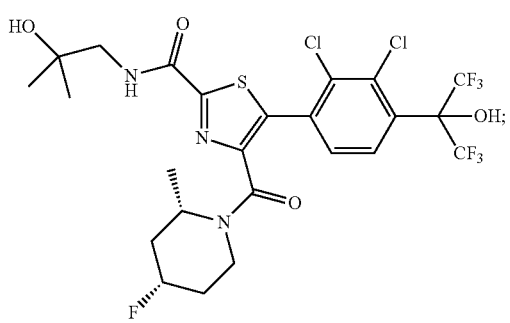
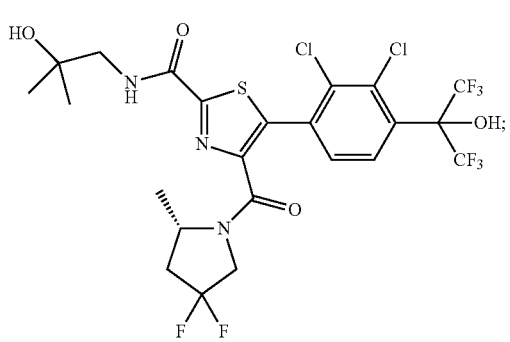
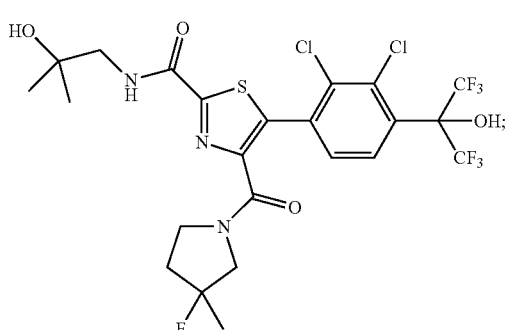
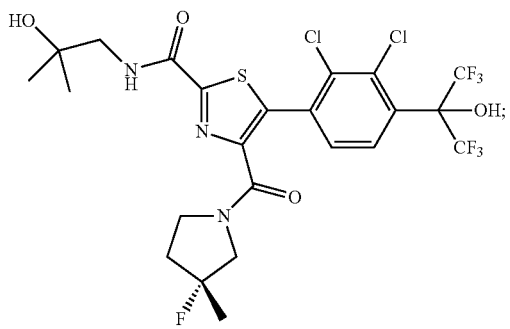
-continued
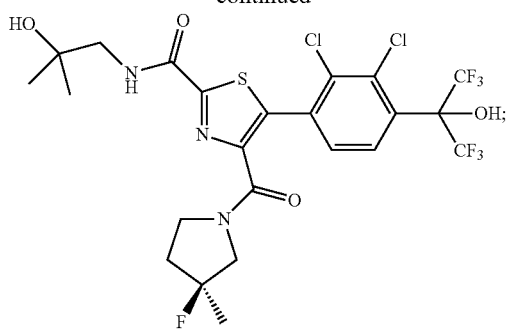
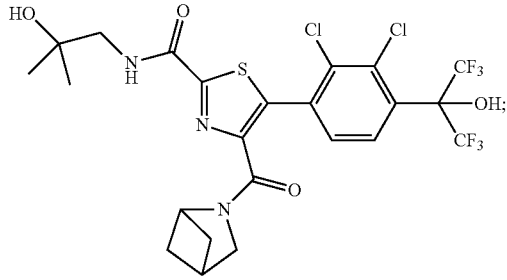
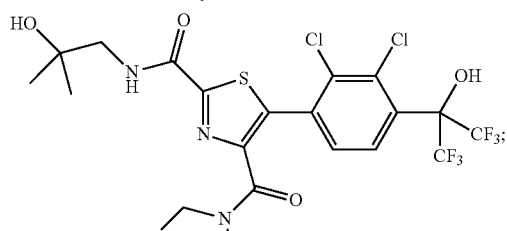
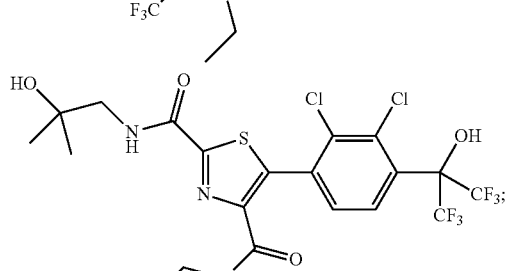
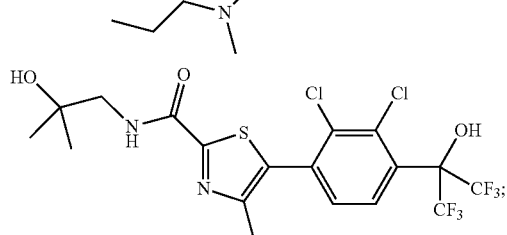
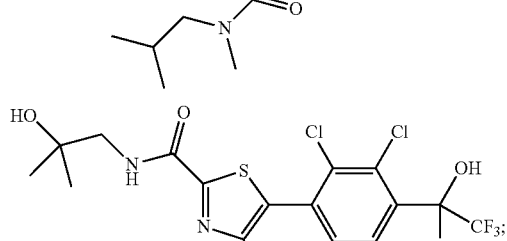

219
-continued
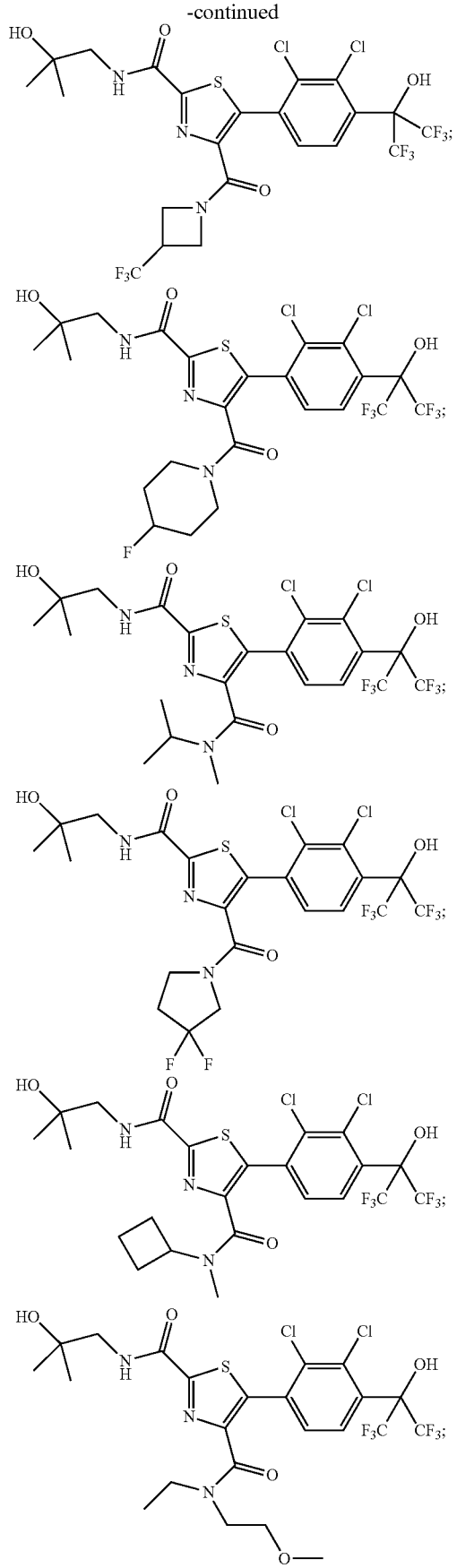
220
-continued
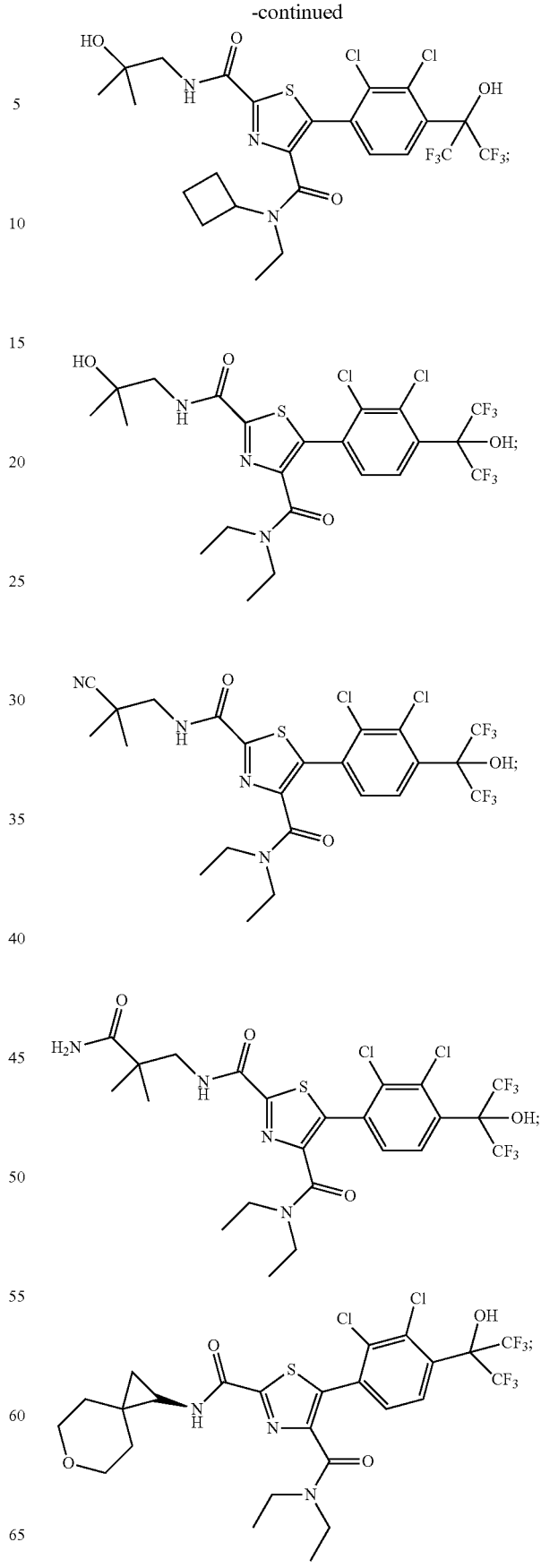

221
-continued
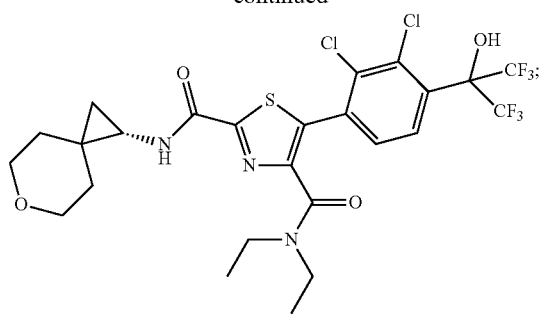
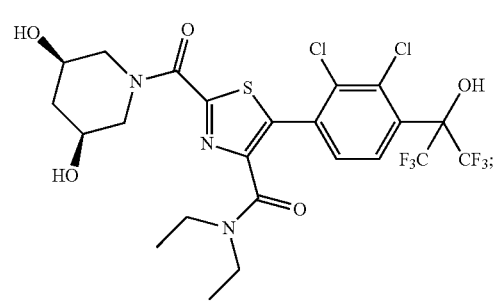
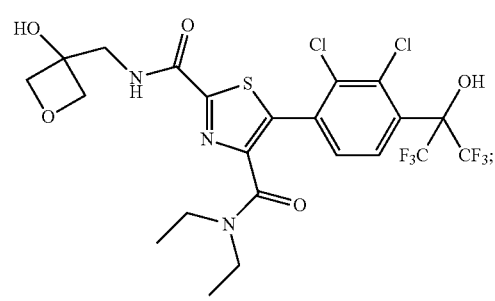
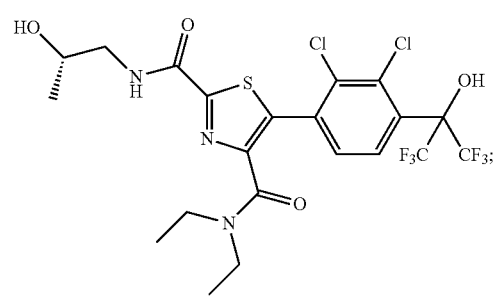
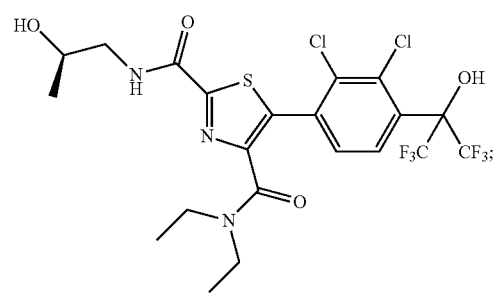
222
-continued
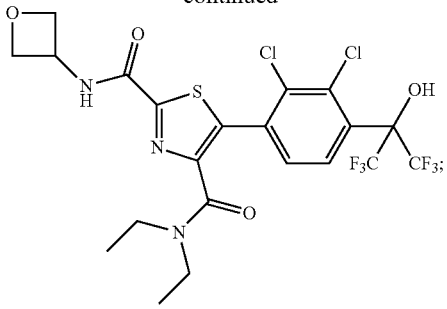
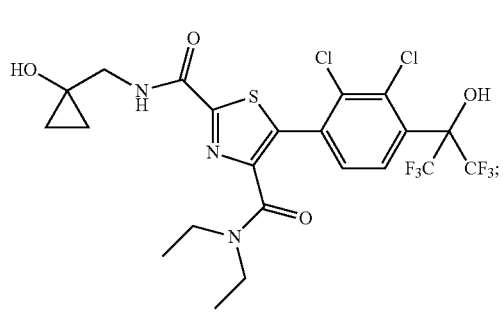
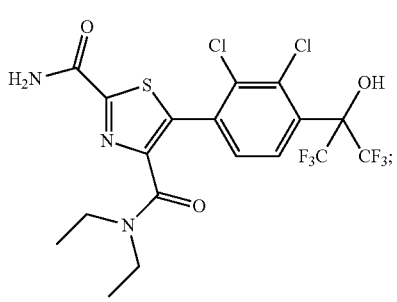
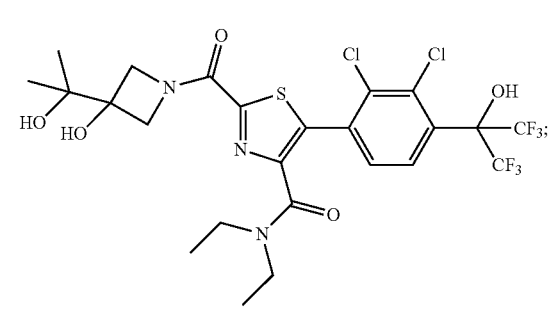
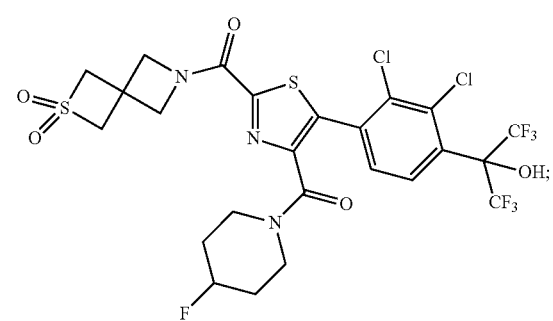

223
-continued
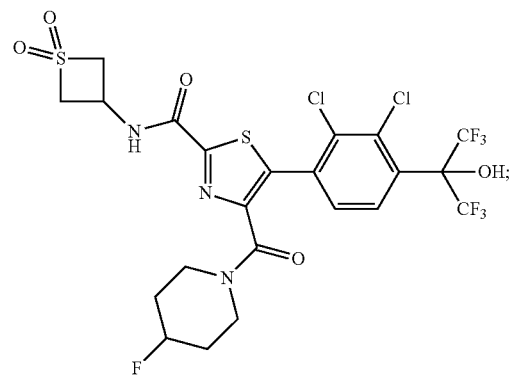
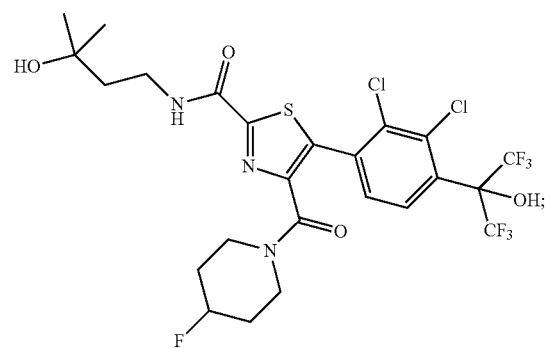
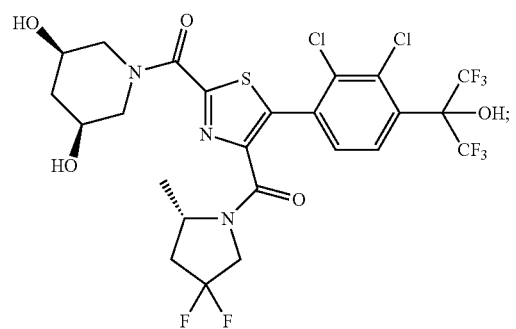
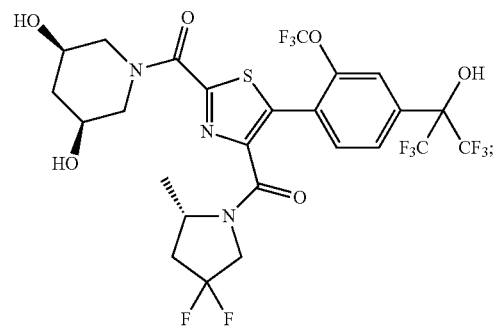
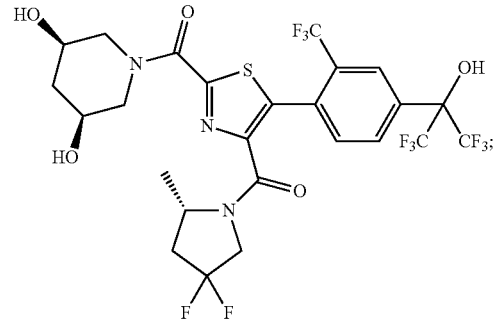
224
-continued
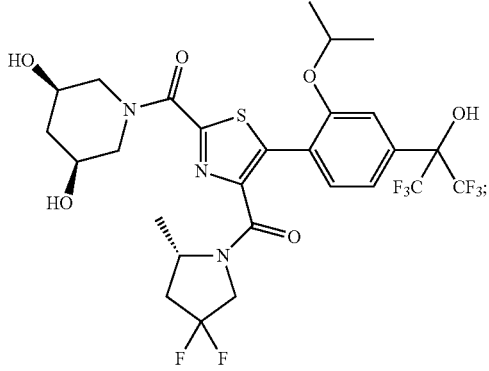
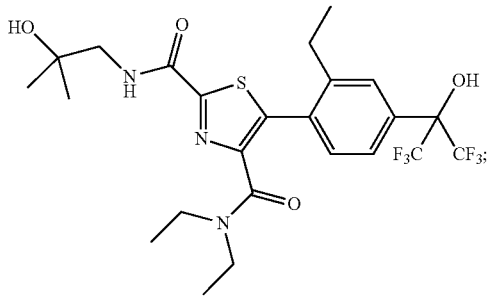
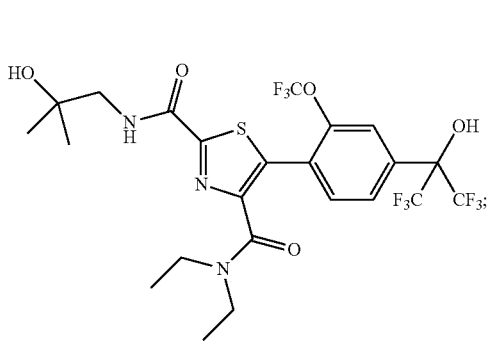
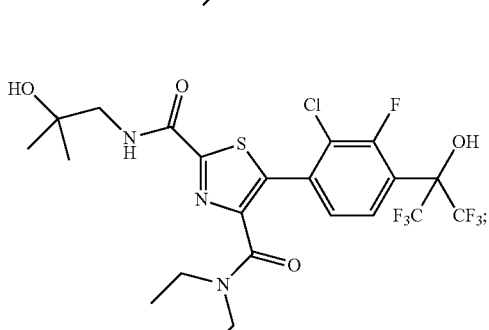
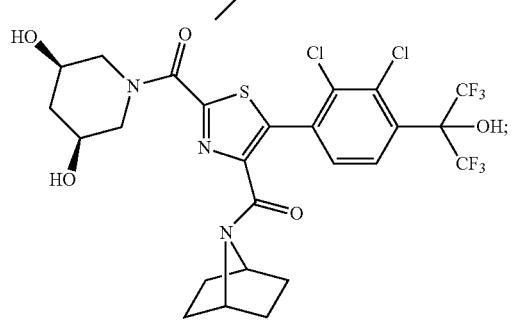

225
-continued
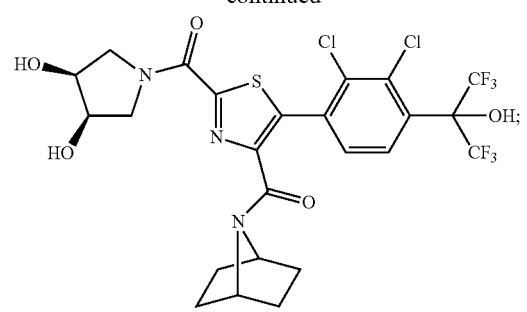
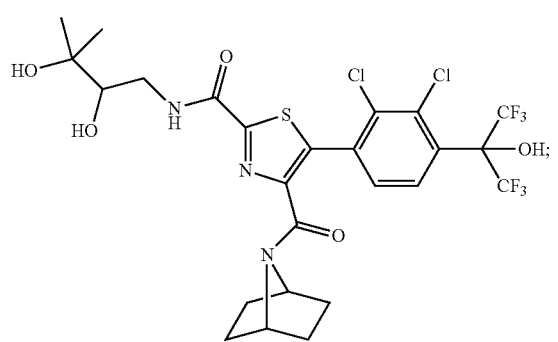
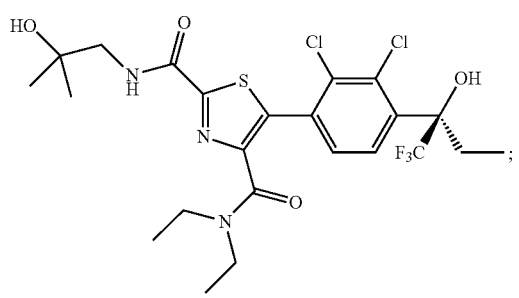
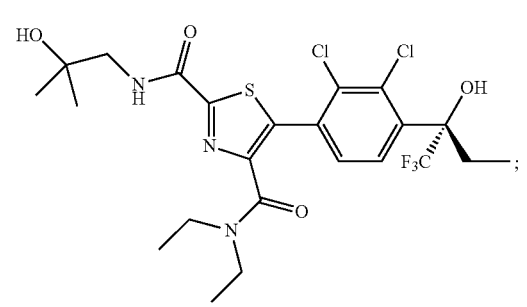
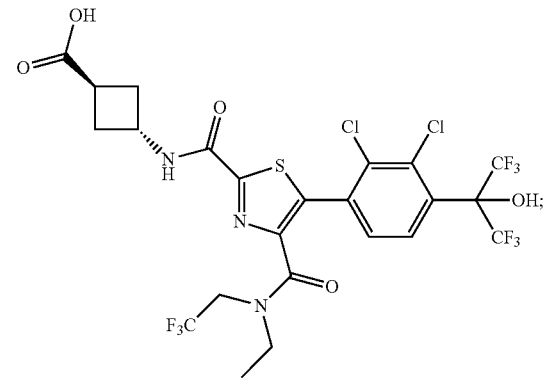
226
-continued
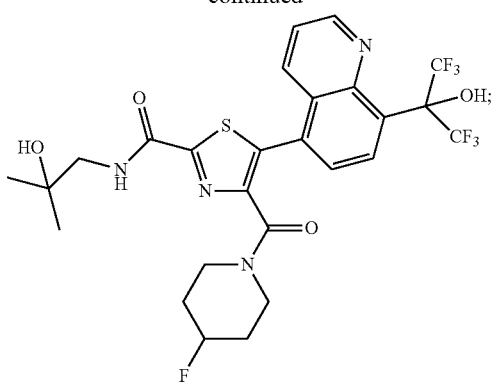
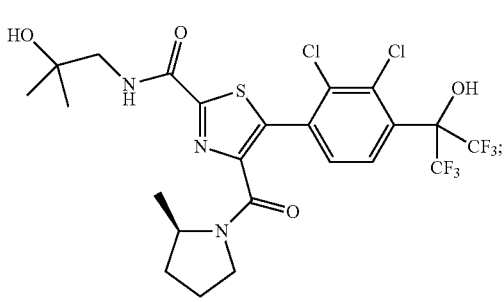
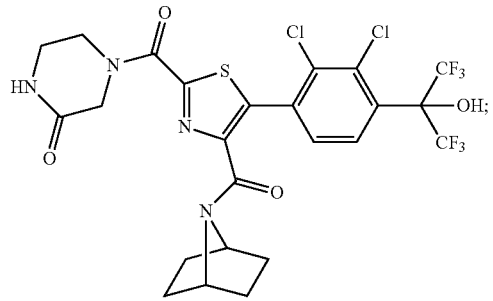
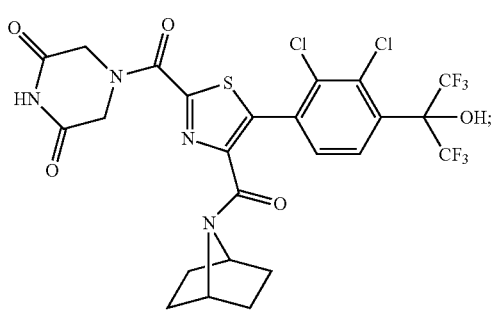
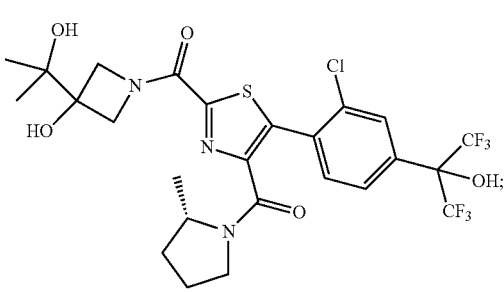

227
-continued
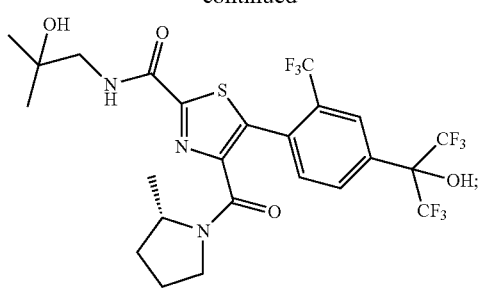
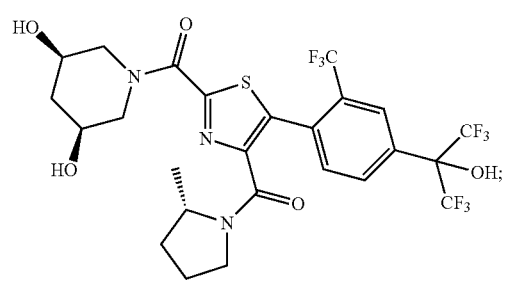
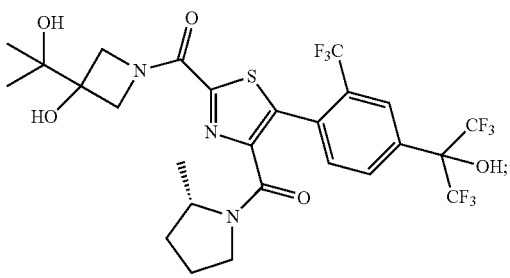
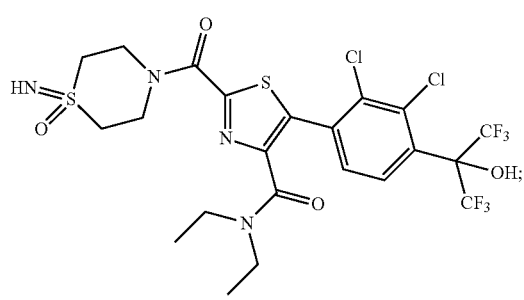
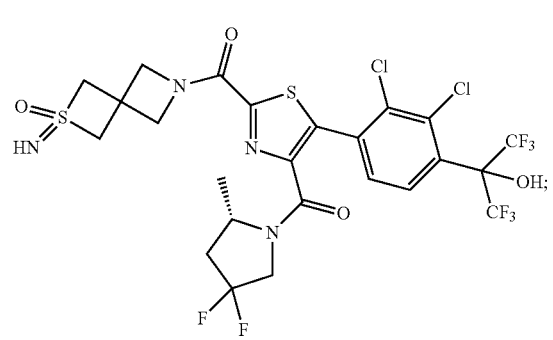
228
-continued
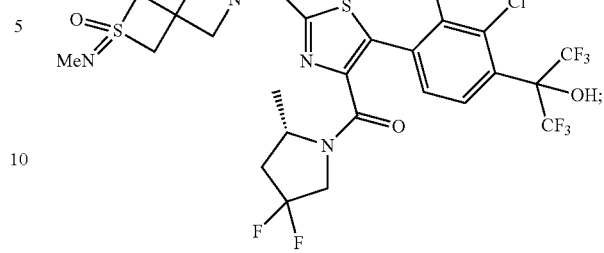
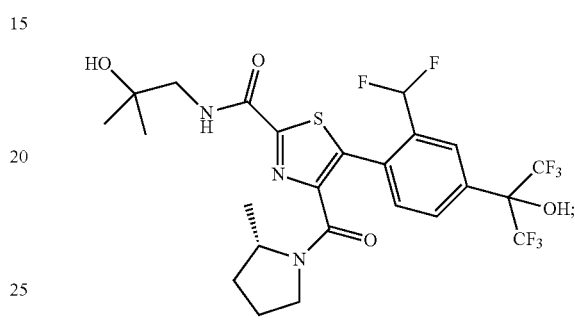
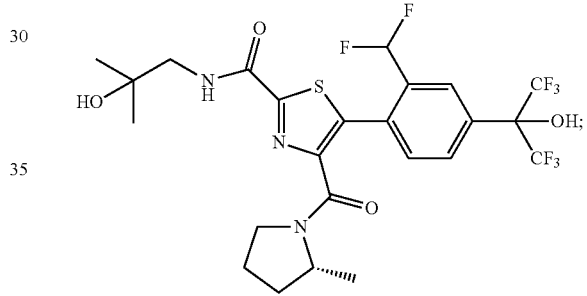
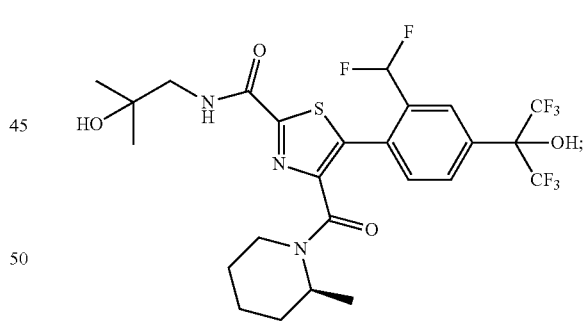
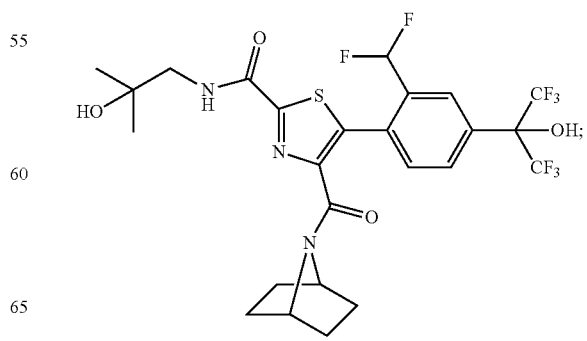

229
-continued
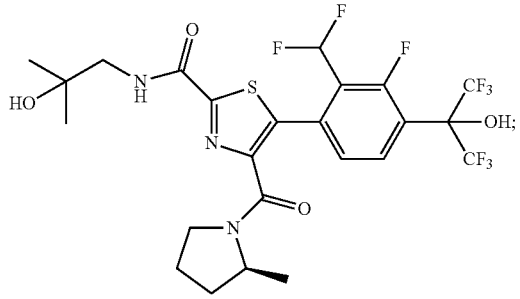
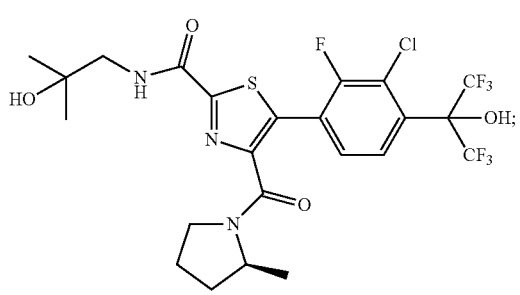
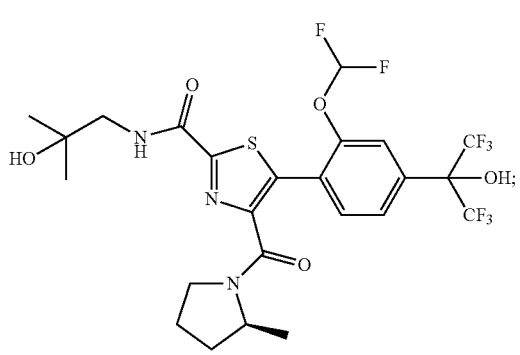
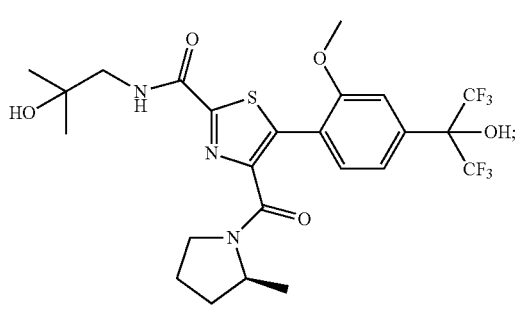
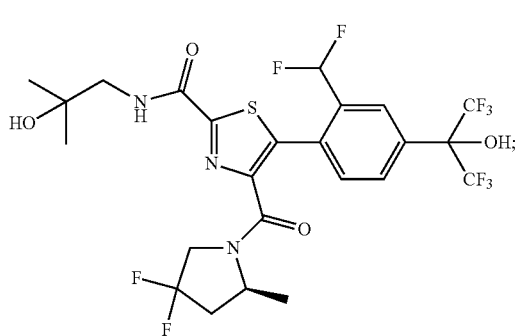
230
-continued
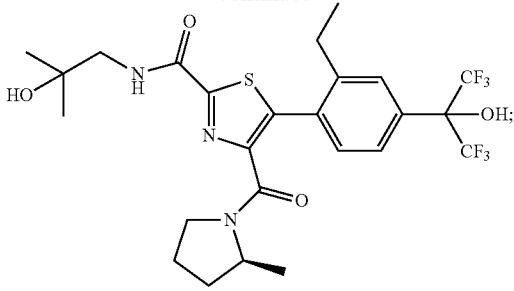
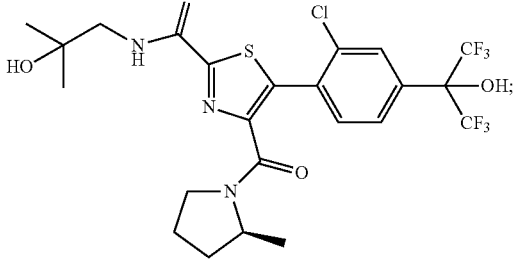
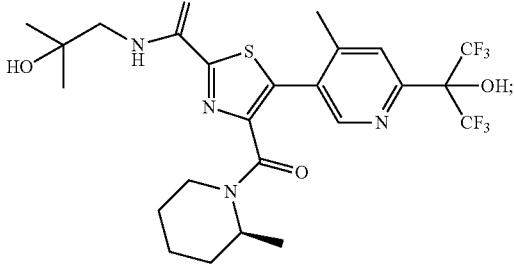
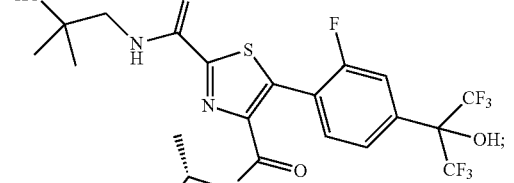
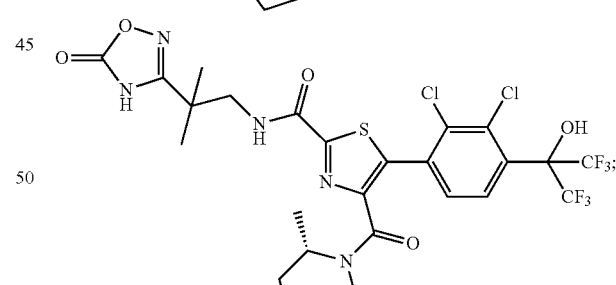
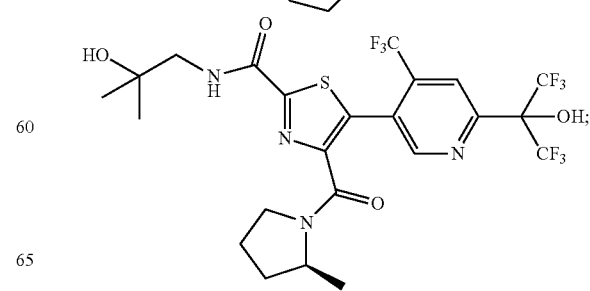

231
-continued
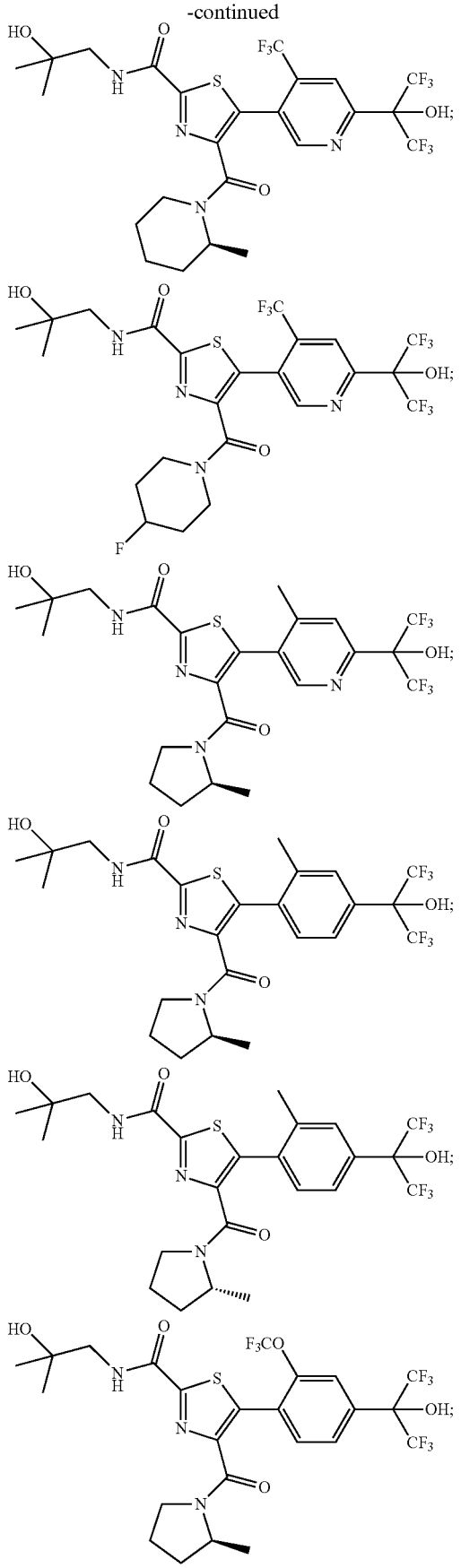
232
-continued
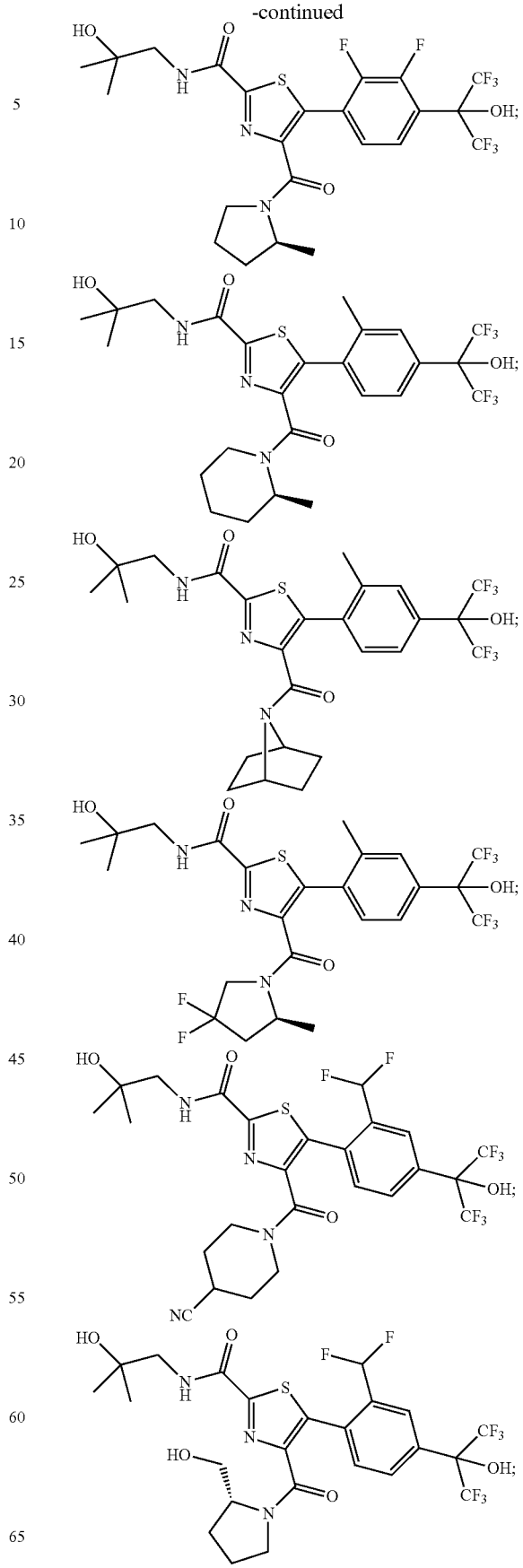

233
-continued
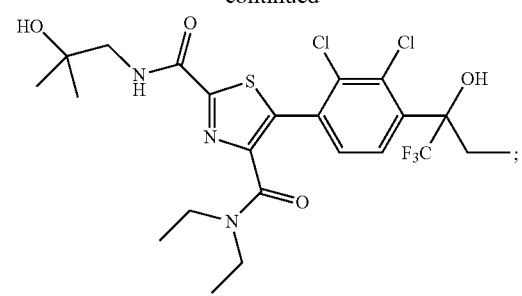
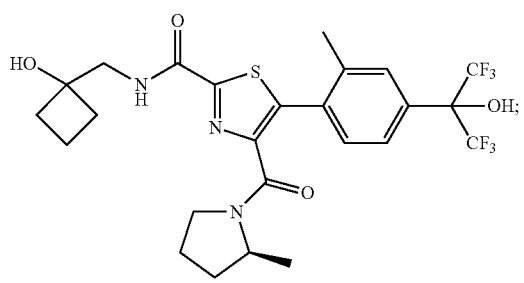
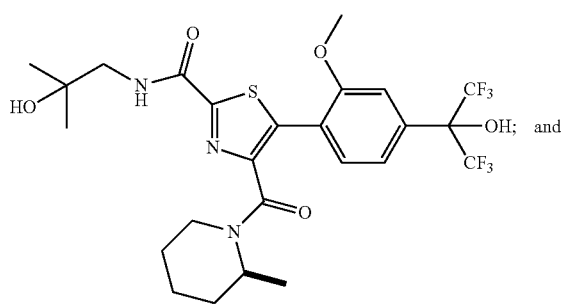
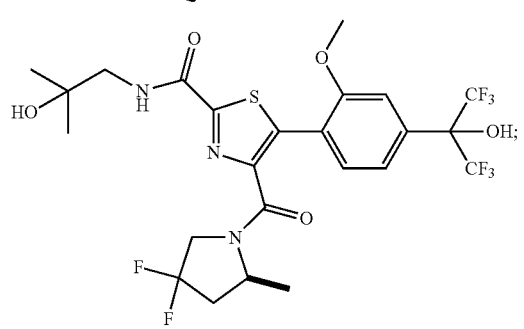
and pharmaceutically acceptable salts thereof.
6. The compound of claim 1 selected from the group consisting of:
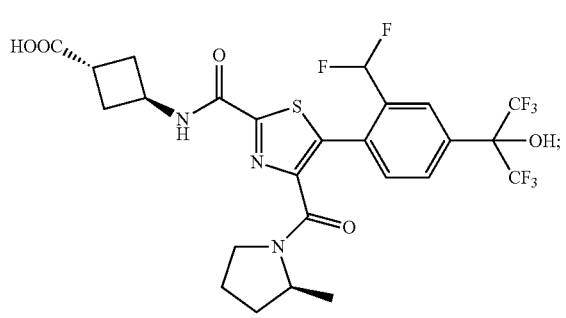
234
-continued
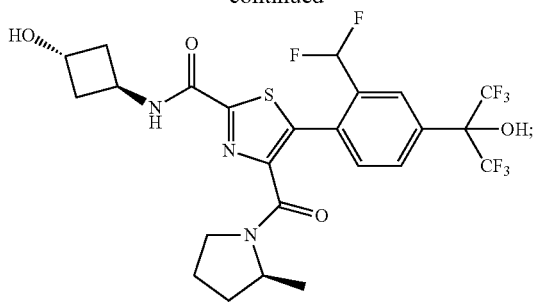
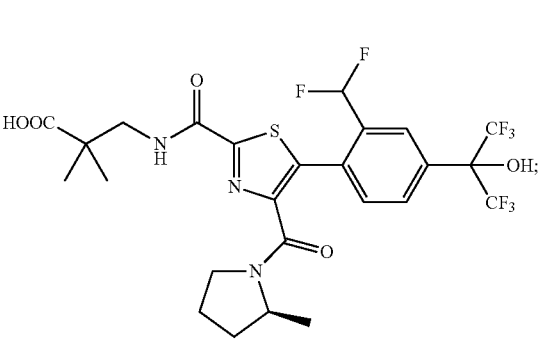
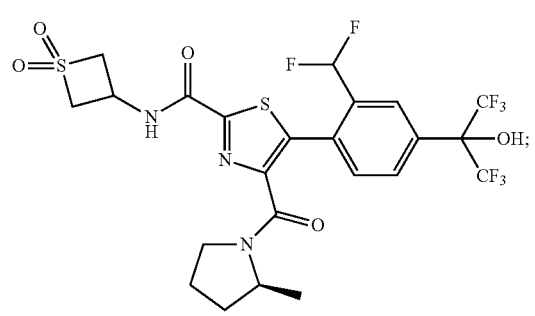
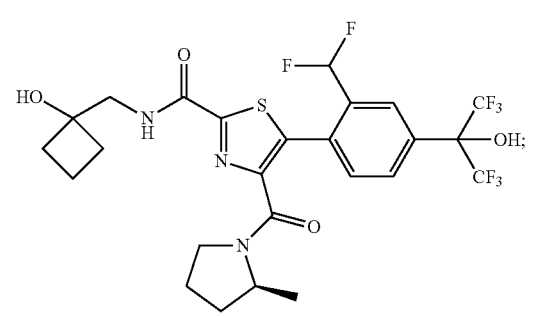
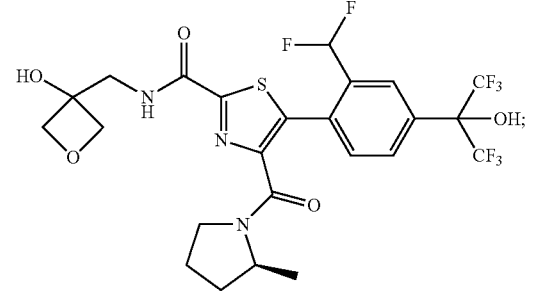

235
-continued
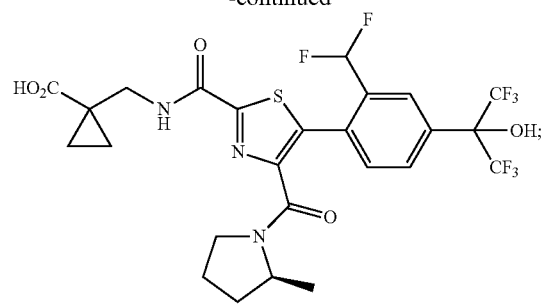
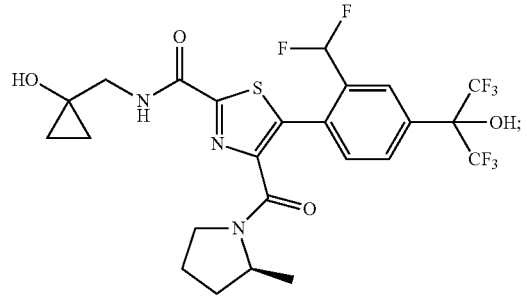
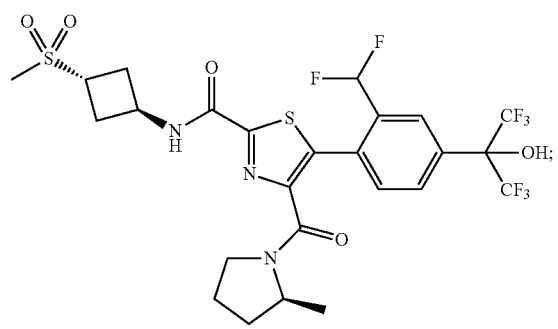
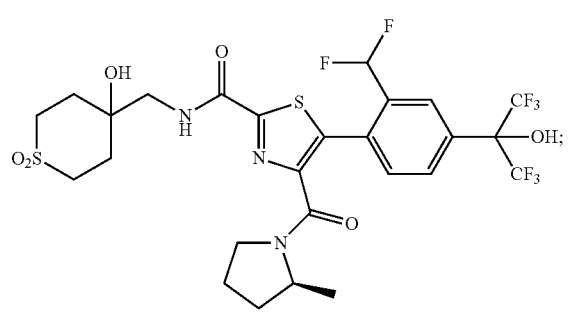
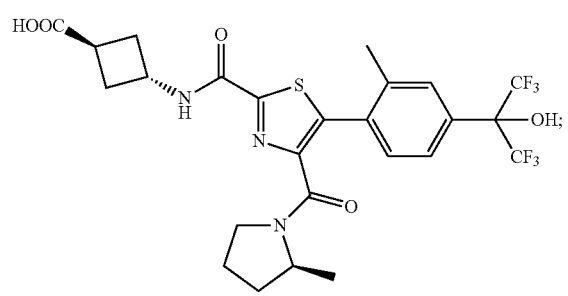
236
-continued
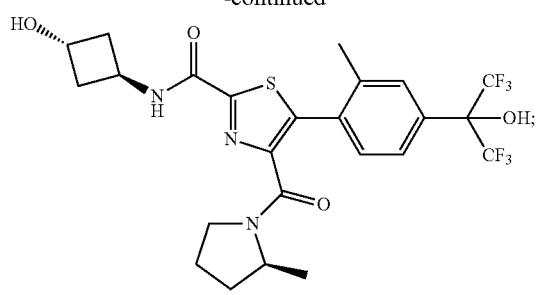
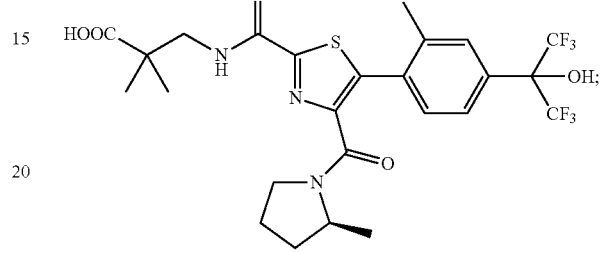
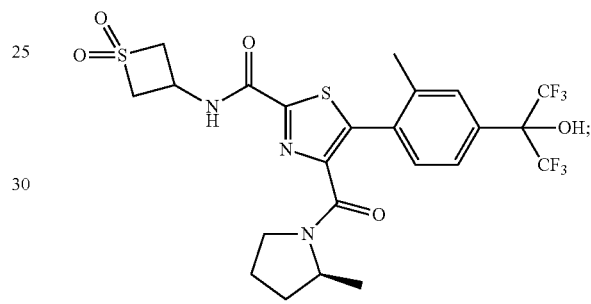
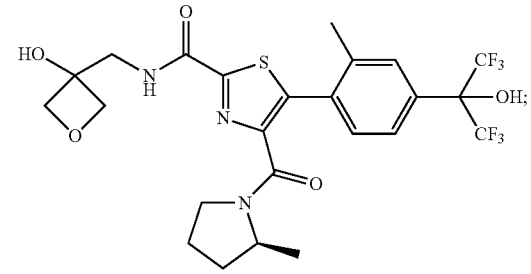
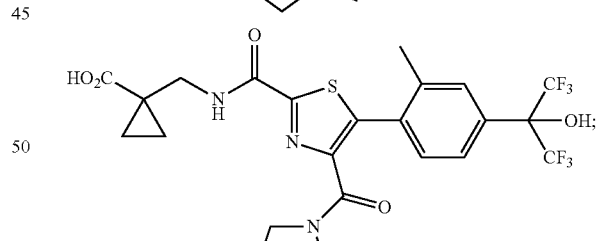
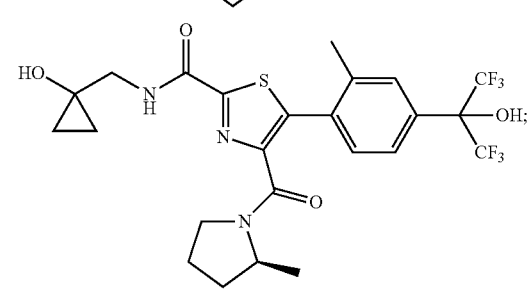

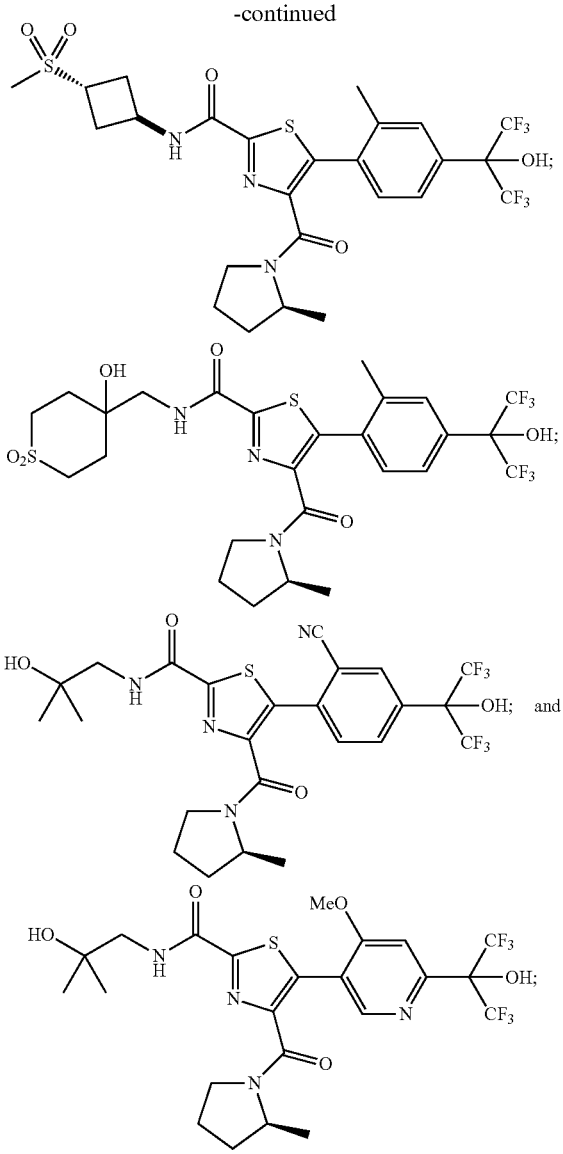

and pharmaceutically acceptable salts thereof.

7. A pharmaceutical composition, comprising a compound of claim 1 and a pharmaceutically acceptable carrier.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

10. A method for treating or ameliorating a RORγt mediated inflammatory syndrome, disorder or disease selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus, comprising administering to a subject in need thereof an effective amount of a compound of claim 1.

11. The method of claim 10, wherein the disease is psoriasis.

12. The method of claim 10, wherein the disease is rheumatoid arthritis.

13. The method of claim 10, wherein the inflammatory bowel disease is ulcerative colitis.

14. The method of claim 10, wherein the inflammatory bowel disease is Crohn's disease.

15. The method of claim 10, wherein the disease is multiple sclerosis.

16. The method of claim 10, wherein the disease is neutrophilic asthma.

17. The method of claim 10, wherein the disease is steroid resistant asthma.

18. The method of claim 10, wherein the disease is psoriatic arthritis.

19. The method of claim 10, wherein the disease is ankylosing spondylitis.

20. The method of claim 10, wherein the disease is systemic lupus erythematosus.

21. The method of claim 10, wherein the disease is chronic obstructive pulmonary disorder.

22. The compound of claim 5 selected from the group consisting of:

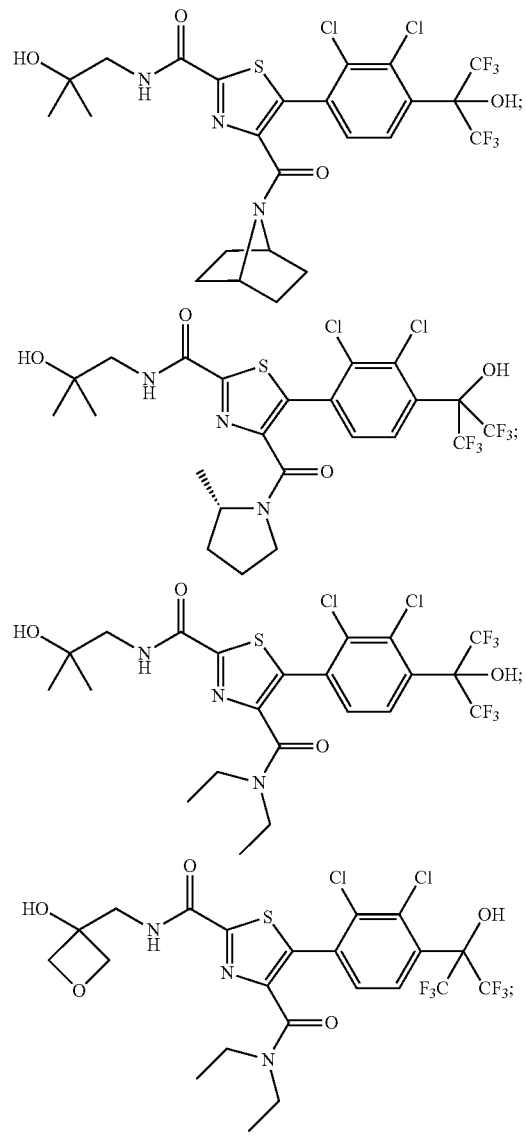

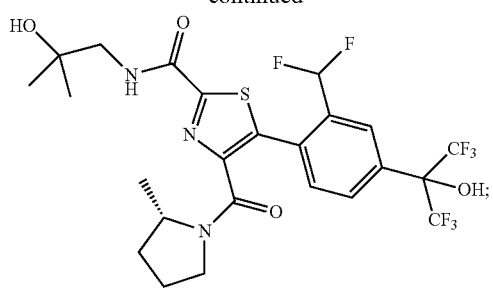
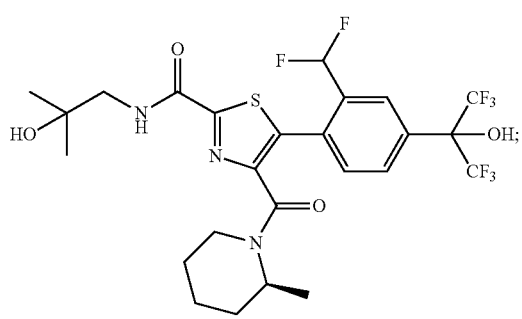
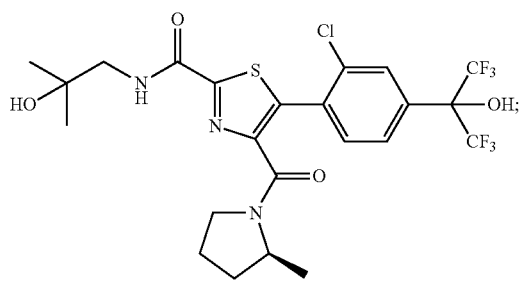
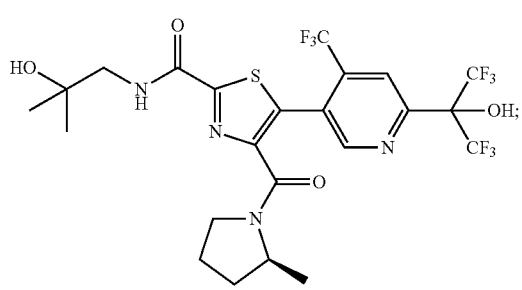
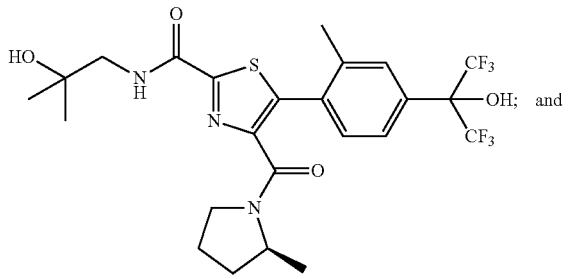
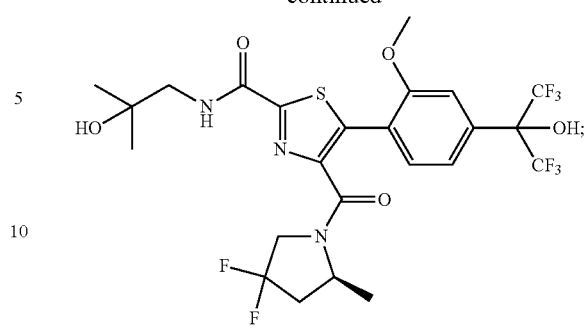
and pharmaceutically acceptable salts thereof.
23. The compound of claim 22 that is:
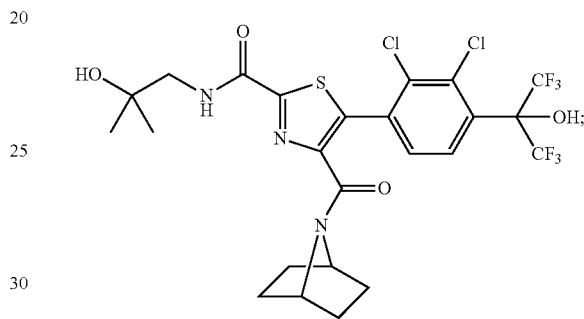
and pharmaceutically acceptable salts thereof.
24. The compound of claim 22 that is:
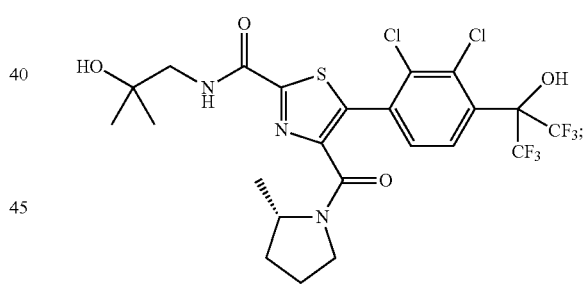
and pharmaceutically acceptable salts thereof.
25. The compound of claim 22 that is:
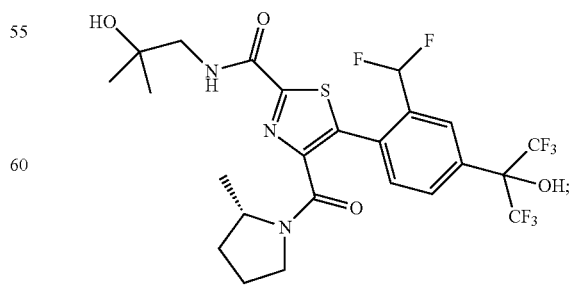
and pharmaceutically acceptable salts thereof.

26. The compound of claim 22 that is:

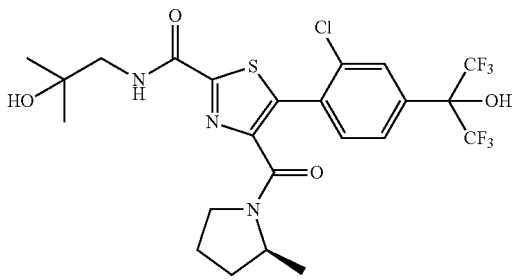 [SMILES: C[C@H]1CCCN1C(=O)c1nc(C(=O)NCC(C)(C)O)sc1-c1ccc(C(O)(C(F)(F)F)C(F)(F)F)cc1Cl]

and pharmaceutically acceptable salts thereof.

27. The compound of claim 22 that is:

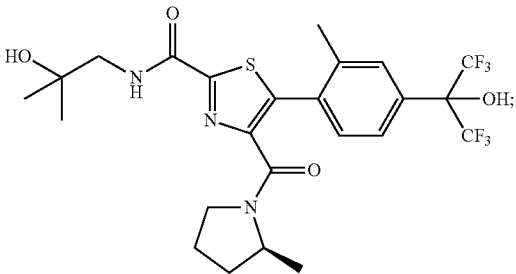 [SMILES: Cc1cc(C(O)(C(F)(F)F)C(F)(F)F)ccc1-c1sc(C(=O)NCC(C)(C)O)nc1C(=O)N1CCC[C@@H]1C]

and pharmaceutically acceptable salts thereof.

28. The compound of claim 22 that is:

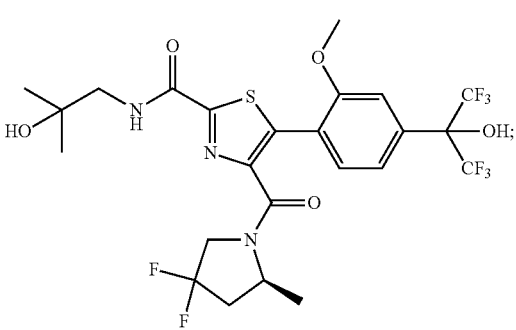 [SMILES: COc1cc(C(O)(C(F)(F)F)C(F)(F)F)ccc1-c1sc(C(=O)NCC(C)(C)O)nc1C(=O)N1CC(F)(F)C[C@@H]1C]

and pharmaceutically acceptable salts thereof.

29. A pharmaceutical composition, comprising a compound of claim 22 and a pharmaceutically acceptable carrier.

30. A pharmaceutical composition made by mixing a compound of claim 22 and a pharmaceutically acceptable carrier.

31. A process for making a pharmaceutical composition comprising mixing a compound of claim 22 and a pharmaceutically acceptable carrier.

32. A method for treating or ameliorating a RORγt mediated inflammatory syndrome, disorder or disease selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus, comprising administering to a subject in need thereof an effective amount of a compound of claim 22.

33. The method of claim 32, wherein the disease is psoriasis.

34. The method of claim 32, wherein the disease is rheumatoid arthritis.

35. The method of claim 32, wherein the inflammatory bowel disease is ulcerative colitis.

36. The method of claim 32, wherein the inflammatory bowel disease is Crohn's disease.

37. The method of claim 32, wherein the disease is multiple sclerosis.

38. The method of claim 32, wherein the disease is neutrophilic asthma.

39. The method of claim 32, wherein the disease is steroid resistant asthma.

40. The method of claim 32, wherein the disease is psoriatic arthritis.

41. The method of claim 32, wherein the disease is ankylosing spondylitis.

42. The method of claim 32, wherein the disease is systemic lupus erythematosus.

43. The method of claim 32, wherein the disease is chronic obstructive pulmonary disorder.

* * * * *